US009611310B2

(12) United States Patent
Low et al.

(10) Patent No.: US 9,611,310 B2
(45) Date of Patent: Apr. 4, 2017

(54) SYSTEMS FOR FACTOR VIII PROCESSING AND METHODS THEREOF

(75) Inventors: Susan C. Low, Pepperell, MA (US); Robert T. Peters, West Roxbury, MA (US)

(73) Assignee: Bioverativ Therapeutics Inc., Waltham, MA (US)

( * ) Notice: Subject to any disclaimer, the term of this patent is extended or adjusted under 35 U.S.C. 154(b) by 636 days.

(21) Appl. No.: 13/809,285

(22) PCT Filed: Jul. 11, 2011

(86) PCT No.: PCT/US2011/043568
§ 371 (c)(1), (2), (4) Date: Jun. 5, 2013

(87) PCT Pub. No.: WO2012/006623
PCT Pub. Date: Jan. 12, 2012

(65) Prior Publication Data

US 2013/0281671 A1 Oct. 24, 2013

Related U.S. Application Data

(60) Provisional application No. 61/363,184, filed on Jul. 9, 2010.

(51) Int. Cl.

| | |
|---|---|
| ***C07K 14/755*** | (2006.01) |
| ***C12N 9/64*** | (2006.01) |
| ***C12P 21/06*** | (2006.01) |
| ***C12N 9/60*** | (2006.01) |

(52) U.S. Cl.
CPC .............. *C07K 14/755* (2013.01); *C12N 9/60* (2013.01); *C12N 9/6424* (2013.01); *C12P 21/06* (2013.01); *C07K 2319/00* (2013.01); *C07K 2319/02* (2013.01); *C07K 2319/21* (2013.01); *C07K 2319/23* (2013.01); *C07K 2319/30* (2013.01); *C07K 2319/31* (2013.01); *C07K 2319/43* (2013.01)

(58) Field of Classification Search
CPC ...... C07K 14/755; C12N 9/6424; C12P 21/06
See application file for complete search history.

(56) References Cited

U.S. PATENT DOCUMENTS

| | | | |
|---|---|---|---|
| 4,215,051 A | 7/1980 | Palmer et al. | |
| 4,713,339 A | 12/1987 | Levinson et al. | |
| 4,757,006 A | 7/1988 | Toole, Jr. et al. | |
| 4,868,112 A | 9/1989 | Toole, Jr. | |
| 4,965,199 A | 10/1990 | Capon et al. | |
| 4,994,371 A | 2/1991 | Davie et al. | |
| 5,004,803 A | 4/1991 | Kaufman et al. | |
| 5,112,950 A | 5/1992 | Meulien et al. | |
| 5,116,964 A | 5/1992 | Capon et al. | |
| 5,171,844 A | 12/1992 | Van Ooyen et al. | |
| 5,252,714 A | 10/1993 | Harris et al. | |
| 5,364,771 A | 11/1994 | Lollar et al. | |
| 5,460,950 A * | 10/1995 | Barr ..................... | C12N 9/6454 435/219 |
| 5,480,981 A | 1/1996 | Goodwin et al. | |
| 5,543,502 A | 8/1996 | Nordfang et al. | |
| 5,595,886 A | 1/1997 | Chapman et al. | |
| 5,610,278 A | 3/1997 | Nordfang et al. | |
| 5,624,821 A | 4/1997 | Winter et al. | |
| 5,739,277 A | 4/1998 | Presta et al. | |
| 5,789,203 A | 8/1998 | Chapman et al. | |
| 5,808,029 A | 9/1998 | Brockhaus et al. | |
| 5,859,204 A | 1/1999 | Lollar | |
| 5,935,815 A | 8/1999 | Van de Ven et al. | |
| 5,972,885 A | 10/1999 | Spira et al. | |
| 5,981,216 A | 11/1999 | Kenten et al. | |
| 6,030,613 A | 2/2000 | Blumberg et al. | |
| 6,048,720 A | 4/2000 | Dalborg et al. | |
| 6,060,447 A | 5/2000 | Chapman et al. | |
| 6,086,875 A | 7/2000 | Blumberg et al. | |
| 6,228,620 B1 | 5/2001 | Chapman et al. | |
| 6,251,632 B1 | 6/2001 | Lillicrap et al. | |
| 6,316,226 B1 | 11/2001 | Van Ooyen et al. | |
| 6,346,513 B1 | 2/2002 | Van Ooyen et al. | |
| 6,376,463 B1 | 4/2002 | Lollar | |

(Continued)

FOREIGN PATENT DOCUMENTS

| | | |
|---|---|---|
| EP | 0154316 A2 | 9/1985 |
| EP | 0295597 A2 | 12/1988 |

(Continued)

OTHER PUBLICATIONS

Kaufman, R.J., et al. 1988 The Journal of Biological Chemistry 263(13): 6352-6362.*
Scamuffa, N., et al. 2006 The FASEB Journal 20: 1954-1963.*
Pittman, D.D., et al. Blood 81(11): 2925-2935.*
Aruffo, A., et al., "CD44 Is the Principal Cell Surface Receptor for Hyaluronate," *Cell* 61(7):1303-1313, Cell Press, United States (1990).
Ashkenazi, A., et al., "Protection against Endotoxic Shock by a Tumor Necrosis Factor Receptor Immunoadhesin," *Proceedings of the National Academy of Sciences of the United States of America* 88(23):10535-10539, National Academy of Sciences, United States (1991).
Zheng, X.X., et al., "Administration of Noncytolytic IL-10/Fc in Murine Models of Lipopolysaccharide-Induced Septic Shock and Allogeneic Islet Transplantation," *Journal of Immunology* 154(10):5590-5600, The American Association of Immunologists, United States (1995).

(Continued)

*Primary Examiner* — Marsha Tsay
(74) *Attorney, Agent, or Firm* — Sterne, Kessler, Goldstein & Fox P.L.L.C.

(57) ABSTRACT

The present invention provides methods of reducing non-processed Factor VIII or a chimeric polypeptide comprising Factor VIII comprising co-transfecting in a host cell a polynucleotide encoding Factor VIII with a polynucleotide encoding a protein convertase, where the endogenous processing enzymes of the host cell are insufficient to convert all of the Factor VIII to its processed isoform; expressing a proprotein convertase from a second polynucleotide in the host cell; and reducing the nonprocessed Factor VIII by processing with said proprotein convertase.

25 Claims, 8 Drawing Sheets

(56) References Cited

U.S. PATENT DOCUMENTS

Figure 1:
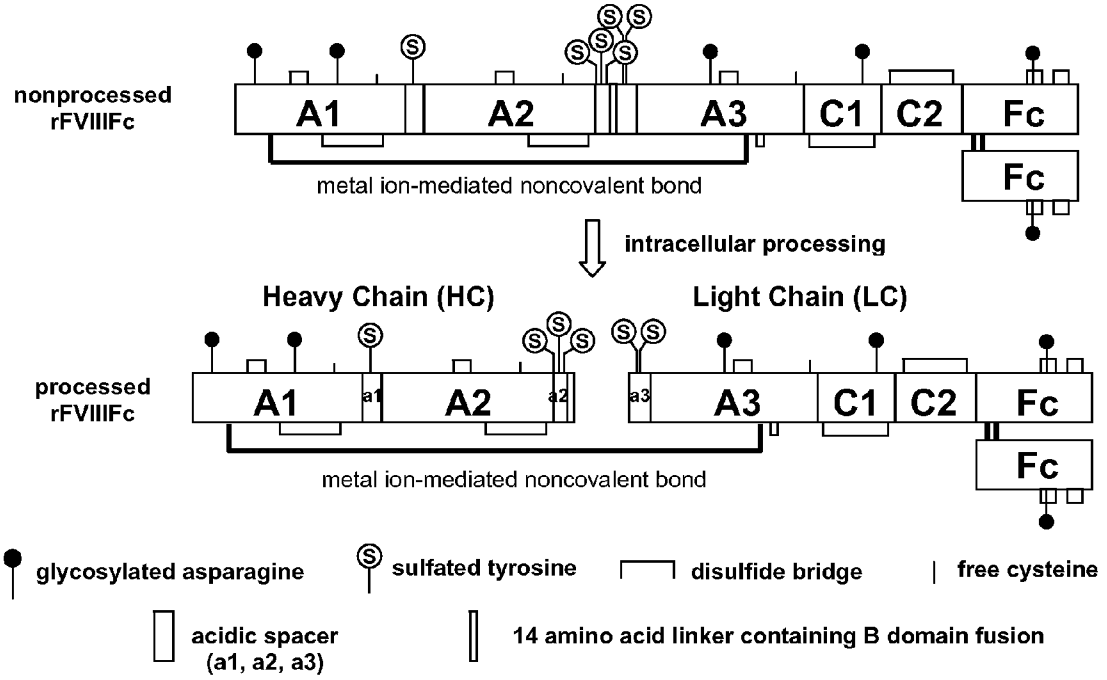

| | | | | |
|---|---|---|---|---|
| 6,380,171 | B1 | 4/2002 | Day et al. | |
| 6,458,563 | B1 | 10/2002 | Lollar | |
| 6,485,726 | B1 | 11/2002 | Blumberg et al. | |
| 7,041,635 | B2 | 5/2006 | Kim et al. | |
| 7,199,223 | B2 | 4/2007 | Bossard et al. | |
| 7,404,956 | B2 | 7/2008 | Peters et al. | |
| 7,566,565 | B2 | 7/2009 | Peters et al. | |
| 7,795,400 | B2 | 9/2010 | Peters et al. | |
| 8,021,880 | B2 | 9/2011 | Peters et al. | |
| 2003/0235536 | A1 | 12/2003 | Blumberg et al. | |
| 2004/0101740 | A1 | 5/2004 | Sanders | |
| 2004/0192599 | A1* | 9/2004 | Schuh et al. | 514/12 |
| 2005/0027109 | A1 | 2/2005 | Mezo et al. | |
| 2005/0100990 | A1 | 5/2005 | Saenko et al. | |
| 2006/0074199 | A1 | 4/2006 | Hirata et al. | |
| 2006/0115876 | A1 | 6/2006 | Pan et al. | |
| 2008/0261877 | A1 | 10/2008 | Ballance et al. | |
| 2008/0280818 | A1 | 11/2008 | DeFrees | |
| 2009/0163699 | A1 | 6/2009 | Chamberlain et al. | |
| 2009/0264627 | A1 | 10/2009 | Gillies et al. | |
| 2012/0021484 | A1* | 1/2012 | McDonnell | C07K 1/22 435/183 |

FOREIGN PATENT DOCUMENTS

| | | | | |
|---|---|---|---|---|
| EP | 0401384 | A1 | 12/1990 | |
| WO | WO-8704187 | A1 | 7/1987 | |
| WO | WO-8800831 | A1 | 2/1988 | |
| WO | WO-8803558 | A1 | 5/1988 | |
| WO | WO-8808035 | A1 | 10/1988 | |
| WO | WO-9109122 | A1 | 6/1991 | |
| WO | WO-9216221 | A1 | 10/1992 | |
| WO | WO-9320093 | A1 | 10/1993 | |
| WO | WO-9411503 | A2 | 5/1994 | |
| WO | WO-9534326 | A1 | 12/1995 | |
| WO | WO-03077834 | A2 | 9/2003 | |
| WO | WO-2004101740 | A2 | 11/2004 | |
| WO | WO-2006074199 | A1 | 7/2006 | |
| WO | WO-2007112005 | A2 | 10/2007 | |
| WO | WO-2009089396 | A2 | 7/2009 | |
| WO | WO 2010048313 | A3 * | 7/2010 | C07K 1/22 |
| WO | WO-2012122611 | A1 | 9/2012 | |

OTHER PUBLICATIONS

Barbero, P., et al., "PC5-A-mediated Processing of Pro-Neurotensin in Early Compartments of the Regulated Secretory Pathway of PC5-Transfected PC12 Cells," *The Journal of Biological Chemistry* 273(39):25339-25346, The American Society for Biochemistry and Molecular Biology, Inc., United States (1998).

Benjannet, S., et al., "PC1 and PC2 are Proprotein Convertases Capable of Cleaving Proopiomelanocortin at Distinct Pairs of Basic Residues," *Proceedings of the National Academy of Sciences USA* 88(9):3564-3568, National Academy of Sciences, United States (1991).

Bennett, B.D., et al., "Extracellular Domain-IgG Fusion Proteins for Three Human Natriuretic Peptide Receptors: Hormone Pharmacology and Application to Solid Phase Screening of Synthetic Peptide Antisera," *The Journal of Biological Chemistry* 266(34):23060-23067, The American Society for Biochemistry and Molecular Biology, Inc., United States (1991).

Burmeister, W.P., et al., "Crystal structure of the complex of rat neonatal Fc receptor with Fc," *Nature* 372(6504):379-383, Nature Publishing Group/Macmillan Journals Ltd., England (1994).

Byrn, R.A., et al., "Biological Properties of a CD4 Immunoadhesin," *Nature* 344(6267):667-670 Nature Publishing Group, UK (1990).

Cameron, C., et al., "The canine factor VIII cDNA and 5' flanking sequence," *Thrombosis and Haemostasis* 79(2):317-322, Schattauer Verlag, Germany (1998).

Capon, D.J., et al., "Designing CD4 Immunoadhesins for AIDS Therapy," *Nature* 337(6207):525-531, Nature Publishing Group, UK (1989).

Chalupny, N.J., et al., "T-Cell Activation Molecule 4-IBB Binds to Extracellular Matrix Proteins," *Proceedings of the National Academy of Sciences USA* 89(21):10360-10364, National Academy of Sciences, United States (1992).

Chamow, S.M., et al., "Modification of CD4 Immunoadhesin With Monomethoxypoly (Ethylene Glycol) Aldehyde Via Reductive Alkylation," *Bioconjugate Chemistry* 5(2):133-140, American Chemical Society, United States of America (1994).

Eaton, D.L., et al., "Construction and characterization of an active factor VIII variant lacking the central one-third of the molecule," *Biochemistry* 25(26):8343-8347, The American Chemical Society, United States (1986).

Francis, G.E., "Protein Modification arid Fusion Proteins," *Focus on Growth Factors* 3(2):4-10, Mediscript, England (1992).

Gascoigne, N.R.J., et al., "Secretion of a Chimeric T-Cell Receptor-Immunoglobulin Protein," *Proceedings of the National Academy of Sciences USA* 84(9):2936-2940, National Academy of Sciences, United States (1987).

GenBank, "Sequence 6 from Patent WO0131007," Accession No. AX127530.1, accessed at https://www.ncbi.nlm.nih.gov/nuccore/AX127530.1, accessed on Sep. 16, 2014, 3 pages.

GenBank, "*Homo sapiens* clone DNA119302 prohormone convertase (UNQ2757) mRNA, complete cds," Accession No. AY358963.1, accessed at https://www.ncbi.nlm.nih.gov/nuccore/AY358963.1, Oct. 3, 2003, accessed on Sep. 16, 2014, 3 pages.

GenBank, "*Homo sapiens* furin (paired basic amino acid cleaving enzyme), mRNA (cDNA clone MGC:20463 Image:4550620), complete cds," Accession No. BC012181.1, accessed at https://www.ncbi.nlm.nih.gov/nuccore/BC012181.1, accessed on Sep. 16, 2014, 5 pages.

GenBank, "*Homo sapiens* membrane-bound transcription factor peptidase, site 1, transcript variant 1, mRNA (cDNA clone MGC:138712 Image:40054075), complete cds," Accession No. BC114555.1, accessed at https://www.ncbi.nlm.nih.gov/nuccore/BC114555.1, accessed on Sep. 16, 2014, 4 pages.

GenBank, "*Homo sapiens* mRNA; cDNA DKFZp66710310 (from clone DKFZp66710310)", Accession No. AL834522.1, accessed at https://www.ncbi.nlm.nih.gov/nuccore/AL834522.1, accessed on Sep. 16, 2014, 4 pages.

GenBank, "*Homo sapiens* proprotein convertase subtilisin/kexin Type 7 mRNA, complete cds," Accession No. BT006870.1, accessed at https://www.ncbi.nlm.nih.gov/nuccore/BT006870.1, accessed on Sep. 16, 2014, 3 pages.

GenBank, "*H. sapiens* PC1 (NEC1) mRNA, complete cds," Accession No. M90753.1, accessed at https://www.ncbi.nlm.nih.gov/nuccore/M90753.1, accessed on Sep. 16, 2014, 3 pages.

GenBank, "Human Prohormone Converting Enzyme (NEC2) Gene," Accession No. AH002912.1, accessed at https://www.ncbi.nlm.nih.gov/nuccore/AH002912.1, accessed on Sep. 16, 2014, 9 pages.

GenBank, "Human subtilisin-like protein (PACE4) mRNA, complete cds," Accession No. M80482.1, accessed at https://www.ncbi.nlm.nih.gov/nuccore/M80482.1, accessed on Sep. 16, 2014, 4 pages.

GenBank, "Prohormone Convertase [*Homo Sapiens*]," Accession No. AAQ89322.1, accessed at https://www.ncbi.nlm.nih.gov/protein/AAQ89322.1, accessed on Sep. 16, 2014, 3 pages.

GenBank, "prohormone processing enzyme (KEX2) [*Saccharomyces cerevisiae*]," Accession No. AAA34718.1, accessed at https://www.ncbi.nlm.nih.gov/protein/AAA34718, accessed on Sep. 19, 2014, 2 pages.

Gitschier, J. et al., "Characterization of the human factor VIII gene," *Nature* 312(5992):326-330, Nature Publishing Group, UK (1984).

Ridgway, J. and Gorman, C., et al., "Expression and Activity of IgE Receptor Alpha Chain-IgC Chimeric Molecules," *Cell Biology* 115(3):1448, Rockefeller University Press, United States (1991).

Harrison, S., et al., "The Manufacturing Process for Recombinant Factor IX," *Seminars in Hematology* 35(2 Suppl 2):4-10, W.B. Saunders Company, United States (1998).

Healey, J.F. et al., "The cDNA and derived amino acid sequence of porcine factor VIII," *Blood* 88(11):4209-4214, The American Society of Hematology, United States of America (1996).

(56) References Cited

OTHER PUBLICATIONS

Hoeben, R.C., et al., "Expression of functional factor VIII in primary human skin fibroblasts after retrovirus-mediated gene transfer," *The Journal of Biological Chemistry* 265(13):7318-7323, The American Society for Biochemistry and Molecular Biology, Inc., United States (1990).
International Search Report and Written Opinion for Application No. PCT/US2011/043568, ISA/US, United States, mailed on Nov. 25, 2011, 10 pages.
Zettmeissi, G. et al., "Expression and Characterization of Human CD4: Immunoglobulin Fusion Proteins," *DNA Cell Biology* 9(5):347-353, Mary Ann Liebert, United States (1990).
Kürschner, C., et al., "Construction, Purification, and Characterization of New Interferon γ (IFNγ) Inhibitor Proteins: Three IFNγ Receptor-Immunoglobulin Hybrid Molecules," *Journal of Biological Chemistry* 267(13):9354-9360, The American Society for Biochemistry and Molecular Biology, Inc., United States (1992).
Langner, K.D., et al., "Synthesis of biologically active deletion mutants of human factor VIII:C," *Behring Institute Mitteilungen* 82:16-25, Behringwerke AG, Germany, (1988).
Lesslauer, W., et al., "Recombinant Soluble Tumor Necrosis Factor Receptor Proteins Protect Mice From Lipopolysaccharide-Induced Lethality," *European Journal of Immunology* 21(11):2883-2886, Verlagsgesellschaft mbH, Germany (1991).
Linsley, P.S., et al., "Binding of the B Cell Activation Antigen B7 to CD28 Costimulates T Cell Proliferation and Interleukin 2 mRNA Accumulation," *Journal of Experimental Medicine* 173(3):721-730, The Rockefeller University Press, United States (1991).
Linsley, P.S., et al., "CTLA-4 is a Second Receptor for the B Cell Activation Antigen B7," *Journal of Experimental Medicine* 174(3):561-569, The Rockefeller University Press, United States (1991).
Logan, J., et al., "Adenovirus Tripartite Leader Sequence Enhances Translation of mRNAs Late After Infection," *Proceedings of the National Academy of Sciences USA* 81(12):3655-3659, National Academy of Sciences, United States (1984).
Mackett, M., et al., "General Method for Production and Selection of Infectious Vaccinia Virus Recombinants Expressing Foreign Genes," *Journal of Virology* 49(3):857-864, American Society for Microbiology, United States (1984).
Mackett, M., et al., "Vaccinia Virus: A Selectable Eukaryotic Cloning and Expression Vector," *Proceedings of the National Academy of Sciences USA* 79(23):7415-7419, National Academy of Sciences, United States (1982).
Malik, F., et al., "Polyethylene Glycol (PEG)-Modified Granulocyte-Macrophage Colony-Stimulating Factor (GM-CSF) With Conserved Biological Activity," *Experimental Hematology* 20(8):1028-1035, International Society for Experimental Hematology, United States (1992).
Mei, B., et al., "Expression of Human Coagulation Factor VIII in a Human Hybrid Cell Line, HKB11," *Molecular Biotechnology* 34(2):165-178, Humana Press Inc., United States (2006).
Mei, B., et al., "Rational Design of a Fully Active, Long-Acting PEGylated Factor VIII for Hemophilia A Treatment," *Blood* 116(2):270-279, The American Society of Hematology, United States of America (2010).
Meulien, P., et al, "A new recombinant procoagulant protein derived from the cDNA encoding human factor VIII," *Protein Engineering* 2(4):301-306, IRL Press Ltd., England (1988).
Miao, H.Z., et al., "Bioengineering of coagulation factor VIII for improved secretion," *Blood* 103(9):3412-3419, The American Society of Hematology, United States of America (2004).
Mount, J.D., et al., "Sustained Phenotypic Correction of Hemophilia B dogs with a Factor IX Null Mutation by Liver-Directed Gene Therapy," *Bood* 99(8):2670-2676, The American Society of Hematology, United States of America (2002).
Nakayama, K., "Furin: A Mammalian Subtilisin/Kex2p-like Endoprotease Involved in Processing of a Wide Variety of Precursor Proteins," *Biochemical Journal* 327:625-635, Biochemical Society, Great Britain (1997).
NCBI, "*Homo Sapiens* Proprotein Convertase Subtilisin/Kexin Type 5 (PCSK5), Transcript Variant 1, mRNA," Accession No. NM_001190482.1, accessed at http://www.ncbi.nlm.nih.gov/nuccore/NM_001190482.1, accessed on Sep. 16, 2014, 12 pages.
NCBI, "*Homo Sapiens* Proprotein Convertase Subtilisin/Kexin Type 5 (PCSK5), Transcript Variant 2, mRNA," Accession No. NM_006200.5, accessed at http://www.ncbi.nlm.nih.gov/nuccore/NM_006200.5, accessed on Sep. 16, 2014, 8 pages.
NCBI, "Proprotein Convertase Subtilisin/Kexin Type 5 Isoform PC6A Preproprotein [*Homo Sapiens*]," Accession No. NP_006191.2, accessed at http://www.ncbi.nlm.nih.gov/protein/NP_006191.2, accessed on Sep. 16, 2014, 5 pages.
NCBI, "Proprotein Convertase Subtilisin/Kexin Type 5 Isoform PC6B Preproprotein [*Homo Sapiens*]," Accession No. NP_001177411.1, accessed at http://www.ncbi.nlm.nih.gov/protein/NP_001177411.1, accessed on Sep. 16, 2014, 7 pages.
Oganesyan, V., et al., "Structural characterization of a human Fc fragment engineered for extended serum half-life," *Molecular Immunology* 46(8-9):1750-1755, Elsevier, United States (2009).
Panicali, D., et al., "Construction of Poxviruses as Cloning Vectors: Insertion of the Thymidine Proceedings Kinase Gene from Herpes Simplex Virus into the DNA of Infectious Vaccinia Virus," *Proceedings of the National Academy of Sciences of the United States of America* 79(16):4927-4931, National Academy of Sciences, USA (1982).
Peppel, K., et al., "A Tumor Necrosis Factor (TNT) Receptor-IgG Heavy Chain Chimeric Protein as a Bivalent Antagonist of TNF Activity," *The Journal of Experimental Medicine* 174(6):1483-1489, The Rockefeller University Press, United States (1991).
Peters, R.T., et al., "Biochemical and Functional Characterization of a Recombinant Monomeric Factor VIII-Fc Fusion Protein," *Journal of Thrombosis and Haemostasis* 11(1):132-141, Blackwell Publishing, England (2012).
Plantier., J-L., et al:, "B-Domain Deleted Factor VIII is Aggregated and Degraded Through Proteasomal and Lysosomal Pathways," *Thrombosis and Haemostasis* 93(5):824-832, Stuttgart, Schattauer, Germany (2005).
Rockwell, N.C., et al., "Precursor Processing by Kex2/Furin Proteases," *Chemical Reviews* 102(12):4525-4548, American Chemical Society, United States of America (2002).
Rouille, Y., et al., "Proglucagon is Processed to Glucagon by Prohormone Convertase PC2 in αTC1-6 Cells," *Proceedings of the National Academy of Sciences USA* 91(8):3242-3246, National Academy of Sciences, United States (1994).
Rouille, Y., et al., "Proteolytic Processing Mechanisms in the Biosynthesis of Neuroendocrine Peptides: The Subtilisin-Like Proprotein Convertases," *Frontiers in Neuroendocrinology* 16(4):322-361, Academic Press, United States (1995).
Rovere, C., et al., "Evidence That PC2 is the Endogenous Pro-Neurotensin Convertase in rMTC 6-23 Cells and That PC1- and PC2-Transfected PC12 Cells Differentially Process Pro-Neurotensin," *Journal of Biological Chemistry* 271(19):11368-11375, The American Society for Biochemistry and Molecular Biology, Inc., United States (1996).
Ruther, U., et al., "Easy Identification of cDNA Clones," *EMBO J* 2(10):1791-1794, IRL Press Ltd, England (1983).
Sarver, N., et al., "Stable expression of recombinant factor VIII molecules using a bovine papillomavirus vector," *DNA* 6(6):553-564, Mary Ann Liebert. Inc., United States (1987).
Schellenberger, V., et al., "A recombinant polypeptide extends the in vivo half-life of peptides and proteins in a tunable manner," *Nature Biotechnology* 27(12):1186-1190, Nature America, Inc., United States (2009).
Seidah, N.G., et al., "Testicular Expression of PC4 in the Rat: Molecular Diversity of a Novel Germ Cell-Specific Kex2/Subtilisin-like Proprotein Convertase," *Molecular Endocrinology* 6(10):1559-1570, Endocrine Society, United States (1992).
Seidah, N.G., et al., "The Prohormone and Proprotein Processing Enzymes PC1 and PC2: Structure, Selective Cleavage of Mouse Pomc and Human Renin at Pairs of Basic Residues, Cellular Expression, Tissue Distribution, and mRNA Regulation," *NIDA Research Monograph* 126:132-150, U.S. Department of Health and Human Services, United States (1992).

(56) References Cited

OTHER PUBLICATIONS

Simonsen, C.C., et al., "Isolation and Expression of an Altered Mouse Dihydrofolate Reductase cDNA," *Proceedings of the National Academy of Sciences 80*(9):2495-2499, National Academy of Sciences, United States (1983).
Smeekens, S.P., et al., "Proinsulin Processing by the Subtilisin-Related Proprotein Convertases Furin, PC2, and PC3," *Proceedings of the National Academy of Sciences* 89(18):8822-8826, National Academy of Sciences, United States (1992).
Smith, G.E., et al., "Molecular Engineering of the *Autographa californica* Nuclear Polyhedrosis Virus Genome: Deletion Mutations Within the Polyhedrin Gene," *Journal of Virology* 46(2):584-593, American Society for Microbiology, United States of America (1983).
Stamenkovic, I., et al., "The B Lymphocyte Adhesion Molecule CD22 Interacts with Leukocyte Common Antigen CD45RO on T Cells and α2-6 Sialyltransferase, CD75, on B Cells," *Cell* 66(6):1133-1144, Cell Press, United States (1991).
Story, C.M., et al., "A major histocompatibility complex class I-like Fc receptor cloned from human placenta: possible role in transfer of immunoglobulin G from mother to fetus," *The Journal of Experimental Medicine* 180(6):2377-2381, The Rockefeller University Press, United States (1994).
Supplementary European Search Report for Application No. EP11804475, Munich, Germany, mailed on Jan. 2, 2014, 7 pages.
Toole, J.J. et al., "A large region (≈95 kDa) of human factor VIII is dispensable for *in vitro* procoagulant activity," *Proceedings of the National Academy of Sciences USA* 83(16):5939-5942, National Academy of Sciences, United States (1986).
Toole, J.J. et al., "Molecular cloning of a cDNA encoding human antihaemophilic factor," *Nature* 312(5992):342-347, Nature Publishing Group, UK (1984).
Traunecker, A., et al., "Highly Efficient Neutralization of HIV with Recombinant CD4-Immunoglobulin Molecules," *Nature* 339(6219):68-70, Nature Publishing Group, UK (1989).
UniProtKB/Swiss-Prot, "Furin_Human," Accession No. P09958.2, accessed at http://www.uniprot.org/uniprot/P09958, accessed on Sep. 16, 2014, 14 pages.
UniProtKB/Swiss-Prot, "KEX2_Yeast," Accession No. P13134.1, accessed at http://www.uniprot.org/uniprot/P13134, accessed on Sep. 16, 2014, 10 pages.
UniProtKB/Swiss-Prot, "MBTP1_Human," Accession No. Q14703.1, accessed at http://www.uniprot.org/uniprot/Q14703, accessed on Sep. 16, 2014, 12 pages.
UniProtKB/Swiss-Prot, "NEC1_Human," Accession No. P29120.2, accessed at http://www.uniprot.org/uniprot/P29120, accessed on Sep. 16, 2014, 14 pages.
UniProtKB'Swiss-Prot. "NEC2_Human," Accession No. P16519.2, accessed at http://www.uniprot.org/uniprot/P16519, accessed on Sep. 16, 2014, 12 pages.
UniProtKB/Swiss-Prot, "PCSK6_Human," Accession No. P29122.1, accessed at http://www.uniprot.org/uniprot/P29122, accessed on Sep. 16, 2014, 13 pages.
UniProtKB/Swiss-Prot, "PCSK7_Human," Accession No. Q16549.2, accessed at http://www.uniprot.org/uniprot/Q16549, accessed on Sep. 16, 2014, 12 pages.
UniProtK13/Swiss-Prot, "PCSK9_Human," Accession No. Q8NBP7.3, accessed at http://www.uniprot.org/uniprot/Q8NBP7, accessed on Sep. 16, 2014, 20 pages.
Vaccaro, C., et al., "Engineering the Fc region of immunoglobulin G to modulate *in vivo* antibody levels," *Nature Biotechnology* 23(10):1283-1288, Nature Publishing Group, United States (2005).
Vehar, G.A. et al., "Structure of human factor VIII," *Nature* 312(5992):337-342, Nature Publishing Group, UK (1984).
Viale, A., et al., "Cellular Localization and Role of Prohormone Convertases in the Processing of Pro-Melanin Concentrating Hormone in Mammals," *Journal of Biological Chemistry* 274(10):6536-6545, The American Society for Biochemistry and Molecular Biology, Inc., United States (1999).
Wasley, L.C., et al., "PACE/Furin Can Process the Vitamin K-Dependent Pro-Factor IX Precursor within The Secretory Pathway," *The Journal of Biological Chemistry* 268(12):8458-8465, The American Society for Biochemistry and Molecular Biology, Inc., United States (1993).
Watson, S.R., et al., "A Homing Receptor-IgG chimera as a Probe for Adhesive Ligands of Lymph Node High Endothelial Venules," *Journal of Cell Biology* 110(6):2221-2229, The Rockefeller University Press, United States (1990).
Watson, S.R., et al., "Neutrophil Influx into an Inflammatory Site Inhibited by a Soluble Homing Receptor-IgG Chimaera," *Nature* 349(6305):164-167, Nature Publishing Group, United States (1991).
Wood, W.I. et al., "Expression of active human factor VIII from recombinant DNA clones," *Nature* 312(5992):330-337, Nature Publishing Group, UK (1984).
Xu, H et al., "Prohormone Processing in Permeabilized Cells: Endoproteolytic Cleavage of Prosomatostatin in the Trans-Golgi Network," *Biochimie* 76(3-4):257-264, Elsevier, France (1994).
International Search Report for International Application No. PCT/US2007/007252, European Patent Office, Rijswijk, Netherlands, mailed Nov. 5, 2007, 4 pages.
Lind, P., et al., "Novel forms of B-Domain-Deleted Recombinant Factor VIII Molecules. Construction and Biochemical Characterization," *European Journal of Biochemistry* 232(1):19-27, Wiley-Blackwell Publishing Ltd., England (1995).

* cited by examiner

Figure 3A: Western Blot
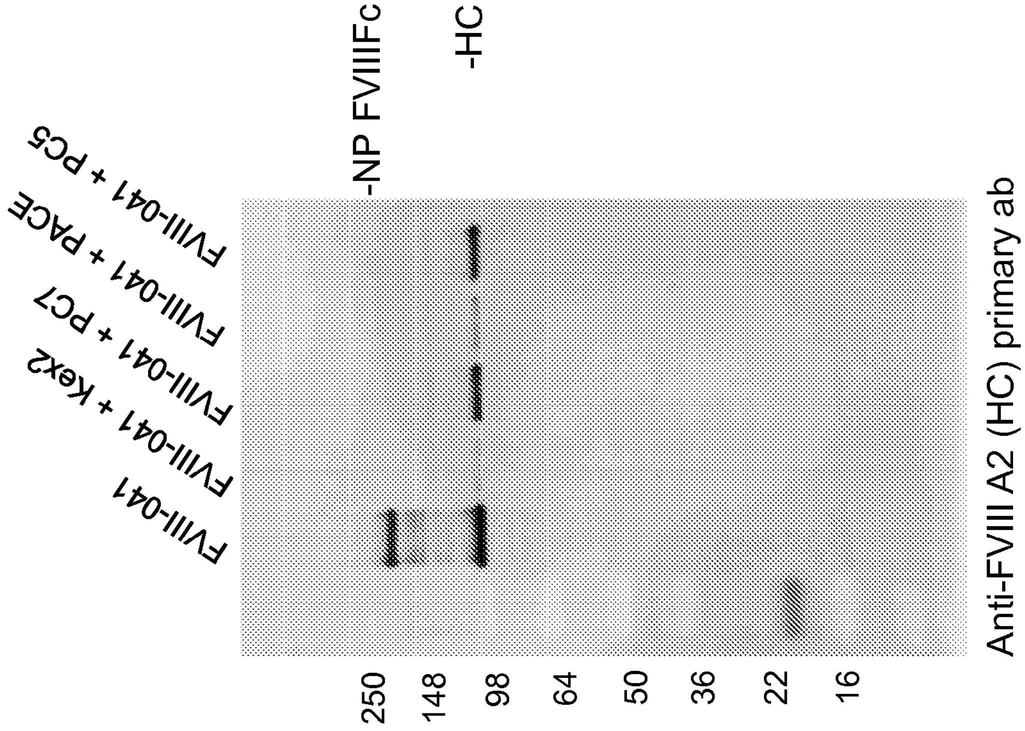

Figure 3B: Western Blot
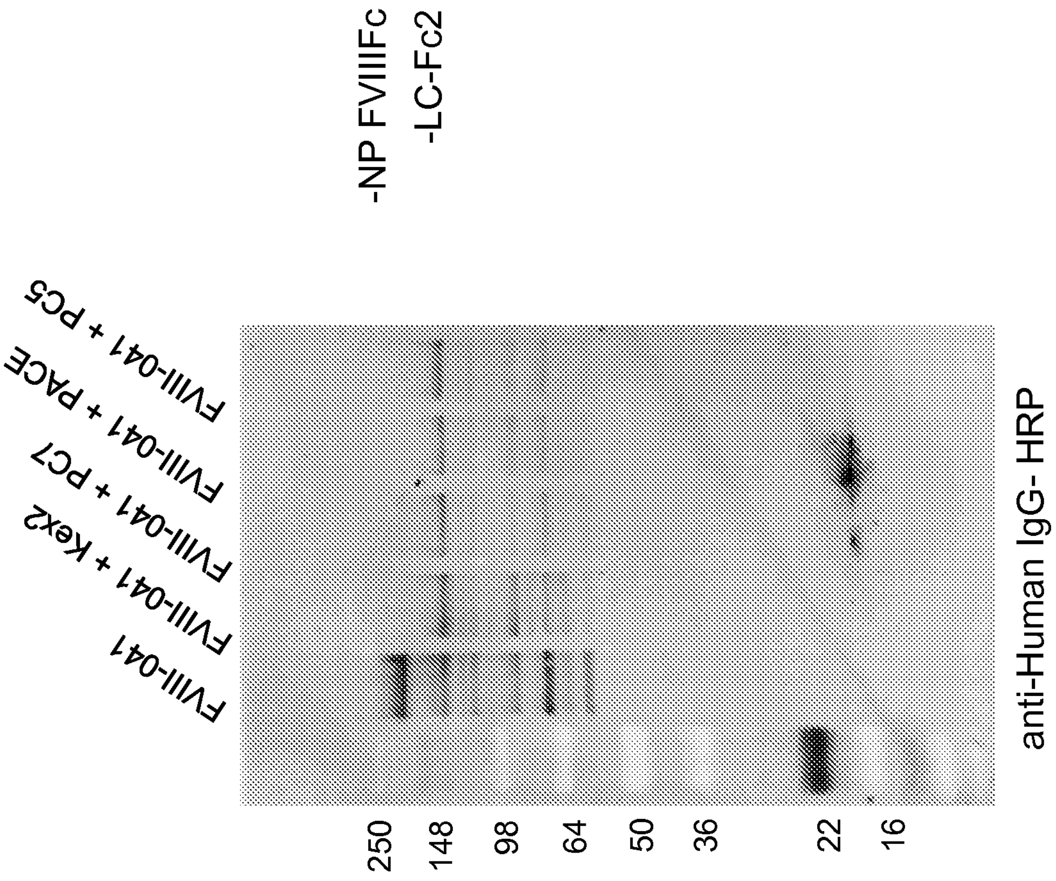

Figure 4A: SYPRO Ruby gel staining
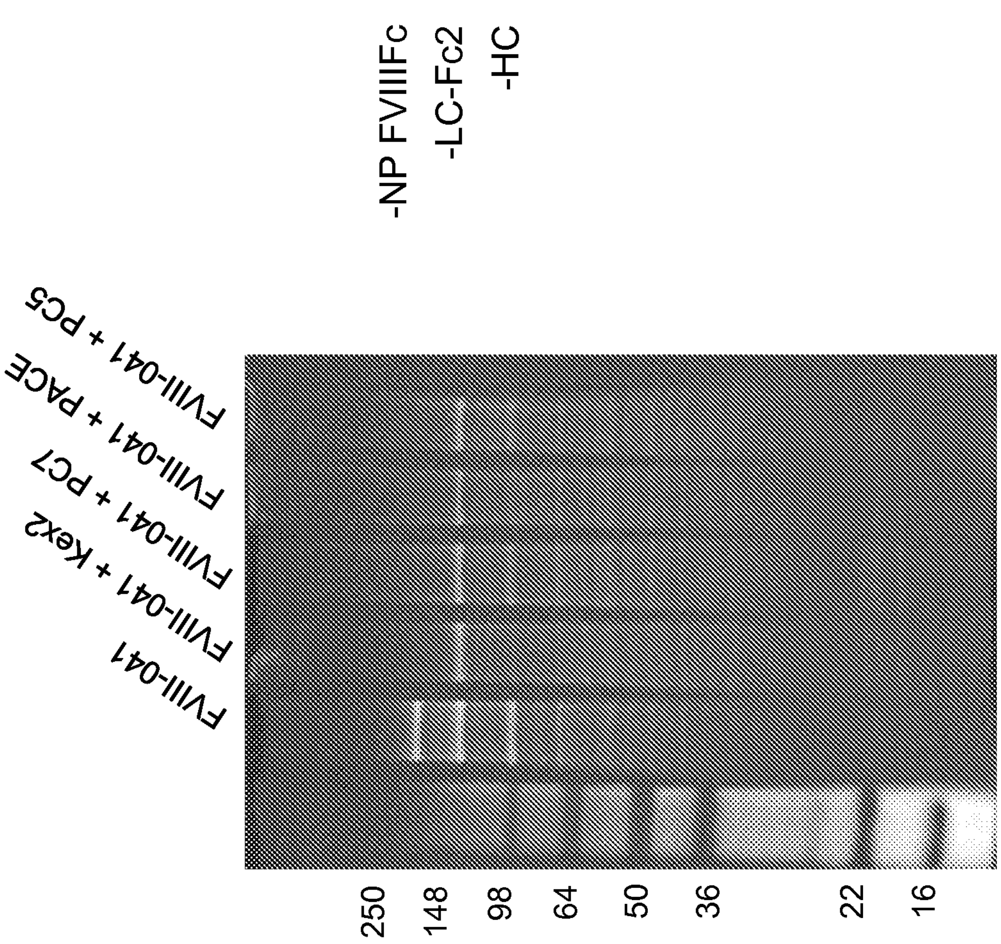

Figure 4B: Coomassie gel staining
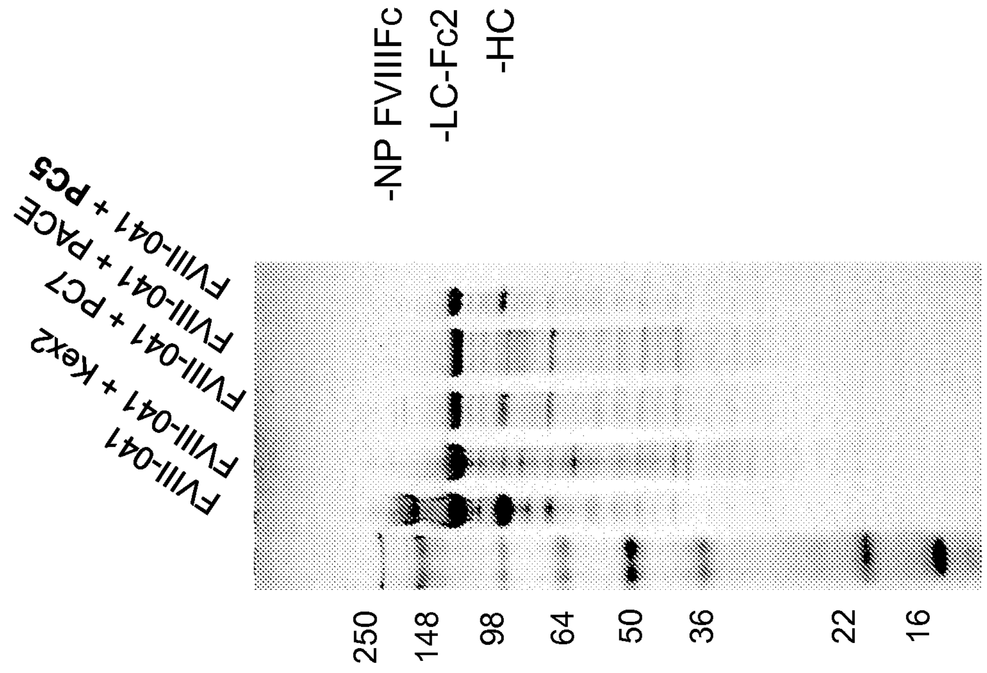

Figure 5B: Nonreduced SDS-PAGE
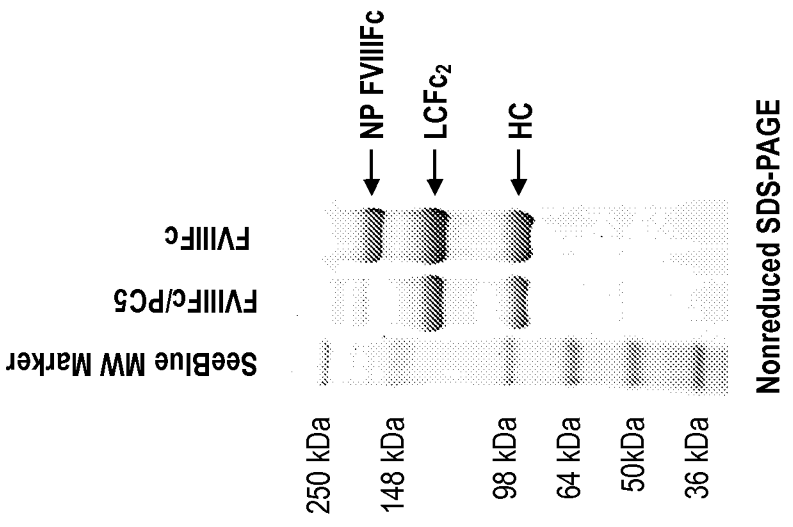
Figure 5A: Reduced SDS-PAGE
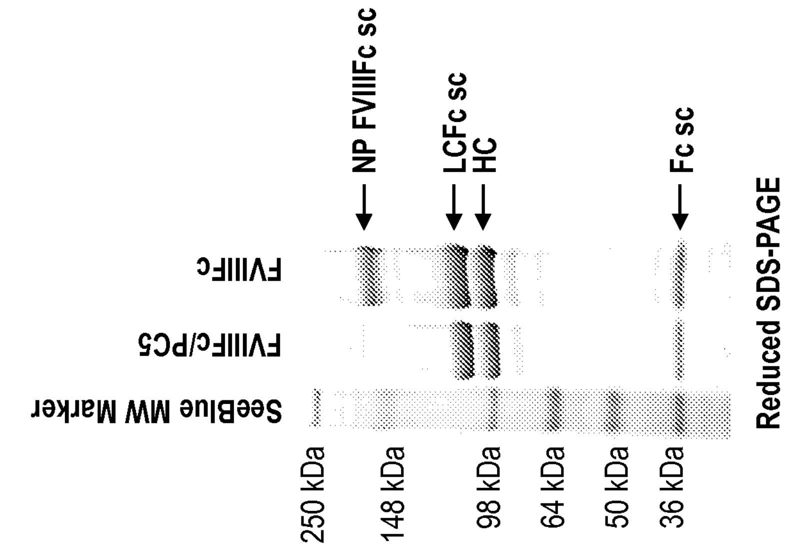

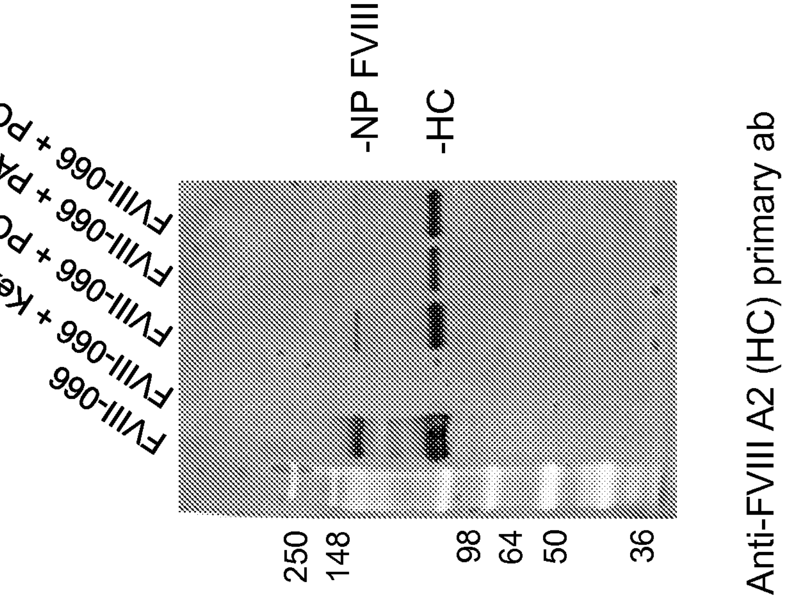
Figure 6B: Western Blot
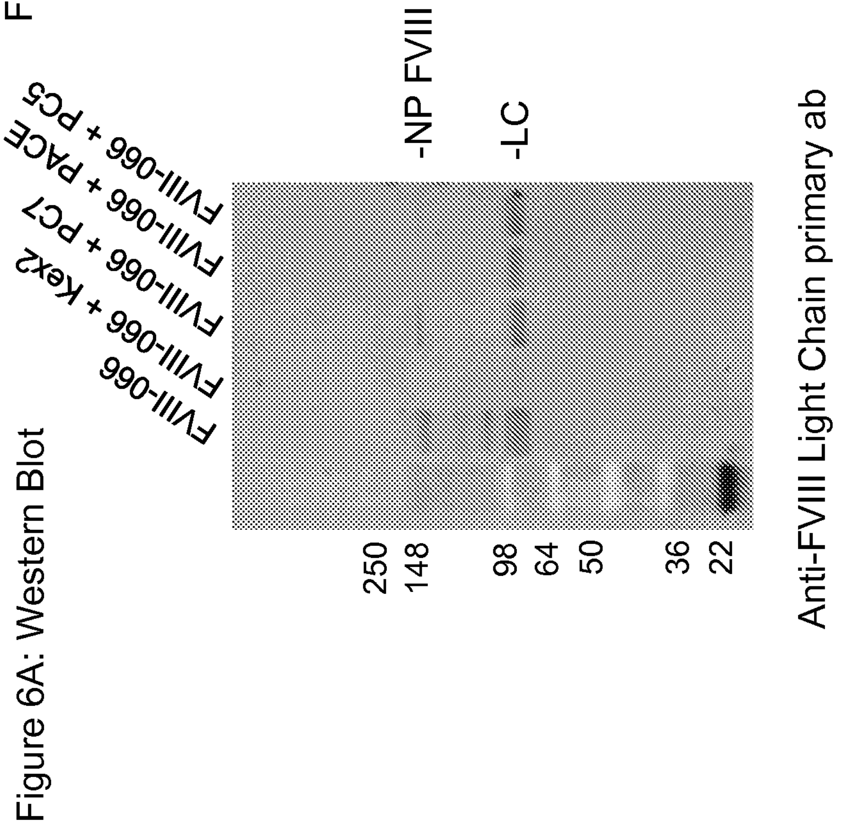
Figure 6A: Western Blot

SEQUENCE LISTING

<160> NUMBER OF SEQ ID NOS: 63

<210> SEQ ID NO 1
<211> LENGTH: 4314
<212> TYPE: DNA
<213> ORGANISM: Artificial Sequence
<220> FEATURE:
<223> OTHER INFORMATION: B-domain deleted Factor VIII (S743/Q1638)

<400> SEQUENCE: 1
gccaccagaa gatactacct gggtgcagtg gaactgtcat gggactatat gcaaagtgat 60
ctcggtgagc tgcctgtgga cgcaagattt cctcctagag tgccaaaatc ttttccattc 120
aacacctcag tcgtgtacaa aaagactctg tttgtagaat tcacggatca ccttttcaac 180
atcgctaagc caaggccacc ctggatgggt ctgctaggtc ctaccatcca ggctgaggtt 240
tatgatacag tggtcattac acttaagaac atggcttccc atcctgtcag tcttcatgct 300
gttggtgtat cctactggaa agcttctgag ggagctgaat atgatgatca gaccagtcaa 360
agggagaaag aagatgataa agtcttccct ggtggaagcc atacatatgt ctggcaggtc 420
ctgaaagaga atggtccaat ggcctctgac ccactgtgcc ttacctactc atatctttct 480
catgtggacc tggtaaaaga cttgaattca ggcctcattg gagccctact agtatgtaga 540
gaagggagtc tggccaagga aaagacacag accttgcaca aatttatact actttttgct 600
gtatttgatg aagggaaaag ttggcactca gaaacaaaga actccttgat gcaggatagg 660

-continued

```
gatgctgcat ctgctcgggc ctggcctaaa atgcacacag tcaatggtta tgtaaacagg    720
tctctgccag gtctgattgg atgccacagg aaatcagtct attggcatgt gattggaatg    780
ggcaccactc ctgaagtgca ctcaatattc ctcgaaggtc acacatttct tgtgaggaac    840
catcgccagg cgtccttgga aatctcgcca ataactttcc ttactgctca aacactcttg    900
atggaccttg gacagtttct actgttttgt catatctctt cccaccaaca tgatggcatg    960
gaagcttatg tcaaagtaga cagctgtcca gaggaacccc aactacgaat gaaaaataat   1020
gaagaagcgg aagactatga tgatgatctt actgattctg aaatggatgt ggtcaggttt   1080
gatgatgaca actctccttc ctttatccaa attcgctcag ttgccaagaa gcatcctaaa   1140
acttgggtac attacattgc tgctgaagag gaggactggg actatgctcc cttagtcctc   1200
gcccccgatg acagaagtta taaaagtcaa tatttgaaca atggccctca gcggattggt   1260
aggaagtaca aaaaagtccg atttatggca tacacagatg aaacctttaa gactcgtgaa   1320
gctattcagc atgaatcagg aatcttggga cctttacttt atggggaagt tggagacaca   1380
ctgttgatta tatttaagaa tcaagcaagc agaccatata acatctaccc tcacggaatc   1440
actgatgtcc gtcctttgta ttcaaggaga ttaccaaaag gtgtaaaaca tttgaaggat   1500
tttccaattc tgccaggaga aatattcaaa tataaatgga cagtgactgt agaagatggg   1560
ccaactaaat cagatcctcg gtgcctgacc cgctattact ctagtttcgt taatatggag   1620
agagatctag cttcaggact cattggccct ctcctcatct gctacaaaga atctgtagat   1680
caaagaggaa accagataat gtcagacaag aggaatgtca tcctgttttc tgtatttgat   1740
gagaaccgaa gctggtacct cacagagaat atacaacgct ttctccccaa tccagctgga   1800
gtgcagcttg aggatccaga gttccaagcc tccaacatca tgcacagcat caatggctat   1860
gtttttgata gtttgcagtt gtcagtttgt ttgcatgagg tggcatactg gtacattcta   1920
agcattggag cacagactga cttcctttct gtcttcttct ctggatatac cttcaaacac   1980
aaaatggtct atgaagacac actcacccta ttcccattct caggagaaac tgtcttcatg   2040
tcgatggaaa acccaggtct atggattctg gggtgccaca actcagactt tcggaacaga   2100
ggcatgaccg ccttactgaa ggtttctagt tgtgacaaga acactggtga ttattacgag   2160
gacagttatg aagatatttc agcatacttg ctgagtaaaa acaatgccat tgaaccaaga   2220
agcttctctc aaaacccacc agtcttgaaa cgccatcaac gggaaataac tcgtactact   2280
cttcagtcag atcaagagga aattgactat gatgatacca tatcagttga aatgaagaag   2340
gaagattttg acatttatga tgaggatgaa aatcagagcc cccgcagctt tcaaaagaaa   2400
acacgacact attttattgc tgcagtggag aggctctggg attatgggat gagtagctcc   2460
ccacatgttc taagaaacag ggctcagagt ggcagtgtcc ctcagttcaa gaaagttgtt   2520
ttccaggaat ttactgatgg ctcctttact cagcccttat accgtggaga actaaatgaa   2580
catttgggac tcctggggcc atatataaga gcagaagttg aagataatat catggtaact   2640
ttcagaaatc aggcctctcg tccctattcc ttctattcta gccttatttc ttatgaggaa   2700
gatcagaggc aaggagcaga acctagaaaa aactttgtca agcctaatga aaccaaaact   2760
tacttttgga aagtgcaaca tcatatggca cccactaaag atgagtttga ctgcaaagcc   2820
tgggcttatt tctctgatgt tgacctggaa aaagatgtgc actcaggcct gattggaccc   2880
cttctggtct gccacactaa cacactgaac cctgctcatg ggagacaagt gacagtacag   2940
gaatttgctc tgtttttcac catctttgat gagaccaaaa gctggtactt cactgaaaat   3000
```

```
atggaaagaa actgcagggc tccctgcaat atccagatgg aagatcccac ttttaaagag   3060
aattatcgct tccatgcaat caatggctac ataatggata cactacctgg cttagtaatg   3120
gctcaggatc aaaggattcg atggtatctg ctcagcatgg gcagcaatga aaacatccat   3180
tctattcatt tcagtggaca tgtgttcact gtacgaaaaa aagaggagta taaaatggca   3240
ctgtacaatc tctatccagg tgtttttgag acagtggaaa tgttaccatc caaagctgga   3300
atttggcggg tggaatgcct tattggcgag catctacatg ctgggatgag cacacttttt   3360
ctggtgtaca gcaataagtg tcagactccc ctgggaatgg cttctggaca cattagagat   3420
tttcagatta cagcttcagg acaatatgga cagtgggccc caaagctggc cagacttcat   3480
tattccggat caatcaatgc ctggagcacc aaggagccct tttcttggat caaggtggat   3540
ctgttggcac caatgattat tcacggcatc aagacccagg gtgcccgtca gaagttctcc   3600
agcctctaca tctctcagtt tatcatcatg tatagtcttg atgggaagaa gtggcagact   3660
tatcgaggaa attccactgg aaccttaatg gtcttctttg gcaatgtgga ttcatctggg   3720
ataaaacaca atatttttaa ccctccaatt attgctcgat acatccgttt gcacccaact   3780
cattatagca ttcgcagcac tcttcgcatg gagttgatgg gctgtgattt aaatagttgc   3840
agcatgccat tgggaatgga gagtaaagca atatcagatg cacagattac tgcttcatcc   3900
tactttacca atatgtttgc cacctggtct ccttcaaaag ctcgacttca cctccaaggg   3960
aggagtaatg cctggagacc tcaggtgaat aatccaaaag agtggctgca agtggacttc   4020
cagaagacaa tgaaagtcac aggagtaact actcagggag taaaatctct gcttaccagc   4080
atgtatgtga aggagttcct catctccagc agtcaagatg gccatcagtg gactctcttt   4140
tttcagaatg gcaaagtaaa ggtttttcag ggaaatcaag actccttcac acctgtggtg   4200
aactctctag acccaccgtt actgactcgc taccttcgaa ttcacccccca gagttgggtg   4260
caccagattg ccctgaggat ggaggttctg ggctgcgagg cacaggacct ctac         4314
```

```
<210> SEQ ID NO 2
<211> LENGTH: 1438
<212> TYPE: PRT
<213> ORGANISM: Artificial Sequence
<220> FEATURE:
<223> OTHER INFORMATION: B-domain deleted Factor VIII (S743/Q1638)

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
```

-continued

```
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560
```

```
Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
        915                 920                 925

Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975
```

-continued

```
Val Thr Val Gln Glu Phe Ala Leu Phe Phe Thr Ile Phe Asp Glu Thr
            980                 985                 990

Lys Ser Trp Tyr Phe Thr Glu Asn  Met Glu Arg Asn Cys  Arg Ala Pro
        995                 1000                1005

Cys Asn  Ile Gln Met Glu Asp  Pro Thr Phe Lys Glu  Asn Tyr Arg
    1010                 1015                 1020

Phe His  Ala Ile Asn Gly Tyr  Ile Met Asp Thr Leu  Pro Gly Leu
    1025                 1030                 1035

Val Met  Ala Gln Asp Gln Arg  Ile Arg Trp Tyr Leu  Leu Ser Met
    1040                 1045                 1050

Gly Ser  Asn Glu Asn Ile His  Ser Ile His Phe Ser  Gly His Val
    1055                 1060                 1065

Phe Thr  Val Arg Lys Lys Glu  Glu Tyr Lys Met Ala  Leu Tyr Asn
    1070                 1075                 1080

Leu Tyr  Pro Gly Val Phe Glu  Thr Val Glu Met Leu  Pro Ser Lys
    1085                 1090                 1095

Ala Gly  Ile Trp Arg Val Glu  Cys Leu Ile Gly Glu  His Leu His
    1100                 1105                 1110

Ala Gly  Met Ser Thr Leu Phe  Leu Val Tyr Ser Asn  Lys Cys Gln
    1115                 1120                 1125

Thr Pro  Leu Gly Met Ala Ser  Gly His Ile Arg Asp  Phe Gln Ile
    1130                 1135                 1140

Thr Ala  Ser Gly Gln Tyr Gly  Gln Trp Ala Pro Lys  Leu Ala Arg
    1145                 1150                 1155

Leu His  Tyr Ser Gly Ser Ile  Asn Ala Trp Ser Thr  Lys Glu Pro
    1160                 1165                 1170

Phe Ser  Trp Ile Lys Val Asp  Leu Leu Ala Pro Met  Ile Ile His
    1175                 1180                 1185

Gly Ile  Lys Thr Gln Gly Ala  Arg Gln Lys Phe Ser  Ser Leu Tyr
    1190                 1195                 1200

Ile Ser  Gln Phe Ile Ile Met  Tyr Ser Leu Asp Gly  Lys Lys Trp
    1205                 1210                 1215

Gln Thr  Tyr Arg Gly Asn Ser  Thr Gly Thr Leu Met  Val Phe Phe
    1220                 1225                 1230

Gly Asn  Val Asp Ser Ser Gly  Ile Lys His Asn Ile  Phe Asn Pro
    1235                 1240                 1245

Pro Ile  Ile Ala Arg Tyr Ile  Arg Leu His Pro Thr  His Tyr Ser
    1250                 1255                 1260

Ile Arg  Ser Thr Leu Arg Met  Glu Leu Met Gly Cys  Asp Leu Asn
    1265                 1270                 1275

Ser Cys  Ser Met Pro Leu Gly  Met Glu Ser Lys Ala  Ile Ser Asp
    1280                 1285                 1290

Ala Gln  Ile Thr Ala Ser Ser  Tyr Phe Thr Asn Met  Phe Ala Thr
    1295                 1300                 1305

Trp Ser  Pro Ser Lys Ala Arg  Leu His Leu Gln Gly  Arg Ser Asn
    1310                 1315                 1320

Ala Trp  Arg Pro Gln Val Asn  Asn Pro Lys Glu Trp  Leu Gln Val
    1325                 1330                 1335

Asp Phe  Gln Lys Thr Met Lys  Val Thr Gly Val Thr  Thr Gln Gly
    1340                 1345                 1350

Val Lys  Ser Leu Leu Thr Ser  Met Tyr Val Lys Glu  Phe Leu Ile
    1355                 1360                 1365

Ser Ser  Ser Gln Asp Gly His  Gln Trp Thr Leu Phe  Phe Gln Asn
```

```
    1370                1375                1380

Gly Lys  Val Lys Val Phe Gln  Gly Asn Gln Asp Ser  Phe Thr Pro
    1385                1390                1395

Val Val  Asn Ser Leu Asp Pro  Pro Leu Leu Thr Arg  Tyr Leu Arg
    1400                1405                1410

Ile His  Pro Gln Ser Trp Val  His Gln Ile Ala Leu  Arg Met Glu
    1415                1420                1425

Val Leu  Gly Cys Glu Ala Gln  Asp Leu Tyr
    1430                1435
```

<210> SEQ ID NO 3
<211> LENGTH: 741
<212> TYPE: DNA
<213> ORGANISM: Artificial Sequence
<220> FEATURE:
<223> OTHER INFORMATION: Fc fragment

<400> SEQUENCE: 3

```
atggagacag acacactcct gctatgggta ctgctgctct gggttccagg ttccactggt     60

gacaaaactc acacatgccc accgtgccca gcacctgaac tcctgggagg accgtcagtc    120

ttcctcttcc ccccaaaacc caaggacacc ctcatgatct cccggacccc tgaggtcaca    180

tgcgtggtgg tggacgtgag ccacgaagac cctgaggtca agttcaactg gtacgtggac    240

ggcgtggagg tgcataatgc caagacaaag ccgcgggagg agcagtacaa cagcacgtac    300

cgtgtggtca gcgtcctcac cgtcctgcac caggactggc tgaatggcaa ggagtacaag    360

tgcaaggtct ccaacaaagc cctcccagcc cccatcgaga aaaccatctc caaagccaaa    420

gggcagcccc gagaaccaca ggtgtacacc ctgcccccat cccgcgatga gctgaccaag    480

aaccaggtca gcctgacctg cctggtcaaa ggcttctatc ccagcgacat cgccgtggag    540

tgggagagca atgggcagcc ggagaacaac tacaagacca cgcctcccgt gttggactcc    600

gacggctcct tcttcctcta cagcaagctc accgtggaca agagcaggtg gcagcagggg    660

aacgtcttct catgctccgt gatgcatgag gctctgcaca accactacac gcagaagagc    720

ctctccctgt ctccgggtaa a                                              741
```

<210> SEQ ID NO 4
<211> LENGTH: 247
<212> TYPE: PRT
<213> ORGANISM: Artificial Sequence
<220> FEATURE:
<223> OTHER INFORMATION: Fc fragment

<400> SEQUENCE: 4

```
Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
```

-continued

```
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245


<210> SEQ ID NO 5
<211> LENGTH: 6996
<212> TYPE: DNA
<213> ORGANISM: Homo sapiens

<400> SEQUENCE: 5

gccaccagaa gatactacct gggtgcagtg gaactgtcat gggactatat gcaaagtgat     60

ctcggtgagc tgcctgtgga cgcaagattt cctcctagag tgccaaaatc ttttccattc    120

aacacctcag tcgtgtacaa aaagactctg tttgtagaat tcacggatca ccttttcaac    180

atcgctaagc caaggccacc ctggatgggt ctgctaggtc ctaccatcca ggctgaggtt    240

tatgatacag tggtcattac acttaagaac atggcttccc atcctgtcag tcttcatgct    300

gttggtgtat cctactggaa agcttctgag ggagctgaat atgatgatca gaccagtcaa    360

agggagaaag aagatgataa agtcttccct ggtggaagcc atacatatgt ctggcaggtc    420

ctgaaagaga atggtccaat ggcctctgac ccactgtgcc ttacctactc atatctttct    480

catgtggacc tggtaaaaga cttgaattca ggcctcattg gagccctact agtatgtaga    540

gaagggagtc tggccaagga aaagacacag accttgcaca aatttatact actttttgct    600

gtatttgatg aagggaaaag ttggcactca gaaacaaaga actccttgat gcaggatagg    660

gatgctgcat ctgctcgggc ctggcctaaa atgcacacag tcaatggtta tgtaaacagg    720

tctctgccag gtctgattgg atgccacagg aaatcagtct attggcatgt gattggaatg    780

ggcaccactc ctgaagtgca ctcaatattc ctcgaaggtc acacatttct tgtgaggaac    840

catcgccagg cgtccttgga aatctcgcca ataactttcc ttactgctca aacactcttg    900

atggaccttg gacagtttct actgttttgt catatctctt cccaccaaca tgatggcatg    960

gaagcttatg tcaaagtaga cagctgtcca gaggaacccc aactacgaat gaaaaataat   1020

gaagaagcgg aagactatga tgatgatctt actgattctg aaatggatgt ggtcaggttt   1080

gatgatgaca actctccttc ctttatccaa attcgctcag ttgccaagaa gcatcctaaa   1140

acttgggtac attacattgc tgctgaagag gaggactggg actatgctcc cttagtcctc   1200

gcccccgatg acagaagtta taaaagtcaa tatttgaaca atggccctca gcggattggt   1260
```

-continued

```
aggaagtaca aaaaagtccg atttatggca tacacagatg aaacctttaa gactcgtgaa   1320
gctattcagc atgaatcagg aatcttggga cctttacttt atggggaagt tggagacaca   1380
ctgttgatta tatttaagaa tcaagcaagc agaccatata acatctaccc tcacggaatc   1440
actgatgtcc gtcctttgta ttcaaggaga ttaccaaaag gtgtaaaaca tttgaaggat   1500
tttccaattc tgccaggaga aatattcaaa tataaatgga cagtgactgt agaagatggg   1560
ccaactaaat cagatcctcg gtgcctgacc cgctattact ctagtttcgt taatatggag   1620
agagatctag cttcaggact cattggccct ctcctcatct gctacaaaga atctgtagat   1680
caaagaggaa accagataat gtcagacaag aggaatgtca tcctgttttc tgtatttgat   1740
gagaaccgaa gctggtacct cacagagaat atacaacgct ttctccccaa tccagctgga   1800
gtgcagcttg aggatccaga gttccaagcc tccaacatca tgcacagcat caatggctat   1860
gtttttgata gtttgcagtt gtcagtttgt ttgcatgagg tggcatactg gtacattcta   1920
agcattggag cacagactga cttcctttct gtcttcttct ctggatatac cttcaaacac   1980
aaaatggtct atgaagacac actcacccta ttcccattct caggagaaac tgtcttcatg   2040
tcgatggaaa acccaggtct atggattctg gggtgccaca actcagactt tcggaacaga   2100
ggcatgaccg ccttactgaa ggtttctagt tgtgacaaga acactggtga ttattacgag   2160
gacagttatg aagatatttc agcatacttg ctgagtaaaa acaatgccat tgaaccaaga   2220
agcttctccc agaattcaag acaccctagc actaggcaaa agcaatttaa tgccaccaca   2280
attccagaaa atgacataga gaagactgac ccttggtttg cacacagaac acctatgcct   2340
aaaatacaaa atgtctcctc tagtgatttg ttgatgctct tgcgacagag tcctactcca   2400
catgggctat ccttatctga tctccaagaa gccaaatatg agactttttc tgatgatcca   2460
tcacctggag caatagacag taataacagc ctgtctgaaa tgacacactt caggccacag   2520
ctccatcaca gtggggacat ggtatttacc cctgagtcag gcctccaatt aagattaaat   2580
gagaaactgg ggacaactgc agcaacagag ttgaagaaac ttgatttcaa agtttctagt   2640
acatcaaata atctgatttc aacaattcca tcagacaatt tggcagcagg tactgataat   2700
acaagttcct taggaccccc aagtatgcca gttcattatg atagtcaatt agataccact   2760
ctatttggca aaaagtcatc tccccttact gagtctggtg gacctctgag cttgagtgaa   2820
gaaaataatg attcaaagtt gttagaatca ggtttaatga atagccaaga aagttcatgg   2880
ggaaaaaatg tatcgtcaac agagagtggt aggttattta aagggaaaag agctcatgga   2940
cctgctttgt tgactaaaga taatgcctta ttcaaagtta gcatctcttt gttaaagaca   3000
aacaaaactt ccaataattc agcaactaat agaaagactc acattgatgg cccatcatta   3060
ttaattgaga atagtccatc agtctggcaa aatatattag aaagtgacac tgagtttaaa   3120
aaagtgacac ctttgattca tgacagaatg cttatggaca aaaatgctac agctttgagg   3180
ctaaatcata tgtcaaataa aactacttca tcaaaaaaca tggaaatggt ccaacagaaa   3240
aaagagggcc ccattccacc agatgcacaa aatccagata tgtcgttctt taagatgcta   3300
ttcttgccag aatcagcaag gtggatacaa aggactcatg gaaagaactc tctgaactct   3360
gggcaaggcc ccagtccaaa gcaattagta tccttaggac cagaaaaatc tgtggaaggt   3420
cagaatttct tgtctgagaa aaacaaagtg gtagtaggaa agggtgaatt tacaaaggac   3480
gtaggactca aagagatggt tttccaagc agcagaaacc tatttcttac taacttggat   3540
aatttacatg aaaataatac acacaatcaa gaaaaaaaaa ttcaggaaga aatagaaaag   3600
aaggaaacat taatccaaga gaatgtagtt ttgcctcaga tacatacagt gactggcact   3660
```

-continued

```
aagaatttca tgaagaacct tttcttactg agcactaggc aaaatgtaga aggttcatat   3720
gacggggcat atgctccagt acttcaagat tttaggtcat taaatgattc aacaaataga   3780
acaaagaaac acacagctca tttctcaaaa aaaggggagg aagaaaactt ggaaggcttg   3840
ggaaatcaaa ccaagcaaat tgtagagaaa tatgcatgca ccacaaggat atctcctaat   3900
acaagccagc agaattttgt cacgcaacgt agtaagagag ctttgaaaca attcagactc   3960
ccactagaag aaacagaact tgaaaaaagg ataattgtgg atgacacctc aacccagtgg   4020
tccaaaaaca tgaaacattt gaccccgagc accctcacac agatagacta caatgagaag   4080
gagaaagggg ccattactca gtctccctta tcagattgcc ttacgaggag tcatagcatc   4140
cctcaagcaa atagatctcc attacccatt gcaaaggtat catcatttcc atctattaga   4200
cctatatatc tgaccagggt cctattccaa gacaactctt ctcatcttcc agcagcatct   4260
tatagaaaga aagattctgg ggtccaagaa agcagtcatt tcttacaagg agccaaaaaa   4320
aataaccttt ctttagccat tctaaccttg gagatgactg gtgatcaaag agaggttggc   4380
tccctgggga caagtgccac aaattcagtc acatacaaga aagttgagaa cactgttctc   4440
ccgaaaccag acttgcccaa aacatctggc aaagttgaat tgcttccaaa agttcacatt   4500
tatcagaagg acctattccc tacggaaact agcaatgggt ctcctggcca tctggatctc   4560
gtggaaggga gccttcttca gggaacagag ggagcgatta agtggaatga agcaaacaga   4620
cctggaaaag ttccctttct gagagtagca acagaaagct ctgcaaagac tccctccaag   4680
ctattggatc ctcttgcttg ggataaccac tatggtactc agataccaaa agaagagtgg   4740
aaatcccaag agaagtcacc agaaaaaaca gcttttaaga aaaaggatac cattttgtcc   4800
ctgaacgctt gtgaaagcaa tcatgcaata gcagcaataa atgagggaca aaataagccc   4860
gaaatagaag tcacctgggc aaagcaaggt aggactgaaa ggctgtgctc tcaaaaccca   4920
ccagtcttga aacgccatca acgggaaata actcgtacta ctcttcagtc agatcaagag   4980
gaaattgact atgatgatac catatcagtt gaaatgaaga aggaagattt tgacatttat   5040
gatgaggatg aaaatcagag cccccgcagc tttcaaaaga aaacacgaca ctattttatt   5100
gctgcagtgg agaggctctg ggattatggg atgagtagct ccccacatgt tctaagaaac   5160
agggctcaga gtggcagtgt ccctcagttc aagaaagttg ttttccagga atttactgat   5220
ggctccttta ctcagccctt ataccgtgga gaactaaatg aacatttggg actcctgggg   5280
ccatatataa gagcagaagt tgaagataat atcatggtaa ctttcagaaa tcaggcctct   5340
cgtccctatt ccttctattc tagccttatt tcttatgagg aagatcagag gcaaggagca   5400
gaacctagaa aaaactttgt caagcctaat gaaaccaaaa cttacttttg gaaagtgcaa   5460
catcatatgg cacccactaa agatgagttt gactgcaaag cctgggctta tttctctgat   5520
gttgacctgg aaaaagatgt gcactcaggc ctgattggac cccttctggt ctgccacact   5580
aacacactga accctgctca tgggagacaa gtgacagtac aggaatttgc tctgtttttc   5640
accatctttg atgagaccaa aagctggtac ttcactgaaa atatggaaag aaactgcagg   5700
gctccctgca atatccagat ggaagatccc acttttaaag agaattatcg cttccatgca   5760
atcaatggct acataatgga tacactacct ggcttagtaa tggctcagga tcaaaggatt   5820
cgatggtatc tgctcagcat gggcagcaat gaaaacatcc attctattca tttcagtgga   5880
catgtgttca ctgtacgaaa aaaagaggag tataaaatgg cactgtacaa tctctatcca   5940
ggtgtttttg agacagtgga aatgttacca tccaaagctg gaatttggcg ggtggaatgc   6000
```

-continued

```
cttattggcg agcatctaca tgctgggatg agcacacttt ttctggtgta cagcaataag   6060

tgtcagactc ccctgggaat ggcttctgga cacattagag attttcagat tacagcttca   6120

ggacaatatg gacagtgggc cccaaagctg gccagacttc attattccgg atcaatcaat   6180

gcctggagca ccaaggagcc cttttcttgg atcaaggtgg atctgttggc accaatgatt   6240

attcacggca tcaagaccca gggtgcccgt cagaagttct ccagcctcta catctctcag   6300

tttatcatca tgtatagtct tgatgggaag aagtggcaga cttatcgagg aaattccact   6360

ggaaccttaa tggtcttctt tggcaatgtg gattcatctg ggataaaaca caatattttt   6420

aaccctccaa ttattgctcg atacatccgt ttgcacccaa ctcattatag cattcgcagc   6480

actcttcgca tggagttgat gggctgtgat ttaaatagtt gcagcatgcc attgggaatg   6540

gagagtaaag caatatcaga tgcacagatt actgcttcat cctactttac caatatgttt   6600

gccacctggt ctccttcaaa agctcgactt cacctccaag ggaggagtaa tgcctggaga   6660

cctcaggtga ataatccaaa agagtggctg caagtggact tccagaagac aatgaaagtc   6720

acaggagtaa ctactcaggg agtaaaatct ctgcttacca gcatgtatgt gaaggagttc   6780

ctcatctcca gcagtcaaga tggccatcag tggactctct tttttcagaa tggcaaagta   6840

aaggtttttc agggaaatca agactccttc acacctgtgg tgaactctct agacccaccg   6900

ttactgactc gctaccttcg aattcacccc cagagttggg tgcaccagat tgccctgagg   6960

atggaggttc tgggctgcga ggcacaggac ctctac                             6996
```

<210> SEQ ID NO 6
<211> LENGTH: 2332
<212> TYPE: PRT
<213> ORGANISM: Homo sapiens

<400> SEQUENCE: 6

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
```

-continued

```
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620
```

-continued

```
Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr  Asn Lys Thr Ser Asn  Asn Ser Ala
        995                 1000                1005

Thr Asn  Arg Lys Thr His Ile  Asp Gly Pro Ser Leu  Leu Ile Glu
    1010                1015                1020

Asn Ser  Pro Ser Val Trp Gln  Asn Ile Leu Glu Ser  Asp Thr Glu
    1025                1030                1035
```

-continued

```
Phe Lys  Lys Val Thr Pro Leu  Ile His Asp Arg Met  Leu Met Asp
    1040                 1045                 1050

Lys Asn  Ala Thr Ala Leu Arg  Leu Asn His Met Ser  Asn Lys Thr
    1055                 1060                 1065

Thr Ser  Ser Lys Asn Met Glu  Met Val Gln Gln Lys  Lys Glu Gly
    1070                 1075                 1080

Pro Ile  Pro Pro Asp Ala Gln  Asn Pro Asp Met Ser  Phe Phe Lys
    1085                 1090                 1095

Met Leu  Phe Leu Pro Glu Ser  Ala Arg Trp Ile Gln  Arg Thr His
    1100                 1105                 1110

Gly Lys  Asn Ser Leu Asn Ser  Gly Gln Gly Pro Ser  Pro Lys Gln
    1115                 1120                 1125

Leu Val  Ser Leu Gly Pro Glu  Lys Ser Val Glu Gly  Gln Asn Phe
    1130                 1135                 1140

Leu Ser  Glu Lys Asn Lys Val  Val Val Gly Lys Gly  Glu Phe Thr
    1145                 1150                 1155

Lys Asp  Val Gly Leu Lys Glu  Met Val Phe Pro Ser  Ser Arg Asn
    1160                 1165                 1170

Leu Phe  Leu Thr Asn Leu Asp  Asn Leu His Glu Asn  Asn Thr His
    1175                 1180                 1185

Asn Gln  Glu Lys Lys Ile Gln  Glu Glu Ile Glu Lys  Lys Glu Thr
    1190                 1195                 1200

Leu Ile  Gln Glu Asn Val Val  Leu Pro Gln Ile His  Thr Val Thr
    1205                 1210                 1215

Gly Thr  Lys Asn Phe Met Lys  Asn Leu Phe Leu Leu  Ser Thr Arg
    1220                 1225                 1230

Gln Asn  Val Glu Gly Ser Tyr  Asp Gly Ala Tyr Ala  Pro Val Leu
    1235                 1240                 1245

Gln Asp  Phe Arg Ser Leu Asn  Asp Ser Thr Asn Arg  Thr Lys Lys
    1250                 1255                 1260

His Thr  Ala His Phe Ser Lys  Lys Gly Glu Glu Glu  Asn Leu Glu
    1265                 1270                 1275

Gly Leu  Gly Asn Gln Thr Lys  Gln Ile Val Glu Lys  Tyr Ala Cys
    1280                 1285                 1290

Thr Thr  Arg Ile Ser Pro Asn  Thr Ser Gln Gln Asn  Phe Val Thr
    1295                 1300                 1305

Gln Arg  Ser Lys Arg Ala Leu  Lys Gln Phe Arg Leu  Pro Leu Glu
    1310                 1315                 1320

Glu Thr  Glu Leu Glu Lys Arg  Ile Ile Val Asp Asp  Thr Ser Thr
    1325                 1330                 1335

Gln Trp  Ser Lys Asn Met Lys  His Leu Thr Pro Ser  Thr Leu Thr
    1340                 1345                 1350

Gln Ile  Asp Tyr Asn Glu Lys  Glu Lys Gly Ala Ile  Thr Gln Ser
    1355                 1360                 1365

Pro Leu  Ser Asp Cys Leu Thr  Arg Ser His Ser Ile  Pro Gln Ala
    1370                 1375                 1380

Asn Arg  Ser Pro Leu Pro Ile  Ala Lys Val Ser Ser  Phe Pro Ser
    1385                 1390                 1395

Ile Arg  Pro Ile Tyr Leu Thr  Arg Val Leu Phe Gln  Asp Asn Ser
    1400                 1405                 1410

Ser His  Leu Pro Ala Ala Ser  Tyr Arg Lys Lys Asp  Ser Gly Val
    1415                 1420                 1425

Gln Glu  Ser Ser His Phe Leu  Gln Gly Ala Lys Lys  Asn Asn Leu
```

```
    1430                1435                1440

Ser Leu  Ala Ile Leu Thr Leu  Glu Met Thr Gly Asp  Gln Arg Glu
    1445                1450                1455

Val Gly  Ser Leu Gly Thr Ser  Ala Thr Asn Ser Val  Thr Tyr Lys
    1460                1465                1470

Lys Val  Glu Asn Thr Val Leu  Pro Lys Pro Asp Leu  Pro Lys Thr
    1475                1480                1485

Ser Gly  Lys Val Glu Leu Leu  Pro Lys Val His Ile  Tyr Gln Lys
    1490                1495                1500

Asp Leu  Phe Pro Thr Glu Thr  Ser Asn Gly Ser Pro  Gly His Leu
    1505                1510                1515

Asp Leu  Val Glu Gly Ser Leu  Leu Gln Gly Thr Glu  Gly Ala Ile
    1520                1525                1530

Lys Trp  Asn Glu Ala Asn Arg  Pro Gly Lys Val Pro  Phe Leu Arg
    1535                1540                1545

Val Ala  Thr Glu Ser Ser Ala  Lys Thr Pro Ser Lys  Leu Leu Asp
    1550                1555                1560

Pro Leu  Ala Trp Asp Asn His  Tyr Gly Thr Gln Ile  Pro Lys Glu
    1565                1570                1575

Glu Trp  Lys Ser Gln Glu Lys  Ser Pro Glu Lys Thr  Ala Phe Lys
    1580                1585                1590

Lys Lys  Asp Thr Ile Leu Ser  Leu Asn Ala Cys Glu  Ser Asn His
    1595                1600                1605

Ala Ile  Ala Ala Ile Asn Glu  Gly Gln Asn Lys Pro  Glu Ile Glu
    1610                1615                1620

Val Thr  Trp Ala Lys Gln Gly  Arg Thr Glu Arg Leu  Cys Ser Gln
    1625                1630                1635

Asn Pro  Pro Val Leu Lys Arg  His Gln Arg Glu Ile  Thr Arg Thr
    1640                1645                1650

Thr Leu  Gln Ser Asp Gln Glu  Glu Ile Asp Tyr Asp  Asp Thr Ile
    1655                1660                1665

Ser Val  Glu Met Lys Lys Glu  Asp Phe Asp Ile Tyr  Asp Glu Asp
    1670                1675                1680

Glu Asn  Gln Ser Pro Arg Ser  Phe Gln Lys Lys Thr  Arg His Tyr
    1685                1690                1695

Phe Ile  Ala Ala Val Glu Arg  Leu Trp Asp Tyr Gly  Met Ser Ser
    1700                1705                1710

Ser Pro  His Val Leu Arg Asn  Arg Ala Gln Ser Gly  Ser Val Pro
    1715                1720                1725

Gln Phe  Lys Lys Val Val Phe  Gln Glu Phe Thr Asp  Gly Ser Phe
    1730                1735                1740

Thr Gln  Pro Leu Tyr Arg Gly  Glu Leu Asn Glu His  Leu Gly Leu
    1745                1750                1755

Leu Gly  Pro Tyr Ile Arg Ala  Glu Val Glu Asp Asn  Ile Met Val
    1760                1765                1770

Thr Phe  Arg Asn Gln Ala Ser  Arg Pro Tyr Ser Phe  Tyr Ser Ser
    1775                1780                1785

Leu Ile  Ser Tyr Glu Glu Asp  Gln Arg Gln Gly Ala  Glu Pro Arg
    1790                1795                1800

Lys Asn  Phe Val Lys Pro Asn  Glu Thr Lys Thr Tyr  Phe Trp Lys
    1805                1810                1815

Val Gln  His His Met Ala Pro  Thr Lys Asp Glu Phe  Asp Cys Lys
    1820                1825                1830
```

-continued

```
Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
    1970                1975                1980

Glu Thr Val Glu Met Leu Pro Ser Lys Ala Gly Ile Trp Arg Val
    1985                1990                1995

Glu Cys Leu Ile Gly Glu His Leu His Ala Gly Met Ser Thr Leu
    2000                2005                2010

Phe Leu Val Tyr Ser Asn Lys Cys Gln Thr Pro Leu Gly Met Ala
    2015                2020                2025

Ser Gly His Ile Arg Asp Phe Gln Ile Thr Ala Ser Gly Gln Tyr
    2030                2035                2040

Gly Gln Trp Ala Pro Lys Leu Ala Arg Leu His Tyr Ser Gly Ser
    2045                2050                2055

Ile Asn Ala Trp Ser Thr Lys Glu Pro Phe Ser Trp Ile Lys Val
    2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220
```

```
Asn Asn  Pro Lys Glu Trp Leu  Gln Val Asp Phe Gln  Lys Thr Met
    2225                 2230                 2235

Lys Val  Thr Gly Val Thr Thr  Gln Gly Val Lys Ser  Leu Leu Thr
    2240                 2245                 2250

Ser Met  Tyr Val Lys Glu Phe  Leu Ile Ser Ser Ser  Gln Asp Gly
    2255                 2260                 2265

His Gln  Trp Thr Leu Phe Phe  Gln Asn Gly Lys Val  Lys Val Phe
    2270                 2275                 2280

Gln Gly  Asn Gln Asp Ser Phe  Thr Pro Val Val Asn  Ser Leu Asp
    2285                 2290                 2295

Pro Pro  Leu Leu Thr Arg Tyr  Leu Arg Ile His Pro  Gln Ser Trp
    2300                 2305                 2310

Val His  Gln Ile Ala Leu Arg  Met Glu Val Leu Gly  Cys Glu Ala
    2315                 2320                 2325

Gln Asp  Leu Tyr
    2330

<210> SEQ ID NO 7
<211> LENGTH: 2262
<212> TYPE: DNA
<213> ORGANISM: Homo sapiens

<400> SEQUENCE: 7

atggagcgaa gagcctggag tctgcagtgc actgctttcg tcctcttttg cgcttggtgt      60

gcactgaaca gtgcaaaagc gaaaaggcaa tttgtcaatg aatgggcagc ggagatcccc     120

gggggcccgg aagcagcctc ggccatcgcc gaggagctgg gctatgacct tttgggtcag     180

attggttcac ttgaaaatca ctacttattc aaacataaaa accaccccag aaggtctcga     240

aggagtgcct ttcatatcac taagagatta tctgatgatg atcgtgtgat atgggctgaa     300

caacagtatg aaaaagaaag aagtaaacgt tcagctctaa gggactcagc actaaatctc     360

ttcaatgatc ccatgtggaa tcagcaatgg tacttgcaag ataccaggat gacggcagcc     420

ctgcccaagc tggaccttca tgtgatacct gtttggcaaa aaggcattac gggcaaagga     480

gttgttatca ccgtactgga tgatggtttg gagtggaatc acacggacat ttatgccaac     540

tatgatccag aggctagcta tgattttaat gataatgacc atgatccatt tccccgatat     600

gatcccacaa acgagaacaa acacgggacc agatgtgcag gagaaattgc catgcaagca     660

aataatcaca aatgcggggt tggagttgca tacaattcca aagttggagg cataagaatg     720

ctggatggca ttgtgacgga tgctattgag gccagttcaa ttggattcaa tcctggacac     780

gtggatattt acagtgcaag ctggggccct aatgatgatg ggaaaactgt ggaggggcct     840

ggccggctag cccagaaggc ttttgaatat ggtgtcaaac aggggagaca ggggaagggg     900

tccatcttcg tctgggcttc gggaaacggg gggcgtcagg gagataattg tgactgtgat     960

ggctacacag acagcatcta caccatctcc atcagcagtg cctcccagca aggcctatcc    1020

ccctggtacg ctgagaagtg ctcctccaca ctggccacct cttacagcag cggagattac    1080

accgaccaga gaatcacgag cgctgacctg cacaatgact gcacggagac gcacacaggc    1140

acctcggcct ctgcacctct ggctgctggc atcttcgctc tggccctgga agcaaaccca    1200

aatctcacct ggcgagatat gcagcacctg gttgtctgga cctctgagta tgacccgctg    1260

gccaataacc ctggatggaa aaagaatgga gcaggcttga tggtgaatag tcgatttgga    1320

tttggcttgc taaatgccaa agctctggtg gatttagctg accccaggac ctggaggagc    1380

gtgcctgaga agaaagagtg tgttgtaaag gacaatgact ttgagcccag agccctgaaa    1440
```

```
gctaatggag aagttatcat tgaaattcca acaagagctt gtgaaggaca agaaaatgct   1500

atcaagtccc tggagcatgt acaatttgaa gcaacaattg aatattcccg aagaggagac   1560

cttcatgtca cacttacttc tgctgctgga actagcactg tgctcttggc tgaaagagaa   1620

cgggatacat ctcctaatgg ctttaagaac tgggacttca tgtctgttca cacatgggga   1680

gagaacccta taggtacttg gactttgaga attacagaca tgtctggaag aattcaaaat   1740

gaaggaagaa ttgtgaactg gaagctgatt ttgcacggga cctcttctca gccagagcat   1800

atgaagcagc ctcgtgtgta cacgtcctac aacactgttc agaatgacag aagaggggtg   1860

gagaagatgg tggatccagg ggaggagcag cccacacaag agaaccctaa ggagaacacc   1920

ctggtgtcca aaagccccag cagcagcagc gtagggggcc ggagggatga gttggaggag   1980

ggagcccctt cccaggccat gctgcgactc ctgcaaagtg ctttcagtaa aaactcaccg   2040

ccaaagcaat caccaaagaa gtccccaagt gcaaagctca acatccctta tgaaaacttc   2100

tacgaagccc tggaaaagct gaacaaacct tcccagctta aagactctga agacagtctg   2160

tataatgact atgttgatgt tttttataac actaaacctt acaagcacag agacgaccgg   2220

ctgcttcaag ctctggtgga cattctgaat gaggaaaatt aa                       2262
```

<210> SEQ ID NO 8
<211> LENGTH: 753
<212> TYPE: PRT
<213> ORGANISM: Homo sapiens

<400> SEQUENCE: 8

```
Met Glu Arg Arg Ala Trp Ser Leu Gln Cys Thr Ala Phe Val Leu Phe
1               5                   10                  15

Cys Ala Trp Cys Ala Leu Asn Ser Ala Lys Ala Lys Arg Gln Phe Val
            20                  25                  30

Asn Glu Trp Ala Ala Glu Ile Pro Gly Gly Pro Glu Ala Ala Ser Ala
        35                  40                  45

Ile Ala Glu Glu Leu Gly Tyr Asp Leu Leu Gly Gln Ile Gly Ser Leu
    50                  55                  60

Glu Asn His Tyr Leu Phe Lys His Lys Asn His Pro Arg Arg Ser Arg
65                  70                  75                  80

Arg Ser Ala Phe His Ile Thr Lys Arg Leu Ser Asp Asp Asp Arg Val
                85                  90                  95

Ile Trp Ala Glu Gln Gln Tyr Glu Lys Glu Arg Ser Lys Arg Ser Ala
            100                 105                 110

Leu Arg Asp Ser Ala Leu Asn Leu Phe Asn Asp Pro Met Trp Asn Gln
        115                 120                 125

Gln Trp Tyr Leu Gln Asp Thr Arg Met Thr Ala Ala Leu Pro Lys Leu
    130                 135                 140

Asp Leu His Val Ile Pro Val Trp Gln Lys Gly Ile Thr Gly Lys Gly
145                 150                 155                 160

Val Val Ile Thr Val Leu Asp Asp Gly Leu Glu Trp Asn His Thr Asp
                165                 170                 175

Ile Tyr Ala Asn Tyr Asp Pro Glu Ala Ser Tyr Asp Phe Asn Asp Asn
            180                 185                 190

Asp His Asp Pro Phe Pro Arg Tyr Asp Pro Thr Asn Glu Asn Lys His
        195                 200                 205

Gly Thr Arg Cys Ala Gly Glu Ile Ala Met Gln Ala Asn Asn His Lys
    210                 215                 220
```

Cys Gly Val Gly Val Ala Tyr Asn Ser Lys Val Gly Gly Ile Arg Met
225 230 235 240

Leu Asp Gly Ile Val Thr Asp Ala Ile Glu Ala Ser Ser Ile Gly Phe
245 250 255

Asn Pro Gly His Val Asp Ile Tyr Ser Ala Ser Trp Gly Pro Asn Asp
260 265 270

Asp Gly Lys Thr Val Glu Gly Pro Gly Arg Leu Ala Gln Lys Ala Phe
275 280 285

Glu Tyr Gly Val Lys Gln Gly Arg Gln Gly Lys Gly Ser Ile Phe Val
290 295 300

Trp Ala Ser Gly Asn Gly Gly Arg Gln Gly Asp Asn Cys Asp Cys Asp
305 310 315 320

Gly Tyr Thr Asp Ser Ile Tyr Thr Ile Ser Ile Ser Ser Ala Ser Gln
325 330 335

Gln Gly Leu Ser Pro Trp Tyr Ala Glu Lys Cys Ser Ser Thr Leu Ala
340 345 350

Thr Ser Tyr Ser Ser Gly Asp Tyr Thr Asp Gln Arg Ile Thr Ser Ala
355 360 365

Asp Leu His Asn Asp Cys Thr Glu Thr His Thr Gly Thr Ser Ala Ser
370 375 380

Ala Pro Leu Ala Ala Gly Ile Phe Ala Leu Ala Leu Glu Ala Asn Pro
385 390 395 400

Asn Leu Thr Trp Arg Asp Met Gln His Leu Val Val Trp Thr Ser Glu
405 410 415

Tyr Asp Pro Leu Ala Asn Asn Pro Gly Trp Lys Lys Asn Gly Ala Gly
420 425 430

Leu Met Val Asn Ser Arg Phe Gly Phe Gly Leu Leu Asn Ala Lys Ala
435 440 445

Leu Val Asp Leu Ala Asp Pro Arg Thr Trp Arg Ser Val Pro Glu Lys
450 455 460

Lys Glu Cys Val Val Lys Asp Asn Asp Phe Glu Pro Arg Ala Leu Lys
465 470 475 480

Ala Asn Gly Glu Val Ile Ile Glu Ile Pro Thr Arg Ala Cys Glu Gly
485 490 495

Gln Glu Asn Ala Ile Lys Ser Leu Glu His Val Gln Phe Glu Ala Thr
500 505 510

Ile Glu Tyr Ser Arg Arg Gly Asp Leu His Val Thr Leu Thr Ser Ala
515 520 525

Ala Gly Thr Ser Thr Val Leu Leu Ala Glu Arg Glu Arg Asp Thr Ser
530 535 540

Pro Asn Gly Phe Lys Asn Trp Asp Phe Met Ser Val His Thr Trp Gly
545 550 555 560

Glu Asn Pro Ile Gly Thr Trp Thr Leu Arg Ile Thr Asp Met Ser Gly
565 570 575

Arg Ile Gln Asn Glu Gly Arg Ile Val Asn Trp Lys Leu Ile Leu His
580 585 590

Gly Thr Ser Ser Gln Pro Glu His Met Lys Gln Pro Arg Val Tyr Thr
595 600 605

Ser Tyr Asn Thr Val Gln Asn Asp Arg Arg Gly Val Glu Lys Met Val
610 615 620

Asp Pro Gly Glu Glu Gln Pro Thr Gln Glu Asn Pro Lys Glu Asn Thr
625 630 635 640

Leu Val Ser Lys Ser Pro Ser Ser Ser Ser Val Gly Gly Arg Arg Asp

```
                645                 650                 655

Glu Leu Glu Glu Gly Ala Pro Ser Gln Ala Met Leu Arg Leu Leu Gln
            660                 665                 670

Ser Ala Phe Ser Lys Asn Ser Pro Pro Lys Gln Ser Pro Lys Lys Ser
        675                 680                 685

Pro Ser Ala Lys Leu Asn Ile Pro Tyr Glu Asn Phe Tyr Glu Ala Leu
    690                 695                 700

Glu Lys Leu Asn Lys Pro Ser Gln Leu Lys Asp Ser Glu Asp Ser Leu
705                 710                 715                 720

Tyr Asn Asp Tyr Val Asp Val Phe Tyr Asn Thr Lys Pro Tyr Lys His
                725                 730                 735

Arg Asp Asp Arg Leu Leu Gln Ala Leu Val Asp Ile Leu Asn Glu Glu
            740                 745                 750

Asn


<210> SEQ ID NO 9
<211> LENGTH: 1917
<212> TYPE: DNA
<213> ORGANISM: Homo sapiens

<400> SEQUENCE: 9

atgaagggtg gttgtgtctc ccagtggaag gcggccgccg ggttcctctt ctgtgtcatg      60

gtttttgcat ctgctgagcg accggtcttc acgaatcatt ttcttgtgga gttgcataaa     120

gggggagagg acaaagctcg ccaagttgca gcagaacacg gctttggagt ccgaaagctt     180

ccctttgctg aaggtctgta ccacttttat cacaatggcc ttgcaaaggc caagagaaga     240

cgcagcctac accacaagca gcagctggag agagacccca gggtaaagat ggctttgcag     300

caggaaggat ttgaccgaaa aaagcgaggt tacagagaca tcaatgagat cgacatcaac     360

atgaacgatc ctctttttac aaagcagtgg tatctgatca atactgggca agctgatggc     420

actcctggcc ttgatttgaa tgtggctgaa gcctgggagc tgggatacac agggaaaggt     480

gttaccattg gaattatgga tgatgggatt gactatctcc acccggacct ggcctccaac     540

tataatgccg aagcaagtta cgacttcagc agcaacgacc cctatcctta ccctcggtac     600

acagatgact ggtttaacag ccacgggacc cgatgtgcag gagaagtttc tgctgccgcc     660

aacaacaata tctgtggagt tggagtagca tacaactcca aggttgcagg catccggatg     720

ctggaccagc cattcatgac agacatcatc gaggcctcct ccatcagtca tatgccacag     780

ctgattgaca tctacagcgc cagctggggc cccacagaca acggcaagac agtggatggg     840

ccccgggagc tcacgctgca ggccatggcc gatggcgtga acaagggccg cggcggcaaa     900

ggcagcatct acgtgtgggc ctccggggac ggcggcagct atgacgactg caactgcgac     960

ggctacgcct ccagcatgtg gaccatctcc atcaactcag ccatcaacga cggcaggact    1020

gccctgtacg acgagagctg ctcttccacc ttggcttcca ccttcagcaa cgggaggaaa    1080

aggaaccccg aggccggtgt ggcaaccaca gatttgtacg gcaactgcac tctgaggcat    1140

tctgggacat ctgcagctgc ccccgaggca gctggtgtgt ttgcactggc tctggaggct    1200

aacctgggtc tgacctggcg ggacatgcag catctgactg tgctcacctc caaacggaac    1260

cagcttcacg acgaggtcca tcagtggcgg cgcaatgggg tcggcctgga atttaatcac    1320

ctctttggct acggggtcct tgatgcaggt gccatggtga aaatggctaa agactggaaa    1380

accgtgcctg agagattcca ctgtgtggga ggctccgtgc aggaccctga gaaaatacca    1440

tccactggca agttggtgct gacactcaca accgacgcct gtgaggggaa ggaaaatttt    1500
```

gtccgctacc tggagcatgt ccaggctgtc atcacggtca acgcaaccag aagaggagac 1560
ctgaacatca acatgacttc ccctatgggc accaagtcca ttttgctgag ccggcgtcca 1620
agggatgacg actccaaggt gggctttgac aagtggcctt tcatgaccac tcacacgtgg 1680
ggggaagacg cccgaggcac ctggaccctg gagctgggat ttgtcggcag cgccccgcag 1740
aagggggtgc tgaaggagtg gaccctgatg ctgcatggca ctcagagtgc cccgtacatc 1800
gaccaggtgg tgcgggatta ccagtccaag ttggccatgt ccaagaaaga ggagctggag 1860
gaagagctgg acgaagccgt ggagagaagc ctgaaaagca tccttaacaa gaactag 1917

<210> SEQ ID NO 10
<211> LENGTH: 638
<212> TYPE: PRT
<213> ORGANISM: Homo sapiens

<400> SEQUENCE: 10

Met Lys Gly Gly Cys Val Ser Gln Trp Lys Ala Ala Ala Gly Phe Leu
1 5 10 15

Phe Cys Val Met Val Phe Ala Ser Ala Glu Arg Pro Val Phe Thr Asn
20 25 30

His Phe Leu Val Glu Leu His Lys Gly Gly Glu Asp Lys Ala Arg Gln
35 40 45

Val Ala Ala Glu His Gly Phe Gly Val Arg Lys Leu Pro Phe Ala Glu
50 55 60

Gly Leu Tyr His Phe Tyr His Asn Gly Leu Ala Lys Ala Lys Arg Arg
65 70 75 80

Arg Ser Leu His His Lys Gln Gln Leu Glu Arg Asp Pro Arg Val Lys
85 90 95

Met Ala Leu Gln Gln Glu Gly Phe Asp Arg Lys Lys Arg Gly Tyr Arg
100 105 110

Asp Ile Asn Glu Ile Asp Ile Asn Met Asn Asp Pro Leu Phe Thr Lys
115 120 125

Gln Trp Tyr Leu Ile Asn Thr Gly Gln Ala Asp Gly Thr Pro Gly Leu
130 135 140

Asp Leu Asn Val Ala Glu Ala Trp Glu Leu Gly Tyr Thr Gly Lys Gly
145 150 155 160

Val Thr Ile Gly Ile Met Asp Asp Gly Ile Asp Tyr Leu His Pro Asp
165 170 175

Leu Ala Ser Asn Tyr Asn Ala Glu Ala Ser Tyr Asp Phe Ser Ser Asn
180 185 190

Asp Pro Tyr Pro Tyr Pro Arg Tyr Thr Asp Asp Trp Phe Asn Ser His
195 200 205

Gly Thr Arg Cys Ala Gly Glu Val Ser Ala Ala Ala Asn Asn Asn Ile
210 215 220

Cys Gly Val Gly Val Ala Tyr Asn Ser Lys Val Ala Gly Ile Arg Met
225 230 235 240

Leu Asp Gln Pro Phe Met Thr Asp Ile Ile Glu Ala Ser Ser Ile Ser
245 250 255

His Met Pro Gln Leu Ile Asp Ile Tyr Ser Ala Ser Trp Gly Pro Thr
260 265 270

Asp Asn Gly Lys Thr Val Asp Gly Pro Arg Glu Leu Thr Leu Gln Ala
275 280 285

Met Ala Asp Gly Val Asn Lys Gly Arg Gly Gly Lys Gly Ser Ile Tyr
290 295 300

```
Val Trp Ala Ser Gly Asp Gly Gly Ser Tyr Asp Asp Cys Asn Cys Asp
305                 310                 315                 320

Gly Tyr Ala Ser Ser Met Trp Thr Ile Ser Ile Asn Ser Ala Ile Asn
                325                 330                 335

Asp Gly Arg Thr Ala Leu Tyr Asp Glu Ser Cys Ser Ser Thr Leu Ala
            340                 345                 350

Ser Thr Phe Ser Asn Gly Arg Lys Arg Asn Pro Glu Ala Gly Val Ala
        355                 360                 365

Thr Thr Asp Leu Tyr Gly Asn Cys Thr Leu Arg His Ser Gly Thr Ser
    370                 375                 380

Ala Ala Ala Pro Glu Ala Ala Gly Val Phe Ala Leu Ala Leu Glu Ala
385                 390                 395                 400

Asn Leu Gly Leu Thr Trp Arg Asp Met Gln His Leu Thr Val Leu Thr
                405                 410                 415

Ser Lys Arg Asn Gln Leu His Asp Glu Val His Gln Trp Arg Arg Asn
            420                 425                 430

Gly Val Gly Leu Glu Phe Asn His Leu Phe Gly Tyr Gly Val Leu Asp
        435                 440                 445

Ala Gly Ala Met Val Lys Met Ala Lys Asp Trp Lys Thr Val Pro Glu
    450                 455                 460

Arg Phe His Cys Val Gly Gly Ser Val Gln Asp Pro Glu Lys Ile Pro
465                 470                 475                 480

Ser Thr Gly Lys Leu Val Leu Thr Leu Thr Thr Asp Ala Cys Glu Gly
                485                 490                 495

Lys Glu Asn Phe Val Arg Tyr Leu Glu His Val Gln Ala Val Ile Thr
            500                 505                 510

Val Asn Ala Thr Arg Arg Gly Asp Leu Asn Ile Asn Met Thr Ser Pro
        515                 520                 525

Met Gly Thr Lys Ser Ile Leu Leu Ser Arg Arg Pro Arg Asp Asp Asp
    530                 535                 540

Ser Lys Val Gly Phe Asp Lys Trp Pro Phe Met Thr Thr His Thr Trp
545                 550                 555                 560

Gly Glu Asp Ala Arg Gly Thr Trp Thr Leu Glu Leu Gly Phe Val Gly
                565                 570                 575

Ser Ala Pro Gln Lys Gly Val Leu Lys Glu Trp Thr Leu Met Leu His
            580                 585                 590

Gly Thr Gln Ser Ala Pro Tyr Ile Asp Gln Val Val Arg Asp Tyr Gln
        595                 600                 605

Ser Lys Leu Ala Met Ser Lys Lys Glu Glu Leu Glu Glu Glu Leu Asp
    610                 615                 620

Glu Ala Val Glu Arg Ser Leu Lys Ser Ile Leu Asn Lys Asn
625                 630                 635
```

<210> SEQ ID NO 11
<211> LENGTH: 2385
<212> TYPE: DNA
<213> ORGANISM: Homo sapiens

<400> SEQUENCE: 11

```
atggagctga ggccctggtt gctatgggtg gtagcagcaa caggaacctt ggtcctgcta      60

gcagctgatg ctcagggcca gaaggtcttc accaacacgt gggctgtgcg catccctgga     120

ggcccagcgg tggccaacag tgtggcacgg aagcatgggt tcctcaacct gggccagatc     180

ttcggggact attaccactt ctggcatcga ggagtgacga agcggtccct gtcgcctcac     240
```

-continued

```
cgcccgcggc acagccggct gcagagggag cctcaagtac agtggctgga acagcaggtg    300
gcaaagcgac ggactaaacg ggacgtgtac caggagccca cagaccccaa gtttcctcag    360
cagtggtacc tgtctggtgt cactcagcgg gacctgaatg tgaaggcggc ctgggcgcag    420
ggctacacag ggcacggcat tgtggtctcc attctggacg atggcatcga gaagaaccac    480
ccggacttgg caggcaatta tgatcctggg gccagttttg atgtcaatga ccaggaccct    540
gacccccagc ctcggtacac acagatgaat gacaacaggc acggcacacg gtgtgcgggg    600
gaagtggctg cggtggccaa caacggtgtc tgtggtgtag gtgtggccta caacgcccgc    660
attggagggg tgcgcatgct ggatggcgag gtgacagatg cagtggaggc acgctcgctg    720
ggcctgaacc ccaaccacat ccacatctac agtgccagct ggggccccga ggatgacggc    780
aagacagtgg atgggccagc ccgcctcgcc gaggaggcct tcttccgtgg ggttagccag    840
ggccgagggg ggctgggctc catctttgtc tgggcctcgg ggaacggggg ccgggaacat    900
gacagctgca actgcgacgg ctacaccaac agtatctaca cgctgtccat cagcagcgcc    960
acgcagtttg gcaacgtgcc gtggtacagc gaggcctgct cgtccacact ggccacgacc   1020
tacagcagtg gcaaccagaa tgagaagcag atcgtgacga ctgacttgcg gcagaagtgc   1080
acggagtctc acacgggcac ctcagcctct gcccccttag cagccggcat cattgctctc   1140
accctggagg ccaataagaa cctcacatgg cgggacatgc aacacctggt ggtacagacc   1200
tcgaagccag cccacctcaa tgccaacgac tgggccacca atggtgtggg ccggaaagtg   1260
agccactcat atggctacgg gcttttggac gcaggcgcca tggtggccct ggcccagaat   1320
tggaccacag tggcccccca gcggaagtgc atcatcgaca tcctcaccga gcccaaagac   1380
atcgggaaac ggctcgaggt gcggaagacc gtgaccgcgt gcctgggcga gcccaaccac   1440
atcactcggc tggagcacgc tcaggcgcgg ctcaccctgt cctataatcg ccgtggcgac   1500
ctggccatcc acctggtcag ccccatgggc acccgctcca ccctgctggc agccaggcca   1560
catgactact ccgcagatgg gtttaatgac tgggccttca tgacaactca ttcctgggat   1620
gaggatccct ctggcgagtg ggtcctagag attgaaaaca ccagcgaagc caacaactat   1680
gggacgctga ccaagttcac cctcgtactc tatggcaccg cccctgaggg gctgcccgta   1740
cctccagaaa gcagtggctg caagaccctc acgtccagtc aggcctgtgt ggtgtgcgag   1800
gaaggcttct ccctgcacca gaagagctgt gtccagcact gccctccagg cttcgccccc   1860
caagtcctcg atacgcacta tagcaccgag aatgacgtgg agaccatccg ggccagcgtc   1920
tgcgccccct gccacgcctc atgtgccaca tgccaggggc cggccctgac agactgcctc   1980
agctgcccca gccacgcctc cttggaccct gtggagcaga cttgctcccg gcaaagccag   2040
agcagccgag agtccccgcc acagcagcag ccacctcggc tgcccccgga ggtggaggcg   2100
gggcaacggc tgcgggcagg gctgctgccc tcacacctgc ctgaggtggt ggccggcctc   2160
agctgcgcct tcatcgtgct ggtcttcgtc actgtcttcc tggtcctgca gctgcgctct   2220
ggctttagtt ttcgggggt gaaggtgtac accatggacc gtggcctcat ctcctacaag   2280
gggctgcccc ctgaagcctg gcaggaggag tgcccgtctg actcagaaga ggacgagggc   2340
cggggcgaga ggaccgcctt tatcaaagac cagagcgccc tctga                   2385
```

<210> SEQ ID NO 12
<211> LENGTH: 794
<212> TYPE: PRT
<213> ORGANISM: Homo sapiens

<400> SEQUENCE: 12

Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45

Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val
    210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
        275                 280                 285

Phe Val Trp Ala Ser Gly Asn Gly Gly Arg Glu His Asp Ser Cys Asn
    290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
            340                 345                 350

Thr Thr Asp Leu Arg Gln Lys Cys Thr Glu Ser His Thr Gly Thr Ser
        355                 360                 365

Ala Ser Ala Pro Leu Ala Ala Gly Ile Ile Ala Leu Thr Leu Glu Ala
    370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
                405                 410                 415

```
Gly Arg Lys Val Ser His Ser Tyr Gly Tyr Gly Leu Leu Asp Ala Gly
            420                 425                 430

Ala Met Val Ala Leu Ala Gln Asn Trp Thr Thr Val Ala Pro Gln Arg
        435                 440                 445

Lys Cys Ile Ile Asp Ile Leu Thr Glu Pro Lys Asp Ile Gly Lys Arg
    450                 455                 460

Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
                485                 490                 495

Arg Arg Gly Asp Leu Ala Ile His Leu Val Ser Pro Met Gly Thr Arg
            500                 505                 510

Ser Thr Leu Leu Ala Ala Arg Pro His Asp Tyr Ser Ala Asp Gly Phe
        515                 520                 525

Asn Asp Trp Ala Phe Met Thr Thr His Ser Trp Asp Glu Asp Pro Ser
    530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
                565                 570                 575

Gly Leu Pro Val Pro Pro Glu Ser Ser Gly Cys Lys Thr Leu Thr Ser
            580                 585                 590

Ser Gln Ala Cys Val Val Cys Glu Glu Gly Phe Ser Leu His Gln Lys
        595                 600                 605

Ser Cys Val Gln His Cys Pro Pro Gly Phe Ala Pro Gln Val Leu Asp
    610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
                645                 650                 655

Thr Asp Cys Leu Ser Cys Pro Ser His Ala Ser Leu Asp Pro Val Glu
            660                 665                 670

Gln Thr Cys Ser Arg Gln Ser Gln Ser Ser Arg Glu Ser Pro Pro Gln
        675                 680                 685

Gln Gln Pro Pro Arg Leu Pro Pro Glu Val Glu Ala Gly Gln Arg Leu
    690                 695                 700

Arg Ala Gly Leu Leu Pro Ser His Leu Pro Glu Val Val Ala Gly Leu
705                 710                 715                 720

Ser Cys Ala Phe Ile Val Leu Val Phe Val Thr Val Phe Leu Val Leu
                725                 730                 735

Gln Leu Arg Ser Gly Phe Ser Phe Arg Gly Val Lys Val Tyr Thr Met
            740                 745                 750

Asp Arg Gly Leu Ile Ser Tyr Lys Gly Leu Pro Pro Glu Ala Trp Gln
        755                 760                 765

Glu Glu Cys Pro Ser Asp Ser Glu Glu Asp Glu Gly Arg Gly Glu Arg
    770                 775                 780

Thr Ala Phe Ile Lys Asp Gln Ser Ala Leu
785                 790

<210> SEQ ID NO 13
<211> LENGTH: 2268
<212> TYPE: DNA
<213> ORGANISM: Homo sapiens
```

-continued

<400> SEQUENCE: 13

```
atgcggcccg ccccgattgc gctgtggctg cgcctggtct tggccctggc ccttgtccgc     60
ccccgggctg tggggtgggc cccggtccga gcccccatct atgtcagcag ctgggccgtc    120
caggtgtccc agggtaaccg ggaggtcgag cgcctggcac gcaaattcgg cttcgtcaac    180
ctggggccga tcttctctga cgggcagtac tttcacctgc ggcaccgggg cgtggtccag    240
cagtccctga ccccgcactg gggccaccgc ctgcacctga agaaaaaccc caaggtgcag    300
tggttccagc agcagacgct gcagcggcgg gtgaaacgct ctgtcgtggt gcccacggac    360
ccctggttct ccaagcagtg gtacatgaac agcgaggccc aaccagacct gagcatcctg    420
caggcctgga gtcaggggct gtcaggccag ggcatcgtgg tctctgtgct ggacgatggc    480
atcgagaagg accacccgga cctctgggcc aactacgacc ccctggccag ctatgacttc    540
aatgactacg acccggaccc ccagccccgc tacaccccca gcaaagagaa ccggcacggg    600
acccgctgtg ctggggaggt ggccgcgatg gccaacaatg gcttctgtgg tgtgggggtc    660
gctttcaacg cccgaatcgg aggcgtacgg atgctggacg gtaccatcac cgatgtcatc    720
gaggcccagt cgctgagcct gcagccgcag cacatccaca tttacagcgc cagctggggt    780
cccgaggacg acggccgcac ggtggacggc cccggcatcc tcacccgcga ggccttccgg    840
cgtggtgtga ccaagggccg cggcgggctg ggcacgctct tcatctgggc ctcgggcaac    900
ggcggcctgc actacgacaa ctgcaactgc gacggctaca ccaacagcat ccacacgctt    960
tccgtgggca gcaccaccca gcagggccgc gtgccctggt acagcgaagc ctgcgcctcc   1020
accctcacca ccacctacag cagcggcgtg gccaccgacc cccagatcgt caccacggac   1080
ctgcatcacg ggtgcacaga ccagcacacg ggcacctcgg cctcagcccc actggcggcc   1140
ggcatgatcg ccctagcgct ggaggccaac ccgttcctga cgtggagaga catgcagcac   1200
ctggtggtcc gcgcgtccaa gccggcgcac ctgcaggccg aggactggag gaccaacggc   1260
gtggggcgcc aagtgagcca tcactacgga tacgggctgc tggacgccgg gctgctggtg   1320
gacaccgccc gcacctggct gcccacccag ccgcagagga agtgcgccgt ccgggtccag   1380
agccgcccca cccccatcct gccgctgatc tacatcaggg aaaacgtatc ggcctgcgcc   1440
ggcctccaca actccatccg ctcgctggag cacgtgcagg cgcagctgac gctgtcctac   1500
agccggcgcg gagacctgga gatctcgctc accagcccca tgggcacgcg ctccacactc   1560
gtggccatac gacccttgga cgtcagcact gaaggctaca acaactgggt cttcatgtcc   1620
acccacttct gggatgagaa cccacagggc gtgtggaccc tgggcctaga gaacaagggc   1680
tactatttca acacggggac gttgtaccgc tacacgctgc tgctctatgg gacggccgag   1740
gacatgacag cgcggcctac aggcccccag gtgaccagca gcgcgtgtgt gcagcgggac   1800
acagaggggc tgtgccaggc gtgtgacggc cccgcctaca tcctgggaca gctctgcctg   1860
gcctactgcc ccccgcggtt cttcaaccac acaaggctgg tgaccgctgg gcctgggcac   1920
acggcggcgc ccgcgctgag ggtctgctcc agctgccatg cctcctgcta cacctgccgc   1980
ggcggctccc cgagggactg cacctcctgt cccccatcct ccacgctgga ccagcagcag   2040
ggctcctgca tgggacccac cacccccgac agccgccccc ggcttagagc tgccgcctgt   2100
ccccaccacc gctgcccagc ctcggccatg gtgctgagcc tcctggccgt gaccctcgga   2160
ggccccgtcc tctgcggcat gtccatggac ctcccactat acgcctggct ctcccgtgcc   2220
agggccaccc ccaccaaacc ccaggtctgg ctgccagctg gaacctga                 2268
```

```
<210> SEQ ID NO 14
<211> LENGTH: 755
<212> TYPE: PRT
<213> ORGANISM: Homo sapiens

<400> SEQUENCE: 14

Met Arg Pro Ala Pro Ile Ala Leu Trp Leu Arg Leu Val Leu Ala Leu
1               5                   10                  15

Ala Leu Val Arg Pro Arg Ala Val Gly Trp Ala Pro Val Arg Ala Pro
            20                  25                  30

Ile Tyr Val Ser Ser Trp Ala Val Gln Val Ser Gln Gly Asn Arg Glu
        35                  40                  45

Val Glu Arg Leu Ala Arg Lys Phe Gly Phe Val Asn Leu Gly Pro Ile
    50                  55                  60

Phe Ser Asp Gly Gln Tyr Phe His Leu Arg His Arg Gly Val Val Gln
65                  70                  75                  80

Gln Ser Leu Thr Pro His Trp Gly His Arg Leu His Leu Lys Lys Asn
                85                  90                  95

Pro Lys Val Gln Trp Phe Gln Gln Gln Thr Leu Gln Arg Arg Val Lys
            100                 105                 110

Arg Ser Val Val Val Pro Thr Asp Pro Trp Phe Ser Lys Gln Trp Tyr
        115                 120                 125

Met Asn Ser Glu Ala Gln Pro Asp Leu Ser Ile Leu Gln Ala Trp Ser
    130                 135                 140

Gln Gly Leu Ser Gly Gln Gly Ile Val Val Ser Val Leu Asp Asp Gly
145                 150                 155                 160

Ile Glu Lys Asp His Pro Asp Leu Trp Ala Asn Tyr Asp Pro Leu Ala
                165                 170                 175

Ser Tyr Asp Phe Asn Asp Tyr Asp Pro Asp Pro Gln Pro Arg Tyr Thr
            180                 185                 190

Pro Ser Lys Glu Asn Arg His Gly Thr Arg Cys Ala Gly Glu Val Ala
        195                 200                 205

Ala Met Ala Asn Asn Gly Phe Cys Gly Val Gly Val Ala Phe Asn Ala
    210                 215                 220

Arg Ile Gly Gly Val Arg Met Leu Asp Gly Thr Ile Thr Asp Val Ile
225                 230                 235                 240

Glu Ala Gln Ser Leu Ser Leu Gln Pro Gln His Ile His Ile Tyr Ser
                245                 250                 255

Ala Ser Trp Gly Pro Glu Asp Asp Gly Arg Thr Val Asp Gly Pro Gly
            260                 265                 270

Ile Leu Thr Arg Glu Ala Phe Arg Arg Gly Val Thr Lys Gly Arg Gly
        275                 280                 285

Gly Leu Gly Thr Leu Phe Ile Trp Ala Ser Gly Asn Gly Gly Leu His
    290                 295                 300

Tyr Asp Asn Cys Asn Cys Asp Gly Tyr Thr Asn Ser Ile His Thr Leu
305                 310                 315                 320

Ser Val Gly Ser Thr Thr Gln Gln Gly Arg Val Pro Trp Tyr Ser Glu
                325                 330                 335

Ala Cys Ala Ser Thr Leu Thr Thr Thr Tyr Ser Ser Gly Val Ala Thr
            340                 345                 350

Asp Pro Gln Ile Val Thr Thr Asp Leu His His Gly Cys Thr Asp Gln
        355                 360                 365

His Thr Gly Thr Ser Ala Ser Ala Pro Leu Ala Ala Gly Met Ile Ala
    370                 375                 380
```

-continued

Leu Ala Leu Glu Ala Asn Pro Phe Leu Thr Trp Arg Asp Met Gln His
385 390 395 400

Leu Val Val Arg Ala Ser Lys Pro Ala His Leu Gln Ala Glu Asp Trp
405 410 415

Arg Thr Asn Gly Val Gly Arg Gln Val Ser His His Tyr Gly Tyr Gly
420 425 430

Leu Leu Asp Ala Gly Leu Leu Val Asp Thr Ala Arg Thr Trp Leu Pro
435 440 445

Thr Gln Pro Gln Arg Lys Cys Ala Val Arg Val Gln Ser Arg Pro Thr
450 455 460

Pro Ile Leu Pro Leu Ile Tyr Ile Arg Glu Asn Val Ser Ala Cys Ala
465 470 475 480

Gly Leu His Asn Ser Ile Arg Ser Leu Glu His Val Gln Ala Gln Leu
485 490 495

Thr Leu Ser Tyr Ser Arg Arg Gly Asp Leu Glu Ile Ser Leu Thr Ser
500 505 510

Pro Met Gly Thr Arg Ser Thr Leu Val Ala Ile Arg Pro Leu Asp Val
515 520 525

Ser Thr Glu Gly Tyr Asn Asn Trp Val Phe Met Ser Thr His Phe Trp
530 535 540

Asp Glu Asn Pro Gln Gly Val Trp Thr Leu Gly Leu Glu Asn Lys Gly
545 550 555 560

Tyr Tyr Phe Asn Thr Gly Thr Leu Tyr Arg Tyr Thr Leu Leu Leu Tyr
565 570 575

Gly Thr Ala Glu Asp Met Thr Ala Arg Pro Thr Gly Pro Gln Val Thr
580 585 590

Ser Ser Ala Cys Val Gln Arg Asp Thr Glu Gly Leu Cys Gln Ala Cys
595 600 605

Asp Gly Pro Ala Tyr Ile Leu Gly Gln Leu Cys Leu Ala Tyr Cys Pro
610 615 620

Pro Arg Phe Phe Asn His Thr Arg Leu Val Thr Ala Gly Pro Gly His
625 630 635 640

Thr Ala Ala Pro Ala Leu Arg Val Cys Ser Ser Cys His Ala Ser Cys
645 650 655

Tyr Thr Cys Arg Gly Gly Ser Pro Arg Asp Cys Thr Ser Cys Pro Pro
660 665 670

Ser Ser Thr Leu Asp Gln Gln Gln Gly Ser Cys Met Gly Pro Thr Thr
675 680 685

Pro Asp Ser Arg Pro Arg Leu Arg Ala Ala Ala Cys Pro His His Arg
690 695 700

Cys Pro Ala Ser Ala Met Val Leu Ser Leu Leu Ala Val Thr Leu Gly
705 710 715 720

Gly Pro Val Leu Cys Gly Met Ser Met Asp Leu Pro Leu Tyr Ala Trp
725 730 735

Leu Ser Arg Ala Arg Ala Thr Pro Thr Lys Pro Gln Val Trp Leu Pro
740 745 750

Ala Gly Thr
755

<210> SEQ ID NO 15
<211> LENGTH: 729
<212> TYPE: DNA
<213> ORGANISM: Homo sapiens

<400> SEQUENCE: 15

```
atgggcacgc gctccacact cgtggccata cgacccttgg acgtcagcac tgaaggctac     60

aacaactggg tcttcatgtc cacccacttc tgggatgaga acccacaggg cgtgtggacc    120

ctgggcctag agaacaaggg ctactatttc aacacgggga cgttgtaccg ctacacgctg    180

ctgctctatg ggacggccga ggacatgaca gcgcggccta caggccccca ggtgaccagc    240

agcgcgtgtg tgcagcggga cacagagggg ctgtgccagg cgtgtgacgg ccccgcctac    300

atcctgggac agctctgcct ggcctactgc cccccgcggt tcttcaacca cacaaggctg    360

gtgaccgctg ggcctgggca cacggcggcg cccgcgctga gggtctgctc cagctgccat    420

gcctcctgct acacctgccg cggcggctcc ccgagggact gcacctcctg tcccccatcc    480

tccacgctgg accagcagca gggctcctgc atgggaccca ccacccccga cagccgcccc    540

cggcttagag ctgccgcctg tccccaccac cgctgcccag cctcggccat ggtgctgagc    600

ctcctggccg tgaccctcgg aggccccgtc ctctgcggca tgtccatgga cctcccacta    660

tacgcctggc tctcccgtgc cagggccacc cccaccaaac cccaggtctg gctgccagct    720

ggaacctga                                                            729
```

<210> SEQ ID NO 16
<211> LENGTH: 242
<212> TYPE: PRT
<213> ORGANISM: Homo sapiens

<400> SEQUENCE: 16

```
Met Gly Thr Arg Ser Thr Leu Val Ala Ile Arg Pro Leu Asp Val Ser
1               5                   10                  15

Thr Glu Gly Tyr Asn Asn Trp Val Phe Met Ser Thr His Phe Trp Asp
            20                  25                  30

Glu Asn Pro Gln Gly Val Trp Thr Leu Gly Leu Glu Asn Lys Gly Tyr
        35                  40                  45

Tyr Phe Asn Thr Gly Thr Leu Tyr Arg Tyr Thr Leu Leu Leu Tyr Gly
    50                  55                  60

Thr Ala Glu Asp Met Thr Ala Arg Pro Thr Gly Pro Gln Val Thr Ser
65                  70                  75                  80

Ser Ala Cys Val Gln Arg Asp Thr Glu Gly Leu Cys Gln Ala Cys Asp
                85                  90                  95

Gly Pro Ala Tyr Ile Leu Gly Gln Leu Cys Leu Ala Tyr Cys Pro Pro
            100                 105                 110

Arg Phe Phe Asn His Thr Arg Leu Val Thr Ala Gly Pro Gly His Thr
        115                 120                 125

Ala Ala Pro Ala Leu Arg Val Cys Ser Ser Cys His Ala Ser Cys Tyr
    130                 135                 140

Thr Cys Arg Gly Gly Ser Pro Arg Asp Cys Thr Ser Cys Pro Pro Ser
145                 150                 155                 160

Ser Thr Leu Asp Gln Gln Gln Gly Ser Cys Met Gly Pro Thr Thr Pro
                165                 170                 175

Asp Ser Arg Pro Arg Leu Arg Ala Ala Ala Cys Pro His His Arg Cys
            180                 185                 190

Pro Ala Ser Ala Met Val Leu Ser Leu Leu Ala Val Thr Leu Gly Gly
        195                 200                 205

Pro Val Leu Cys Gly Met Ser Met Asp Leu Pro Leu Tyr Ala Trp Leu
    210                 215                 220

Ser Arg Ala Arg Ala Thr Pro Thr Lys Pro Gln Val Trp Leu Pro Ala
225                 230                 235                 240
```

Gly Thr

<210> SEQ ID NO 17
<211> LENGTH: 2742
<212> TYPE: DNA
<213> ORGANISM: Homo sapiens

<400> SEQUENCE: 17
atgggctggg ggagccgctg ctgctgcccg ggacgtttgg acctgctgtg cgtgctggcg 60
ctgctcgggg gctgcctgct ccccgtgtgt cggacgcgcg tctacaccaa ccactgggca 120
gtcaaaatcg ccgggggctt cccggaggcc aaccgtatcg ccagcaagta cggattcatc 180
aacataggac agatagggc cctgaaggac tactaccact tctaccatag caggacgatt 240
aaaaggtcag ttatctcgag cagagggacc cacagtttca tttcaatgga accaaaggtg 300
gaatggatcc aacagcaagt ggtaaaaaag cggacaaaga gggattatga cttcagtcgt 360
gcccagtcta cctatttcaa tgatcccaag tggcccagca tgtggtatat gcactgcagt 420
gacaatacac atccctgcca gtctgacatg aatatcgaag gagcctggaa gagaggctac 480
acgggaaaga acattgtggt cactatcctg gatgacggaa ttgagagaac ccatccagat 540
ctgatgcaaa actacgatgc tctggcaagt tgcgacgtga atgggaatga cttggaccca 600
atgcctcgtt atgatgcaag caacgagaac aagcatggga ctcgctgtgc tggagaagtg 660
gcagccgctg caaacaattc gcactgcaca gtcggaattg ctttcaacgc caagatcgga 720
ggagtgcgaa tgctggacgg agatgtcacg gacatggttg aagcaaaatc agttagcttc 780
aacccccagc acgtgcacat ttacagcgcc agctggggcc cggatgatga tggcaagact 840
gtggacggac cagcccccct cacccggcaa gcctttgaaa acggcgttag aatggggcgg 900
agaggcctcg gctctgtgtt tgtttgggca tctggaaatg gtggaaggag caaagaccac 960
tgctcctgtg atggctacac caacagcatc tacaccatct ccatcagcag cactgcagaa 1020
agcggaaaga aaccttggta cctggaagag tgttcatcca cgctggccac aacctacagc 1080
agcggggagt cctacgataa gaaaatcatc actacagatc tgaggcagcg ttgcacggac 1140
aaccacactg ggacgtcagc ctcagccccc atggctgcag gcatcattgc gctggccctg 1200
gaagccaatc cgtttctgac ctggagagac gtacagcatg ttattgtcag gacttcccgt 1260
gcgggacatt tgaacgctaa tgactggaaa accaatgctg ctggttttaa ggtgagccat 1320
ctttatggat ttggactgat ggacgcagaa gccatggtga tggaggcaga gaagtggacc 1380
accgttcccc ggcagcacgt gtgtgtggag agcacagacc gacaaatcaa gacaatccgc 1440
cctaacagtg cagtgcgctc catctacaaa gcttcaggct gctcggataa ccccaaccgc 1500
catgtcaact acctggagca cgtcgttgtg cgcatcacca tcacccaccc caggagagga 1560
gacctggcca tctacctgac ctcgccctct ggaactaggt ctcagctttt ggccaacagg 1620
ctatttgatc actccatgga aggattcaaa aactgggagt tcatgaccat tcattgctgg 1680
ggagaaagag ctgctggtga ctgggtcctt gaagtttatg atactccctc tcagctaagg 1740
aactttaaga ctccaggtaa attgaaagaa tggtctttgg tcctctacgg cacctccgtg 1800
cagccatatt caccaaccaa tgaatttccg aaagtggaac ggttccgcta tagccgagtt 1860
gaagacccca cagacgacta tggcacagag gattatgcag gtccctgcga ccctgagtgc 1920
agtgaggttg gctgtgacgg gccaggacca gaccactgca atgactgttt gcactactac 1980
tacaagctga aaaacaatac caggatctgt gtctccagct gcccccctgg ccactaccac 2040

```
gccgacaaga agcgctgcag gaagtgtgcc cccaactgtg agtcctgctt tgggagccat   2100

ggtgaccaat gcatgtcctg caaatatgga tactttctga atgaagaaac caacagctgt   2160

gttactcact gccctgatgg gtcatatcag gataccaaga aaaatctttg ccggaaatgc   2220

agtgaaaact gcaagacatg tactgaattc cataactgta cagaatgtag ggatgggtta   2280

agcctgcagg gatcccggtg ctctgtctcc tgtgaagatg gacggtattt caacggccag   2340

gactgccagc cctgccaccg cttctgcgcc acttgtgctg gggcaggagc tgatgggtgc   2400

attaactgca cagagggcta cttcatggag gatgggagat gcgtgcagag ctgtagtatc   2460

agctattact ttgaccactc ttcagagaat ggatacaaat cctgcaaaaa atgtgatatc   2520

agttgtttga cgtgcaatgg cccaggattc aagaactgta caagctgccc tagtgggtat   2580

ctcttagact taggaatgtg tcaaatggga gccatttgca aggatgcaac ggaagagtcc   2640

tgggcggaag gaggcttctg tatgcttgtg aaaaagaaca atctgtgcca acggaaggtt   2700

cttcaacaac tttgctgcaa aacatgtaca tttcaaggct ga                      2742
```

<210> SEQ ID NO 18
<211> LENGTH: 913
<212> TYPE: PRT
<213> ORGANISM: Homo sapiens

<400> SEQUENCE: 18

```
Met Gly Trp Gly Ser Arg Cys Cys Cys Pro Gly Arg Leu Asp Leu Leu
1               5                   10                  15

Cys Val Leu Ala Leu Leu Gly Gly Cys Leu Leu Pro Val Cys Arg Thr
            20                  25                  30

Arg Val Tyr Thr Asn His Trp Ala Val Lys Ile Ala Gly Gly Phe Pro
        35                  40                  45

Glu Ala Asn Arg Ile Ala Ser Lys Tyr Gly Phe Ile Asn Ile Gly Gln
    50                  55                  60

Ile Gly Ala Leu Lys Asp Tyr Tyr His Phe Tyr His Ser Arg Thr Ile
65                  70                  75                  80

Lys Arg Ser Val Ile Ser Ser Arg Gly Thr His Ser Phe Ile Ser Met
                85                  90                  95

Glu Pro Lys Val Glu Trp Ile Gln Gln Gln Val Val Lys Lys Arg Thr
            100                 105                 110

Lys Arg Asp Tyr Asp Phe Ser Arg Ala Gln Ser Thr Tyr Phe Asn Asp
        115                 120                 125

Pro Lys Trp Pro Ser Met Trp Tyr Met His Cys Ser Asp Asn Thr His
    130                 135                 140

Pro Cys Gln Ser Asp Met Asn Ile Glu Gly Ala Trp Lys Arg Gly Tyr
145                 150                 155                 160

Thr Gly Lys Asn Ile Val Val Thr Ile Leu Asp Asp Gly Ile Glu Arg
                165                 170                 175

Thr His Pro Asp Leu Met Gln Asn Tyr Asp Ala Leu Ala Ser Cys Asp
            180                 185                 190

Val Asn Gly Asn Asp Leu Asp Pro Met Pro Arg Tyr Asp Ala Ser Asn
        195                 200                 205

Glu Asn Lys His Gly Thr Arg Cys Ala Gly Glu Val Ala Ala Ala Ala
    210                 215                 220

Asn Asn Ser His Cys Thr Val Gly Ile Ala Phe Asn Ala Lys Ile Gly
225                 230                 235                 240

Gly Val Arg Met Leu Asp Gly Asp Val Thr Asp Met Val Glu Ala Lys
                245                 250                 255
```

-continued

```
Ser Val Ser Phe Asn Pro Gln His Val His Ile Tyr Ser Ala Ser Trp
            260                 265                 270

Gly Pro Asp Asp Asp Gly Lys Thr Val Asp Gly Pro Ala Pro Leu Thr
        275                 280                 285

Arg Gln Ala Phe Glu Asn Gly Val Arg Met Gly Arg Arg Gly Leu Gly
    290                 295                 300

Ser Val Phe Val Trp Ala Ser Gly Asn Gly Gly Arg Ser Lys Asp His
305                 310                 315                 320

Cys Ser Cys Asp Gly Tyr Thr Asn Ser Ile Tyr Thr Ile Ser Ile Ser
                325                 330                 335

Ser Thr Ala Glu Ser Gly Lys Lys Pro Trp Tyr Leu Glu Glu Cys Ser
            340                 345                 350

Ser Thr Leu Ala Thr Thr Tyr Ser Ser Gly Glu Ser Tyr Asp Lys Lys
        355                 360                 365

Ile Ile Thr Thr Asp Leu Arg Gln Arg Cys Thr Asp Asn His Thr Gly
    370                 375                 380

Thr Ser Ala Ser Ala Pro Met Ala Ala Gly Ile Ile Ala Leu Ala Leu
385                 390                 395                 400

Glu Ala Asn Pro Phe Leu Thr Trp Arg Asp Val Gln His Val Ile Val
                405                 410                 415

Arg Thr Ser Arg Ala Gly His Leu Asn Ala Asn Asp Trp Lys Thr Asn
            420                 425                 430

Ala Ala Gly Phe Lys Val Ser His Leu Tyr Gly Phe Gly Leu Met Asp
        435                 440                 445

Ala Glu Ala Met Val Met Glu Ala Glu Lys Trp Thr Thr Val Pro Arg
    450                 455                 460

Gln His Val Cys Val Glu Ser Thr Asp Arg Gln Ile Lys Thr Ile Arg
465                 470                 475                 480

Pro Asn Ser Ala Val Arg Ser Ile Tyr Lys Ala Ser Gly Cys Ser Asp
                485                 490                 495

Asn Pro Asn Arg His Val Asn Tyr Leu Glu His Val Val Val Arg Ile
            500                 505                 510

Thr Ile Thr His Pro Arg Arg Gly Asp Leu Ala Ile Tyr Leu Thr Ser
        515                 520                 525

Pro Ser Gly Thr Arg Ser Gln Leu Leu Ala Asn Arg Leu Phe Asp His
    530                 535                 540

Ser Met Glu Gly Phe Lys Asn Trp Glu Phe Met Thr Ile His Cys Trp
545                 550                 555                 560

Gly Glu Arg Ala Ala Gly Asp Trp Val Leu Glu Val Tyr Asp Thr Pro
                565                 570                 575

Ser Gln Leu Arg Asn Phe Lys Thr Pro Gly Lys Leu Lys Glu Trp Ser
            580                 585                 590

Leu Val Leu Tyr Gly Thr Ser Val Gln Pro Tyr Ser Pro Thr Asn Glu
        595                 600                 605

Phe Pro Lys Val Glu Arg Phe Arg Tyr Ser Arg Val Glu Asp Pro Thr
    610                 615                 620

Asp Asp Tyr Gly Thr Glu Asp Tyr Ala Gly Pro Cys Asp Pro Glu Cys
625                 630                 635                 640

Ser Glu Val Gly Cys Asp Gly Pro Gly Pro Asp His Cys Asn Asp Cys
                645                 650                 655

Leu His Tyr Tyr Tyr Lys Leu Lys Asn Asn Thr Arg Ile Cys Val Ser
            660                 665                 670
```

-continued

```
Ser Cys Pro Pro Gly His Tyr His Ala Asp Lys Lys Arg Cys Arg Lys
        675                 680                 685

Cys Ala Pro Asn Cys Glu Ser Cys Phe Gly Ser His Gly Asp Gln Cys
    690                 695                 700

Met Ser Cys Lys Tyr Gly Tyr Phe Leu Asn Glu Glu Thr Asn Ser Cys
705                 710                 715                 720

Val Thr His Cys Pro Asp Gly Ser Tyr Gln Asp Thr Lys Lys Asn Leu
                725                 730                 735

Cys Arg Lys Cys Ser Glu Asn Cys Lys Thr Cys Thr Glu Phe His Asn
            740                 745                 750

Cys Thr Glu Cys Arg Asp Gly Leu Ser Leu Gln Gly Ser Arg Cys Ser
        755                 760                 765

Val Ser Cys Glu Asp Gly Arg Tyr Phe Asn Gly Gln Asp Cys Gln Pro
    770                 775                 780

Cys His Arg Phe Cys Ala Thr Cys Ala Gly Ala Gly Ala Asp Gly Cys
785                 790                 795                 800

Ile Asn Cys Thr Glu Gly Tyr Phe Met Glu Asp Gly Arg Cys Val Gln
                805                 810                 815

Ser Cys Ser Ile Ser Tyr Tyr Phe Asp His Ser Ser Glu Asn Gly Tyr
            820                 825                 830

Lys Ser Cys Lys Lys Cys Asp Ile Ser Cys Leu Thr Cys Asn Gly Pro
        835                 840                 845

Gly Phe Lys Asn Cys Thr Ser Cys Pro Ser Gly Tyr Leu Leu Asp Leu
    850                 855                 860

Gly Met Cys Gln Met Gly Ala Ile Cys Lys Asp Ala Thr Glu Glu Ser
865                 870                 875                 880

Trp Ala Glu Gly Gly Phe Cys Met Leu Val Lys Lys Asn Asn Leu Cys
                885                 890                 895

Gln Arg Lys Val Leu Gln Gln Leu Cys Cys Lys Thr Cys Thr Phe Gln
            900                 905                 910

Gly
```

<210> SEQ ID NO 19
<211> LENGTH: 2910
<212> TYPE: DNA
<213> ORGANISM: Homo sapiens

<400> SEQUENCE: 19

```
atgcctccgc gcgcgccgcc tgcgcccggg ccccggccgc cgccccgggc cgccgccgcc      60

accgacaccg ccgcgggcgc ggggggcgcg gggggcgcgg ggggcgccgg cgggcccggg     120

ttccggccgc tcgcgccgcg tccctggcgc tggctgctgc tgctggcgct gcctgccgcc     180

tgctccgcgc ccccgccgcg ccccgtctac accaaccact gggcggtgca agtgctgggc     240

ggcccggccg aggcggaccg cgtggcggcg gcgcacggct acctcaactt gggccagatt     300

ggaaacctgg aagattacta ccatttttat cacagcaaaa cctttaaaag atcaaccttg     360

agtagcagag gccctcacac cttcctcaga atggaccccc aggtgaaatg gctccagcaa     420

caggaagtga aacgaagggt gaagagacag gtgcgaagtg acccgcaggc cctttacttc     480

aacgacccca tttggtccaa catgtggtac ctgcattgtg gcgacaagaa cagtcgctgc     540

cggtcggaaa tgaatgtcca ggcagcgtgg aagaggggct acacaggaaa aaacgtggtg     600

gtcaccatcc ttgatgatgg catagagaga aatcaccctg acctggcccc aaattatgat     660

tcctacgcca gctacgacgt gaacggcaat gattatgacc catctccacg atatgatgcc     720
```

-continued

```
agcaatgaaa ataaacacgg cactcgttgt gcgggagaag ttgctgcttc agcaaacaat    780
tcctactgca tcgtgggcat agcgtacaat gccaaaatag gaggcatccg catgctggac    840
ggcgatgtca cagatgtggt cgaggcaaag tcgctgggca tcagacccaa ctacatcgac    900
atttacagtg ccagctgggg gccggacgac gacggcaaga cggtggacgg gcccggccga    960
ctggctaagc aggctttcga gtatggcatt aaaaagggcc ggcagggcct gggctccatt   1020
ttcgtctggg catctgggaa tggcgggaga gagggggact actgctcgtg cgatggctac   1080
accaacagca tctacaccat ctccgtcagc agcgccaccg agaatggcta caagccctgg   1140
tacctggaag agtgtgcctc caccctggcc accacctaca gcagtggggc cttttatgag   1200
cgaaaaatcg tcaccacgga tctgcgtcag cgctgtaccg atggccacac tgggacctca   1260
gtctctgccc ccatggtggc gggcatcatc gccttggctc tagaagcaaa cagccagtta   1320
acctggaggg acgtccagca cctgctagtg aagacatccc ggccggccca cctgaaagcg   1380
agcgactgga aagtaaacgg cgcgggtcat aaagttagcc atttctatgg atttggtttg   1440
gtggacgcag aagctctcgt tgtggaggca aagaagtgga cagcagtgcc atcgcagcac   1500
atgtgtgtgg ccgcctcgga caagagaccc aggagcatcc ccttagtgca ggtgctgcgg   1560
actacggccc tgaccagcgc ctgcgcggag cactcggacc agcgggtggt ctacttggag   1620
cacgtggtgg ttcgcacctc catctcacac ccacgccgag gagacctcca gatctacctg   1680
gtttctccct cgggaaccaa gtctcaactt ttggcaaaga ggttgctgga tctttccaat   1740
gaagggttta caaactggga attcatgact gtccactgct ggggagaaaa ggctgaaggg   1800
cagtggacct tggaaatcca agatctgcca tcccaggtcc gcaacccgga gaagcaaggg   1860
aagttgaaag aatggagcct catactgtat ggcacagcag agcacccgta ccacaccttc   1920
agtgcccatc agtcccgctc gcggatgctg gagctctcag ccccagagct ggagccaccc   1980
aaggctgccc tgtcaccctc ccaggtggaa gttcctgaag atgaggaaga ttacacagct   2040
caatccaccc caggctctgc taatatttta cagaccagtg tgtgccatcc ggagtgtggt   2100
gacaaaggct gtgatggccc caatgcagac cagtgcttga actgcgtcca cttcagcctg   2160
gggagtgtca agaccagcag gaagtgcgtg agtgtgtgcc ccttgggcta ctttggggac   2220
acagcagcaa gacgctgtcg ccggtgccac aaggggtgtg agacctgctc cagcagagct   2280
gcgacgcagt gcctgtcttg ccgccgcggg ttctatcacc accaggagat gaacacctgt   2340
gtgaccctct gtcctgcagg attttatgct gatgaaagtc agaaaaattg ccttaaatgc   2400
cacccaagct gtaaaaagtg cgtggatgaa cctgagaaat gtactgtctg taaagaagga   2460
ttcagccttg cacggggcag ctgcattcct gactgtgagc caggcaccta ctttgactca   2520
gagctgatca gatgtgggga atgccatcac acctgcggaa cctgcgtggg gccaggcaga   2580
gaagagtgca ttcactgtgc gaaaaacttc cacttccacg actggaagtg tgtgccagcc   2640
tgtggtgagg gcttctaccc agaagagatg ccgggcttgc cccacaaagt gtgtcgaagg   2700
tgtgacgaga actgcttgag ctgtgcaggc tccagcagga actgtagcag gtgtaagacg   2760
ggcttcacac agctggggac ctcctgcatc accaaccaca cgtgcagcaa cgctgacgag   2820
acattctgcg agatggtgaa gtccaaccgg ctgtgcgaac ggaagctctt cattcagttc   2880
tgctgccgca cgtgcctcct ggccgggtaa                                    2910
```

<210> SEQ ID NO 20
<211> LENGTH: 969
<212> TYPE: PRT
<213> ORGANISM: Homo sapiens

<400> SEQUENCE: 20

Met Pro Pro Arg Ala Pro Pro Ala Pro Gly Pro Arg Pro Pro Pro Arg
1 5 10 15

Ala Ala Ala Ala Thr Asp Thr Ala Ala Gly Ala Gly Gly Ala Gly Gly
20 25 30

Ala Gly Gly Ala Gly Gly Pro Gly Phe Arg Pro Leu Ala Pro Arg Pro
35 40 45

Trp Arg Trp Leu Leu Leu Leu Ala Leu Pro Ala Ala Cys Ser Ala Pro
50 55 60

Pro Pro Arg Pro Val Tyr Thr Asn His Trp Ala Val Gln Val Leu Gly
65 70 75 80

Gly Pro Ala Glu Ala Asp Arg Val Ala Ala Ala His Gly Tyr Leu Asn
85 90 95

Leu Gly Gln Ile Gly Asn Leu Glu Asp Tyr Tyr His Phe Tyr His Ser
100 105 110

Lys Thr Phe Lys Arg Ser Thr Leu Ser Ser Arg Gly Pro His Thr Phe
115 120 125

Leu Arg Met Asp Pro Gln Val Lys Trp Leu Gln Gln Gln Glu Val Lys
130 135 140

Arg Arg Val Lys Arg Gln Val Arg Ser Asp Pro Gln Ala Leu Tyr Phe
145 150 155 160

Asn Asp Pro Ile Trp Ser Asn Met Trp Tyr Leu His Cys Gly Asp Lys
165 170 175

Asn Ser Arg Cys Arg Ser Glu Met Asn Val Gln Ala Ala Trp Lys Arg
180 185 190

Gly Tyr Thr Gly Lys Asn Val Val Val Thr Ile Leu Asp Asp Gly Ile
195 200 205

Glu Arg Asn His Pro Asp Leu Ala Pro Asn Tyr Asp Ser Tyr Ala Ser
210 215 220

Tyr Asp Val Asn Gly Asn Asp Tyr Asp Pro Ser Pro Arg Tyr Asp Ala
225 230 235 240

Ser Asn Glu Asn Lys His Gly Thr Arg Cys Ala Gly Glu Val Ala Ala
245 250 255

Ser Ala Asn Asn Ser Tyr Cys Ile Val Gly Ile Ala Tyr Asn Ala Lys
260 265 270

Ile Gly Gly Ile Arg Met Leu Asp Gly Asp Val Thr Asp Val Val Glu
275 280 285

Ala Lys Ser Leu Gly Ile Arg Pro Asn Tyr Ile Asp Ile Tyr Ser Ala
290 295 300

Ser Trp Gly Pro Asp Asp Asp Gly Lys Thr Val Asp Gly Pro Gly Arg
305 310 315 320

Leu Ala Lys Gln Ala Phe Glu Tyr Gly Ile Lys Lys Gly Arg Gln Gly
325 330 335

Leu Gly Ser Ile Phe Val Trp Ala Ser Gly Asn Gly Gly Arg Glu Gly
340 345 350

Asp Tyr Cys Ser Cys Asp Gly Tyr Thr Asn Ser Ile Tyr Thr Ile Ser
355 360 365

Val Ser Ser Ala Thr Glu Asn Gly Tyr Lys Pro Trp Tyr Leu Glu Glu
370 375 380

Cys Ala Ser Thr Leu Ala Thr Thr Tyr Ser Ser Gly Ala Phe Tyr Glu
385 390 395 400

Arg Lys Ile Val Thr Thr Asp Leu Arg Gln Arg Cys Thr Asp Gly His

```
                405                 410                 415

Thr Gly Thr Ser Val Ser Ala Pro Met Val Ala Gly Ile Ile Ala Leu
            420                 425                 430

Ala Leu Glu Ala Asn Ser Gln Leu Thr Trp Arg Asp Val Gln His Leu
        435                 440                 445

Leu Val Lys Thr Ser Arg Pro Ala His Leu Lys Ala Ser Asp Trp Lys
    450                 455                 460

Val Asn Gly Ala Gly His Lys Val Ser His Phe Tyr Gly Phe Gly Leu
465                 470                 475                 480

Val Asp Ala Glu Ala Leu Val Val Glu Ala Lys Lys Trp Thr Ala Val
                485                 490                 495

Pro Ser Gln His Met Cys Val Ala Ala Ser Asp Lys Arg Pro Arg Ser
            500                 505                 510

Ile Pro Leu Val Gln Val Leu Arg Thr Thr Ala Leu Thr Ser Ala Cys
        515                 520                 525

Ala Glu His Ser Asp Gln Arg Val Val Tyr Leu Glu His Val Val Val
    530                 535                 540

Arg Thr Ser Ile Ser His Pro Arg Arg Gly Asp Leu Gln Ile Tyr Leu
545                 550                 555                 560

Val Ser Pro Ser Gly Thr Lys Ser Gln Leu Leu Ala Lys Arg Leu Leu
                565                 570                 575

Asp Leu Ser Asn Glu Gly Phe Thr Asn Trp Glu Phe Met Thr Val His
            580                 585                 590

Cys Trp Gly Glu Lys Ala Glu Gly Gln Trp Thr Leu Glu Ile Gln Asp
        595                 600                 605

Leu Pro Ser Gln Val Arg Asn Pro Glu Lys Gln Gly Lys Leu Lys Glu
    610                 615                 620

Trp Ser Leu Ile Leu Tyr Gly Thr Ala Glu His Pro Tyr His Thr Phe
625                 630                 635                 640

Ser Ala His Gln Ser Arg Ser Arg Met Leu Glu Leu Ser Ala Pro Glu
                645                 650                 655

Leu Glu Pro Pro Lys Ala Ala Leu Ser Pro Ser Gln Val Glu Val Pro
            660                 665                 670

Glu Asp Glu Glu Asp Tyr Thr Ala Gln Ser Thr Pro Gly Ser Ala Asn
        675                 680                 685

Ile Leu Gln Thr Ser Val Cys His Pro Glu Cys Gly Asp Lys Gly Cys
    690                 695                 700

Asp Gly Pro Asn Ala Asp Gln Cys Leu Asn Cys Val His Phe Ser Leu
705                 710                 715                 720

Gly Ser Val Lys Thr Ser Arg Lys Cys Val Ser Val Cys Pro Leu Gly
                725                 730                 735

Tyr Phe Gly Asp Thr Ala Ala Arg Arg Cys Arg Arg Cys His Lys Gly
            740                 745                 750

Cys Glu Thr Cys Ser Ser Arg Ala Ala Thr Gln Cys Leu Ser Cys Arg
        755                 760                 765

Arg Gly Phe Tyr His His Gln Glu Met Asn Thr Cys Val Thr Leu Cys
    770                 775                 780

Pro Ala Gly Phe Tyr Ala Asp Glu Ser Gln Lys Asn Cys Leu Lys Cys
785                 790                 795                 800

His Pro Ser Cys Lys Lys Cys Val Asp Glu Pro Glu Lys Cys Thr Val
                805                 810                 815

Cys Lys Glu Gly Phe Ser Leu Ala Arg Gly Ser Cys Ile Pro Asp Cys
            820                 825                 830
```

```
Glu Pro Gly Thr Tyr Phe Asp Ser Glu Leu Ile Arg Cys Gly Glu Cys
        835                 840                 845

His His Thr Cys Gly Thr Cys Val Gly Pro Gly Arg Glu Glu Cys Ile
    850                 855                 860

His Cys Ala Lys Asn Phe His Phe His Asp Trp Lys Cys Val Pro Ala
865                 870                 875                 880

Cys Gly Glu Gly Phe Tyr Pro Glu Glu Met Pro Gly Leu Pro His Lys
                885                 890                 895

Val Cys Arg Arg Cys Asp Glu Asn Cys Leu Ser Cys Ala Gly Ser Ser
            900                 905                 910

Arg Asn Cys Ser Arg Cys Lys Thr Gly Phe Thr Gln Leu Gly Thr Ser
        915                 920                 925

Cys Ile Thr Asn His Thr Cys Ser Asn Ala Asp Glu Thr Phe Cys Glu
    930                 935                 940

Met Val Lys Ser Asn Arg Leu Cys Glu Arg Lys Leu Phe Ile Gln Phe
945                 950                 955                 960

Cys Cys Arg Thr Cys Leu Leu Ala Gly
                965


<210> SEQ ID NO 21
<211> LENGTH: 2358
<212> TYPE: DNA
<213> ORGANISM: Homo sapiens

<400> SEQUENCE: 21

atgccgaagg ggaggcagaa agtgccacac ttggatgccc ccctgggcct gcccacctgc      60

ctctggctgg aattagccgg gctcttctta ctggttccct gggtcatggg cctggcaggg     120

acaggtgggc ctgatggcca gggcacaggg gggccgagct gggctgtgca cctggaaagc     180

ctggaaggtg acggggagga agagactctg gagcagcagg cggatgcctt ggcccaggca     240

gcagggctgg tgaatgctgg acgcatcgga gagcttcagg ggcactacct ctttgtccag     300

cctgctgggc acaggccggc cctggaggtg gaggccatcc ggcagcaggt ggaggctgtg     360

ttggctgggc atgaagctgt gcgctggcac tcagagcaga ggctgctaag gcgggccaag     420

cgcagcgtcc acttcaacga ccccaagtac ccgcagcaat ggcacctgaa taaccgacgg     480

agcccgggca gggacatcaa cgtgacgggt gtgtgggaac gcaatgtgac tgggcgaggg     540

gtgacggtgg tggtagtgga tgacggagtg gaacacacca tccaggacat tgcacccaac     600

tatagccctg agggtagcta tgacctcaac tctaatgacc ctgaccccat gccccacccg     660

gatgtggaga atggcaacca ccatggcacg cgatgtgcag gagagatcgc ggctgtgccc     720

aacaacagct tctgtgccgt gggcgtggcc tacgggagcc gcatcgcagg tatccgggta     780

ctggatggac ctctcacaga cagcatggag gcagtggcgt tcaacaagca ctatcagatc     840

aatgacatct acagctgcag ctggggacca gatgacgatg ggaagacagt ggatggcccc     900

catcagcttg gaaaggctgc cttacaacat ggggtgattg ctggtcgcca gggctttggg     960

agcatctttg tggtagccag tggcaacgga ggccaacaca acgacaactg caactacgat    1020

ggctacgcca actccatcta caccgtcacc ataggagctg tggatgagga gggacgcatg    1080

cctttctatg cagaagaatg tgcctccatg ctggcagtca ccttcagtgg tggggacaag    1140

atgcttcgga gcattgtgac cactgactgg gaccttcaga agggcactgg ctgcactgag    1200

ggccacacag ggacctcagc tgcagcgcct ctggcagctg gcatgatagc cttaatgctg    1260

caggtgcggc cctgcctcac gtggcgtgac gtccagcaca tcattgtctt cacagccacc    1320
```

```
cggtatgagg atcgccgtgc agagtgggtc accaacgagg caggcttcag ccatagccac   1380

cagcacggtt tcggcctcct caacgcctgg aggctcgtga atgcagccaa gatctggaca   1440

tctgtccctt acttagcatc ctacgtcagt cccgtgttaa aagaaaacaa ggcgattccg   1500

cagtcccccc gttccctgga ggtcctgtgg aatgtcagca ggatggacct ggagatgtca   1560

gggctgaaga ccctggagca tgtggcagtg acagtctcca tcactcaccc acggcgcggc   1620

agcttggagc tgaagctgtt ctgccccagt ggcatgatgt ccctcatcgg cgcccccgc    1680

agcatggact cggatcccaa cggcttcaat gactggacct tctccactgt gcgatgctgg   1740

ggggagagag cccgagggac ctacaggctt gtcatcaggg atgtcgggga tgagtcattc   1800

caggtcggca tcctccggca atggcagctg accctatatg gctctgtgtg gagtgcagta   1860

gacatcaggg acagacaaag gctgttagag agtgccatga gtggaaaata cctgcacgat   1920

gacttcgccc tgccctgccc accggggctg aaaattcctg aggaagatgg ttacaccatc   1980

acccccaaca ccctcaagac cctggtgctg gtaggctgtt tcaccgtctt ctggactgtt   2040

tactacatgc tggaagtata tttgagccag aggaatgtgg cttccaatca agtttgtagg   2100

agtggaccct gccactggcc ccatcggagc cggaaagcca aggaggaagg gacagagcta   2160

gaatcagtgc cactttgcag cagcaaggat ccagacgaag tggaaacaga gagcaggggc   2220

cctcccacca cctctgacct ccttgcccca gacctgctgg agcaagggga ctggagcctg   2280

tcccagaaca agagcgccct ggactgccct catcagcacc tagacgtacc gcacgggaag   2340

gaggagcaga tctgctag                                                 2358
```

<210> SEQ ID NO 22
<211> LENGTH: 785
<212> TYPE: PRT
<213> ORGANISM: Homo sapiens

<400> SEQUENCE: 22

```
Met Pro Lys Gly Arg Gln Lys Val Pro His Leu Asp Ala Pro Leu Gly
1               5                   10                  15

Leu Pro Thr Cys Leu Trp Leu Glu Leu Ala Gly Leu Phe Leu Leu Val
            20                  25                  30

Pro Trp Val Met Gly Leu Ala Gly Thr Gly Gly Pro Asp Gly Gln Gly
        35                  40                  45

Thr Gly Gly Pro Ser Trp Ala Val His Leu Glu Ser Leu Glu Gly Asp
    50                  55                  60

Gly Glu Glu Glu Thr Leu Glu Gln Gln Ala Asp Ala Leu Ala Gln Ala
65                  70                  75                  80

Ala Gly Leu Val Asn Ala Gly Arg Ile Gly Glu Leu Gln Gly His Tyr
                85                  90                  95

Leu Phe Val Gln Pro Ala Gly His Arg Pro Ala Leu Glu Val Glu Ala
            100                 105                 110

Ile Arg Gln Gln Val Glu Ala Val Leu Ala Gly His Glu Ala Val Arg
        115                 120                 125

Trp His Ser Glu Gln Arg Leu Leu Arg Arg Ala Lys Arg Ser Val His
    130                 135                 140

Phe Asn Asp Pro Lys Tyr Pro Gln Gln Trp His Leu Asn Asn Arg Arg
145                 150                 155                 160

Ser Pro Gly Arg Asp Ile Asn Val Thr Gly Val Trp Glu Arg Asn Val
                165                 170                 175

Thr Gly Arg Gly Val Thr Val Val Val Val Asp Asp Gly Val Glu His
```

-continued

```
            180                 185                 190

Thr Ile Gln Asp Ile Ala Pro Asn Tyr Ser Pro Glu Gly Ser Tyr Asp
        195                 200                 205

Leu Asn Ser Asn Asp Pro Asp Pro Met Pro His Pro Asp Val Glu Asn
    210                 215                 220

Gly Asn His His Gly Thr Arg Cys Ala Gly Glu Ile Ala Ala Val Pro
225                 230                 235                 240

Asn Asn Ser Phe Cys Ala Val Gly Val Ala Tyr Gly Ser Arg Ile Ala
                245                 250                 255

Gly Ile Arg Val Leu Asp Gly Pro Leu Thr Asp Ser Met Glu Ala Val
            260                 265                 270

Ala Phe Asn Lys His Tyr Gln Ile Asn Asp Ile Tyr Ser Cys Ser Trp
        275                 280                 285

Gly Pro Asp Asp Asp Gly Lys Thr Val Asp Gly Pro His Gln Leu Gly
    290                 295                 300

Lys Ala Ala Leu Gln His Gly Val Ile Ala Gly Arg Gln Gly Phe Gly
305                 310                 315                 320

Ser Ile Phe Val Val Ala Ser Gly Asn Gly Gly Gln His Asn Asp Asn
                325                 330                 335

Cys Asn Tyr Asp Gly Tyr Ala Asn Ser Ile Tyr Thr Val Thr Ile Gly
            340                 345                 350

Ala Val Asp Glu Glu Gly Arg Met Pro Phe Tyr Ala Glu Glu Cys Ala
        355                 360                 365

Ser Met Leu Ala Val Thr Phe Ser Gly Gly Asp Lys Met Leu Arg Ser
    370                 375                 380

Ile Val Thr Thr Asp Trp Asp Leu Gln Lys Gly Thr Gly Cys Thr Glu
385                 390                 395                 400

Gly His Thr Gly Thr Ser Ala Ala Ala Pro Leu Ala Ala Gly Met Ile
                405                 410                 415

Ala Leu Met Leu Gln Val Arg Pro Cys Leu Thr Trp Arg Asp Val Gln
            420                 425                 430

His Ile Ile Val Phe Thr Ala Thr Arg Tyr Glu Asp Arg Arg Ala Glu
        435                 440                 445

Trp Val Thr Asn Glu Ala Gly Phe Ser His Ser His Gln His Gly Phe
    450                 455                 460

Gly Leu Leu Asn Ala Trp Arg Leu Val Asn Ala Ala Lys Ile Trp Thr
465                 470                 475                 480

Ser Val Pro Tyr Leu Ala Ser Tyr Val Ser Pro Val Leu Lys Glu Asn
                485                 490                 495

Lys Ala Ile Pro Gln Ser Pro Arg Ser Leu Glu Val Leu Trp Asn Val
            500                 505                 510

Ser Arg Met Asp Leu Glu Met Ser Gly Leu Lys Thr Leu Glu His Val
        515                 520                 525

Ala Val Thr Val Ser Ile Thr His Pro Arg Arg Gly Ser Leu Glu Leu
    530                 535                 540

Lys Leu Phe Cys Pro Ser Gly Met Met Ser Leu Ile Gly Ala Pro Arg
545                 550                 555                 560

Ser Met Asp Ser Asp Pro Asn Gly Phe Asn Asp Trp Thr Phe Ser Thr
                565                 570                 575

Val Arg Cys Trp Gly Glu Arg Ala Arg Gly Thr Tyr Arg Leu Val Ile
            580                 585                 590

Arg Asp Val Gly Asp Glu Ser Phe Gln Val Gly Ile Leu Arg Gln Trp
        595                 600                 605
```

-continued

Gln Leu Thr Leu Tyr Gly Ser Val Trp Ser Ala Val Asp Ile Arg Asp
    610                 615                 620

Arg Gln Arg Leu Leu Glu Ser Ala Met Ser Gly Lys Tyr Leu His Asp
625                 630                 635                 640

Asp Phe Ala Leu Pro Cys Pro Pro Gly Leu Lys Ile Pro Glu Glu Asp
                645                 650                 655

Gly Tyr Thr Ile Thr Pro Asn Thr Leu Lys Thr Leu Val Leu Val Gly
            660                 665                 670

Cys Phe Thr Val Phe Trp Thr Val Tyr Tyr Met Leu Glu Val Tyr Leu
        675                 680                 685

Ser Gln Arg Asn Val Ala Ser Asn Gln Val Cys Arg Ser Gly Pro Cys
    690                 695                 700

His Trp Pro His Arg Ser Arg Lys Ala Lys Glu Glu Gly Thr Glu Leu
705                 710                 715                 720

Glu Ser Val Pro Leu Cys Ser Ser Lys Asp Pro Asp Glu Val Glu Thr
                725                 730                 735

Glu Ser Arg Gly Pro Pro Thr Thr Ser Asp Leu Leu Ala Pro Asp Leu
            740                 745                 750

Leu Glu Gln Gly Asp Trp Ser Leu Ser Gln Asn Lys Ser Ala Leu Asp
        755                 760                 765

Cys Pro His Gln His Leu Asp Val Pro His Gly Lys Glu Glu Gln Ile
    770                 775                 780

Cys
785

<210> SEQ ID NO 23
<211> LENGTH: 3159
<212> TYPE: DNA
<213> ORGANISM: Homo sapiens

<400> SEQUENCE: 23
atgaagcttg tcaacatctg gctgcttctg ctcgtggttt tgctctgtgg gaagaaacat 60
ctgggcgaca gactggaaaa gaaatctttt gaaaaggccc catgccctgg ctgttcccac 120
ctgactttga aggtggaatt ctcatcaaca gttgtggaat atgaatatat tgtggctttc 180
aatggatact ttacagccaa agctagaaat tcatttattt caagtgccct gaagagcagt 240
gaagtagaca attggagaat tatacctcga aacaatccat ccagtgacta ccctagtgat 300
tttgaggtga ttcagataaa agaaaaacag aaagcggggc tgctaacact tgaagatcat 360
ccaaacatca aacgggtcac gccccaacga aaagtctttc gttccctcaa gtatgctgaa 420
tctgacccca cagtaccctg caatgaaacc cggtggagcc agaagtggca atcatcacgt 480
cccctgcgaa gagccagcct ctccctgggc tctggcttct ggcatgctac gggaaggcat 540
tcgagcagac ggctgctgag agccatcccg cgccaggttg cccagacact gcaggcagat 600
gtgctctggc agatgggata tacaggtgct aatgtaagag ttgctgtttt tgacactggg 660
ctgagcgaga agcatcccca cttcaaaaat gtgaaggaga gaaccaactg gaccaacgag 720
cgaacgctgg acgatgggtt gggccatggc acattcgtgg caggtgtgat agccagcatg 780
agggagtgcc aaggatttgc tccagatgca gaacttcaca ttttcagggt ctttaccaat 840
aatcaggtat cttacacatc ttggtttttg gacgccttca actatgccat tttaaagaag 900
atcgacgtgt taaacctcag catcggcggc ccggacttca tggatcatcc gtttgttgac 960
aaggtgtggg aattaacagc taacaatgta atcatggttt ctgctattgg caatgacgga 1020
cctctttatg gcactctgaa taaccctgct gatcaaatgg atgtgattgg agtaggcggc 1080
attgactttg aagataacat cgcccgcttt tcttcaaggg gaatgactac ctgggagcta 1140
ccaggaggct acggtcgcat gaaacctgac attgtcacct atggtgctgg cgtgcggggt 1200
tctggcgtga aggggggtg ccgggccctc tcagggacca gtgttgcttc tccagtggtt 1260
gcaggtgctg tcaccttgtt agtgagcaca gtccagaagc gtgagctggt gaatcccgcc 1320
agtatgaagc aggccctgat cgcgtcagcc cggaggctcc ccggggtcaa catgtttgag 1380
caaggccacg gcaagctcga tctgctcaga gcctatcaga tcctcaacag ctacaagcca 1440
caggcaagtt tgagccccag ctacatagat ctgactgagt gtccctacat gtggccctac 1500
tgctcccagc ccatctacta tggaggaatg ccgacagttg ttaatgtcac catcctcaac 1560
ggcatgggag tcacaggaag aattgtagat aagcctgact ggcagcccta tttgccacag 1620
aacggagaca acattgaagt tgccttctcc tactcctcgg tcttatggcc ttggtcgggc 1680
tacctggcca tctccatttc tgtgaccaag aaagcggctt cctgggaagg cattgctcag 1740
ggccatgtca tgatcactgt ggcttcccca gcagagacag agtcaaaaaa tggtgcagaa 1800
cagacttcaa cagtaaagct ccccattaag gtgaagataa ttcctactcc cccgcgaagc 1860
aagagagttc tctgggatca gtaccacaac ctccgctatc cacctggcta tttccccagg 1920
gataatttaa ggatgaagaa tgaccccttta gactggaatg gtgatcacat ccacaccaat 1980
ttcagggata tgtaccagca tctgagaagc atgggctact ttgtagaggt cctcggggcc 2040
cccttcacgt gttttgatgc cagtcagtat ggcactttgc tgatggtgga cagtgaggag 2100
gagtacttcc ctgaagagat cgccaagctc cggagggacg tggacaacgg cctctcgctc 2160
gtcatcttca gtgactggta caacacttct gttatgagaa aagtgaagtt ttatgatgaa 2220
aacacaaggc agtggtggat gccggatacc ggaggagcta acatcccagc tctgaatgag 2280
ctgctgtctg tgtggaacat ggggttcagc gatggcctgt atgaagggga gttcaccctg 2340
gccaaccatg acatgtatta tgcgtcaggg tgcagcatcg cgaagtttcc agaagatggc 2400
gtcgtgataa cacagacttt caaggaccaa ggattggagg ttttaaagca ggaaacagca 2460
gttgttgaaa acgtccccat tttgggactt tatcagattc cagctgaggg tggaggccgg 2520
attgtactgt atggggactc caattgcttg gatgacagtc accgacagaa ggactgcttt 2580
tggcttctgg atgccctcct ccagtacaca tcgtatgggg tgacaccgcc tagcctcagt 2640
cactctggga accgccagcg ccctcccagt ggagcaggct cagtcactcc agagaggatg 2700
gaaggaaacc atcttcatcg gtactccaag gttctggagg cccatttggg agacccaaaa 2760
cctcggcctc taccagcctg tccacgcttg tcttgggcca agccacagcc tttaaacgag 2820
acggcgccca gtaacctttg gaaacatcag aagctactct ccattgacct ggacaaggtg 2880
gtgttaccca actttcgatc gaatcgccct caagtgaggc ccttgtcccc tggagagagc 2940
ggcgcctggg acattcctgg agggatcatg cctggccgct acaaccagga ggtgggccag 3000
accattcctg tctttgcctt cctgggagcc atggtggtcc tggccttctt tgtggtacaa 3060
atcaacaagg ccaagagcag gccgaagcgg aggaagccca gggtgaagcg cccgcagctc 3120
atgcagcagg ttcacccgcc aaagacccct tcggtgtga 3159

<210> SEQ ID NO 24
<211> LENGTH: 3159
<212> TYPE: PRT
<213> ORGANISM: Homo sapiens

<400> SEQUENCE: 24

Ala Thr Gly Ala Ala Gly Cys Thr Thr Gly Thr Cys Ala Ala Cys Ala
1 5 10 15

Thr Cys Thr Gly Gly Cys Thr Gly Cys Thr Thr Cys Thr Gly Cys Thr
20 25 30

Cys Gly Thr Gly Gly Thr Thr Thr Thr Gly Cys Thr Cys Thr Gly Thr
35 40 45

Gly Gly Gly Ala Ala Gly Ala Ala Ala Cys Ala Thr Cys Thr Gly Gly
50 55 60

Gly Cys Gly Ala Cys Ala Gly Ala Cys Thr Gly Gly Ala Ala Ala Ala
65 70 75 80

Gly Ala Ala Ala Thr Cys Thr Thr Thr Thr Gly Ala Ala Ala Ala Gly
85 90 95

Gly Cys Cys Cys Cys Ala Thr Gly Cys Cys Cys Thr Gly Gly Cys Thr
100 105 110

Gly Thr Thr Cys Cys Cys Ala Cys Cys Thr Gly Ala Cys Thr Thr Thr
115 120 125

Gly Ala Ala Gly Gly Thr Gly Gly Ala Ala Thr Thr Cys Thr Cys Ala
130 135 140

Thr Cys Ala Ala Cys Ala Gly Thr Thr Gly Thr Gly Gly Ala Ala Thr
145 150 155 160

Ala Thr Gly Ala Ala Thr Ala Thr Ala Thr Thr Gly Thr Gly Gly Cys
165 170 175

Thr Thr Thr Cys Ala Ala Thr Gly Gly Ala Thr Ala Cys Thr Thr Thr
180 185 190

Ala Cys Ala Gly Cys Cys Ala Ala Ala Gly Cys Thr Ala Gly Ala Ala
195 200 205

Ala Thr Thr Cys Ala Thr Thr Thr Ala Thr Thr Thr Cys Ala Ala Gly
210 215 220

Thr Gly Cys Cys Cys Thr Gly Ala Ala Gly Ala Gly Cys Ala Gly Thr
225 230 235 240

Gly Ala Ala Gly Thr Ala Gly Ala Cys Ala Ala Thr Thr Gly Gly Ala
245 250 255

Gly Ala Ala Thr Thr Ala Thr Ala Cys Cys Thr Cys Gly Ala Ala Ala
260 265 270

Cys Ala Ala Thr Cys Cys Ala Thr Cys Cys Ala Gly Thr Gly Ala Cys
275 280 285

Thr Ala Cys Cys Cys Thr Ala Gly Thr Gly Ala Thr Thr Thr Thr Gly
290 295 300

Ala Gly Gly Thr Gly Ala Thr Thr Cys Ala Gly Ala Thr Ala Ala Ala
305 310 315 320

Ala Gly Ala Ala Ala Ala Ala Cys Ala Gly Ala Ala Ala Gly Cys Gly
325 330 335

Gly Gly Gly Cys Thr Gly Cys Thr Ala Ala Cys Ala Cys Thr Thr Gly
340 345 350

Ala Ala Gly Ala Thr Cys Ala Thr Cys Cys Ala Ala Ala Cys Ala Thr
355 360 365

Cys Ala Ala Ala Cys Gly Gly Gly Thr Cys Ala Cys Gly Cys Cys Cys
370 375 380

Cys Ala Ala Cys Gly Ala Ala Ala Ala Gly Thr Cys Thr Thr Thr Cys
385 390 395 400

Gly Thr Thr Cys Cys Cys Thr Cys Ala Ala Gly Thr Ala Thr Gly Cys
405 410 415

Thr Gly Ala Ala Thr Cys Thr Gly Ala Cys Cys Cys Cys Ala Cys Ala
420 425 430

Gly Thr Ala Cys Cys Cys Thr Gly Cys Ala Ala Thr Gly Ala Ala Ala
435 440 445

Cys Cys Cys Gly Gly Thr Gly Gly Ala Gly Cys Cys Ala Gly Ala Ala
450 455 460

Gly Thr Gly Gly Cys Ala Ala Thr Cys Ala Thr Cys Ala Cys Gly Thr
465 470 475 480

Cys Cys Cys Cys Thr Gly Cys Gly Ala Ala Gly Ala Gly Cys Cys Ala
485 490 495

Gly Cys Cys Thr Cys Thr Cys Cys Cys Thr Gly Gly Gly Cys Thr Cys
500 505 510

Thr Gly Gly Cys Thr Thr Cys Thr Gly Gly Cys Ala Thr Gly Cys Thr
515 520 525

Ala Cys Gly Gly Gly Ala Ala Gly Gly Cys Ala Thr Thr Cys Gly Ala
530 535 540

Gly Cys Ala Gly Ala Cys Gly Gly Cys Thr Gly Cys Thr Gly Ala Gly
545 550 555 560

Ala Gly Cys Cys Ala Thr Cys Cys Cys Gly Cys Gly Cys Cys Ala Gly
565 570 575

Gly Thr Thr Gly Cys Cys Cys Ala Gly Ala Cys Ala Cys Thr Gly Cys
580 585 590

Ala Gly Gly Cys Ala Gly Ala Thr Gly Thr Gly Cys Thr Cys Thr Gly
595 600 605

Gly Cys Ala Gly Ala Thr Gly Gly Gly Ala Thr Ala Thr Ala Cys Ala
610 615 620

Gly Gly Thr Gly Cys Thr Ala Ala Thr Gly Thr Ala Ala Gly Ala Gly
625 630 635 640

Thr Thr Gly Cys Thr Gly Thr Thr Thr Thr Thr Gly Ala Cys Ala Cys
645 650 655

Thr Gly Gly Gly Cys Thr Gly Ala Gly Cys Gly Ala Gly Ala Ala Gly
660 665 670

Cys Ala Thr Cys Cys Cys Cys Ala Cys Thr Thr Cys Ala Ala Ala Ala
675 680 685

Ala Thr Gly Thr Gly Ala Ala Gly Gly Ala Gly Ala Gly Ala Ala Cys
690 695 700

Cys Ala Ala Cys Thr Gly Gly Ala Cys Cys Ala Ala Cys Gly Ala Gly
705 710 715 720

Cys Gly Ala Ala Cys Gly Cys Thr Gly Gly Ala Cys Gly Ala Thr Gly
725 730 735

Gly Gly Thr Thr Gly Gly Gly Cys Cys Ala Thr Gly Gly Cys Ala Cys
740 745 750

Ala Thr Thr Cys Gly Thr Gly Gly Cys Ala Gly Gly Thr Gly Thr Gly
755 760 765

Ala Thr Ala Gly Cys Cys Ala Gly Cys Ala Thr Gly Ala Gly Gly Gly
770 775 780

Ala Gly Thr Gly Cys Cys Ala Ala Gly Gly Ala Thr Thr Thr Gly Cys
785 790 795 800

Thr Cys Cys Ala Gly Ala Thr Gly Cys Ala Gly Ala Ala Cys Thr Thr
805 810 815

Cys Ala Cys Ala Thr Thr Thr Thr Cys Ala Gly Gly Gly Thr Cys Thr
820 825 830

Thr Thr Ala Cys Cys Ala Ala Thr Ala Ala Thr Cys Ala Gly Gly Thr

-continued

```
        835                 840                 845

Ala Thr Cys Thr Thr Ala Cys Ala Cys Ala Thr Cys Thr Thr Gly Gly
    850                 855                 860

Thr Thr Thr Thr Thr Gly Gly Ala Cys Gly Cys Cys Thr Thr Cys Ala
865                 870                 875                 880

Ala Cys Thr Ala Thr Gly Cys Cys Ala Thr Thr Thr Thr Ala Ala Ala
                885                 890                 895

Gly Ala Ala Gly Ala Thr Cys Gly Ala Cys Gly Thr Gly Thr Thr Ala
            900                 905                 910

Ala Ala Cys Cys Thr Cys Ala Gly Cys Ala Thr Cys Gly Gly Cys Gly
        915                 920                 925

Gly Cys Cys Cys Gly Gly Ala Cys Thr Thr Cys Ala Thr Gly Gly Ala
    930                 935                 940

Thr Cys Ala Thr Cys Cys Gly Thr Thr Thr Gly Thr Thr Gly Ala Cys
945                 950                 955                 960

Ala Ala Gly Gly Thr Gly Thr Gly Gly Gly Ala Ala Thr Thr Ala Ala
                965                 970                 975

Cys Ala Gly Cys Thr Ala Ala Cys Ala Ala Thr Gly Thr Ala Ala Thr
            980                 985                 990

Cys Ala Thr Gly Gly Thr Thr Thr  Cys Thr Gly Cys Thr  Ala Thr Thr
        995                 1000                1005

Gly Gly  Cys Ala Ala Thr Gly  Ala Cys Gly Gly Ala  Cys Cys Thr
    1010                1015                1020

Cys Thr  Thr Thr Ala Thr Gly  Gly Cys Ala Cys Thr  Cys Thr Gly
    1025                1030                1035

Ala Ala  Thr Ala Ala Cys Cys  Cys Thr Gly Cys Thr  Gly Ala Thr
    1040                1045                1050

Cys Ala  Ala Ala Thr Gly Gly  Ala Thr Gly Thr Gly  Ala Thr Thr
    1055                1060                1065

Gly Gly  Ala Gly Thr Ala Gly  Gly Cys Gly Gly Cys  Ala Thr Thr
    1070                1075                1080

Gly Ala  Cys Thr Thr Thr Gly  Ala Ala Gly Ala Thr  Ala Ala Cys
    1085                1090                1095

Ala Thr  Cys Gly Cys Cys Cys  Gly Cys Thr Thr Thr  Thr Cys Thr
    1100                1105                1110

Thr Cys  Ala Ala Gly Gly Gly  Gly Ala Ala Thr Gly  Ala Cys Thr
    1115                1120                1125

Ala Cys  Cys Thr Gly Gly Gly  Ala Gly Cys Thr Ala  Cys Cys Ala
    1130                1135                1140

Gly Gly  Ala Gly Gly Cys Thr  Ala Cys Gly Gly Thr  Cys Gly Cys
    1145                1150                1155

Ala Thr  Gly Ala Ala Ala Cys  Cys Thr Gly Ala Cys  Ala Thr Thr
    1160                1165                1170

Gly Thr  Cys Ala Cys Cys Thr  Ala Thr Gly Gly Thr  Gly Cys Thr
    1175                1180                1185

Gly Gly  Cys Gly Thr Gly Cys  Gly Gly Gly Gly Thr  Thr Cys Thr
    1190                1195                1200

Gly Gly  Cys Gly Thr Gly Ala  Ala Ala Gly Gly Gly  Gly Gly Gly
    1205                1210                1215

Thr Gly  Cys Cys Gly Gly Gly  Cys Cys Cys Thr Cys  Thr Cys Ala
    1220                1225                1230

Gly Gly  Gly Ala Cys Cys Ala  Gly Thr Gly Thr Thr  Gly Cys Thr
    1235                1240                1245
```

-continued

```
Thr Cys  Thr Cys Cys Ala Gly  Thr Gly Gly Thr Thr  Gly Cys Ala
    1250                 1255                 1260

Gly Gly  Thr Gly Cys Thr Gly  Thr Cys Ala Cys Cys  Thr Thr Gly
    1265                 1270                 1275

Thr Thr  Ala Gly Thr Gly Ala  Gly Cys Ala Cys Ala  Gly Thr Cys
    1280                 1285                 1290

Cys Ala  Gly Ala Ala Gly Cys  Gly Thr Gly Ala Gly  Cys Thr Gly
    1295                 1300                 1305

Gly Thr  Gly Ala Ala Thr Cys  Cys Cys Gly Cys Cys  Ala Gly Thr
    1310                 1315                 1320

Ala Thr  Gly Ala Ala Gly Cys  Ala Gly Gly Cys Cys  Cys Thr Gly
    1325                 1330                 1335

Ala Thr  Cys Gly Cys Gly Thr  Cys Ala Gly Cys Cys  Cys Gly Gly
    1340                 1345                 1350

Ala Gly  Gly Cys Thr Cys Cys  Cys Cys Gly Gly Gly  Gly Thr Cys
    1355                 1360                 1365

Ala Ala  Cys Ala Thr Gly Thr  Thr Thr Gly Ala Gly  Cys Ala Ala
    1370                 1375                 1380

Gly Gly  Cys Cys Ala Cys Gly  Gly Cys Ala Ala Gly  Cys Thr Cys
    1385                 1390                 1395

Gly Ala  Thr Cys Thr Gly Cys  Thr Cys Ala Gly Ala  Gly Cys Cys
    1400                 1405                 1410

Thr Ala  Thr Cys Ala Gly Ala  Thr Cys Cys Thr Cys  Ala Ala Cys
    1415                 1420                 1425

Ala Gly  Cys Thr Ala Cys Ala  Ala Gly Cys Cys Ala  Cys Ala Gly
    1430                 1435                 1440

Gly Cys  Ala Ala Gly Thr Thr  Thr Gly Ala Gly Cys  Cys Cys Cys
    1445                 1450                 1455

Ala Gly  Cys Thr Ala Cys Ala  Thr Ala Gly Ala Thr  Cys Thr Gly
    1460                 1465                 1470

Ala Cys  Thr Gly Ala Gly Thr  Gly Thr Cys Cys Cys  Thr Ala Cys
    1475                 1480                 1485

Ala Thr  Gly Thr Gly Gly Cys  Cys Cys Thr Ala Cys  Thr Gly Cys
    1490                 1495                 1500

Thr Cys  Cys Cys Ala Gly Cys  Cys Cys Ala Thr Cys  Thr Ala Cys
    1505                 1510                 1515

Thr Ala  Thr Gly Gly Ala Gly  Gly Ala Ala Thr Gly  Cys Cys Gly
    1520                 1525                 1530

Ala Cys  Ala Gly Thr Thr Gly  Thr Thr Ala Ala Thr  Gly Thr Cys
    1535                 1540                 1545

Ala Cys  Cys Ala Thr Cys Cys  Thr Cys Ala Ala Cys  Gly Gly Cys
    1550                 1555                 1560

Ala Thr  Gly Gly Gly Ala Gly  Thr Cys Ala Cys Ala  Gly Gly Ala
    1565                 1570                 1575

Ala Gly  Ala Ala Thr Thr Gly  Thr Ala Gly Ala Thr  Ala Ala Gly
    1580                 1585                 1590

Cys Cys  Thr Gly Ala Cys Thr  Gly Gly Cys Ala Gly  Cys Cys Cys
    1595                 1600                 1605

Thr Ala  Thr Thr Thr Gly Cys  Cys Ala Cys Ala Gly  Ala Ala Cys
    1610                 1615                 1620

Gly Gly  Ala Gly Ala Cys Ala  Ala Cys Ala Thr Thr  Gly Ala Ala
    1625                 1630                 1635
```

```
Gly Thr  Thr Gly Cys Cys Thr  Thr Cys Thr Cys Cys  Thr Ala Cys
    1640                 1645                 1650

Thr Cys  Cys Thr Cys Gly Gly  Thr Cys Thr Thr Ala  Thr Gly Gly
    1655                 1660                 1665

Cys Cys  Thr Thr Gly Gly Thr  Cys Gly Gly Gly Cys  Thr Ala Cys
    1670                 1675                 1680

Cys Thr  Gly Gly Cys Cys Ala  Thr Cys Thr Cys Cys  Ala Thr Thr
    1685                 1690                 1695

Thr Cys  Thr Gly Thr Gly Ala  Cys Cys Ala Ala Gly  Ala Ala Ala
    1700                 1705                 1710

Gly Cys  Gly Gly Cys Thr Thr  Cys Cys Thr Gly Gly  Gly Ala Ala
    1715                 1720                 1725

Gly Gly  Cys Ala Thr Thr Gly  Cys Thr Cys Ala Gly  Gly Gly Cys
    1730                 1735                 1740

Cys Ala  Thr Gly Thr Cys Ala  Thr Gly Ala Thr Cys  Ala Cys Thr
    1745                 1750                 1755

Gly Thr  Gly Gly Cys Thr Thr  Cys Cys Cys Cys Ala  Gly Cys Ala
    1760                 1765                 1770

Gly Ala  Gly Ala Cys Ala Gly  Ala Gly Thr Cys Ala  Ala Ala Ala
    1775                 1780                 1785

Ala Ala  Thr Gly Gly Thr Gly  Cys Ala Gly Ala Ala  Cys Ala Gly
    1790                 1795                 1800

Ala Cys  Thr Thr Cys Ala Ala  Cys Ala Gly Thr Ala  Ala Ala Gly
    1805                 1810                 1815

Cys Thr  Cys Cys Cys Cys Ala  Thr Thr Ala Ala Gly  Gly Thr Gly
    1820                 1825                 1830

Ala Ala  Gly Ala Thr Ala Ala  Thr Thr Cys Cys Thr  Ala Cys Thr
    1835                 1840                 1845

Cys Cys  Cys Cys Cys Gly Cys  Gly Ala Ala Gly Cys  Ala Ala Gly
    1850                 1855                 1860

Ala Gly  Ala Gly Thr Thr Cys  Thr Cys Thr Gly Gly  Gly Ala Thr
    1865                 1870                 1875

Cys Ala  Gly Thr Ala Cys Cys  Ala Cys Ala Ala Cys  Cys Thr Cys
    1880                 1885                 1890

Cys Gly  Cys Thr Ala Thr Cys  Cys Ala Cys Cys Thr  Gly Gly Cys
    1895                 1900                 1905

Thr Ala  Thr Thr Thr Cys Cys  Cys Cys Ala Gly Gly  Gly Ala Thr
    1910                 1915                 1920

Ala Ala  Thr Thr Thr Ala Ala  Gly Gly Ala Thr Gly  Ala Ala Gly
    1925                 1930                 1935

Ala Ala  Thr Gly Ala Cys Cys  Cys Thr Thr Thr Ala  Gly Ala Cys
    1940                 1945                 1950

Thr Gly  Gly Ala Ala Thr Gly  Gly Thr Gly Ala Thr  Cys Ala Cys
    1955                 1960                 1965

Ala Thr  Cys Cys Ala Cys Ala  Cys Cys Ala Ala Thr  Thr Thr Cys
    1970                 1975                 1980

Ala Gly  Gly Gly Ala Thr Ala  Thr Gly Thr Ala Cys  Cys Ala Gly
    1985                 1990                 1995

Cys Ala  Thr Cys Thr Gly Ala  Gly Ala Ala Gly Cys  Ala Thr Gly
    2000                 2005                 2010

Gly Gly  Cys Thr Ala Cys Thr  Thr Thr Gly Thr Ala  Gly Ala Gly
    2015                 2020                 2025

Gly Thr  Cys Cys Thr Cys Gly  Gly Gly Gly Cys Cys  Cys Cys Cys
```

-continued

```
    2030                2035                2040

Thr Thr  Cys Ala Cys Gly Thr  Gly Thr Thr Thr Thr  Gly Ala Thr
    2045                2050                2055

Gly Cys  Cys Ala Gly Thr Cys  Ala Gly Thr Ala Thr  Gly Gly Cys
    2060                2065                2070

Ala Cys  Thr Thr Thr Gly Cys  Thr Gly Ala Thr Gly  Gly Thr Gly
    2075                2080                2085

Gly Ala  Cys Ala Gly Thr Gly  Ala Gly Gly Ala Gly  Gly Ala Gly
    2090                2095                2100

Thr Ala  Cys Thr Thr Cys Cys  Cys Thr Gly Ala Ala  Gly Ala Gly
    2105                2110                2115

Ala Thr  Cys Gly Cys Cys Ala  Ala Gly Cys Thr Cys  Cys Gly Gly
    2120                2125                2130

Ala Gly  Gly Gly Ala Cys Gly  Thr Gly Gly Ala Cys  Ala Ala Cys
    2135                2140                2145

Gly Gly  Cys Cys Thr Cys Thr  Cys Gly Cys Thr Cys  Gly Thr Cys
    2150                2155                2160

Ala Thr  Cys Thr Thr Cys Ala  Gly Thr Gly Ala Cys  Thr Gly Gly
    2165                2170                2175

Thr Ala  Cys Ala Ala Cys Ala  Cys Thr Thr Cys Thr  Gly Thr Thr
    2180                2185                2190

Ala Thr  Gly Ala Gly Ala Ala  Ala Ala Gly Thr Gly  Ala Ala Gly
    2195                2200                2205

Thr Thr  Thr Thr Ala Thr Gly  Ala Thr Gly Ala Ala  Ala Ala Cys
    2210                2215                2220

Ala Cys  Ala Ala Gly Gly Cys  Ala Gly Thr Gly Gly  Thr Gly Gly
    2225                2230                2235

Ala Thr  Gly Cys Cys Gly Gly  Ala Thr Ala Cys Cys  Gly Gly Ala
    2240                2245                2250

Gly Gly  Ala Gly Cys Thr Ala  Ala Cys Ala Thr Cys  Cys Cys Ala
    2255                2260                2265

Gly Cys  Thr Cys Thr Gly Ala  Ala Thr Gly Ala Gly  Cys Thr Gly
    2270                2275                2280

Cys Thr  Gly Thr Cys Thr Gly  Thr Gly Thr Gly Gly  Ala Ala Cys
    2285                2290                2295

Ala Thr  Gly Gly Gly Gly Thr  Thr Cys Ala Gly Cys  Gly Ala Thr
    2300                2305                2310

Gly Gly  Cys Cys Thr Gly Thr  Ala Thr Gly Ala Ala  Gly Gly Gly
    2315                2320                2325

Gly Ala  Gly Thr Thr Cys Ala  Cys Cys Cys Thr Gly  Gly Cys Cys
    2330                2335                2340

Ala Ala  Cys Cys Ala Thr Gly  Ala Cys Ala Thr Gly  Thr Ala Thr
    2345                2350                2355

Thr Ala  Thr Gly Cys Gly Thr  Cys Ala Gly Gly Gly  Thr Gly Cys
    2360                2365                2370

Ala Gly  Cys Ala Thr Cys Gly  Cys Gly Ala Ala Gly  Thr Thr Thr
    2375                2380                2385

Cys Cys  Ala Gly Ala Ala Gly  Ala Thr Gly Gly Cys  Gly Thr Cys
    2390                2395                2400

Gly Thr  Gly Ala Thr Ala Ala  Cys Ala Cys Ala Gly  Ala Cys Thr
    2405                2410                2415

Thr Thr  Cys Ala Ala Gly Gly  Ala Cys Cys Ala Ala  Gly Gly Ala
    2420                2425                2430
```

```
Thr Thr Gly Gly Ala Gly Gly Thr Thr Thr Thr Ala Ala Ala Gly
    2435                2440                2445

Cys Ala Gly Gly Ala Ala Ala Cys Ala Gly Cys Ala Gly Thr Thr
    2450                2455                2460

Gly Thr Thr Gly Ala Ala Ala Ala Cys Gly Thr Cys Cys Cys Cys
    2465                2470                2475

Ala Thr Thr Thr Thr Gly Gly Gly Ala Cys Thr Thr Thr Ala Thr
    2480                2485                2490

Cys Ala Gly Ala Thr Thr Cys Cys Ala Gly Cys Thr Gly Ala Gly
    2495                2500                2505

Gly Gly Thr Gly Gly Ala Gly Gly Cys Cys Gly Gly Ala Thr Thr
    2510                2515                2520

Gly Thr Ala Cys Thr Gly Thr Ala Thr Gly Gly Gly Gly Ala Cys
    2525                2530                2535

Thr Cys Cys Ala Ala Thr Thr Gly Cys Thr Thr Gly Gly Ala Thr
    2540                2545                2550

Gly Ala Cys Ala Gly Thr Cys Ala Cys Cys Gly Ala Cys Ala Gly
    2555                2560                2565

Ala Ala Gly Gly Ala Cys Thr Gly Cys Thr Thr Thr Thr Gly Gly
    2570                2575                2580

Cys Thr Thr Cys Thr Gly Gly Ala Thr Gly Cys Cys Cys Thr Cys
    2585                2590                2595

Cys Thr Cys Cys Ala Gly Thr Ala Cys Ala Cys Ala Thr Cys Gly
    2600                2605                2610

Thr Ala Thr Gly Gly Gly Gly Thr Gly Ala Cys Ala Cys Cys Gly
    2615                2620                2625

Cys Cys Thr Ala Gly Cys Cys Thr Cys Ala Gly Thr Cys Ala Cys
    2630                2635                2640

Thr Cys Thr Gly Gly Gly Ala Ala Cys Cys Gly Cys Cys Ala Gly
    2645                2650                2655

Cys Gly Cys Cys Cys Thr Cys Cys Cys Ala Gly Thr Gly Gly Ala
    2660                2665                2670

Gly Cys Ala Gly Gly Cys Thr Cys Ala Gly Thr Cys Ala Cys Thr
    2675                2680                2685

Cys Cys Ala Gly Ala Gly Ala Gly Gly Ala Thr Gly Gly Ala Ala
    2690                2695                2700

Gly Gly Ala Ala Ala Cys Cys Ala Thr Cys Thr Thr Cys Ala Thr
    2705                2710                2715

Cys Gly Gly Thr Ala Cys Thr Cys Cys Ala Ala Gly Gly Thr Thr
    2720                2725                2730

Cys Thr Gly Gly Ala Gly Gly Cys Cys Cys Ala Thr Thr Thr Gly
    2735                2740                2745

Gly Gly Ala Gly Ala Cys Cys Cys Ala Ala Ala Ala Cys Cys Thr
    2750                2755                2760

Cys Gly Gly Cys Cys Thr Cys Thr Ala Cys Cys Ala Gly Cys Cys
    2765                2770                2775

Thr Gly Thr Cys Cys Ala Cys Gly Cys Thr Thr Gly Thr Cys Thr
    2780                2785                2790

Thr Gly Gly Gly Cys Cys Ala Ala Gly Cys Cys Ala Cys Ala Gly
    2795                2800                2805

Cys Cys Thr Thr Thr Ala Ala Ala Cys Gly Ala Gly Ala Cys Gly
    2810                2815                2820
```

Gly Cys Gly Cys Cys Cys Ala Gly Thr Ala Ala Cys Cys Thr Thr
2825 2830 2835

Thr Gly Gly Ala Ala Ala Cys Ala Thr Cys Ala Gly Ala Ala Gly
2840 2845 2850

Cys Thr Ala Cys Thr Cys Thr Cys Cys Ala Thr Thr Gly Ala Cys
2855 2860 2865

Cys Thr Gly Gly Ala Cys Ala Ala Gly Gly Thr Gly Gly Thr Gly
2870 2875 2880

Thr Thr Ala Cys Cys Cys Ala Ala Cys Thr Thr Thr Cys Gly Ala
2885 2890 2895

Thr Cys Gly Ala Ala Thr Cys Gly Cys Cys Cys Thr Cys Ala Ala
2900 2905 2910

Gly Thr Gly Ala Gly Gly Cys Cys Cys Thr Thr Gly Thr Cys Cys
2915 2920 2925

Cys Cys Thr Gly Gly Ala Gly Ala Gly Ala Gly Cys Gly Gly Cys
2930 2935 2940

Gly Cys Cys Thr Gly Gly Gly Ala Cys Ala Thr Thr Cys Cys Thr
2945 2950 2955

Gly Gly Ala Gly Gly Gly Ala Thr Cys Ala Thr Gly Cys Cys Thr
2960 2965 2970

Gly Gly Cys Cys Gly Cys Thr Ala Cys Ala Ala Cys Cys Ala Gly
2975 2980 2985

Gly Ala Gly Gly Thr Gly Gly Gly Cys Cys Ala Gly Ala Cys Cys
2990 2995 3000

Ala Thr Thr Cys Cys Thr Gly Thr Cys Thr Thr Thr Gly Cys Cys
3005 3010 3015

Thr Thr Cys Cys Thr Gly Gly Gly Ala Gly Cys Cys Ala Thr Gly
3020 3025 3030

Gly Thr Gly Gly Thr Cys Cys Thr Gly Gly Cys Cys Thr Thr Cys
3035 3040 3045

Thr Thr Thr Gly Thr Gly Gly Thr Ala Cys Ala Ala Ala Thr Cys
3050 3055 3060

Ala Ala Cys Ala Ala Gly Gly Cys Cys Ala Ala Gly Ala Gly Cys
3065 3070 3075

Ala Gly Gly Cys Cys Gly Ala Ala Gly Cys Gly Gly Ala Gly Gly
3080 3085 3090

Ala Ala Gly Cys Cys Cys Ala Gly Gly Gly Thr Gly Ala Ala Gly
3095 3100 3105

Cys Gly Cys Cys Cys Gly Cys Ala Gly Cys Thr Cys Ala Thr Gly
3110 3115 3120

Cys Ala Gly Cys Ala Gly Gly Thr Thr Cys Ala Cys Cys Cys Gly
3125 3130 3135

Cys Cys Ala Ala Ala Gly Ala Cys Cys Cys Cys Thr Thr Cys Gly
3140 3145 3150

Gly Thr Gly Thr Gly Ala
3155

<210> SEQ ID NO 25
<211> LENGTH: 2079
<212> TYPE: DNA
<213> ORGANISM: Homo sapiens

<400> SEQUENCE: 25
atgggcaccg tcagctccag gcggtcctgg tggccgctgc cactgctgct gctgctgctg 60
ctgctcctgg gtcccgcggg cgcccgtgcg caggaggacg aggacggcga ctacgaggag 120
ctggtgctag ccttgcgttc cgaggaggac ggcctggccg aagcacccga gcacggaacc 180
acagccacct tccaccgctg cgccaaggat ccgtggaggt tgcctggcac ctacgtggtg 240
gtgctgaagg aggagaccca cctctcgcag tcagagcgca ctgcccgccg cctgcaggcc 300
caggctgccc gccggggata cctcaccaag atcctgcatg tcttccatgg ccttcttcct 360
ggcttcctgg tgaagatgag tggcgacctg ctggagctgg ccttgaagtt gccccatgtc 420
gactacatcg aggaggactc ctctgtcttt gcccagagca tcccgtggaa cctggagcgg 480
attacccctc cacggtaccg ggcggatgaa taccagcccc ccgacggagg cagcctggtg 540
gaggtgtatc tcctagacac cagcatacag agtgaccacc gggaaatcga gggcagggtc 600
atggtcaccg acttcgagaa tgtgcccgag gaggacggga cccgcttcca cagacaggcc 660
agcaagtgtg acagtcatgg cacccacctg gcaggggtgg tcagcggccg ggatgccggc 720
gtggccaagg gtgccagcat gcgcagcctg cgcgtgctca actgccaagg gaagggcacg 780
gttagcggca ccctcatagg cctggagttt attcggaaaa gccagctggt ccagcctgtg 840
gggccactgg tggtgctgct gcccctggcg ggtgggtaca gccgcgtcct caacgccgcc 900
tgccagcgcc tggcgagggc tggggtcgtg ctggtcaccg ctgccggcaa cttccgggac 960
gatgcctgcc tctactcccc agcctcagct cccgaggtca tcacagttgg ggccaccaat 1020
gcccaggacc agccggtgac cctggggact ttggggacca actttggccg ctgtgtggac 1080
ctctttgccc caggggagga catcattggt gcctccagcg actgcagcac ctgctttgtg 1140
tcacagagtg ggacatcaca ggctgctgcc cacgtggctg gcattgcagc catgatgctg 1200
tctgccgagc cggagctcac cctggccgag ttgaggcaga gactgatcca cttctctgcc 1260
aaagatgtca tcaatgaggc ctggttccct gaggaccagc gggtactgac ccccaacctg 1320
gtggccgccc tgccccccag cacccatggg gcaggttggc agctgttttg caggactgtg 1380
tggtcagcac actcggggcc tacacggatg gccacagcca tcgcccgctg cgccccagat 1440
gaggagctgc tgagctgctc cagtttctcc aggagtggga agcggcgggg cgagcgcatg 1500
gaggcccaag gggcaagct ggtctgccgg gcccacaacg cttttggggg tgagggtgtc 1560
tacgccattg ccaggtgctg cctgctaccc caggccaact gcagcgtcca cacagctcca 1620
ccagctgagg ccagcatggg gacccgtgtc cactgccacc aacagggcca cgtcctcaca 1680
ggctgcagct cccactggga ggtggaggac cttggcaccc acaagccgcc tgtgctgagg 1740
ccacgaggtc agcccaacca gtgcgtgggc cacagggagg ccagcatcca cgcttcctgc 1800
tgccatgccc caggtctgga atgcaaagtc aaggagcatg gaatcccggc ccctcaggag 1860
caggtgaccg tggcctgcga ggagggctgg accctgactg gctgcagtgc cctccctggg 1920
acctcccacg tcctgggggc ctacgccgta gacaacacgt gtgtagtcag gagccgggac 1980
gtcagcacta caggcagcac cagcgaagag gccgtgacag ccgttgccat ctgctgccgg 2040
agccggcacc tggcgcaggc ctcccaggag ctccagtga 2079

<210> SEQ ID NO 26
<211> LENGTH: 692
<212> TYPE: PRT
<213> ORGANISM: Homo sapiens

<400> SEQUENCE: 26

Met Gly Thr Val Ser Ser Arg Arg Ser Trp Trp Pro Leu Pro Leu Leu
1 5 10 15

-continued

```
Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
```

```
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln
    690
```

<210> SEQ ID NO 27
<211> LENGTH: 1665
<212> TYPE: DNA
<213> ORGANISM: Homo sapiens

<400> SEQUENCE: 27

```
tatggtctag acgtaaacga tatatattca tgctcatggg gtcccgctga tgacggaaga      60

catttacaag gccctagtga cctggtgaaa aaggctttag taaaaggtgt tactgaggga     120

agagattcca aaggagcgat ttacgttttt gccagtggaa atggtggaac tcgtggtgat     180

aattgcaatt acgacggcta tactaattcc atatattcta ttactattgg ggctattgat     240

cacaaagatc tacatcctcc ttattccgaa ggttgttccg ccgtcatggc agtcacgtat     300

tcttcaggtt caggcgaata tattcattcg agtgatatca acggcagatg cagtaatagc     360

cacggtggaa cgtctgcggc tgctccatta gctgccggtg tttacacttt gttactagaa     420

gccaacccaa acctaacttg gagagacgta cagtatttat caatcttgtc tgcggtaggg     480

ttagaaaaga acgctgacgg agattggaga gatagcgcca tggggaagaa atactctcat     540

cgctatggct ttggtaaaat cgatgcccat aagttaattg aaatgtccaa gacctgggag     600

aatgttaacg cacaaacctg gttttacctg ccaacattgt atgtttccca gtccacaaac     660
```

```
tccacggaag agacattaga atccgtcata accatatcag aaaaaagtct tcaagatgct    720

aacttcaaga gaattgagca cgtcacggta actgtagata ttgatacaga aattagggga    780

actacgactg tcgatttaat atcaccagcg ggataatttt caaaccttgg cgttgtaaga    840

ccaagagatg tttcatcaga gggattcaaa gactggacat tcatgtctgt agcacattgg    900

ggtgagaacg gcgtaggtga ttggaaaatc aaggttaaga caacagaaaa tggacacagg    960

attgacttcc acagttggag gctgaagctc tttggggaat ccattgattc atctaaaaca   1020

gaaactttcg tctttggaaa cgataaagag gaggttgaac cagctgctac agaaagtacc   1080

gtatcacaat attctgccag ttcaacttct atttccatca gcgctacttc tacatcttct   1140

atctcaattg gtgtggaaac gtcggccatt ccccaaacga ctactgcgag taccgatcct   1200

gattctgatc caaacactcc taaaaaactt tcctctccta ggcaagccat gcattatttt   1260

ttaacaatat ttttgattgg cgccacattt ttggtgttat acttcatgtt ttttatgaaa   1320

tcaaggagaa ggatcagaag gtcaagagcg gaaacgtatg aattcgatat cattgataca   1380

gactctgagt acgattctac tttggacaat ggaacttccg gaattactga gcccgaagag   1440

gttgaggact tcgattttga tttgtccgat gaagaccatc ttgcaagttt gtcttcatca   1500

gaaaacggtg atgctgaaca tacaattgat agtgtactaa caaacgaaaa tccatttagt   1560

gaccctataa agcaaaagtt cccaaatgac gccaacgcag aatctgcttc caataaatta   1620

caagaattac agcctgatgt tcctccatct tccggacgat cgtga                   1665
```

```
<210> SEQ ID NO 28
<211> LENGTH: 814
<212> TYPE: PRT
<213> ORGANISM: Homo sapiens

<400> SEQUENCE: 28

Met Lys Val Arg Lys Tyr Ile Thr Leu Cys Phe Trp Trp Ala Phe Ser
1               5                   10                  15

Thr Ser Ala Leu Val Ser Ser Gln Gln Ile Pro Leu Lys Asp His Thr
            20                  25                  30

Ser Arg Gln Tyr Phe Ala Val Glu Ser Asn Glu Thr Leu Ser Arg Leu
        35                  40                  45

Glu Glu Met His Pro Asn Trp Lys Tyr Glu His Asp Val Arg Gly Leu
    50                  55                  60

Pro Asn His Tyr Val Phe Ser Lys Glu Leu Leu Lys Leu Gly Lys Arg
65                  70                  75                  80

Ser Ser Leu Glu Glu Leu Gln Gly Asp Asn Asn Asp His Ile Leu Ser
                85                  90                  95

Val His Asp Leu Phe Pro Arg Asn Asp Leu Phe Lys Arg Leu Pro Val
            100                 105                 110

Pro Ala Pro Pro Met Asp Ser Ser Leu Leu Pro Val Lys Glu Ala Glu
        115                 120                 125

Asp Lys Leu Ser Ile Asn Asp Pro Leu Phe Glu Arg Gln Trp His Leu
    130                 135                 140

Val Asn Pro Ser Phe Pro Gly Ser Asp Ile Asn Val Leu Asp Leu Trp
145                 150                 155                 160

Tyr Asn Asn Ile Thr Gly Ala Gly Val Val Ala Ala Ile Val Asp Asp
                165                 170                 175

Gly Leu Asp Tyr Glu Asn Glu Asp Leu Lys Asp Asn Phe Cys Ala Glu
            180                 185                 190
```

-continued

```
Gly Ser Trp Asp Phe Asn Asp Asn Thr Asn Leu Pro Lys Pro Arg Leu
        195                 200                 205

Ser Asp Asp Tyr His Gly Thr Arg Cys Ala Gly Glu Ile Ala Ala Lys
    210                 215                 220

Lys Gly Asn Asn Phe Cys Gly Val Gly Val Gly Tyr Asn Ala Lys Ile
225                 230                 235                 240

Ser Gly Ile Arg Ile Leu Ser Gly Asp Ile Thr Thr Glu Asp Glu Ala
                245                 250                 255

Ala Ser Leu Ile Tyr Gly Leu Asp Val Asn Asp Ile Tyr Ser Cys Ser
            260                 265                 270

Trp Gly Pro Ala Asp Asp Gly Arg His Leu Gln Gly Pro Ser Asp Leu
        275                 280                 285

Val Lys Lys Ala Leu Val Lys Gly Val Thr Glu Gly Arg Asp Ser Lys
    290                 295                 300

Gly Ala Ile Tyr Val Phe Ala Ser Gly Asn Gly Gly Thr Arg Gly Asp
305                 310                 315                 320

Asn Cys Asn Tyr Asp Gly Tyr Thr Asn Ser Ile Tyr Ser Ile Thr Ile
                325                 330                 335

Gly Ala Ile Asp His Lys Asp Leu His Pro Pro Tyr Ser Glu Gly Cys
            340                 345                 350

Ser Ala Val Met Ala Val Thr Tyr Ser Ser Gly Ser Gly Glu Tyr Ile
        355                 360                 365

His Ser Ser Asp Ile Asn Gly Arg Cys Ser Asn Ser His Gly Gly Thr
    370                 375                 380

Ser Ala Ala Ala Pro Leu Ala Ala Gly Val Tyr Thr Leu Leu Leu Glu
385                 390                 395                 400

Ala Asn Pro Asn Leu Thr Trp Arg Asp Val Gln Tyr Leu Ser Ile Leu
                405                 410                 415

Ser Ala Val Gly Leu Glu Lys Asn Ala Asp Gly Asp Trp Arg Asp Ser
            420                 425                 430

Ala Met Gly Lys Lys Tyr Ser His Arg Tyr Gly Phe Gly Lys Ile Asp
        435                 440                 445

Ala His Lys Leu Ile Glu Met Ser Lys Thr Trp Glu Asn Val Asn Ala
    450                 455                 460

Gln Thr Trp Phe Tyr Leu Pro Thr Leu Tyr Val Ser Gln Ser Thr Asn
465                 470                 475                 480

Ser Thr Glu Glu Thr Leu Glu Ser Val Ile Thr Ile Ser Glu Lys Ser
                485                 490                 495

Leu Gln Asp Ala Asn Phe Lys Arg Ile Glu His Val Thr Val Thr Val
            500                 505                 510

Asp Ile Asp Thr Glu Ile Arg Gly Thr Thr Thr Val Asp Leu Ile Ser
        515                 520                 525

Pro Ala Gly Ile Ile Ser Asn Leu Gly Val Val Arg Pro Arg Asp Val
    530                 535                 540

Ser Ser Glu Gly Phe Lys Asp Trp Thr Phe Met Ser Val Ala His Trp
545                 550                 555                 560

Gly Glu Asn Gly Val Gly Asp Trp Lys Ile Lys Val Lys Thr Thr Glu
                565                 570                 575

Asn Gly His Arg Ile Asp Phe His Ser Trp Arg Leu Lys Leu Phe Gly
            580                 585                 590

Glu Ser Ile Asp Ser Ser Lys Thr Glu Thr Phe Val Phe Gly Asn Asp
        595                 600                 605

Lys Glu Glu Val Glu Pro Ala Ala Thr Glu Ser Thr Val Ser Gln Tyr
```

```
    610                 615                 620

Ser Ala Ser Ser Thr Ser Ile Ser Ile Ser Ala Thr Ser Thr Ser Ser
625                 630                 635                 640

Ile Ser Ile Gly Val Glu Thr Ser Ala Ile Pro Gln Thr Thr Thr Ala
                645                 650                 655

Ser Thr Asp Pro Asp Ser Asp Pro Asn Thr Pro Lys Lys Leu Ser Ser
            660                 665                 670

Pro Arg Gln Ala Met His Tyr Phe Leu Thr Ile Phe Leu Ile Gly Ala
        675                 680                 685

Thr Phe Leu Val Leu Tyr Phe Met Phe Phe Met Lys Ser Arg Arg Arg
    690                 695                 700

Ile Arg Arg Ser Arg Ala Glu Thr Tyr Glu Phe Asp Ile Ile Asp Thr
705                 710                 715                 720

Asp Ser Glu Tyr Asp Ser Thr Leu Asp Asn Gly Thr Ser Gly Ile Thr
                725                 730                 735

Glu Pro Glu Glu Val Glu Asp Phe Asp Phe Asp Leu Ser Asp Glu Asp
            740                 745                 750

His Leu Ala Ser Leu Ser Ser Ser Glu Asn Gly Asp Ala Glu His Thr
        755                 760                 765

Ile Asp Ser Val Leu Thr Asn Glu Asn Pro Phe Ser Asp Pro Ile Lys
    770                 775                 780

Gln Lys Phe Pro Asn Asp Ala Asn Ala Glu Ser Ala Ser Asn Lys Leu
785                 790                 795                 800

Gln Glu Leu Gln Pro Asp Val Pro Pro Ser Ser Gly Arg Ser
                805                 810


<210> SEQ ID NO 29
<211> LENGTH: 24
<212> TYPE: DNA
<213> ORGANISM: Artificial Sequence
<220> FEATURE:
<223> OTHER INFORMATION: primer

<400> SEQUENCE: 29

atctacacca tctccatcag cagc                                            24


<210> SEQ ID NO 30
<211> LENGTH: 37
<212> TYPE: DNA
<213> ORGANISM: Artificial Sequence
<220> FEATURE:
<223> OTHER INFORMATION: primer

<400> SEQUENCE: 30

aaggcggccg ctcagccttg aaatgtacat gttttgc                              37


<210> SEQ ID NO 31
<211> LENGTH: 18
<212> TYPE: DNA
<213> ORGANISM: Artificial Sequence
<220> FEATURE:
<223> OTHER INFORMATION: primer

<400> SEQUENCE: 31

agcgagggag cagcgagg                                                   18


<210> SEQ ID NO 32
<211> LENGTH: 21
<212> TYPE: DNA
<213> ORGANISM: Artificial Sequence
```

<220> FEATURE:
<223> OTHER INFORMATION: primer

<400> SEQUENCE: 32
ggtagttgac atggcggttg g 21

<210> SEQ ID NO 33
<211> LENGTH: 34
<212> TYPE: DNA
<213> ORGANISM: Artificial Sequence
<220> FEATURE:
<223> OTHER INFORMATION: primer

<400> SEQUENCE: 33
cagcgactta agccaccatg ggctggggga gccg 34

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
gtaggttgtg gccagcgtgg 20

<210> SEQ ID NO 35
<211> LENGTH: 2739
<212> TYPE: DNA
<213> ORGANISM: Artificial Sequence
<220> FEATURE:
<223> OTHER INFORMATION: p55N-PC5-005

<400> SEQUENCE: 35
atgggctggg ggagccgctg ctgctgcccg ggacgtttgg acctgctgtg cgtgctggcg 60
ctgctcgggg gctgcctgct ccccgtgtgt cggacgcgcg tctacaccaa ccactgggca 120
gtcaaaatcg ccgggggctt cccggaggcc aaccgtatcg ccagcaagta cggattcatc 180
aacataggac agataggggc cctgaaggac tactaccact tctaccatag caggacgatt 240
aaaaggtcag ttatctcgag cagagggacc cacagtttca tttcaatgga accaaaggtg 300
gaatggatcc aacagcaagt ggtaaaaaag cggacaaaga gggattatga cttcagtcgt 360
gcccagtcta cctatttcaa tgatcccaag tggcccagta tgtggtatat gcactgcagt 420
gacaatacac atccctgcca gtctgacatg aatatcgaag gagcctggaa gagaggctac 480
acgggaaaga acattgtggt cactatcctg gatgacggaa ttgagagaac ccatccagat 540
ctgatgcaaa actacgatgc tctggcaagt tgcgacgtga atgggaatga cttggaccca 600
atgcctcgtt atgatgcaag caacgagaac aagcatggga ctcgctgtgc tggagaagtg 660
gcagccgctg caaacaattc gcactgcaca gtcggaattg ctttcaacgc caagatcgga 720
ggagtgcgaa tgctggacgg agatgtcacg gacatggttg aagcaaaatc agttagcttc 780
aacccccagc acgtgcacat ttacagcgcc agctggggcc cggatgatga tggcaagact 840
gtggacggac cagcccccct cacccggcaa gcctttgaaa acggcgttag aatggggcgg 900
agaggcctcg gctctgtgtt tgtttgggca tctggaaatg gtggaaggag caaagaccac 960
tgctcctgtg atggctacac caacagcatc tacaccatct ccatcagcag cactgcagaa 1020
agcggaaaga aaccttggta cctggaagag tgttcatcca cgctggccac aacctacagc 1080
agcggggagt cctacgataa gaaaatcatc actacagatc tgaggcagcg ttgcacggac 1140

-continued aaccacactg ggacgtcagc ctcagccccc atggctgcag gcatcattgc gctggccctg 1200
gaagccaatc cgtttctgac ctggagagac gtacagcatg ttattgtcag gacttcccgt 1260
gcgggacatt tgaacgctaa tgactggaaa accaatgctg ctggttttaa ggtgagccat 1320
ctttatggat ttggactgat ggacgcagaa gccatggtga tggaggcaga gaagtggacc 1380
accgttcccc ggcagcacgt gtgtgtggag agcacagacc gacaaatcaa gacaatccgc 1440
cctaacagtg cagtgcgctc catctacaaa gcctcaggct gctcagataa ccccaaccgc 1500
catgtcaact acctggagca cgtcgttgtg cgcatcacca tcacccaccc caggagagga 1560
gacctggcca tctacctgac ctcgccctct ggaactaggt ctcagctttt ggccaacagg 1620
ctatttgatc actccatgga aggattcaaa aactgggagt tcatgaccat tcattgctgg 1680
ggagaaagag ctgctggtga ctgggtcctt gaagtttatg atactccctc tcagctaagg 1740
aactttaaga ctccaggtaa attgaaagaa tggtctttgg tcctctacgg cacctccgtg 1800
cagccatatt caccaaccaa tgaatttccg aaagtggaac ggttccgcta tagccgagtt 1860
gaagacccca cagacgacta tggcacagag gattatgcag gtccctgcga ccctgagtgc 1920
agtgaggttg gctgtgacgg gccaggacca gaccactgca atgactgttt gcactactac 1980
tacaagctga aaaacaatac caggatctgt gtctccagct gccccccctgg ccactaccac 2040 gccgacaaga agcgctgcag gaagtgtgcc cccaactgtg agtcctgctt tgggagccat 2100
ggtgaccaat gcatgtcctg caaatatgga tactttctga atgaagaaac caacagctgt 2160
gttactcact gccctgatgg gtcatatcag gataccaaga aaaatctttg ccggaaatgc 2220
agtgaaaact gcaagacatg tactgaattc cataactgta cagaatgtag ggatgggtta 2280
agcctgcagg gatcccggtg ctctgtctcc tgtgaagatg gacggtattt caacggccag 2340
gactgccagc cctgccaccg cttctgcgcc acttgtgctg gggcaggagc tgatgggtgc 2400
attaactgca cagagggcta cttcatggag gatgggagat gcgtgcagag ctgtagtatc 2460
agctattact ttgaccactc ttcagagaat ggatacaaat cctgcaaaaa atgtgatatc 2520
agttgtttga cgtgcaatgg cccaggattc aagaactgta caagctgccc tagtgggtat 2580
ctcttagact taggaatgtg tcaaatggga gccatttgca aggatgcaac ggaagagtcc 2640
tgggcggaag gaggcttctg tatgcttgtg aaaaagaaca atctgtgcca acggaaggtt 2700
cttcaacaac tttgctgcaa aacatgtaca tttcaaggc 2739

<210> SEQ ID NO 36
<211> LENGTH: 34
<212> TYPE: DNA
<213> ORGANISM: Artificial Sequence
<220> FEATURE:
<223> OTHER INFORMATION: primer

<400> SEQUENCE: 36
ggtaagcttg ccatggagct gaggccctgg ttgc 34

<210> SEQ ID NO 37
<211> LENGTH: 27
<212> TYPE: DNA
<213> ORGANISM: Artificial Sequence
<220> FEATURE:
<223> OTHER INFORMATION: primer

<400> SEQUENCE: 37
gttttcaatc tctaggaccc actcgcc 27

<210> SEQ ID NO 38
<211> LENGTH: 23
<212> TYPE: DNA
<213> ORGANISM: Artificial Sequence
<220> FEATURE:
<223> OTHER INFORMATION: primer

<400> SEQUENCE: 38
gccaggccac atgactactc cgc 23

<210> SEQ ID NO 39
<211> LENGTH: 34
<212> TYPE: DNA
<213> ORGANISM: Artificial Sequence
<220> FEATURE:
<223> OTHER INFORMATION: primer

<400> SEQUENCE: 39
ggtgaattct cactcaggca ggtgtgaggg cagc 34

<210> SEQ ID NO 40
<211> LENGTH: 53
<212> TYPE: DNA
<213> ORGANISM: Artificial Sequence
<220> FEATURE:
<223> OTHER INFORMATION: primer

<400> SEQUENCE: 40
gcgctagccg tacggccgcc accatgaaag tgaggaaata tattacttta tgc 53

<210> SEQ ID NO 41
<211> LENGTH: 29
<212> TYPE: DNA
<213> ORGANISM: Artificial Sequence
<220> FEATURE:
<223> OTHER INFORMATION: primer

<400> SEQUENCE: 41
gctattgatc acaaagatct acatcctcc 29

<210> SEQ ID NO 42
<211> LENGTH: 29
<212> TYPE: DNA
<213> ORGANISM: Artificial Sequence
<220> FEATURE:
<223> OTHER INFORMATION: primer

<400> SEQUENCE: 42
ggaggatgta gatctttgtg atcaatagc 29

<210> SEQ ID NO 43
<211> LENGTH: 59
<212> TYPE: DNA
<213> ORGANISM: Artificial Sequence
<220> FEATURE:
<223> OTHER INFORMATION: primer

<400> SEQUENCE: 43
gcgaattccg gtccgtcatt gcctagggct cgagagtttt ttaggagtgt ttggatcag 59

<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
gcatggactc cgatcccaac g 21

<210> SEQ ID NO 45
<211> LENGTH: 21
<212> TYPE: DNA
<213> ORGANISM: Artificial Sequence
<220> FEATURE:
<223> OTHER INFORMATION: primer

<400> SEQUENCE: 45
cgttgggatc ggagtccatg c 21

<210> SEQ ID NO 46
<211> LENGTH: 40
<212> TYPE: DNA
<213> ORGANISM: Artificial Sequence
<220> FEATURE:
<223> OTHER INFORMATION: primer

<400> SEQUENCE: 46
ggtaagcttg ccgccaccat gccgaagggg aggcagaaag 40

<210> SEQ ID NO 47
<211> LENGTH: 33
<212> TYPE: DNA
<213> ORGANISM: Artificial Sequence
<220> FEATURE:
<223> OTHER INFORMATION: primer

<400> SEQUENCE: 47
tttgaattct cagttggggg tgatggtgta acc 33

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
ggcacctgaa taaccgacgg 20

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
cgtcacgttg atgtccctgc 20

<210> SEQ ID NO 50
<211> LENGTH: 8
<212> TYPE: PRT
<213> ORGANISM: Artificial Sequence
<220> FEATURE:
<223> OTHER INFORMATION: linker

<400> SEQUENCE: 50

Glu Phe Ala Gly Ala Ala Ala Val
1 5

<210> SEQ ID NO 51

<211> LENGTH: 7
<212> TYPE: PRT
<213> ORGANISM: Artificial Sequence
<220> FEATURE:
<223> OTHER INFORMATION: linker

<400> SEQUENCE: 51

```
Ser Gly Gly Ser Gly Gly Ser
1               5
```

<210> SEQ ID NO 52
<211> LENGTH: 15
<212> TYPE: PRT
<213> ORGANISM: Artificial Sequence
<220> FEATURE:
<223> OTHER INFORMATION: linker

<400> SEQUENCE: 52

```
Gly Gly Ser Gly Gly Ser Gly Gly Ser Gly Gly Ser Gly Gly Gly
1               5                   10                  15
```

<210> SEQ ID NO 53
<211> LENGTH: 16
<212> TYPE: PRT
<213> ORGANISM: Artificial Sequence
<220> FEATURE:
<223> OTHER INFORMATION: linker

<400> SEQUENCE: 53

```
Gly Gly Ser Gly Gly Ser Gly Gly Gly Gly Ser Gly Gly Gly Gly Ser
1               5                   10                  15
```

<210> SEQ ID NO 54
<211> LENGTH: 18
<212> TYPE: PRT
<213> ORGANISM: Artificial Sequence
<220> FEATURE:
<223> OTHER INFORMATION: linker

<400> SEQUENCE: 54

```
Gly Gly Ser Gly Gly Ser Gly Gly Ser Gly Gly Ser Gly Gly Ser Gly
1               5                   10                  15

Gly Ser
```

<210> SEQ ID NO 55
<211> LENGTH: 5
<212> TYPE: PRT
<213> ORGANISM: Artificial Sequence
<220> FEATURE:
<223> OTHER INFORMATION: linker

<400> SEQUENCE: 55

```
Gly Gly Gly Gly Ser
1               5
```

<210> SEQ ID NO 56
<211> LENGTH: 15
<212> TYPE: PRT
<213> ORGANISM: Artificial Sequence
<220> FEATURE:
<223> OTHER INFORMATION: linker

<400> SEQUENCE: 56

```
Gly Gly Gly Gly Ser Gly Gly Gly Gly Ser Gly Gly Gly Gly Ser
1               5                   10                  15
```

<210> SEQ ID NO 57
<211> LENGTH: 1860
<212> TYPE: PRT
<213> ORGANISM: Homo sapiens

<400> SEQUENCE: 57

Met Gly Trp Gly Ser Arg Cys Cys Cys Pro Gly Arg Leu Asp Leu Leu
1 5 10 15

Cys Val Leu Ala Leu Leu Gly Gly Cys Leu Leu Pro Val Cys Arg Thr
20 25 30

Arg Val Tyr Thr Asn His Trp Ala Val Lys Ile Ala Gly Gly Phe Pro
35 40 45

Glu Ala Asn Arg Ile Ala Ser Lys Tyr Gly Phe Ile Asn Ile Gly Gln
50 55 60

Ile Gly Ala Leu Lys Asp Tyr Tyr His Phe Tyr His Ser Arg Thr Ile
65 70 75 80

Lys Arg Ser Val Ile Ser Ser Arg Gly Thr His Ser Phe Ile Ser Met
85 90 95

Glu Pro Lys Val Glu Trp Ile Gln Gln Gln Val Val Lys Lys Arg Thr
100 105 110

Lys Arg Asp Tyr Asp Phe Ser Arg Ala Gln Ser Thr Tyr Phe Asn Asp
115 120 125

Pro Lys Trp Pro Ser Met Trp Tyr Met His Cys Ser Asp Asn Thr His
130 135 140

Pro Cys Gln Ser Asp Met Asn Ile Glu Gly Ala Trp Lys Arg Gly Tyr
145 150 155 160

Thr Gly Lys Asn Ile Val Val Thr Ile Leu Asp Asp Gly Ile Glu Arg
165 170 175

Thr His Pro Asp Leu Met Gln Asn Tyr Asp Ala Leu Ala Ser Cys Asp
180 185 190

Val Asn Gly Asn Asp Leu Asp Pro Met Pro Arg Tyr Asp Ala Ser Asn
195 200 205

Glu Asn Lys His Gly Thr Arg Cys Ala Gly Glu Val Ala Ala Ala Ala
210 215 220

Asn Asn Ser His Cys Thr Val Gly Ile Ala Phe Asn Ala Lys Ile Gly
225 230 235 240

Gly Val Arg Met Leu Asp Gly Asp Val Thr Asp Met Val Glu Ala Lys
245 250 255

Ser Val Ser Phe Asn Pro Gln His Val His Ile Tyr Ser Ala Ser Trp
260 265 270

Gly Pro Asp Asp Asp Gly Lys Thr Val Asp Gly Pro Ala Pro Leu Thr
275 280 285

Arg Gln Ala Phe Glu Asn Gly Val Arg Met Gly Arg Arg Gly Leu Gly
290 295 300

Ser Val Phe Val Trp Ala Ser Gly Asn Gly Gly Arg Ser Lys Asp His
305 310 315 320

Cys Ser Cys Asp Gly Tyr Thr Asn Ser Ile Tyr Thr Ile Ser Ile Ser
325 330 335

Ser Thr Ala Glu Ser Gly Lys Lys Pro Trp Tyr Leu Glu Glu Cys Ser
340 345 350

Ser Thr Leu Ala Thr Thr Tyr Ser Ser Gly Glu Ser Tyr Asp Lys Lys
355 360 365

Ile Ile Thr Thr Asp Leu Arg Gln Arg Cys Thr Asp Asn His Thr Gly
370 375 380

-continued

```
Thr Ser Ala Ser Ala Pro Met Ala Ala Gly Ile Ile Ala Leu Ala Leu
385                 390                 395                 400

Glu Ala Asn Pro Phe Leu Thr Trp Arg Asp Val Gln His Val Ile Val
                405                 410                 415

Arg Thr Ser Arg Ala Gly His Leu Asn Ala Asn Asp Trp Lys Thr Asn
            420                 425                 430

Ala Ala Gly Phe Lys Val Ser His Leu Tyr Gly Phe Gly Leu Met Asp
        435                 440                 445

Ala Glu Ala Met Val Met Glu Ala Glu Lys Trp Thr Thr Val Pro Arg
    450                 455                 460

Gln His Val Cys Val Glu Ser Thr Asp Arg Gln Ile Lys Thr Ile Arg
465                 470                 475                 480

Pro Asn Ser Ala Val Arg Ser Ile Tyr Lys Ala Ser Gly Cys Ser Asp
                485                 490                 495

Asn Pro Asn Arg His Val Asn Tyr Leu Glu His Val Val Val Arg Ile
            500                 505                 510

Thr Ile Thr His Pro Arg Arg Gly Asp Leu Ala Ile Tyr Leu Thr Ser
        515                 520                 525

Pro Ser Gly Thr Arg Ser Gln Leu Leu Ala Asn Arg Leu Phe Asp His
    530                 535                 540

Ser Met Glu Gly Phe Lys Asn Trp Glu Phe Met Thr Ile His Cys Trp
545                 550                 555                 560

Gly Glu Arg Ala Ala Gly Asp Trp Val Leu Glu Val Tyr Asp Thr Pro
                565                 570                 575

Ser Gln Leu Arg Asn Phe Lys Thr Pro Gly Lys Leu Lys Glu Trp Ser
            580                 585                 590

Leu Val Leu Tyr Gly Thr Ser Val Gln Pro Tyr Ser Pro Thr Asn Glu
        595                 600                 605

Phe Pro Lys Val Glu Arg Phe Arg Tyr Ser Arg Val Glu Asp Pro Thr
    610                 615                 620

Asp Asp Tyr Gly Thr Glu Asp Tyr Ala Gly Pro Cys Asp Pro Glu Cys
625                 630                 635                 640

Ser Glu Val Gly Cys Asp Gly Pro Gly Pro Asp His Cys Asn Asp Cys
                645                 650                 655

Leu His Tyr Tyr Tyr Lys Leu Lys Asn Asn Thr Arg Ile Cys Val Ser
            660                 665                 670

Ser Cys Pro Pro Gly His Tyr His Ala Asp Lys Lys Arg Cys Arg Lys
        675                 680                 685

Cys Ala Pro Asn Cys Glu Ser Cys Phe Gly Ser His Gly Asp Gln Cys
    690                 695                 700

Met Ser Cys Lys Tyr Gly Tyr Phe Leu Asn Glu Glu Thr Asn Ser Cys
705                 710                 715                 720

Val Thr His Cys Pro Asp Gly Ser Tyr Gln Asp Thr Lys Lys Asn Leu
                725                 730                 735

Cys Arg Lys Cys Ser Glu Asn Cys Lys Thr Cys Thr Glu Phe His Asn
            740                 745                 750

Cys Thr Glu Cys Arg Asp Gly Leu Ser Leu Gln Gly Ser Arg Cys Ser
        755                 760                 765

Val Ser Cys Glu Asp Gly Arg Tyr Phe Asn Gly Gln Asp Cys Gln Pro
    770                 775                 780

Cys His Arg Phe Cys Ala Thr Cys Ala Gly Ala Gly Ala Asp Gly Cys
785                 790                 795                 800

Ile Asn Cys Thr Glu Gly Tyr Phe Met Glu Asp Gly Arg Cys Val Gln
```

-continued

```
                805                 810                 815

Ser Cys Ser Ile Ser Tyr Tyr Phe Asp His Ser Ser Glu Asn Gly Tyr
            820                 825                 830

Lys Ser Cys Lys Lys Cys Asp Ile Ser Cys Leu Thr Cys Asn Gly Pro
        835                 840                 845

Gly Phe Lys Asn Cys Thr Ser Cys Pro Ser Gly Tyr Leu Leu Asp Leu
    850                 855                 860

Gly Met Cys Gln Met Gly Ala Ile Cys Lys Asp Gly Glu Tyr Val Asp
865                 870                 875                 880

Glu His Gly His Cys Gln Thr Cys Glu Ala Ser Cys Ala Lys Cys Gln
                885                 890                 895

Gly Pro Thr Gln Glu Asp Cys Thr Thr Cys Pro Met Thr Arg Ile Phe
            900                 905                 910

Asp Asp Gly Arg Cys Val Ser Asn Cys Pro Ser Trp Lys Phe Glu Phe
        915                 920                 925

Glu Asn Gln Cys His Pro Cys His His Thr Cys Gln Arg Cys Gln Gly
    930                 935                 940

Ser Gly Pro Thr His Cys Thr Ser Cys Gly Ala Asp Asn Tyr Gly Arg
945                 950                 955                 960

Glu His Phe Leu Tyr Gln Gly Glu Cys Gly Asp Ser Cys Pro Glu Gly
                965                 970                 975

His Tyr Ala Thr Glu Gly Asn Thr Cys Leu Pro Cys Pro Asp Asn Cys
            980                 985                 990

Glu Leu Cys His Ser Val His Val  Cys Thr Arg Cys Met  Lys Gly Tyr
        995                 1000                1005

Phe Ile  Ala Pro Thr Asn His  Thr Cys Gln Lys Leu  Glu Cys Gly
    1010                1015                1020

Gln Gly  Glu Val Gln Asp Pro  Asp Tyr Glu Glu Cys  Val Pro Cys
    1025                1030                1035

Glu Glu  Gly Cys Leu Gly Cys  Ser Leu Asp Asp Pro  Gly Thr Cys
    1040                1045                1050

Thr Ser  Cys Ala Met Gly Tyr  Tyr Arg Phe Asp His  His Cys Tyr
    1055                1060                1065

Lys Thr  Cys Pro Glu Lys Thr  Tyr Ser Glu Glu Val  Glu Cys Lys
    1070                1075                1080

Ala Cys  Asp Ser Asn Cys Gly  Ser Cys Asp Gln Asn  Gly Cys Tyr
    1085                1090                1095

Trp Cys  Glu Glu Gly Phe Phe  Leu Leu Gly Gly Ser  Cys Val Arg
    1100                1105                1110

Lys Cys  Gly Pro Gly Phe Tyr  Gly Asp Gln Glu Met  Gly Glu Cys
    1115                1120                1125

Glu Ser  Cys His Arg Ala Cys  Glu Thr Cys Thr Gly  Pro Gly His
    1130                1135                1140

Asp Glu  Cys Ser Ser Cys Gln  Glu Gly Leu Gln Leu  Leu Arg Gly
    1145                1150                1155

Met Cys  Val His Ala Thr Lys  Thr Gln Glu Glu Gly  Lys Phe Trp
    1160                1165                1170

Asn Asp  Ile Leu Arg Lys Leu  Gln Pro Cys His Ser  Ser Cys Lys
    1175                1180                1185

Thr Cys  Asn Gly Ser Ala Thr  Leu Cys Thr Ser Cys  Pro Lys Gly
    1190                1195                1200

Ala Tyr  Leu Leu Ala Gln Ala  Cys Val Ser Ser Cys  Pro Gln Gly
    1205                1210                1215
```

```
Thr Trp  Pro Ser Val Arg Ser  Gly Ser Cys Glu Asn  Cys Thr Glu
    1220                 1225                 1230

Ala Cys  Ala Ile Cys Ser Gly  Ala Asp Leu Cys Lys  Lys Cys Gln
    1235                 1240                 1245

Met Gln  Pro Gly His Pro Leu  Phe Leu His Glu Gly  Arg Cys Tyr
    1250                 1255                 1260

Ser Lys  Cys Pro Glu Gly Ser  Tyr Ala Glu Asp Gly  Ile Cys Glu
    1265                 1270                 1275

Arg Cys  Ser Ser Pro Cys Arg  Thr Cys Glu Gly Asn  Ala Thr Asn
    1280                 1285                 1290

Cys His  Ser Cys Glu Gly Gly  His Val Leu His His  Gly Val Cys
    1295                 1300                 1305

Gln Glu  Asn Cys Pro Glu Arg  His Val Ala Val Lys  Gly Val Cys
    1310                 1315                 1320

Lys His  Cys Pro Glu Met Cys  Gln Asp Cys Ile His  Glu Lys Thr
    1325                 1330                 1335

Cys Lys  Glu Cys Thr Pro Glu  Phe Phe Leu His Asp  Asp Met Cys
    1340                 1345                 1350

His Gln  Ser Cys Pro Arg Gly  Phe Tyr Ala Asp Ser  Arg His Cys
    1355                 1360                 1365

Val Pro  Cys His Lys Asp Cys  Leu Glu Cys Ser Gly  Pro Lys Ala
    1370                 1375                 1380

Asp Asp  Cys Glu Leu Cys Leu  Glu Ser Ser Trp Val  Leu Tyr Asp
    1385                 1390                 1395

Gly Leu  Cys Leu Glu Glu Cys  Pro Ala Gly Thr Tyr  Tyr Glu Lys
    1400                 1405                 1410

Glu Thr  Lys Glu Cys Arg Asp  Cys His Lys Ser Cys  Leu Thr Cys
    1415                 1420                 1425

Ser Ser  Ser Gly Thr Cys Thr  Thr Cys Gln Lys Gly  Leu Ile Met
    1430                 1435                 1440

Asn Pro  Arg Gly Ser Cys Met  Ala Asn Glu Lys Cys  Ser Pro Ser
    1445                 1450                 1455

Glu Tyr  Trp Asp Glu Asp Ala  Pro Gly Cys Lys Pro  Cys His Val
    1460                 1465                 1470

Lys Cys  Phe His Cys Met Gly  Pro Ala Glu Asp Gln  Cys Gln Thr
    1475                 1480                 1485

Cys Pro  Met Asn Ser Leu Leu  Leu Asn Thr Thr Cys  Val Lys Asp
    1490                 1495                 1500

Cys Pro  Glu Gly Tyr Tyr Ala  Asp Glu Asp Ser Asn  Arg Cys Ala
    1505                 1510                 1515

His Cys  His Ser Ser Cys Arg  Thr Cys Glu Gly Arg  His Ser Arg
    1520                 1525                 1530

Gln Cys  His Ser Cys Arg Pro  Gly Trp Phe Gln Leu  Gly Lys Glu
    1535                 1540                 1545

Cys Leu  Leu Gln Cys Arg Glu  Gly Tyr Tyr Ala Asp  Asn Ser Thr
    1550                 1555                 1560

Gly Arg  Cys Glu Arg Cys Asn  Arg Ser Cys Lys Gly  Cys Gln Gly
    1565                 1570                 1575

Pro Arg  Pro Thr Asp Cys Leu  Ser Cys Asp Arg Phe  Phe Phe Leu
    1580                 1585                 1590

Leu Arg  Ser Lys Gly Glu Cys  His Arg Ser Cys Pro  Asp His Tyr
    1595                 1600                 1605
```

```
Tyr Val  Glu Gln Ser Thr Gln  Thr Cys Glu Arg Cys  His Pro Thr
    1610                 1615                 1620

Cys Asp  Gln Cys Lys Gly Lys  Gly Ala Leu Asn Cys  Leu Ser Cys
    1625                 1630                 1635

Val Trp  Ser Tyr His Leu Met  Gly Gly Ile Cys Thr  Ser Asp Cys
    1640                 1645                 1650

Leu Val  Gly Glu Tyr Arg Val  Gly Glu Gly Glu Lys  Phe Asn Cys
    1655                 1660                 1665

Glu Lys  Cys His Glu Ser Cys  Met Glu Cys Lys Gly  Pro Gly Ala
    1670                 1675                 1680

Lys Asn  Cys Thr Leu Cys Pro  Ala Asn Leu Val Leu  His Met Asp
    1685                 1690                 1695

Asp Ser  His Cys Leu His Cys  Cys Asn Thr Ser Asp  Pro Pro Ser
    1700                 1705                 1710

Ala Gln  Glu Cys Cys Asp Cys  Gln Asp Thr Thr Asp  Glu Cys Ile
    1715                 1720                 1725

Leu Arg  Thr Ser Lys Val Arg  Pro Ala Thr Glu His  Phe Lys Thr
    1730                 1735                 1740

Ala Leu  Phe Ile Thr Ser Ser  Met Met Leu Val Leu  Leu Leu Gly
    1745                 1750                 1755

Ala Ala  Val Val Val Trp Lys  Lys Ser Arg Gly Arg  Val Gln Pro
    1760                 1765                 1770

Ala Ala  Lys Ala Gly Tyr Glu  Lys Leu Ala Asp Pro  Asn Lys Ser
    1775                 1780                 1785

Tyr Ser  Ser Tyr Lys Ser Ser  Tyr Arg Glu Ser Thr  Ser Phe Glu
    1790                 1795                 1800

Glu Asp  Gln Val Ile Glu Tyr  Arg Asp Arg Asp Tyr  Asp Glu Asp
    1805                 1810                 1815

Asp Asp  Asp Asp Ile Val Tyr  Met Gly Gln Asp Gly  Thr Val Tyr
    1820                 1825                 1830

Arg Lys  Phe Lys Tyr Gly Leu  Leu Asp Asp Asp Asp  Ile Asp Glu
    1835                 1840                 1845

Leu Glu  Tyr Asp Asp Glu Ser  Tyr Ser Tyr Tyr Gln
    1850                 1855                 1860
```

<210> SEQ ID NO 58
<211> LENGTH: 9538
<212> TYPE: DNA
<213> ORGANISM: Homo sapiens

<400> SEQUENCE: 58

```
atttatgcag agcaggagct gctgccattg ccactcagaa tcctcgcgcg ctgctcggag      60

ccggagggag cgctgggagc gagcaagcga gcgtttggag cccgggccag cagagggggc     120

gcccggtcgc tgcctgtacc gctcccgctg gtcatctccg ccgcgctcgg gggcccccggg     180

aggagcgaga ccgagtcgga gagtccggga gccaagccgg gcgaaaccca actgcggagg     240

acgcccgccc cactcagcct cctcctgcgt ccgagccggg gagcatcgcc gagcgcccca     300

cgggccggag agctgggagc acaggtcccg gcagccccag ggatggtcta ggagccggcg     360

taaggctcgc tgctctgctc cctgccgggg ctagccgcct cctgccgatc gcccggggct     420

gcgagctgcg gcggcccggg gctgctcgcc gggcggcgca ggccggagaa gttagttgtg     480

cgcgccctta gtgcgcggaa ccagccagcg agcgagggag cagcgaggcg ccgggaccat     540

gggctggggg agccgctgct gctgcccggg acgtttggac ctgctgtgcg tgctggcgct     600
```

-continued

```
gctcgggggc tgcctgctcc ccgtgtgtcg gacgcgcgtc tacaccaacc actgggcagt    660
caaaatcgcc gggggcttcc cggaggccaa ccgtatcgcc agcaagtacg gattcatcaa    720
cataggacag ataggggccc tgaaggacta ctaccacttc taccatagca ggacgattaa    780
aaggtcagtt atctcgagca gagggaccca cagtttcatt tcaatggaac caaaggtgga    840
atggatccaa cagcaagtgg taaaaaagcg gacaaagagg gattatgact tcagtcgtgc    900
ccagtctacc tatttcaatg atcccaagtg gcccagcatg tggtatatgc actgcagtga    960
caatacacat ccctgccagt ctgacatgaa tatcgaagga gcctggaaga gaggctacac   1020
gggaaagaac attgtggtca ctatcctgga tgacggaatt gagagaaccc atccagatct   1080
gatgcaaaac tacgatgctc tggcaagttg cgacgtgaat gggaatgact tggacccaat   1140
gcctcgttat gatgcaagca acgagaacaa gcatgggact cgctgtgctg gagaagtggc   1200
agccgctgca aacaattcgc actgcacagt cggaattgct ttcaacgcca agatcggagg   1260
agtgcgaatg ctggacggag atgtcacgga catggttgaa gcaaaatcag ttagcttcaa   1320
cccccagcac gtgcacattt acagcgccag ctggggcccg gatgatgatg gcaagactgt   1380
ggacggacca gccccccctca cccggcaagc ctttgaaaac ggcgttagaa tggggcggag   1440
aggcctcggc tctgtgtttg tttgggcatc tggaaatggt ggaaggagca aagaccactg   1500
ctcctgtgat ggctacacca acagcatcta caccatctcc atcagcagca ctgcagaaag   1560
cggaaagaaa ccttggtacc tggaagagtg ttcatccacg ctggccacaa cctacagcag   1620
cggggagtcc tacgataaga aaatcatcac tacagatctg aggcagcgtt gcacggacaa   1680
ccacactggg acgtcagcct cagcccccat ggctgcaggc atcattgcgc tggccctgga   1740
agccaatccg tttctgacct ggagagacgt acagcatgtt attgtcagga cttcccgtgc   1800
gggacatttg aacgctaatg actggaaaac caatgctgct ggttttaagg tgagccatct   1860
ttatggattt ggactgatgg acgcagaagc catggtgatg gaggcagaga agtggaccac   1920
cgttccccgg cagcacgtgt gtgtggagag cacagaccga caaatcaaga caatccgccc   1980
taacagtgca gtgcgctcca tctacaaagc ttcaggctgc tcggataacc ccaaccgcca   2040
tgtcaactac ctggagcacg tcgttgtgcg catcaccatc acccaccccca ggagaggaga   2100
cctggccatc tacctgacct cgccctctgg aactaggtct cagcttttgg ccaacaggct   2160
atttgatcac tccatggaag gattcaaaaa ctgggagttc atgaccattc attgctgggg   2220
agaaagagct gctggtgact gggtccttga agtttatgat actccctctc agctaaggaa   2280
ctttaagact ccaggtaaat tgaaagaatg gtctttggtc ctctacggca cctccgtgca   2340
gccatattca ccaaccaatg aatttccgaa agtggaacgg ttccgctata gccgagttga   2400
agaccccaca gacgactatg gcacagagga ttatgcaggt ccctgcgacc ctgagtgcag   2460
tgaggttggc tgtgacgggc caggaccaga ccactgcaat gactgtttgc actactacta   2520
caagctgaaa aacaatacca ggatctgtgt ctccagctgc ccccctggcc actaccacgc   2580
cgacaagaag cgctgcagga agtgtgcccc caactgtgag tcctgctttg ggagccatgg   2640
tgaccaatgc atgtcctgca aatatggata ctttctgaat gaagaaacca acagctgtgt   2700
tactcactgc cctgatgggt catatcagga taccaagaaa aatctttgcc ggaaatgcag   2760
tgaaaactgc aagacatgta ctgaattcca taactgtaca gaatgtaggg atgggttaag   2820
cctgcaggga tcccggtgct ctgtctcctg tgaagatgga cggtatttca acggccagga   2880
ctgccagccc tgccaccgct tctgcgccac ttgtgctggg gcaggagctg atgggtgcat   2940
taactgcaca gagggctact tcatggagga tgggagatgc gtgcagagct gtagtatcag   3000
```

-continued ctattacttt gaccactctt cagagaatgg atacaaatcc tgcaaaaaat gtgatatcag 3060
ttgtttgacg tgcaatggcc caggattcaa gaactgtaca agctgcccta gtgggtatct 3120
cttagactta ggaatgtgtc aaatgggagc catttgcaag gatggagaat atgttgatga 3180
gcatggccac tgccagacct gtgaggcctc atgtgccaag tgccagggac caacccagga 3240
agactgcact acctgcccca tgacaaggat tttgatgat ggccgctgtg tttcgaactg 3300
cccctcatgg aaatttgaat ttgagaacca atgccatcca tgccaccaca cctgccagag 3360
atgccaagga agtggcccta cccactgcac ctcctgtgga gcagacaact atggccgaga 3420
gcacttcctg taccagggag agtgtggaga tagctgccca gagggccact atgccactga 3480
ggggaacacc tgcctgccct gcccagacaa ctgtgagctt tgccacagcg tgcatgtctg 3540
cacaagatgc atgaagggct acttcatagc gcccaccaac cacacatgcc agaagttaga 3600
gtgtggacaa ggtgaagtcc aagacccaga ctatgaagaa tgtgtccctt gtgaagaagg 3660
atgtctggga tgcagcttgg atgatccagg aacatgtaca tcttgcgcta tggggtatta 3720
caggtttgat caccattgtt ataaaacctg tcctgagaag acctacagtg aggaagtgga 3780
atgcaaggcg tgtgatagta actgtggcag ctgtgaccag aatgggtgtt actggtgtga 3840
agagggcttc tttctcttag gtggcagttg tgtgaggaaa tgtggtcctg gattctatgg 3900
tgaccaagaa atgggagaat gtgagtcctg ccaccgagca tgcgaaacct gcacaggccc 3960
tggtcatgac gagtgcagca gctgccagga aggactgcag ctgctgcgtg ggatgtgcgt 4020
gcatgccacc aagacccagg aggagggcaa attctggaat gatattttga gaaaactcca 4080
gccttgtcat tcttcttgta aaacctgcaa tggatctgca actctgtgca cttcatgtcc 4140
caaaggtgca tatcttctgg ctcaggcctg tgtttcctcc tgtccccaag gcacatggcc 4200
ttccgtaagg agtgggagct gcgagaactg tacggaggcc tgtgccatct gctctggagc 4260
cgatctttgc aaaaaatgcc agatgcagcc gggccaccct ctcttcctcc atgaaggcag 4320
gtgctactcc aagtgcccgg agggctctta tgcagaagac ggcatatgtg aacgctgtag 4380
ctctccttgc agaacatgtg aaggaaacgc caccaactgc cattcttgtg aaggaggcca 4440
cgtcctgcac cacggagtgt gccaggaaaa ctgccccgag aggcacgtgg ctgtgaaggg 4500
ggtatgcaag cattgcccag agatgtgtca ggactgcatc catgagaaaa catgcaaaga 4560
gtgcacgcct gagttcttcc tgcacgatga tatgtgccac cagtcctgtc cccgtggctt 4620
ctatgcagac tcgcgccact gtgtcccctg ccataaagac tgtctggagt gcagtggccc 4680
caaagccgac gactgcgagc tctgtcttga gagttcctgg gtcctctatg atggactgtg 4740
cttggaggag tgtccagcag gaacctatta tgaaaaggag actaaggagt gcagagattg 4800
ccacaagtcc tgcttgacct gctcatcatc tgggacctgc accacctgtc agaaaggcct 4860
gatcatgaac cctcgtggga gctgcatggc caacgagaag tgctcaccct ccgagtactg 4920
ggatgaggat gctcccgggt gcaagccctg ccatgttaag tgcttccact gcatggggcc 4980
ggcggaggac cagtgtcaaa catgccccat gaacagcctt cttctcaaca caacctgtgt 5040
gaaggactgc ccagagggct attatgccga tgaggacagc aaccggtgtg cccactgcca 5100
cagctcttgc aggacatgtg aagggagaca cagcaggcag tgccactcct gccgaccggg 5160
ctggttccag ctaggaaaag agtgcctgct ccagtgcagg gaaggatatt acgcagacaa 5220
ctccactggc cggtgtgaga ggtgcaacag gagctgcaag ggtgccagg gcccacggcc 5280
cacagactgc ctgtcttgcg atagattttt ctttctgctc cgctccaaag gagagtgtca 5340

-continued

```
tcgctcctgc ccagaccatt actatgtaga gcaaagcaca cagacctgtg agagatgcca   5400
tccgacttgt gatcaatgca aaggaaaagg agcgttgaat tgtttatcct gtgtgtggag   5460
ttaccacctc atgggaggga tctgcacctc ggactgtctt gtgggggaat acagagtggg   5520
agagggagag aagtttaact gtgaaaaatg ccacgagagc tgcatggaat gcaagggacc   5580
aggggccaag aactgcacct tgtgccctgc caacctggtg ctgcacatgg acgacagcca   5640
ctgcctccac tgctgcaaca cctctgatcc ccccagtgcc caggagtgct gtgactgcca   5700
ggacaccacg gacgaatgca tccttcgaac aagcaaggtt aggcctgcaa ctgagcattt   5760
caagacagct ctgttcatca cctcctccat gatgctggtg cttctgctcg ggcagctgt    5820
ggtagtgtgg aagaaatctc gtggccgagt ccagccagca gcaaaggccg gctatgaaaa   5880
actggccgac cccaacaagt cttactcctc ctataagagc agctatagag agagcaccag   5940
ctttgaagag gatcaggtga ttgagtacag ggatcgggac tatgatgagg atgatgatga   6000
tgacatcgtc tacatgggcc aggatggcac agtctaccgg aaatttaaat atgggctgct   6060
ggatgacgat gacatagatg agctggaata tgatgacgag agttactcct actaccagta   6120
aacaggcact cccccaccaa caccaccatt ccactctcag gcatgcctgt gagcatcact   6180
gtttttggtt ttatccccac accaggctga tgtgtgagtt tttctatttg tcttctttaa   6240
ccatgagtcc aaccagaata tgtaagaatg atgaaatact ttgttcttct tttgagtggc   6300
taaactcaat taacagttcc tgttcaaccg taattgaaga gcaaggataa aattcagagg   6360
cattttcctc aaaataatgt gttaagacac aaaaatgaag gaagtgaaaa caaatgagat   6420
ttgtacaaac tcttctatgt gattttaaaa aaaggacagc agatctatag aaattctgtt   6480
tccgagctgc attgtggagg tgtctgctgc ctcctggtat tctaattttt ctttatctaa   6540
ttttggggat aatggaggta caaaggagtt gttggtttgg tggtgttttt cttcccttta   6600
gctgtcttta ggcagaaatt tgttttgtaa gggccaagaa aagagggctc ttatcaattg   6660
actccaggcc acccctggtg agcagaagag accacctggg ctgggctgct caggacctac   6720
ttgagataag ggaagaaaag agaaggtgca tcatagctga ggagccatga ggtcacccca   6780
ggccctagtt cctccgcagg aatccagagt cacaacaatt ctaaaggcag agcaagccca   6840
gcgagaaaga aataactgaa tttccaggaa ctgcactctc atgattttct gggtactttt   6900
cgcctgggag acatcagcta agacatcgaa taataaaaga aaaatggcag tgttaaccta   6960
acataaaatg gaataaaatg acaaacactt catccgctct aaaaaattca gagctttcct   7020
tcatcaacaa cccatcacaa aaccgtggac tctcaataga aagagttgga atagagtcta   7080
acatggaaaa aaaaaaatcc caatatgctg ctcacaagct gtactctagc tgctgaccag   7140
ccttccagca ctgctcatca ctatgatttt tgtttctaga cttcctaggc ttcctttttt   7200
ccattcttct gtcaagtgta ttcttggatt catgcaactg aggacagttt ttgtccagat   7260
tgtaacacag agaagggctc ttgctatgca aaatgatgtt ggcagggtct tacagatttc   7320
cttgtcaaaa tagaccttac aggcagtact agaaatggag caccagaaag caaaaatgac   7380
attttcagag aatgatgata attataatct attgcacacc tactaccaga taacaagcta   7440
agtaattccc ccccaaaaat gccccactta tccattttgg tacttaccat actcccatga   7500
ggttggtatt gctattattc tgttcttgta ggaaacctga ggcttacaag aggttaggta   7560
actagtccaa ggtcatgcaa agctcaacaa aattcaagaa aaaagaatga tcaccctaaa   7620
gcgtgtgttc ttataactat gctactgaaa taaggtggga aaataagcat cctaaatata   7680
attaaagtca tgcctattgt tttagtctat aatatcaatg ttatctttac taaattcatg   7740
```

gattttcttt ttttaacata atgtatcact gacacagaaa atctttatga agaagtcttc 7800
agtttactaa aggcttgtgc ttctttagag gaaagctctt aaaacagggt tgacaaacag 7860
tctctggaaa gagccagcta gtaagtacat taggctttct tggccagaaa gtctctgtca 7920
taaccactca gctctgctat tatagcatga atgcagctgg tacataacgg atgggtgagc 7980
tgtgcttcaa taaaacctta tttatggaca ctgacatttg aaattcaggt aattttcaca 8040
tattataaaa ttttattctt cttttgattt ttttcaacct tttaaaattt aaaaatgcaa 8100
aagctattct cagttcacag cattacaaga acaggtggtg ggtcagattt ggccaacagg 8160
ctgtactttg ctgactttat ctttaaaaca gttttcagag atcatacatg tacatgtatg 8220
atatgcctcc aaaaattttg atcatttaaa attatctcct tggccaggcg tggtggctca 8280
tacctctaat cctagcactt tgggagactg aggcaggcag atcacctgaa gtcaggagtt 8340
tgataccagc ttagccaaca tggtgaaacc ccatttctac taaaaataca ataaaaatct 8400
gggcatgttg gtgcacacct gtaatcccag ctactcagga ggctgaggca ggcaaatcac 8460
ttgagcccgg gaggcagagg ttgcagtgag cggagatggc accattgcac tccagcctgg 8520
gtgacagagc aagactccat ctcaaaaaat aagtaactaa ctaactaact aaataaataa 8580
ataaataaaa ttatctcctt gccaggactg ctggctcatg cctgtaatcc cagcactctg 8640
ggaggctaag gcaggaggat tgctgaccca ccacctgttc ttgagcccag gagttcgaca 8700
tcagccttgg acaacatagt gagactcccg tgtctacaaa aaatttaaaa attagccagg 8760
catggtggca agtgtctgta gtctcagcta ctcaggaggc taaggtggaa ggatcacttg 8820
aacccgggag gtcgaggctg cagtgagctg tgatcttgct attgcacttc agcctgaatg 8880
acagagctaa gaccctgact caaaataaat aaataacatt atctcttcaa aatgtatctg 8940
aagccctgat agttctactt tcaattctta gaaacatata aaaatatatg catgatagcc 9000
atcatatcaa tggaagactt tctcacctct gtggttgcag ttagcttaca aaaacgagca 9060
attttgctta tactgtgttg ttcatcttcc ttgttaattc taaagctctg atagactgag 9120
tttgacattt ctttctgtaa actggaaatt gttttctatg aaaaaaaaac tctatgatac 9180
acagttaaag attggttgag gttgagatga acttcaatac taagaaaaat tgtggtgttc 9240
ctctgtgtgg cctgcaatga aaagaaggct catgcttgtg tattgaggtt tgacatcttt 9300
ccttctttgt ttttagtcat gcaacgtcat tcttagatgg cttttgaata ctatgctaat 9360
gactatctaa atagataaat atgtgattgg aaaacaaagt caccttttag ttttctactt 9420
ggaaatatta agagaatcct tgtagactgg aaacacacca aaaggctggg taaagcatgg 9480
gaggttccag ttaatagaaa gtaattttaa aattggaaat aaaattaaat caagacca 9538

<210> SEQ ID NO 59
<211> LENGTH: 5052
<212> TYPE: DNA
<213> ORGANISM: Artificial Sequence
<220> FEATURE:
<223> OTHER INFORMATION: B-domain deleted FVIII Fc chain (S743/Q1638)

<400> SEQUENCE: 59
atgcaaatag agctctccac ctgcttcttt ctgtgccttt tgcgattctg ctttagtgcc 60
accagaagat actacctggg tgcagtggaa ctgtcatggg actatatgca aagtgatctc 120
ggtgagctgc ctgtggacgc aagatttcct cctagagtgc caaaatcttt tccattcaac 180
acctcagtcg tgtacaaaaa gactctgttt gtagaattca cggatcacct tttcaacatc 240

-continued

```
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaacgc catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
```

-continued

```
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
tttgctctgt tttcaccat ctttgatgag accaaaagct ggtacttcac tgaaaatatg    3060
gaaagaaact gcagggctcc ctgcaatatc cagatggaag atcccacttt taaagagaat   3120
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtggacatgt gttcactgta cgaaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg ggatgagcac actttttctg   3420
gtgtacagca ataagtgtca gactcccctg ggaatggctt ctggacacat tagagatttt   3480
cagattacag cttcaggaca atatggacag tgggccccaa agctggccag acttcattat   3540
tccggatcaa tcaatgcctg gagcaccaag gagccctttt cttggatcaa ggtggatctg   3600
ttggcaccaa tgattattca cggcatcaag acccagggtg cccgtcagaa gttctccagc   3660
ctctacatct ctcagtttat catcatgtat agtcttgatg ggaagaagtg gcagacttat   3720
cgaggaaatt ccactggaac cttaatggtc ttctttggca atgtggattc atctgggata   3780
aaacacaata tttttaaccc tccaattatt gctcgataca tccgtttgca cccaactcat   3840
tatagcattc gcagcactct tcgcatggag ttgatgggct gtgatttaaa tagttgcagc   3900
atgccattgg gaatggagag taaagcaata tcagatgcac agattactgc ttcatcctac   3960
tttaccaata tgtttgccac ctggtctcct tcaaaagctc gacttcacct ccaagggagg   4020
agtaatgcct ggagacctca ggtgaataat ccaaaagagt ggctgcaagt ggacttccag   4080
aagacaatga aagtcacagg agtaactact cagggagtaa aatctctgct taccagcatg   4140
tatgtgaagg agttcctcat ctccagcagt caagatggcc atcagtggac tctctttttt   4200
cagaatggca aagtaaaggt ttttcaggga aatcaagact ccttcacacc tgtggtgaac   4260
tctctagacc caccgttact gactcgctac cttcgaattc acccccagag ttgggtgcac   4320
cagattgccc tgaggatgga ggttctgggc tgcgaggcac aggacctcta cgacaaaact   4380
cacacatgcc caccgtgccc agctccagaa ctcctgggcg gaccgtcagt cttcctcttc   4440
cccccaaaac ccaaggacac cctcatgatc tcccggaccc ctgaggtcac atgcgtggtg   4500
gtggacgtga gccacgaaga ccctgaggtc aagttcaact ggtacgtgga cggcgtggag   4560
gtgcataatg ccaagacaaa gccgcgggag gagcagtaca acagcacgta ccgtgtggtc   4620
agcgtcctca ccgtcctgca ccaggactgg ctgaatggca aggagtacaa gtgcaaggtc   4680
tccaacaaag ccctcccagc ccccatcgag aaaaccatct ccaaagccaa agggcagccc   4740
cgagaaccac aggtgtacac cctgccccca tcccgggatg agctgaccaa gaaccaggtc   4800
agcctgacct gcctggtcaa aggcttctat cccagcgaca tcgccgtgga gtgggagagc   4860
aatgggcagc cggagaacaa ctacaagacc acgcctcccg tgttggactc cgacggctcc   4920
ttcttcctct acagcaagct caccgtggac aagagcaggt ggcagcaggg gaacgtcttc   4980
```

```
tcatgctccg tgatgcatga ggctctgcac aaccactaca cgcagaagag cctctccctg   5040

tctccgggta aa                                                       5052


<210> SEQ ID NO 60
<211> LENGTH: 1684
<212> TYPE: PRT
<213> ORGANISM: Artificial Sequence
<220> FEATURE:
<223> OTHER INFORMATION: B-domain deleted FVIIIFc Chain (S743/Q1638)

<400> SEQUENCE: 60

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350
```

-continued

```
Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765
```

-continued

```
Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
```

1175 1180 1185

Thr Lys Glu Pro Phe Ser Trp Ile Lys Val Asp Leu Leu Ala Pro
1190 1195 1200

Met Ile Ile His Gly Ile Lys Thr Gln Gly Ala Arg Gln Lys Phe
1205 1210 1215

Ser Ser Leu Tyr Ile Ser Gln Phe Ile Ile Met Tyr Ser Leu Asp
1220 1225 1230

Gly Lys Lys Trp Gln Thr Tyr Arg Gly Asn Ser Thr Gly Thr Leu
1235 1240 1245

Met Val Phe Phe Gly Asn Val Asp Ser Ser Gly Ile Lys His Asn
1250 1255 1260

Ile Phe Asn Pro Pro Ile Ile Ala Arg Tyr Ile Arg Leu His Pro
1265 1270 1275

Thr His Tyr Ser Ile Arg Ser Thr Leu Arg Met Glu Leu Met Gly
1280 1285 1290

Cys Asp Leu Asn Ser Cys Ser Met Pro Leu Gly Met Glu Ser Lys
1295 1300 1305

Ala Ile Ser Asp Ala Gln Ile Thr Ala Ser Ser Tyr Phe Thr Asn
1310 1315 1320

Met Phe Ala Thr Trp Ser Pro Ser Lys Ala Arg Leu His Leu Gln
1325 1330 1335

Gly Arg Ser Asn Ala Trp Arg Pro Gln Val Asn Asn Pro Lys Glu
1340 1345 1350

Trp Leu Gln Val Asp Phe Gln Lys Thr Met Lys Val Thr Gly Val
1355 1360 1365

Thr Thr Gln Gly Val Lys Ser Leu Leu Thr Ser Met Tyr Val Lys
1370 1375 1380

Glu Phe Leu Ile Ser Ser Ser Gln Asp Gly His Gln Trp Thr Leu
1385 1390 1395

Phe Phe Gln Asn Gly Lys Val Lys Val Phe Gln Gly Asn Gln Asp
1400 1405 1410

Ser Phe Thr Pro Val Val Asn Ser Leu Asp Pro Pro Leu Leu Thr
1415 1420 1425

Arg Tyr Leu Arg Ile His Pro Gln Ser Trp Val His Gln Ile Ala
1430 1435 1440

Leu Arg Met Glu Val Leu Gly Cys Glu Ala Gln Asp Leu Tyr Asp
1445 1450 1455

Lys Thr His Thr Cys Pro Pro Cys Pro Ala Pro Glu Leu Leu Gly
1460 1465 1470

Gly Pro Ser Val Phe Leu Phe Pro Pro Lys Pro Lys Asp Thr Leu
1475 1480 1485

Met Ile Ser Arg Thr Pro Glu Val Thr Cys Val Val Val Asp Val
1490 1495 1500

Ser His Glu Asp Pro Glu Val Lys Phe Asn Trp Tyr Val Asp Gly
1505 1510 1515

Val Glu Val His Asn Ala Lys Thr Lys Pro Arg Glu Glu Gln Tyr
1520 1525 1530

Asn Ser Thr Tyr Arg Val Val Ser Val Leu Thr Val Leu His Gln
1535 1540 1545

Asp Trp Leu Asn Gly Lys Glu Tyr Lys Cys Lys Val Ser Asn Lys
1550 1555 1560

Ala Leu Pro Ala Pro Ile Glu Lys Thr Ile Ser Lys Ala Lys Gly
1565 1570 1575

```
Gln Pro  Arg Glu Pro Gln Val  Tyr Thr Leu Pro Pro  Ser Arg Asp
    1580                 1585                 1590

Glu Leu  Thr Lys Asn Gln Val  Ser Leu Thr Cys Leu  Val Lys Gly
    1595                 1600                 1605

Phe Tyr  Pro Ser Asp Ile Ala  Val Glu Trp Glu Ser  Asn Gly Gln
    1610                 1615                 1620

Pro Glu  Asn Asn Tyr Lys Thr  Thr Pro Pro Val Leu  Asp Ser Asp
    1625                 1630                 1635

Gly Ser  Phe Phe Leu Tyr Ser  Lys Leu Thr Val Asp  Lys Ser Arg
    1640                 1645                 1650

Trp Gln  Gln Gly Asn Val Phe  Ser Cys Ser Val Met  His Glu Ala
    1655                 1660                 1665

Leu His  Asn His Tyr Thr Gln  Lys Ser Leu Ser Leu  Ser Pro Gly
    1670                 1675                 1680

Lys
```

<210> SEQ ID NO 61
<211> LENGTH: 7734
<212> TYPE: DNA
<213> ORGANISM: Artificial Sequence
<220> FEATURE:
<223> OTHER INFORMATION: Full length FVIIIFc chain

<400> SEQUENCE: 61

```
atgcaaatag agctctccac ctgcttcttt ctgtgccttt tgcgattctg ctttagtgcc     60

accagaagat actacctggg tgcagtggaa ctgtcatggg actatatgca aagtgatctc    120

ggtgagctgc ctgtggacgc aagatttcct cctagagtgc caaaatcttt tccattcaac    180

acctcagtcg tgtacaaaaa gactctgttt gtagaattca cggatcacct tttcaacatc    240

gctaagccaa ggccaccctg gatgggtctg ctaggtccta ccatccaggc tgaggtttat    300

gatacagtgg tcattacact taagaacatg gcttcccatc ctgtcagtct tcatgctgtt    360

ggtgtatcct actggaaagc ttctgaggga gctgaatatg atgatcagac cagtcaaagg    420

gagaaagaag atgataaagt cttccctggt ggaagccata catatgtctg gcaggtcctg    480

aaagagaatg gtccaatggc ctctgaccca ctgtgcctta cctactcata tctttctcat    540

gtggacctgg taaaagactt gaattcaggc ctcattggag ccctactagt atgtagagaa    600

gggagtctgg ccaaggaaaa gacacagacc ttgcacaaat ttatactact ttttgctgta    660

tttgatgaag ggaaaagttg gcactcagaa acaaagaact ccttgatgca ggatagggat    720

gctgcatctg ctcgggcctg gcctaaaatg cacacagtca atggttatgt aaacaggtct    780

ctgccaggtc tgattggatg ccacaggaaa tcagtctatt ggcatgtgat tggaatgggc    840

accactcctg aagtgcactc aatattcctc gaaggtcaca catttcttgt gaggaaccat    900

cgccaggcgt ccttggaaat ctcgccaata actttcctta ctgctcaaac actcttgatg    960

gaccttggac agtttctact gttttgtcat atctcttccc accaacatga tggcatggaa   1020

gcttatgtca aagtagacag ctgtccagag gaaccccaac tacgaatgaa aaataatgaa   1080

gaagcggaag actatgatga tgatcttact gattctgaaa tggatgtggt caggtttgat   1140

gatgacaact ctccttcctt tatccaaatt cgctcagttg ccaagaagca tcctaaaact   1200

tgggtacatt acattgctgc tgaagaggag gactgggact atgctccctt agtcctcgcc   1260

cccgatgaca gaagttataa aagtcaatat ttgaacaatg gccctcagcg gattggtagg   1320

aagtacaaaa aagtccgatt tatggcatac acagatgaaa cctttaagac tcgtgaagct   1380
```

-continued

```
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaga attcaagaca ccctagcact aggcaaaagc aatttaatgc caccacaatt   2340
ccagaaaatg acatagagaa gactgaccct tggtttgcac acagaacacc tatgcctaaa   2400
atacaaaatg tctcctctag tgatttgttg atgctcttgc gacagagtcc tactccacat   2460
gggctatcct tatctgatct ccaagaagcc aaatatgaga ctttttctga tgatccatca   2520
cctggagcaa tagacagtaa taacagcctg tctgaaatga cacacttcag gccacagctc   2580
catcacagtg gggacatggt atttacccct gagtcaggcc tccaattaag attaaatgag   2640
aaactgggga caactgcagc aacagagttg aagaaacttg atttcaaagt ttctagtaca   2700
tcaaataatc tgatttcaac aattccatca gacaatttgg cagcaggtac tgataataca   2760
agttccttag gacccccaag tatgccagtt cattatgata gtcaattaga taccactcta   2820
tttggcaaaa agtcatctcc ccttactgag tctggtggac ctctgagctt gagtgaagaa   2880
aataatgatt caaagttgtt agaatcaggt ttaatgaata gccaagaaag ttcatgggga   2940
aaaaatgtat cgtcaacaga gagtggtagg ttatttaaag ggaaaagagc tcatggacct   3000
gctttgttga ctaaagataa tgccttattc aaagttagca tctctttgtt aaagacaaac   3060
aaaacttcca ataattcagc aactaataga aagactcaca ttgatggccc atcattatta   3120
attgagaata gtccatcagt ctggcaaaat atattagaaa gtgacactga gtttaaaaaa   3180
gtgacacctt tgattcatga cagaatgctt atggacaaaa atgctacagc tttgaggcta   3240
aatcatatgt caaataaaac tacttcatca aaaaacatgg aaatggtcca acagaaaaaa   3300
gagggcccca ttccaccaga tgcacaaaat ccagatatgt cgttctttaa gatgctattc   3360
ttgccagaat cagcaaggtg gatacaaagg actcatggaa agaactctct gaactctggg   3420
caaggcccca gtccaaagca attagtatcc ttaggaccag aaaaatctgt ggaaggtcag   3480
aatttcttgt ctgagaaaaa caaagtggta gtaggaaagg gtgaatttac aaaggacgta   3540
ggactcaaag agatggtttt tccaagcagc agaaacctat ttcttactaa cttggataat   3600
ttacatgaaa ataatacaca caatcaagaa aaaaaaattc aggaagaaat agaaaagaag   3660
gaaacattaa tccaagagaa tgtagttttg cctcagatac atacagtgac tggcactaag   3720
```

```
aatttcatga agaacctttt cttactgagc actaggcaaa atgtagaagg ttcatatgac   3780
ggggcatatg ctccagtact tcaagatttt aggtcattaa atgattcaac aaatagaaca   3840
aagaaacaca cagctcattt ctcaaaaaaa ggggaggaag aaaacttgga aggcttggga   3900
aatcaaacca agcaaattgt agagaaatat gcatgcacca caaggatatc tcctaataca   3960
agccagcaga attttgtcac gcaacgtagt aagagagctt tgaaacaatt cagactccca   4020
ctagaagaaa cagaacttga aaaaaggata attgtggatg acacctcaac ccagtggtcc   4080
aaaaacatga aacatttgac cccgagcacc ctcacacaga tagactacaa tgagaaggag   4140
aaaggggcca ttactcagtc tcccttatca gattgcctta cgaggagtca tagcatccct   4200
caagcaaata gatctccatt acccattgca aaggtatcat catttccatc tattagacct   4260
atatatctga ccagggtcct attccaagac aactcttctc atcttccagc agcatcttat   4320
agaaagaaag attctggggt ccaagaaagc agtcatttct tacaaggagc caaaaaaaat   4380
aacctttctt tagccattct aaccttggag atgactggtg atcaaagaga ggttggctcc   4440
ctggggacaa gtgccacaaa ttcagtcaca tacaagaaag ttgagaacac tgttctcccg   4500
aaaccagact tgcccaaaac atctggcaaa gttgaattgc ttccaaaagt tcacatttat   4560
cagaaggacc tattccctac ggaaactagc aatgggtctc ctggccatct ggatctcgtg   4620
gaagggagcc ttcttcaggg aacagaggga gcgattaagt ggaatgaagc aaacagacct   4680
ggaaaagttc cctttctgag agtagcaaca gaaagctctg caaagactcc ctccaagcta   4740
ttggatcctc ttgcttggga taaccactat ggtactcaga taccaaaaga agagtggaaa   4800
tcccaagaga agtcaccaga aaaaacagct tttaagaaaa aggataccat tttgtccctg   4860
aacgcttgtg aaagcaatca tgcaatagca gcaataaatg agggacaaaa taagcccgaa   4920
atagaagtca cctgggcaaa gcaaggtagg actgaaaggc tgtgctctca aaacccacca   4980
gtcttgaaac gccatcaacg ggaaataact cgtactactc ttcagtcaga tcaagaggaa   5040
attgactatg atgataccat atcagttgaa atgaagaagg aagattttga catttatgat   5100
gaggatgaaa atcagagccc ccgcagcttt caaaagaaaa cacgacacta ttttattgct   5160
gcagtggaga ggctctggga ttatgggatg agtagctccc cacatgttct aagaaacagg   5220
gctcagagtg gcagtgtccc tcagttcaag aaagttgttt tccaggaatt tactgatggc   5280
tcctttactc agcccttata ccgtggagaa ctaaatgaac atttgggact cctggggcca   5340
tatataagag cagaagttga agataatatc atggtaactt tcagaaatca ggcctctcgt   5400
ccctattcct tctattctag ccttatttct tatgaggaag atcagaggca aggagcagaa   5460
cctagaaaaa actttgtcaa gcctaatgaa accaaaactt acttttggaa agtgcaacat   5520
catatggcac ccactaaaga tgagtttgac tgcaaagcct gggcttattt ctctgatgtt   5580
gacctggaaa aagatgtgca ctcaggcctg attggacccc ttctggtctg ccacactaac   5640
acactgaacc ctgctcatgg gagacaagtg acagtacagg aatttgctct gtttttcacc   5700
atctttgatg agaccaaaag ctggtacttc actgaaaata tggaaagaaa ctgcagggct   5760
ccctgcaata tccagatgga agatcccact tttaaagaga attatcgctt ccatgcaatc   5820
aatggctaca taatggatac actacctggc ttagtaatgg ctcaggatca aaggattcga   5880
tggtatctgc tcagcatggg cagcaatgaa aacatccatt ctattcattt cagtggacat   5940
gtgttcactg tacgaaaaaa agaggagtat aaaatggcac tgtacaatct ctatccaggt   6000
gtttttgaga cagtggaaat gttaccatcc aaagctggaa tttggcgggt ggaatgcctt   6060
attggcgagc atctacatgc tgggatgagc acactttttc tggtgtacag caataagtgt   6120
```

```
cagactcccc tgggaatggc ttctggacac attagagatt ttcagattac agcttcagga   6180

caatatggac agtgggcccc aaagctggcc agacttcatt attccggatc aatcaatgcc   6240

tggagcacca aggagccctt ttcttggatc aaggtggatc tgttggcacc aatgattatt   6300

cacggcatca agacccaggg tgcccgtcag aagttctcca gcctctacat ctctcagttt   6360

atcatcatgt atagtcttga tgggaagaag tggcagactt atcgaggaaa ttccactgga   6420

accttaatgg tcttctttgg caatgtggat tcatctggga taaaacacaa tatttttaac   6480

cctccaatta ttgctcgata catccgtttg cacccaactc attatagcat tcgcagcact   6540

cttcgcatgg agttgatggg ctgtgattta aatagttgca gcatgccatt gggaatggag   6600

agtaaagcaa tatcagatgc acagattact gcttcatcct actttaccaa tatgtttgcc   6660

acctggtctc cttcaaaagc tcgacttcac ctccaaggga ggagtaatgc ctggagacct   6720

caggtgaata atccaaaaga gtggctgcaa gtggacttcc agaagacaat gaaagtcaca   6780

ggagtaacta ctcagggagt aaaatctctg cttaccagca tgtatgtgaa ggagttcctc   6840

atctccagca gtcaagatgg ccatcagtgg actctctttt ttcagaatgg caaagtaaag   6900

gtttttcagg gaaatcaaga ctccttcaca cctgtggtga actctctaga cccaccgtta   6960

ctgactcgct accttcgaat tcacccccag agttgggtgc accagattgc cctgaggatg   7020

gaggttctgg gctgcgaggc acaggacctc tacgacaaaa ctcacacatg cccaccgtgc   7080

ccagctccag aactcctggg cggaccgtca gtcttcctct tccccccaaa acccaaggac   7140

accctcatga tctcccggac ccctgaggtc acatgcgtgg tggtggacgt gagccacgaa   7200

gaccctgagg tcaagttcaa ctggtacgtg gacggcgtgg aggtgcataa tgccaagaca   7260

aagccgcggg aggagcagta caacagcacg taccgtgtgg tcagcgtcct caccgtcctg   7320

caccaggact ggctgaatgg caaggagtac aagtgcaagg tctccaacaa agccctccca   7380

gcccccatcg agaaaaccat ctccaaagcc aaagggcagc cccgagaacc acaggtgtac   7440

accctgcccc catcccggga tgagctgacc aagaaccagg tcagcctgac ctgcctggtc   7500

aaaggcttct atcccagcga catcgccgtg gagtgggaga gcaatgggca gccggagaac   7560

aactacaaga ccacgcctcc cgtgttggac tccgacggct ccttcttcct ctacagcaag   7620

ctcaccgtgg acaagagcag gtggcagcag gggaacgtct tctcatgctc cgtgatgcat   7680

gaggctctgc acaaccacta cacgcagaag agcctctccc tgtctccggg taaa         7734
```

<210> SEQ ID NO 62
<211> LENGTH: 2578
<212> TYPE: PRT
<213> ORGANISM: Artificial Sequence
<220> FEATURE:
<223> OTHER INFORMATION: Full-length FVIIIFc chain

<400> SEQUENCE: 62

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80
```

```
Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495
```

His Gly Ile Thr Asp Val Arg Pro Leu Tyr Ser Arg Arg Leu Pro Lys
500 505 510

Gly Val Lys His Leu Lys Asp Phe Pro Ile Leu Pro Gly Glu Ile Phe
515 520 525

Lys Tyr Lys Trp Thr Val Thr Val Glu Asp Gly Pro Thr Lys Ser Asp
530 535 540

Pro Arg Cys Leu Thr Arg Tyr Tyr Ser Ser Phe Val Asn Met Glu Arg
545 550 555 560

Asp Leu Ala Ser Gly Leu Ile Gly Pro Leu Leu Ile Cys Tyr Lys Glu
565 570 575

Ser Val Asp Gln Arg Gly Asn Gln Ile Met Ser Asp Lys Arg Asn Val
580 585 590

Ile Leu Phe Ser Val Phe Asp Glu Asn Arg Ser Trp Tyr Leu Thr Glu
595 600 605

Asn Ile Gln Arg Phe Leu Pro Asn Pro Ala Gly Val Gln Leu Glu Asp
610 615 620

Pro Glu Phe Gln Ala Ser Asn Ile Met His Ser Ile Asn Gly Tyr Val
625 630 635 640

Phe Asp Ser Leu Gln Leu Ser Val Cys Leu His Glu Val Ala Tyr Trp
645 650 655

Tyr Ile Leu Ser Ile Gly Ala Gln Thr Asp Phe Leu Ser Val Phe Phe
660 665 670

Ser Gly Tyr Thr Phe Lys His Lys Met Val Tyr Glu Asp Thr Leu Thr
675 680 685

Leu Phe Pro Phe Ser Gly Glu Thr Val Phe Met Ser Met Glu Asn Pro
690 695 700

Gly Leu Trp Ile Leu Gly Cys His Asn Ser Asp Phe Arg Asn Arg Gly
705 710 715 720

Met Thr Ala Leu Leu Lys Val Ser Ser Cys Asp Lys Asn Thr Gly Asp
725 730 735

Tyr Tyr Glu Asp Ser Tyr Glu Asp Ile Ser Ala Tyr Leu Leu Ser Lys
740 745 750

Asn Asn Ala Ile Glu Pro Arg Ser Phe Ser Gln Asn Ser Arg His Pro
755 760 765

Ser Thr Arg Gln Lys Gln Phe Asn Ala Thr Thr Ile Pro Glu Asn Asp
770 775 780

Ile Glu Lys Thr Asp Pro Trp Phe Ala His Arg Thr Pro Met Pro Lys
785 790 795 800

Ile Gln Asn Val Ser Ser Ser Asp Leu Leu Met Leu Leu Arg Gln Ser
805 810 815

Pro Thr Pro His Gly Leu Ser Leu Ser Asp Leu Gln Glu Ala Lys Tyr
820 825 830

Glu Thr Phe Ser Asp Asp Pro Ser Pro Gly Ala Ile Asp Ser Asn Asn
835 840 845

Ser Leu Ser Glu Met Thr His Phe Arg Pro Gln Leu His His Ser Gly
850 855 860

Asp Met Val Phe Thr Pro Glu Ser Gly Leu Gln Leu Arg Leu Asn Glu
865 870 875 880

Lys Leu Gly Thr Thr Ala Ala Thr Glu Leu Lys Lys Leu Asp Phe Lys
885 890 895

Val Ser Ser Thr Ser Asn Asn Leu Ile Ser Thr Ile Pro Ser Asp Asn
900 905 910

Leu Ala Ala Gly Thr Asp Asn Thr Ser Ser Leu Gly Pro Pro Ser Met

-continued

```
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro  Ala Leu Leu Thr Lys  Asp Asn Ala
        995                 1000                1005

Leu Phe  Lys Val Ser Ile Ser  Leu Leu Lys Thr Asn  Lys Thr Ser
    1010                1015                1020

Asn Asn  Ser Ala Thr Asn Arg  Lys Thr His Ile Asp  Gly Pro Ser
    1025                1030                1035

Leu Leu  Ile Glu Asn Ser Pro  Ser Val Trp Gln Asn  Ile Leu Glu
    1040                1045                1050

Ser Asp  Thr Glu Phe Lys Lys  Val Thr Pro Leu Ile  His Asp Arg
    1055                1060                1065

Met Leu  Met Asp Lys Asn Ala  Thr Ala Leu Arg Leu  Asn His Met
    1070                1075                1080

Ser Asn  Lys Thr Thr Ser Ser  Lys Asn Met Glu Met  Val Gln Gln
    1085                1090                1095

Lys Lys  Glu Gly Pro Ile Pro  Pro Asp Ala Gln Asn  Pro Asp Met
    1100                1105                1110

Ser Phe  Phe Lys Met Leu Phe  Leu Pro Glu Ser Ala  Arg Trp Ile
    1115                1120                1125

Gln Arg  Thr His Gly Lys Asn  Ser Leu Asn Ser Gly  Gln Gly Pro
    1130                1135                1140

Ser Pro  Lys Gln Leu Val Ser  Leu Gly Pro Glu Lys  Ser Val Glu
    1145                1150                1155

Gly Gln  Asn Phe Leu Ser Glu  Lys Asn Lys Val Val  Val Gly Lys
    1160                1165                1170

Gly Glu  Phe Thr Lys Asp Val  Gly Leu Lys Glu Met  Val Phe Pro
    1175                1180                1185

Ser Ser  Arg Asn Leu Phe Leu  Thr Asn Leu Asp Asn  Leu His Glu
    1190                1195                1200

Asn Asn  Thr His Asn Gln Glu  Lys Lys Ile Gln Glu  Glu Ile Glu
    1205                1210                1215

Lys Lys  Glu Thr Leu Ile Gln  Glu Asn Val Val Leu  Pro Gln Ile
    1220                1225                1230

His Thr  Val Thr Gly Thr Lys  Asn Phe Met Lys Asn  Leu Phe Leu
    1235                1240                1245

Leu Ser  Thr Arg Gln Asn Val  Glu Gly Ser Tyr Asp  Gly Ala Tyr
    1250                1255                1260

Ala Pro  Val Leu Gln Asp Phe  Arg Ser Leu Asn Asp  Ser Thr Asn
    1265                1270                1275

Arg Thr  Lys Lys His Thr Ala  His Phe Ser Lys Lys  Gly Glu Glu
    1280                1285                1290

Glu Asn  Leu Glu Gly Leu Gly  Asn Gln Thr Lys Gln  Ile Val Glu
    1295                1300                1305

Lys Tyr  Ala Cys Thr Thr Arg  Ile Ser Pro Asn Thr  Ser Gln Gln
    1310                1315                1320
```

-continued

```
Asn Phe  Val Thr Gln Arg Ser  Lys Arg Ala Leu Lys  Gln Phe Arg
    1325                 1330                 1335

Leu Pro  Leu Glu Glu Thr Glu  Leu Glu Lys Arg Ile  Ile Val Asp
    1340                 1345                 1350

Asp Thr  Ser Thr Gln Trp Ser  Lys Asn Met Lys His  Leu Thr Pro
    1355                 1360                 1365

Ser Thr  Leu Thr Gln Ile Asp  Tyr Asn Glu Lys Glu  Lys Gly Ala
    1370                 1375                 1380

Ile Thr  Gln Ser Pro Leu Ser  Asp Cys Leu Thr Arg  Ser His Ser
    1385                 1390                 1395

Ile Pro  Gln Ala Asn Arg Ser  Pro Leu Pro Ile Ala  Lys Val Ser
    1400                 1405                 1410

Ser Phe  Pro Ser Ile Arg Pro  Ile Tyr Leu Thr Arg  Val Leu Phe
    1415                 1420                 1425

Gln Asp  Asn Ser Ser His Leu  Pro Ala Ala Ser Tyr  Arg Lys Lys
    1430                 1435                 1440

Asp Ser  Gly Val Gln Glu Ser  Ser His Phe Leu Gln  Gly Ala Lys
    1445                 1450                 1455

Lys Asn  Asn Leu Ser Leu Ala  Ile Leu Thr Leu Glu  Met Thr Gly
    1460                 1465                 1470

Asp Gln  Arg Glu Val Gly Ser  Leu Gly Thr Ser Ala  Thr Asn Ser
    1475                 1480                 1485

Val Thr  Tyr Lys Lys Val Glu  Asn Thr Val Leu Pro  Lys Pro Asp
    1490                 1495                 1500

Leu Pro  Lys Thr Ser Gly Lys  Val Glu Leu Leu Pro  Lys Val His
    1505                 1510                 1515

Ile Tyr  Gln Lys Asp Leu Phe  Pro Thr Glu Thr Ser  Asn Gly Ser
    1520                 1525                 1530

Pro Gly  His Leu Asp Leu Val  Glu Gly Ser Leu Leu  Gln Gly Thr
    1535                 1540                 1545

Glu Gly  Ala Ile Lys Trp Asn  Glu Ala Asn Arg Pro  Gly Lys Val
    1550                 1555                 1560

Pro Phe  Leu Arg Val Ala Thr  Glu Ser Ser Ala Lys  Thr Pro Ser
    1565                 1570                 1575

Lys Leu  Leu Asp Pro Leu Ala  Trp Asp Asn His Tyr  Gly Thr Gln
    1580                 1585                 1590

Ile Pro  Lys Glu Glu Trp Lys  Ser Gln Glu Lys Ser  Pro Glu Lys
    1595                 1600                 1605

Thr Ala  Phe Lys Lys Lys Asp  Thr Ile Leu Ser Leu  Asn Ala Cys
    1610                 1615                 1620

Glu Ser  Asn His Ala Ile Ala  Ala Ile Asn Glu Gly  Gln Asn Lys
    1625                 1630                 1635

Pro Glu  Ile Glu Val Thr Trp  Ala Lys Gln Gly Arg  Thr Glu Arg
    1640                 1645                 1650

Leu Cys  Ser Gln Asn Pro Pro  Val Leu Lys Arg His  Gln Arg Glu
    1655                 1660                 1665

Ile Thr  Arg Thr Thr Leu Gln  Ser Asp Gln Glu Glu  Ile Asp Tyr
    1670                 1675                 1680

Asp Asp  Thr Ile Ser Val Glu  Met Lys Lys Glu Asp  Phe Asp Ile
    1685                 1690                 1695

Tyr Asp  Glu Asp Glu Asn Gln  Ser Pro Arg Ser Phe  Gln Lys Lys
    1700                 1705                 1710
```

-continued

```
Thr Arg  His Tyr Phe Ile Ala  Ala Val Glu Arg Leu  Trp Asp Tyr
    1715                 1720                 1725

Gly Met  Ser Ser Ser Pro His  Val Leu Arg Asn Arg  Ala Gln Ser
    1730                 1735                 1740

Gly Ser  Val Pro Gln Phe Lys  Lys Val Val Phe Gln  Glu Phe Thr
    1745                 1750                 1755

Asp Gly  Ser Phe Thr Gln Pro  Leu Tyr Arg Gly Glu  Leu Asn Glu
    1760                 1765                 1770

His Leu  Gly Leu Leu Gly Pro  Tyr Ile Arg Ala Glu  Val Glu Asp
    1775                 1780                 1785

Asn Ile  Met Val Thr Phe Arg  Asn Gln Ala Ser Arg  Pro Tyr Ser
    1790                 1795                 1800

Phe Tyr  Ser Ser Leu Ile Ser  Tyr Glu Glu Asp Gln  Arg Gln Gly
    1805                 1810                 1815

Ala Glu  Pro Arg Lys Asn Phe  Val Lys Pro Asn Glu  Thr Lys Thr
    1820                 1825                 1830

Tyr Phe  Trp Lys Val Gln His  His Met Ala Pro Thr  Lys Asp Glu
    1835                 1840                 1845

Phe Asp  Cys Lys Ala Trp Ala  Tyr Phe Ser Asp Val  Asp Leu Glu
    1850                 1855                 1860

Lys Asp  Val His Ser Gly Leu  Ile Gly Pro Leu Leu  Val Cys His
    1865                 1870                 1875

Thr Asn  Thr Leu Asn Pro Ala  His Gly Arg Gln Val  Thr Val Gln
    1880                 1885                 1890

Glu Phe  Ala Leu Phe Phe Thr  Ile Phe Asp Glu Thr  Lys Ser Trp
    1895                 1900                 1905

Tyr Phe  Thr Glu Asn Met Glu  Arg Asn Cys Arg Ala  Pro Cys Asn
    1910                 1915                 1920

Ile Gln  Met Glu Asp Pro Thr  Phe Lys Glu Asn Tyr  Arg Phe His
    1925                 1930                 1935

Ala Ile  Asn Gly Tyr Ile Met  Asp Thr Leu Pro Gly  Leu Val Met
    1940                 1945                 1950

Ala Gln  Asp Gln Arg Ile Arg  Trp Tyr Leu Leu Ser  Met Gly Ser
    1955                 1960                 1965

Asn Glu  Asn Ile His Ser Ile  His Phe Ser Gly His  Val Phe Thr
    1970                 1975                 1980

Val Arg  Lys Lys Glu Glu Tyr  Lys Met Ala Leu Tyr  Asn Leu Tyr
    1985                 1990                 1995

Pro Gly  Val Phe Glu Thr Val  Glu Met Leu Pro Ser  Lys Ala Gly
    2000                 2005                 2010

Ile Trp  Arg Val Glu Cys Leu  Ile Gly Glu His Leu  His Ala Gly
    2015                 2020                 2025

Met Ser  Thr Leu Phe Leu Val  Tyr Ser Asn Lys Cys  Gln Thr Pro
    2030                 2035                 2040

Leu Gly  Met Ala Ser Gly His  Ile Arg Asp Phe Gln  Ile Thr Ala
    2045                 2050                 2055

Ser Gly  Gln Tyr Gly Gln Trp  Ala Pro Lys Leu Ala  Arg Leu His
    2060                 2065                 2070

Tyr Ser  Gly Ser Ile Asn Ala  Trp Ser Thr Lys Glu  Pro Phe Ser
    2075                 2080                 2085

Trp Ile  Lys Val Asp Leu Leu  Ala Pro Met Ile Ile  His Gly Ile
    2090                 2095                 2100

Lys Thr  Gln Gly Ala Arg Gln  Lys Phe Ser Ser Leu  Tyr Ile Ser
```

-continued

```
    2105                2110                2115

Gln Phe  Ile Ile Met Tyr Ser  Leu Asp Gly Lys Lys  Trp Gln Thr
    2120                2125                2130

Tyr Arg  Gly Asn Ser Thr Gly  Thr Leu Met Val Phe  Phe Gly Asn
    2135                2140                2145

Val Asp  Ser Ser Gly Ile Lys  His Asn Ile Phe Asn  Pro Pro Ile
    2150                2155                2160

Ile Ala  Arg Tyr Ile Arg Leu  His Pro Thr His Tyr  Ser Ile Arg
    2165                2170                2175

Ser Thr  Leu Arg Met Glu Leu  Met Gly Cys Asp Leu  Asn Ser Cys
    2180                2185                2190

Ser Met  Pro Leu Gly Met Glu  Ser Lys Ala Ile Ser  Asp Ala Gln
    2195                2200                2205

Ile Thr  Ala Ser Ser Tyr Phe  Thr Asn Met Phe Ala  Thr Trp Ser
    2210                2215                2220

Pro Ser  Lys Ala Arg Leu His  Leu Gln Gly Arg Ser  Asn Ala Trp
    2225                2230                2235

Arg Pro  Gln Val Asn Asn Pro  Lys Glu Trp Leu Gln  Val Asp Phe
    2240                2245                2250

Gln Lys  Thr Met Lys Val Thr  Gly Val Thr Thr Gln  Gly Val Lys
    2255                2260                2265

Ser Leu  Leu Thr Ser Met Tyr  Val Lys Glu Phe Leu  Ile Ser Ser
    2270                2275                2280

Ser Gln  Asp Gly His Gln Trp  Thr Leu Phe Phe Gln  Asn Gly Lys
    2285                2290                2295

Val Lys  Val Phe Gln Gly Asn  Gln Asp Ser Phe Thr  Pro Val Val
    2300                2305                2310

Asn Ser  Leu Asp Pro Pro Leu  Leu Thr Arg Tyr Leu  Arg Ile His
    2315                2320                2325

Pro Gln  Ser Trp Val His Gln  Ile Ala Leu Arg Met  Glu Val Leu
    2330                2335                2340

Gly Cys  Glu Ala Gln Asp Leu  Tyr Asp Lys Thr His  Thr Cys Pro
    2345                2350                2355

Pro Cys  Pro Ala Pro Glu Leu  Leu Gly Gly Pro Ser  Val Phe Leu
    2360                2365                2370

Phe Pro  Pro Lys Pro Lys Asp  Thr Leu Met Ile Ser  Arg Thr Pro
    2375                2380                2385

Glu Val  Thr Cys Val Val Val  Asp Val Ser His Glu  Asp Pro Glu
    2390                2395                2400

Val Lys  Phe Asn Trp Tyr Val  Asp Gly Val Glu Val  His Asn Ala
    2405                2410                2415

Lys Thr  Lys Pro Arg Glu Glu  Gln Tyr Asn Ser Thr  Tyr Arg Val
    2420                2425                2430

Val Ser  Val Leu Thr Val Leu  His Gln Asp Trp Leu  Asn Gly Lys
    2435                2440                2445

Glu Tyr  Lys Cys Lys Val Ser  Asn Lys Ala Leu Pro  Ala Pro Ile
    2450                2455                2460

Glu Lys  Thr Ile Ser Lys Ala  Lys Gly Gln Pro Arg  Glu Pro Gln
    2465                2470                2475

Val Tyr  Thr Leu Pro Pro Ser  Arg Asp Glu Leu Thr  Lys Asn Gln
    2480                2485                2490

Val Ser  Leu Thr Cys Leu Val  Lys Gly Phe Tyr Pro  Ser Asp Ile
    2495                2500                2505
```

-continued

```
Ala Val  Glu Trp Glu Ser Asn  Gly Gln Pro Glu Asn  Asn Tyr Lys
    2510                 2515                 2520

Thr Thr  Pro Pro Val Leu Asp  Ser Asp Gly Ser Phe  Phe Leu Tyr
    2525                 2530                 2535

Ser Lys  Leu Thr Val Asp Lys  Ser Arg Trp Gln Gln  Gly Asn Val
    2540                 2545                 2550

Phe Ser  Cys Ser Val Met His  Glu Ala Leu His Asn  His Tyr Thr
    2555                 2560                 2565

Gln Lys  Ser Leu Ser Leu Ser  Pro Gly Lys
    2570                 2575


<210> SEQ ID NO 63
<211> LENGTH: 8
<212> TYPE: PRT
<213> ORGANISM: Artificial Sequence
<220> FEATURE:
<223> OTHER INFORMATION: linker

<400> SEQUENCE: 63

Gly Gly Ser Gly Gly Gly Gly Ser
1               5
```

SYSTEMS FOR FACTOR VIII PROCESSING AND METHODS THEREOF

REFERENCE TO EARLIER FILED APPLICATIONS

This application is the national phase application of International Application No. PCT/US2011/043568, filed Jul. 11, 2011, and published as WO 2012/006623, which claims the benefit of U.S. Provisional Application No. 61/363,184, filed Jul. 9, 2010, which is incorporated herein by reference in its entirety.

REFERENCE TO SEQUENCE LISTING SUBMITTED ELECTRONICALLY VIA EFS-WEB

The content of the electronically submitted sequence listing (Name: sequencelisting_ascii.txt, Size: 267,731 bytes; and Date of Creation: Jul. 8, 2011) submitted in this application is incorporated herein by reference in its entirety.

BACKGROUND OF THE INVENTION

Proprotein convertases, also known as prohormone convertases, neuroendocrine convertase, or Proprotein Convertase Subtilisin/Kexin Type (PCSK), are capable of cleaving precursor proteins. The precursor proteins that are known to be cleaved by proprotein convertases include growth factors and hormones, receptors, and bacterial endotoxins. Nakayama, K., *Biochem. J.* 327: 625-635 (1997). The first proprotein processing protease discovered was Kex2 protease from *S. cerevisiae*. Rockwell et al., *Chem. Rev.* 102: 4525-4548 (2002). Kex2 homologues identified in mammalian cells include PC1/3, PC2, PACE4, PC4, PC5/PC6, and PC7. See id.

Each member of the convertase family exhibits a unique tissue distribution; different cell types were found to express individual combinations of these enzymes. PC4 is limited to testicular germ cells. Seidah et al., *Mol. Endocrinol.* 6(10): 1559 (1992). PC1/3 and PC2 are restricted to endocrine and neuroendocrine tissues. Seidah et al., *NIDA Res. Monogr.* 126:132 (1992). PACE 4 and PC5 are expressed in several tissues, while PC7 exhibits an even more common tissue distribution. Furin is expressed ubiquitously.

The cellular sublocalisation of the endoproteases is an important determinant for their physiological function, PC1/3, PC2, and PC5A, an isoform of PC5/6, are involved in the processing of pro-hormones and neuropeptide precursors which are secreted in a regulated manner. PC1/3 and PC2 were shown to cleave neuroendocrine-specific proinsulin (Smeekens et al., *Proc. Natl. Acad. Sci. USA*, 89(18): 8822 (1992)), POMC (Benjannet et al., *Proc. Natl. Acad. Sci. USA,* 88(9): 3564 (1991)), pro-glucagon (Rouille et al., *Proc. Natl. Acad. Sci. USA,* 91(8): 3242 (1994)), pro-somatostatin (Xu and Shields, Biochimie 76: 257 (1994)), pro-neurotensin/neuromedin N (proNT/NN; Rovere et al., *J. Biol. Chem.,* 271(19): 11368 (1996)) and pro-melanin concentrating hormone (MCH; Viale et al., *J. Biol. Chem.,* 274(10): 6536 (1999)) C-terminally to KR or RR motifs (see Rouille et al., *Front Neuroendocrinol.* 16(4):322 (1995)). PC5A is also involved in the processing of proNT/NN and MCH (Barbero et al., *J. Biol. Chem.,* 273(39): 25339 (1998)).

BRIEF SUMMARY OF THE INVENTION

The present invention is directed to a method for decreasing nonprocessed Factor VIII in a culturing medium, comprising, a) expressing Factor VIII from a first polynucleotide in a host cell, where the endogenous processing enzymes of the host cell are insufficient to convert all of the Factor VIII to its processed isoform;

b) contacting the Factor VIII with an exogenous proprotein convertase; and c) decreasing the nonprocessed Factor VIII by processing with the proprotein convertase. The exogenous proprotein convertase can be expressed from a second polypeptide in the host cell expressing said Factor VIII, added to said culture medium, or expressed from a polynucleotide sequence in a host cell different from the host cell expressing the Factor VIII.

The Factor VIII of the invention may be processed by cleaving Arginine located at amino acid residue 1648 in SEQ ID NO: 6 (full-length Factor VIII), which corresponds to amino acid residue 1667 in SEQ ID NO: 62, or amino acid residue 754 in SEQ ID NO: 2 (B-domain-deleted Factor VIII), which corresponds to amino acid residue 773 in SEQ ID NO: 60. By the present method, the level of the nonprocessed Factor VIII can be decreased such that the Factor VIII contains more than 75%, 80%, 85%, 90%, 95%, and 100% of the processed Factor VIII after processing by said proprotein convertase.

In one embodiment, the proprotein convertase used in the invention is selected from the group consisting of proprotein convertase subtilisin/kexin type 1, proprotein convertase subtilisin/kexin type 2, proprotein convertase subtilisin/kexin type 3, proprotein convertase subtilisin/kexin type 4, proprotein convertase subtilisin/kexin type 5, proprotein convertase subtilisin/kexin type 6, proprotein convertase subtilisin/kexin type 7, proprotein convertase subtilisin/kexin type 8, proprotein convertase subtilisin/kexin type 9, a yeast Kex 2 and a combination thereof.

In another embodiment, the proprotein convertase for the invention is selected from the group consisting of proprotein convertase subtilisin/kexin type 3, proprotein convertase subtilisin/kexin type 5, proprotein convertase subtilisin/kexin type 7, a yeast Kex 2 and a combination thereof. In a particular embodiment, the proprotein convertase is selected from the group consisting of proprotein convertase subtilisin/kexin type 5, proprotein convertase subtilisin/kexin type 7, and both.

In certain embodiments, the proprotein convertase of the invention comprises an amino acid sequence at least 60%, 70%, 80%, 90%, 95%, 96%, 97%, 98%, 99%, or 100% identical to proprotein convertase subtilisin/kexin type 5 (SEQ ID NO: 18) wherein the proprotein convertase is capable of cleaving full-length Factor VIII (SEQ ID NO: 6) at amino acid residue 1648 or the B-domain deleted Factor VIII (SEQ ID NO: 2) at amino acid residue 754. In some embodiments, the proprotein convertase of the invention comprises an amino acid sequence at least 60%, 70%, 80%, 90%, 95%, 96%, 97%, 98%, 99%, or 100% identical to proprotein convertase subtilisin/kexin type 7 (SEQ ID NO: 22) wherein the proprotein convertase is capable of cleaving full-length Factor VIII (SEQ ID NO: 6) at amino acid residue 1648 or the B-domain deleted Factor VIII (SEQ ID NO: 2) at 754.

The Factor VIII in the present invention can be expressed as full-length Factor VIII or a fragment, derivative, analog, or variant thereof. In one embodiment, the Factor VIII is partial or full B-domain deleted Factor VIII. For example, the Factor VIII comprises an amino acid sequence at least 60%, 70%, 80%, 90%, 95%, 96%, 97%, 98%, 99%, or 100% identical to SEQ ID NO: 2 or 6 (B-domain-deleted FVIII or full-length Factor VIII, respectively), wherein an activated form of the Factor VIII is capable of restoring clotting activity to FVIII-deficient plasma when activated. In one embodiment, the Factor VIII is fused to an immunoglobulin constant region or a portion thereof, e.g., a neonatal Fc Receptor (FcRn) binding domain, e.g., an Fc fragment. In certain embodiments, the Factor VIII is in a dimer, homodimer, heterodimer, or monomer-dimer hybrid.

In some embodiments, the first polynucleotide encoding Factor VIII and the second polynucleotide encoding a proprotein convertase are located on the same vector or on two different vectors.

In one aspect, the present invention is related to an expression vector comprising a first polynucleotide encoding Factor VIII and a second polynucleotide encoding a proprotein convertase, wherein the Factor VIII is processed by the proprotein convertase when the Factor VIII and the proprotein convertase are expressed in a host cell comprising the vector. Also included in the present invention is a host cell comprising an expression vector comprising a first polynucleotide sequence encoding Factor VIII and a second polynucleotide sequence encoding a proprotein convertase, wherein the Factor VIII is processed by the proprotein convertase.

In another aspect, the present invention is related to a method of producing Factor VIII, comprising a) culturing the host cell in a culture medium that expresses the Factor VIII and the proprotein convertase, and b) processing the Factor VIII by the protein convertase.

In some aspects, the present invention includes a method of producing Factor VIII, comprising a) transfecting the expression vector in a host cell, b) culturing the host cell in a culture medium to express the Factor VIII and the proprotein convertase, wherein the proprotein convertase processes the Factor VIII.

Also included is an isolated polypeptide comprising Factor VIII produced by the methods or methods of treating a hemophilia using the polypeptide produced by the present invention.

BRIEF DESCRIPTION OF THE DRAWINGS/FIGURES

FIG. 1. Schematic Representation of the nonprocessed (upper) and processed rFVIIIBDD-Fc monomer (lower).

Figure 2:
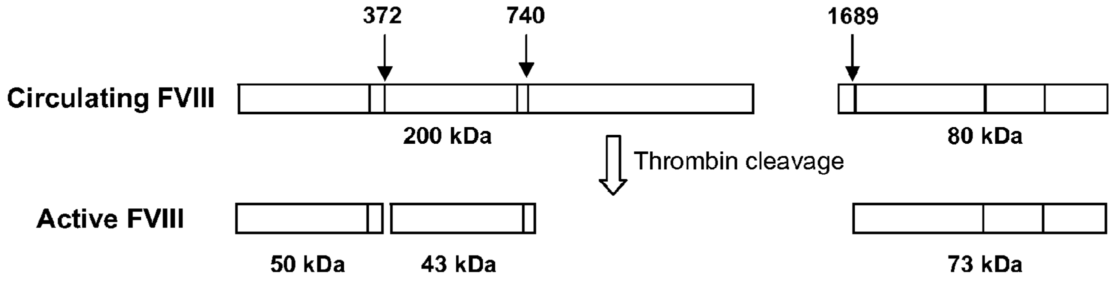

FIG. 2. Schematic diagram of Thrombin activation of full-length Factor VIII.

FIG. 3A-B. A. Western blot analysis using anti-Factor VIII A2 (HC) primary antibody. B. Western blot analysis using anti-human IgG-HRP conjugates. The lanes show expression of processed rFVIIIBDD-Fc (~131 kD for the light chain-Fc fusion and ~86 kD for the heavy chain) and nonprocessed rFVIIIBDD-Fc (~217 kD) in HEK293 cells, which are transiently transfected with (1) rFVIIIBDD-Fc expressing construct alone, (2) rFVIIIBDD-Fc and yeast Kex 2 expressing constructs, (3) rFVIIIBDD-Fc and PC7 expressing constructs, (4) rFVIIIBDD-Fc and PACE expressing constructs, and (5) rFVIIIBDD-Fc and PC5 expressing constructs.

FIG. 4A-B. A. SDS-PAGE gel by SYPRO® ruby gel staining. B. SDS-PAGE gel by Coomassie gel staining. The lanes show expression of processed rFVIIIBDD-Fc 0131 kD for the light chain-Fc fusion and ~86 kD for the heavy chain) and nonprocessed rFVIIIBDD-Fc (~217 kD) in HEK293 cells, which are transiently transfected with (1) rFVIIIBDD-Fc expressing construct alone, (2) rFVIIIBDD-Fc and yeast Kex 2 expressing constructs, (3) rFVIIIBDD-Fc and PC7 expressing constructs, (4) rFVIHBDD-Fc and PACE expressing constructs, and (5) rFVIIIBDD-Fc and PC5 expressing constructs.

FIG. 5A-B. A. Reduced SDS-PAGE gel of rFVIIIBDD-Fc. The first lane shows rFVIIIFcBDD-Fc produced after stably cotransfecting a PC5 expressing construct. The second lane shows rFVIIIFcBDD-Fc produced without stably transfecting a processing enzyme expressing construct.

FIG. 6A-B. Western blot analysis of FVIII:Fc produced in media containing Kex2, PC7, PACE, or PC5. FVIII:Fc was detected by anti-FVIII light chain primary antibody (A) or anti-FVIIIA2 (HC) primary antibody (B).

DETAILED DESCRIPTION OF THE INVENTION

Definitions

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

The term "polynucleotide" or "nucleotide" is intended to encompass a singular nucleic acid as well as plural nucleic acids, and refers to an isolated nucleic acid molecule or construct, e.g., messenger RNA (mRNA) or plasmid DNA (pDNA). In certain embodiments, a polynucleotide comprises a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a Factor VIII polypeptide contained in a vector is considered isolated for the purposes of the present invention. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can include regulatory elements such as promoters, enhancers, ribosome binding sites, or transcription termination signals.

As used herein, a "coding region" or "coding sequence" is a portion of polynucleotide which consists of codons translatable into amino acids. Although a "stop codon" (TAG, TGA, or TAA) is typically not translated into an amino acid, it may be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions of the present invention can be present in a single polynucleotide construct, e.g., on a single vector, or in separate polynucleotide constructs, e.g., on separate (different) vectors. It follows, then, that a single vector can contain just a single coding region, or comprise two or more coding regions, e.g., a single vector can separately encode a binding domain-A and a binding domain-B as described below. In addition, a vector, polynucleotide, or nucleic acid of the invention can encode heterologous coding regions, either fused or unfused to a nucleic acid encoding a binding domain of the invention. Heterologous coding regions include without limitation specialized elements or motifs, such as a secretory signal peptide or a heterologous functional domain.

Certain proteins secreted by mammalian cells are associated with a secretory signal peptide which is cleaved from the mature protein once export of the growing protein chain across the rough endoplasmic reticulum has been initiated. Those of ordinary skill in the art are aware that signal peptides are generally fused to the N-terminus of the polypeptide, and are cleaved from the complete or "full-length" polypeptide to produce a secreted or "mature" form of the polypeptide. In certain embodiments, a native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, e.g., a human tissue plasminogen activator (TPA) or mouse β-glucuronidase signal peptide, or a functional derivative thereof, can be used.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions may include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

A polynucleotide which encodes a gene product, e.g., a polypeptide, can include a promoter and/or other transcription or translation control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other transcription control elements, besides a promoter, for example enhancers, operators, repressors, and transcription termination signals, can also be operably associated with a coding region to direct gene product expression.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit B-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

A "vector" refers to any vehicle for the cloning of and/or transfer of a nucleic acid into a host cell. A vector may be a replicon to which another nucleic acid segment may be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

Vectors may be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), -galactosidase (LacZ), -glucuronidase (Gus), and the like. Selectable markers may also be considered to be reporters.

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

A "cloning vector" refers to a "replicon," which is a unit length of a nucleic acid that replicates sequentially and which comprises an origin of replication, such as a plasmid, phage or cosmid, to which another nucleic acid segment may be attached so as to bring about the replication of the attached segment. Certain cloning vectors are capable of replication in one cell type, e.g., bacteria and expression in another, e.g., eukaryotic cells. Cloning vectors typically comprise one or more sequences that can be used for selection of cells comprising the vector and/or one or more multiple cloning sites for insertion of nucleic acid sequences of interest.

The term "expression vector" refers to a vehicle designed to enable the expression of an inserted nucleic acid sequence following insertion into a host cell. The inserted nucleic acid sequence is placed in operable association with regulatory regions as described above.

Vectors are introduced into host cells by methods well known in the art, e.g., transfection, electroporation, microinjection, transduction, cell fusion, DEAE dextran, calcium phosphate precipitation, lipofection (lysosome fusion), use of a gene gun, or a DNA vector transporter.

"Culture," "to culture" and "culturing," as used herein, means to incubate cells under in vitro conditions that allow for cell growth or division or to maintain cells in a living state. "Cultured cells," as used herein, means cells that are propagated in vitro.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced recombinant technology, but is not necessarily translated from a designated nucleic acid sequence. It can be generated in any manner, including by chemical synthesis.

An "isolated" polypeptide or a fragment, variant, or derivative thereof refers to a polypeptide that is not in its natural milieu. No particular level of purification is required. For example, an isolated polypeptide can simply be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

Also included in the present invention are fragments or variants of polypeptides, and any combination thereof. The term "fragment" or "variant" when referring to polypeptide binding domains or binding molecules of the present invention include any polypeptides which retain at least some of the properties (e.g., FcRn binding affinity for an FcRn binding domain or Fc variant, coagulation activity for an FVIII variant, or Factor VIII cleaving activity for a protein convertase variant) of the reference polypeptide. Fragments of polypeptides include proteolytic fragments, as well as deletion fragments, in addition to specific antibody fragments discussed elsewhere herein. Variants of polypeptide binding domains or binding molecules of the present invention include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

As known in the art, "sequence identity" between two polypeptides is determined by comparing the amino acid sequence of one polypeptide to the sequence of a second polypeptide. When discussed herein, whether any particular polypeptide is at least about 50%, 60%, 70%, 75%, 80%, 85%, 90%, 95%, 99%, or 100% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full-length of the reference polypeptide sequence and that gaps in homology of up to 5% of the total number of amino acids in the reference sequence are allowed.

A "fusion" or chimeric protein comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of a Factor VIII domain of the invention with an immunoglobulin Fc domain. A fusion protein is created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the entity to which it is being compared. For instance, a heterologous polynucleotide or antigen can be derived from a different species, different cell type of an individual, or the same or different type of cell of distinct individuals.

As used herein the term "associate with" refers a covalent or non-covalent bond formed between two sulfur atoms. The amino acid cysteine comprises a thiol group that can form a disulfide bond or bridge with a thiol group on a second cysteine residue. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

Methods of Production

The present invention is directed to a method of producing processed Factor VIII by co-expressing Factor VIII and a proprotein convertase or adding a proprotein convertase protein to the Factor VIII expressing host cell or the medium containing the host cell so that the proprotein convertase cleaves Factor VIII at amino acid 1648 (full-length Factor VIII or SEQ ID NO: 6), which corresponds to amino acid residue 1667 of SEQ ID NO: 62, or the corresponding amino acid residue in other variants (e.g., amino acid 754 in the S743/Q1638 B-domain deleted Factor VIII or SEQ ID NO: 2 or amino acid 773 in SEQ ID NO: 60), and thereby generates a Factor VIII heavy chain and a Factor VIII light chain—processed Factor VIII. In the culture or host cell, the present method therefore increases the level of processed Factor VIII by co-expressing Factor VIII and a proprotein convertase in the same host cell or different host cells or adding a proprotein convertase protein to the Factor VIII expressing host cell or the medium containing the host cell, compared to the level of processed Factor VIII without co-expressing the two proteins together. Alternatively, the present method decreases nonprocessed Factor VIII in a culture medium or host cell compared to the level of nonprocessed Factor VIII in the host cell or culture medium without the proprotein convertase. In some embodiments, the present invention is drawn to a method of cleaving Factor VIII by co-expressing Factor VIII and a proprotein convertase, wherein the proprotein convertase cleaves Factor VIII at amino acid 1648 (full-length FVIII or SEQ ID NO: 6) or the corresponding amino acid residue in other variants (e.g., amino acid 754 in the S743/Q1638 B-domain deleted Factor VIII or SEQ ID NO: 2), and generates a FVIII heavy chain and a FVIII light chain.

Factor VIII can be expressed as a single protein in a cell and processed by intracellular processing enzymes to a heavy chain and a light chain. When Factor VIII is expressed in vitro in an excess amount, the intracellular processing enzymes may not be capable of processing all Factor VIII in the host cell. Thus, the present invention provides that a proprotein convertase co-expressed with Factor VIII can cleave the nonprocessed Factor VIII when endogenous processing enzymes are insufficient to process all Factor VIII produced in the host cell.

The term "processed Factor VIII" as used herein means Factor VIII that has been cleaved right after Arginine at amino acid 1648 (in full-length Factor VIII or SEQ ID NO: 6), amino acid 754 (in the S743/Q1638 B-domain deleted Factor VIII or SEQ ID NO: 2), or the corresponding Arginine residue (in other variants). In one embodiment, a processed Factor VIII comprises a heavy chain and a light chain, which are linked or associated by a metal ion-mediated non-covalent bond. The term "nonprocessed Factor VIII" therefore means Factor VIII that has not been cleaved right after Arginine at amino acid 1648 (in full-length Factor VIII or SEQ ID NO: 6), amino acid 754 (in the S743/Q1638 B-domain-deleted Factor VIII or SEQ ID NO: 2), or the corresponding Arginine residue (in other variants). The term "nonprocessed Factor VIII" is interchangeably used herein with "non-processed Factor VIII," "non processed Factor VIII," "unprocessed Factor VIII," "npFactor VIII," or "npFVIII."

Processed Factor VIII can further be cleaved by thrombin and then activated as Factor VIIIa, serving as a cofactor for activated Factor IX (FIXa). The activated FIX together with activated FVIII forms a Xase complex and converts Factor X to activated Factor X (FXa). For activation, Factor VIII is cleaved by thrombin after three Arginine residues, at amino acids 372, 740, and 1689 (corresponding to amino acids 372, 740, and 795 in the B-domain deleted FVIII sequence), the cleavage generating Factor VIIIa having the 50 kDa A1, 43 kDa A2, and 73 kDa A3-C1-C2 chains.

"Factor VIII," as used herein, means functional factor VIII polypeptide in its normal role in coagulation, unless otherwise specified. Thus, the term Factor VIII includes variant polypeptides that are functional. In one embodiment, the Factor VIII protein is the human, porcine, canine, rat, or murine Factor VIII protein. In addition, comparisons between factor VIII from humans and other species have identified conserved residues that are likely to be required for function (Cameron et al., *Thromb. Haemost.* 79:317-22 (1998); U.S. Pat. No. 6,251,632), incorporated herein by reference in its entirety. In another embodiment, the Factor VIII protein is a chimeric polypeptide, for example, but not limited to, a fusion protein comprising a fully or partially B-domain deleted Factor VIII and at least a portion of an immunoglobulin constant region, e.g., an Fc domain.

The Factor VIII polypeptide and polynucleotide sequences are known, as are many functional fragments, mutants and modified versions. Examples of human factor VIII sequences are shown as subsequences in SEQ ID NO: 2 or 6. Factor VIII polypeptides include full-length Factor VIII, full-length Factor VIII minus Met at the N-terminus, mature Factor VIII (minus the signal sequence), mature Factor VIII with an additional Met at the N-terminus, and/or Factor VIII with a full or partial deletion of the B domain. In certain embodiments, Factor VIII variants include B domain deletions, whether partial or full deletions.

The human factor VIII gene was isolated and expressed in mammalian cells (Toole, J. J., et al., *Nature* 312:342-347 (1984); Gitschier, J., et al., *Nature* 312:326-330 (1984); Wood, W. I., et al., *Nature* 312:330-337 (1984); Vehar, G. A., et al., *Nature* 312:337-342 (1984); WO 87/04187; WO 88/08035; WO 88/03558; and U.S. Pat. No. 4,757,006), each of which is incorporated herein by reference in its entirety. The Factor VIII amino acid sequence was deduced from cDNA as shown in U.S. Pat. No. 4,965,199, which is incorporated herein by reference in its entirety. In addition, partially or fully B-domain deleted Factor VIII is shown in U.S. Pat. Nos. 4,994,371 and 4,868,112, each of which is incorporated herein by reference in its entirety. In some embodiments, the human Factor VIII B-domain is replaced with the human Factor V B-domain as shown in U.S. Pat. No. 5,004,803, incorporated herein by reference in its entirety. The cDNA sequence encoding human Factor VIII and predicted amino acid sequence are shown in SEQ ID NOs:1 and 2, respectively, of US Application Publ. No. 2005/0100990, incorporated herein by reference in its entirety.

The porcine factor VIII sequence is published in Toole, J. J., et al., *Proc. Natl. Acad. Sci. USA* 83:5939-5942 (1986), which is incorporated herein by reference in its entirety. And the complete porcine cDNA sequence obtained from PCR amplification of Factor VIII sequences from a pig spleen cDNA library has been reported in Healey, J. F., et al., *Blood* 88:4209-4214 (1996), incorporated herein by reference in its entirety. Hybrid human/porcine Factor VIII having substitutions of all domains, all subunits, and specific amino acid sequences were disclosed in U.S. Pat. No. 5,364,771 by Lollar and Runge, and in WO 93/20093, incorporated herein by reference in its entirety. More recently, the nucleotide and corresponding amino acid sequences of the A1 and A2 domains of porcine factor VIII and a chimeric factor VIII with porcine A1 and/or A2 domains substituted for the corresponding human domains were reported in WO 94/11503, incorporated herein by reference in its entirety. U.S. Pat. No. 5,859,204, Lollar, J. S., also discloses the porcine cDNA and deduced amino acid sequences. U.S. Pat. No. 6,458,563, incorporated herein by reference in its entirety assigned to Emory discloses a B-domain-deleted porcine Factor VIII.

U.S. Pat. No. 5,859,204, Lollar, J. S., incorporated herein by reference in its entirety, reports functional mutants of Factor VIII having reduced antigenicity and reduced immunoreactivity. U.S. Pat. No. 6,376,463, Lollar, J. S., incorporated herein by reference in its entirety, also reports mutants of Factor VIII having reduced immunoreactivity. US Appl. Publ. No. 2005/0100990, Saenko et al., incorporated herein by reference in its entirety, reports functional mutations in the A2 domain of Factor VIII.

In one embodiment, the Factor VIII (or Factor VIII portion of a chimeric polypeptide) may be at least 50%, 60%, 70%, 80%, 90%, 95%, 96%, 97%, 98%, 99%, or 100% identical to a Factor VIII amino acid sequence of amino acids 1 to 1438 of SEQ ID NO: 2 or amino acids 1 to 2332 of SEQ ID NO: 6 (without a signal sequence) or a Factor VIII amino acid sequence of amino acids-19 to 1438 of SEQ ID NO: 2 or amino acids-19 to 2332 of SEQ ID NO: 6 (with a signal sequence), wherein the Factor VIII has a clotting activity, e.g., activates Factor IX as a cofactor to convert Factor X to activated Factor X. The Factor VIII (or Factor VIII portion of a chimeric polypeptide) may be identical to a Factor VIII amino acid sequence of amino acids 1 to 1438 of SEQ ID NO: 2 or amino acids 1 to 2332 of SEQ ID NO:6 (without a signal sequence). The Factor VIII may further comprise a signal sequence.

"B-domain" of Factor VIII, as used herein, is the same as the B-domain known in the art that is defined by internal amino acid sequence identity and sites of proteolytic cleavage, e.g., residues Ser741-Arg1648 of full-length human Factor VIII. The other human Factor VIII domains are defined by the following amino acid residues: A1, residues Ala1-Arg372; A2, residues Ser373-Arg740; A3, residues Ser1690-Asn2019; C1, residues Lys2020-Asn2172; C2, residues Ser2173-Tyr2332. The A3-C1-C2 sequence includes residues Ser1690-Tyr2332. The remaining sequence, residues Glu1649-Arg1689, is usually referred to as the a3 acidic region. The locations of the boundaries for all of the domains, including the B-domains, for porcine, mouse and canine Factor VIII are also known in the art. In one embodiment, the B domain of Factor VIII is deleted ("B-domain-deleted factor VIII" or "BDD FVIII"). An example of a BDD FVIII is REFACTO® (recombinant BDD FVIII), which has the same sequence as the Factor VIII portion of the sequence in Table 2A(i) (amino acids-19 to 1438 or 1 to 1438 of SEQ ID NO:2).

A "B-domain-deleted Factor VIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a B-domain-deleted Factor VIII sequence of the present invention comprises any one of the deletions disclosed at col. 4, line 4 to col. 5, line 28 and examples 1-5 of U.S. Pat. No. 6,316,226 (also in U.S. Pat. No. 6,346,513). In another embodiment, a B-domain deleted Factor VIII is the S743/Q1638 B-domain deleted Factor VIII (SQ version Factor VIII) (e.g., Factor VIII having a deletion from amino acid 744 to amino acid 1637, e.g., Factor VIII having amino acids 1-743 and amino acids 1638-2332 of SEQ ID NO: 6, i.e., SEQ ID NO: 2). In some embodiments, a B-domain-deleted Factor VIII of the present invention has a deletion disclosed at col. 2, lines 26-51 and examples 5-8 of U.S. Pat. No. 5,789,203 (also U.S. Pat. No. 6,060,447, U.S. Pat. No. 5,595,886, and U.S. Pat. No. 6,228,620). In some embodiments, a B-domain-deleted Factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B-domain-deleted Factor VIII has a deletion of most of the B domain, but still contains amino-terminal sequences of the B domain that are essential for in vivo proteolytic processing of the primary translation product into two polypeptide chain, as disclosed in WO 91/09122, which is incorporated herein by reference in its entirety. In some embodiments, a B-domain-deleted Factor VIII is constructed with a deletion of amino acids 747-1638, i.e., virtually a complete deletion of the B domain. Hoeben R. C., et al. *J. Biol. Chem.* 265 (13): 7318-7323 (1990), incorporated herein by reference in its entirety. A B-domaindeleted Factor VIII may also contain a deletion of amino acids 771-1666 or amino acids 868-1562 of Factor VIII. Meulien P., et al. *Protein Eng.* 2(4): 301-6 (1988), incorporated herein by reference in its entirety. Additional B domain deletions that are part of the invention include: deletion of amino acids 982 through 1562 or 760 through 1639 (Toole et al., *Proc. Natl. Acad. Sci. U.S.A.* (1986) 83, 5939-5942)), 797 through 1562 (Eaton, et al. *Biochemistry* (1986) 25:8343-8347)), 741 through 1646 (Kaufman (PCT published application No. WO 87/04187)), 747-1560 (Sarver, et al., *DNA* (1987) 6:553-564)), 741 though 1648 (Pasek (PCT application No. 88/00831)), or 816 through 1598 or 741 through 1648 (Lagner (Behring Inst. Mitt. (1988) No 82:16-25, EP 295597)), each of which is incorporated herein by reference in its entirety. Each of the foregoing deletions may be made in any Factor VIII sequence.

In one embodiment, Factor VIII processed using the present methods is in a form of a chimeric polypeptide. "Chimeric polypeptide," as used herein, means a polypeptide that includes within it at least two polypeptides (or subsequences or peptides) from different sources, e.g., a heterologous polypeptide. Chimeric polypeptides may include two, three, four, five, six, seven, or more polypeptides from different sources, such as different genes, different cDNAs, or different animal or other species. Chimeric polypeptides may include one or more linkers joining the different subsequences. Thus, the subsequences may be joined directly or indirectly, via linkers, or both, within a single chimeric polypeptide. Chimeric polypeptides may include additional peptides such as signal sequences and sequences such as 6His and FLAG that aid in protein purification or detection. In addition, chimeric polypeptides may have amino acid or peptide additions to the N- and/or C-termini. Exemplary chimeric polypeptides of the invention are Factor VIII-Fc chimeric polypeptides such as SEQ ID NO: 60 or 62, with or without their signal sequences and the chimeric Fc polypeptide of SEQ ID NO:4.

The Factor VIII polypeptide fused to an Fc domain may comprise a sequence at least 50%, 60%, 70%, 80%, 90%, 95%, 96%, 97%, 98%, 99%, or 100% identical to the Factor VIII and Fc amino acid sequence of SEQ ID NO: 60, wherein the Factor VIII portion has the Factor VIII clotting activity, e.g., activating Factor IX as a cofactor to convert Factor X to activated Factor X (FXa) and the Fc domain portion has the FcRn binding affinity.

In some embodiments, the Factor VIII polypeptide fused to an Fc domain may comprise a sequence at least 50%, 60%, 70%, 80%, 90%, 95%, 96%, 97%, 98%, 99%, or 100% identical to the Factor VIII and Fc amino acid sequence of SEQ ID NO: 62, wherein the Factor VIII portion has the Factor VIII clotting activity, e.g., activating Factor IX as a cofactor to convert Factor X to activated Factor X (FXa) and the Fc domain portion has the FcRn binding affinity. The Factor VIII polypeptide fused to an Fc domain may further comprise a signal sequence.

In certain embodiments, Factor VIII used in this invention is conjugated. As used herein, a conjugate refers to any two or more entities bound to one another by any physicochemical means, including, but not limited to, hydrophobic interaction, covalent interaction, hydrogen bond interaction, ionic interaction, or any combination thereof. Thus, in one embodiment, a conjugate of the invention refers to any two or more entities bound to one another by covalent interaction. For example, in one embodiment, a conjugate is a fusion protein. In another embodiment, a conjugate of the invention refers to any two or more entities bound to one another by noncovalent interaction.

In one embodiment, Factor VIII of this invention is fused to an antibody or a fragment thereof, e.g., at least a portion of an immunoglobulin constant region. Immunoglobulins are comprised of four polypeptide chains, two heavy chains and two light chains, which associate via disulfide bonds to form tetramers. Each chain is further comprised of one variable region and one or more constant regions. The variable regions mediate antigen recognition and binding, while the constant regions, particularly the heavy chain constant regions, mediate a variety of effector functions, e.g., complement binding and Fc receptor binding (see, e.g., U.S. Pat. Nos. 6,086,875; 5,624,821; 5,116,964).

The constant region is further comprised of domains denoted CH (constant heavy) domains (CH1, CH2, etc.). Depending on the isotype, (i.e. IgG, IgM, IgA IgD, or IgE) the constant region can be comprised of three or four CH domains. Some isotypes (e.g. IgG) constant regions also contain a hinge region. See Janeway et al. 2001*, Immunobiology*, Garland Publishing, N.Y., N.Y.

The creation of chimeric proteins comprised of immunoglobulin constant regions linked to a protein of interest, or fragment thereof, has been described (see, e.g., U.S. Pat. Nos. 5,480,981 and 5,808,029; Gascoigne et al. 1987, *Proc. Natl. Acad. Sci. USA* 84:2936; Capon et al. 1989, *Nature* 337:525; Traunecker et al. 1989, *Nature* 339:68; Zettmeissl et al. 1990, *DNA Cell Biol. USA* 9:347; Byrn et al. 1990, *Nature* 344:667; Watson et al. 1990, *J. Cell. Biol.* 110:2221; Watson et al. 1991, *Nature* 349:164; Aruffo et al. 1990, *Cell* 61:1303; Linsley et al. 1991, *J. Exp. Med.* 173:721; Linsley et al. 1991, *J. Exp. Med.* 174:561; Stamenkovic et al., 1991, *Cell* 66:1133; Ashkenazi et al. 1991, *Proc. Natl. Acad. Sci. USA* 88:10535; Lesslauer et al. 1991, *Eur. J. Immunol.* 27:2883; Peppel et al. 1991, *J. Exp. Med.* 174:1483; Bennett et al. 1991, *J. Biol. Chem.* 266:23060; Kurschner et al. 1992, *J. Biol. Chem.* 267:9354; Chalupny et al. 1992, *Proc. Natl. Acad. Sci. USA* 89:10360; Ridgway and Gorman, 1991, *J. Cell. Biol.* 115, Abstract No. 1448; Zheng et al. 1995, *J. Immun.* 154:5590). These molecules usually possess both the biological activity associated with the linked molecule of interest as well as the effector function, and possibly some other desired characteristic associated with the immunoglobulin constant region (e.g., biological stability, cellular secretion).

The Fc portion of an immunoglobulin constant region, depending on the immunoglobulin isotype can include the CH2, CH3, and CH4 domains, as well as the hinge region. Chimeric proteins comprising an Fc portion of an immunoglobulin bestow several desirable properties on a chimeric protein including increased stability, increased serum half-life (see Capon et al., 1989, *Nature* 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

FcRn is active in adult epithelial tissues and expressed in the lumen of the intestines, pulmonary airways, nasal surfaces, vaginal surfaces, colon and rectal surfaces (U.S. Pat. No. 6,485,726). Fusion proteins comprising FcRn binding partners (e.g. IgG, Fc fragments) can be effectively shuttled across epithelial barriers by FcRn, thus providing a non-invasive means to systemically administer a desired therapeutic molecule. Additionally, fusion proteins comprising an FcRn binding partner are endocytosed by cells expressing the FcRn. But instead of being marked for degradation, these fusion proteins are recycled out into circulation again, thus increasing the in vivo half-life of these proteins.

Portions of immunoglobulin (e.g., IgG) constant regions, e.g., FcRn binding partners typically associate, via disulfide bonds and other noncovalent interactions, with one another to form dimers. In one embodiment, Factor VIII is fused to an Fc domain as a monomer. In another embodiment, Factor VIII is fused to an Fc domain as a dimer, homodimer or heterodimer. In some embodiments, the Factor VIII-Fc fusion is associated with a second polypeptide chain comprising, consisting essentially of, or consisting of at least a portion of an immunoglobulin constant region comprising an FcRn binding domain ("monomer-dimer hybrid").

"Hybrid" polypeptides and proteins, as used herein, means a combination of a first polypeptide chain, e.g., Factor VIII-Fc fusion, with a second polypeptide chain. In one embodiment, the first polypeptide and the second polypeptide in a hybrid are associated with each other via protein-protein interactions, such as charge-charge or hydrophobic interactions. In another embodiment, the first polypeptide and the second polypeptide in a hybrid are associated with each other via disulfide or other covalent bond(s). Hybrids are described in US 2004/101740 and US 2006/074199, each of which is incorporated herein by reference in its entirety. The second polypeptide may be an identical copy of the first polypeptide or a non-identical polypeptide. In one embodiment, the first polypeptide is a Factor VIII-Fc fusion protein, and the second polypeptide is a polypeptide comprising, consisting essentially of, or consisting of an FcRn binding domain, wherein the first polypeptide and the second polypeptide are associated. In another embodiment, the first polypeptide comprises FVIII-Fc, and the second polypeptide comprises FVIII-Fc, making the hybrid a homodimer.

"Fc," as used herein, comprises functional neonatal Fc receptor (FcRn) binding partners, unless otherwise specified. An FcRn binding partner is any molecule that can be specifically bound by the FcRn receptor with consequent active transport by the FcRn receptor of the FcRn binding partner. Thus, the term Fc includes any variants of IgG Fc that are functional. The region of the Fc portion of IgG that binds to the FcRn receptor has been described based on X-ray crystallography (Burmeister et al. 1994, Nature 372: 379, incorporated herein by reference in its entirety). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U.S. Department of Public Health, Bethesda; MD, incorporated herein by reference in its entirety. (The FcRn receptor has been isolated from several mammalian species including humans. The sequences of the human FcRn, rat FcRn, and mouse FcRn are known (Story et al. 1994, J. Exp. Med. 180: 2377), incorporated herein by reference in its entirety.) An Fc may comprise the CH2 and CH3 domains of an immunoglobulin with or without the hinge region of the immunoglobulin. Exemplary Fc variants are provided in WO 2004/101740 and WO 2006/074199, incorporated herein by reference in their entireties.

Fc (or Fc portion of a chimeric polypeptide) as used herein may contain one or more mutations or combinations of mutations. In one embodiment, a mutation in Fc confers increased half-life; for example, the mutation may include M252Y, S254T, T256E, and/or combinations thereof as disclosed in Oganesyan et al., *Mol. Immunol.* 46:1750 (2009), which is incorporated herein by reference in its entirety; H433K, N434F, and/or combinations thereof, as disclosed in Vaccaro et al., *Nat. Biotechnol.* 23:1283 (2005), which is incorporated herein by reference in its entirety; the mutants disclosed at pages 1-2, paragraph [0012], and Examples 9 and 10 of US 2009/0264627 A1, which is incorporated herein by reference in its entirety; or the mutants disclosed at page 2, paragraphs [0014] to [0021] of US 20090163699 A1, which is incorporated herein by reference in its entirety. In another embodiment, a mutation in Fc preserves or enhances binding to the FcRn; for example, such mutations may include the mutants disclosed in paragraphs [148]-[150] of U.S. Pat. No. 7,404,956 B1, which is incorporated herein by reference in its entirety.

In one embodiment, the FcRn binding domain is a polypeptide including the sequence PKNSSMISNTP (SEQ ID NO: 27) and optionally further including a sequence selected from HQSLGTQ (SEQ ID NO: 28), HQNLSDGK (SEQ ID NO: 29), HQNISDGK (SEQ ID NO: 30), or VISSHLGQ (SEQ ID NO: 31), which are disclosed in U.S. Pat. No. 5,739,277, incorporated herein by reference in its entirety.

In another embodiment, the FcRn binding domain, e.g., Fc (or Fc portion of a chimeric polypeptide), may be at least 60%, 70%, 80%, 85%, 90%, 95%, 96%, 97%, 98%, 99%, or 100% identical to the Fc amino acid sequence of SEQ ID NO: 4.

In some embodiments, Factor VIII may be PEGylated. PEGylated Factor VIII can refer to a conjugate formed between Factor VIII and at least one polyethylene glycol (PEG) molecule. PEG is commercially available in a large variety of molecular weights and average molecular weight ranges. Typical examples of PEG average molecular weight ranges include, but are not limited to, 200, 300, 400, 600, 1000, 1300-1600, 1450, 2000, 3000, 3000-3750, 3350, 3000-7000, 3500-4500, 5000-7000, 7000-9000, 8000, 10000, 8500-11500, 16000-24000, 35000, and 40000. These average molecular weights are provided merely as examples and are not meant to be limiting in any way.

In one embodiment, the Factor VIII portion of the invention may be PEGylated to include mono- or poly- (e.g., 2-4) PEG moieties. PEGylation may be carried out by any of the PEGylation reactions known in the art. Methods for preparing a PEGylated protein product will generally include (a) reacting a polypeptide with polyethylene glycol (such as a reactive ester or aldehyde derivative of PEG) under conditions whereby the peptide of the invention becomes attached to one or more PEG groups; and (b) obtaining the reaction product(s). In general, the optimal reaction conditions for the reactions will be determined case by case based on known parameters and the desired result.

There are a number of PEG attachment methods available to those skilled in the art, for example, EP 0 401 384; Malik F et al. (1992) *Exp Hematol.* 20:1028-35; Francis (1992) *Focus on Growth Factors* 3(2):4-10; EP 0 154 316; EP 0 401 384; WO 92/16221; and WO 95/34326. As a non-limiting example, Factor VIII variants can contain cysteine substitutions at the surface-exposed sites, and the cysteines can be further conjugated to PEG polymer. Mei et al., *Blood*, Mar. 1, 2010, DOI 10.1182/blood-2009-11-254755, which is incorporated herein by reference in its entirety.

The step of PEGylation as described for the proteins of the invention may be carried out via an acylation reaction or an alkylation reaction with a reactive polyethylene glycol molecule. Thus, protein products according to the present invention include PEGylated proteins wherein the PEG group(s) is (are) attached via acyl or alkyl groups. Such products may be mono-PEGylated or poly-PEGylated (for example, those containing 2-6 or 2-5 PEG groups). The PEG groups are generally attached to the protein at the α- or ε-amino groups of amino acids, but it is also contemplated that the PEG groups can be attached to any amino group attached to the protein that is sufficiently reactive to become attached to a PEG group under suitable reaction conditions.

PEGylation by acylation generally involves reacting an active ester derivative of polyethylene glycol with a peptide of the invention. For acylation reactions, the polymer(s) selected typically have a single reactive ester group. Any known or subsequently discovered reactive PEG molecule may be used to carry out the PEGylation reaction. An example of a suitable, activated PEG ester is PEG esterified to N-hydroxysuccinimide (NHS). As used herein, acylation is contemplated to include, without limitation, the following types of linkages between the therapeutic protein and a polymer such as PEG: amide, carbamate, urethane, and the like. See, for example, Chamow S M et al. (1994) *Bioconjug Chem.* 5:133-40. Reaction conditions may be selected from any of those known in the PEGylation art or those subsequently developed, but should avoid conditions such as temperature, solvent, and pH that would inactivate the polypeptide to be modified.

PEGylation by acylation will generally result in a poly-PEGylated protein. The connecting linkage may be an amide. The resulting product may be substantially only (e.g., >95%) mono-, di- or tri-PEGylated. However, some species with higher degrees of PEGylation may be formed in amounts depending on the specific reaction conditions used. If desired, more purified PEGylated species may be separated from the mixture (particularly unreacted species) by standard purification techniques, including among others, dialysis, salting-out, ultrafiltration, ion-exchange chromatography, gel filtration chromatography and electrophoresis.

PEGylation by alkylation generally involves reacting a terminal aldehyde derivative of PEG with a polypeptide in the presence of a reducing agent. For the reductive alkylation reaction, the polymer(s) selected should have a single reactive aldehyde group. An exemplary reactive PEG aldehyde is polyethylene glycol propionaldehyde, which is water stable, or mono C1-C10 alkoxy or aryloxy derivatives thereof. See, for example, U.S. Pat. No. 5,252,714.

The Factor VIII portion of the present invention can also be glycoPEGylated. "GlycoPEGylated" Factor VIII can be produced by conjugating glycosylated or non-glycosylated Factor VIII with a glycosyl moiety that includes a polymer moiety, e.g., poly(ethylene glycol), alkyl derivative (e.g., m-PEG), or reactive derivative (e.g., H2N-PEG, HOOC-PEG), within its structure. In one embodiment, the PEG moiety is attached to the glycosyl moiety directly (i.e., through a single group formed by the reaction of two reactive groups) or through a linker moiety, e.g., substituted or unsubstituted alkyl, substituted or unsubstituted heteroalkyl, etc. The polymer can be attached at any position of a glycosyl moiety of Factor VIII. The glycosyl moiety can be N-linked or O-linked glycosylation. For example, the glycosyl moiety can be O-linked glycosylation, and the polymer moiety can be attached to the O-linked glycosyl moiety. See US2008/0280818 and WO 2009/089396, each of which is incorporated herein by reference in its entirety.

In other embodiments, Factor VIII used in the invention is conjugated to one or more polymers. The polymer can be water-soluble and covalently or non-covalently attached to Factor VIII or other moieties conjugated to Factor VIII. Non-limiting examples of the polymer can be poly(alkylene oxide), poly(vinyl pyrrolidone), poly(vinyl alcohol), polyoxazoline, or poly(acryloylmorpholine). Additional types of polymer-conjugated Factor VIII are disclosed in U.S. Pat. No. 7,199,223, which is disclosed by reference in its entirety.

In certain embodiments, Factor VIII is fused to albumin or albumin fragment or variant. Non-limiting examples of albumin-fused Factor VIII is disclosed in U.S. Application publication no. 2008/0261877, which is incorporated herein by reference in its entirety. The Factor VIII polypeptide can be fused to either the N-terminal end of an albumin or to the C-terminal end of the albumin, provided the Factor VIII component of the Factor VIII-albumin fusion protein can be processed by an enzymatically-active proprotein convertase to yield a processed Factor VIII-containing polypeptide, as described herein. In one embodiment the Factor VIII polypeptide is a human Factor VIII' polypeptide and the albumin polypeptide is a human albumin polypeptide.

In some embodiments, the Factor VIII protein is fused to a transferrin protein. A Factor VIII-transferrin fusion protein as used herein refers to a fusion protein that includes a Factor VIII (full-length or B-domain-deleted) polypeptide covalently bonded to transferrin. The Factor VIII polypeptide can be fused to either the N-terminal end of an transferrin polypeptide or to the C-terminal end of an transferrin polypeptide, provided the Factor VIII component of the Factor VIII-transferrin fusion protein can be processed by an enzymatically-active proprotein convertase to yield a processed Factor VIII-containing polypeptide, as described herein. In one embodiment the Factor VIII polypeptide is a human Factor VIII polypeptide and the transferrin polypeptide is a human transferrin polypeptide.

In some embodiments, the Factor VIII protein is fused to an artificial protein, such as an XTEN sequence (Schellenberger et al. Nature Biotechnology 2009. 27:1186).

The Factor VIII and a heterologous polypeptide, e.g., an immunoglobulin constant region (e.g., an Fc domain), albumin, or transferrin, may be fused by a direct peptide bond or by a linker. The linker can comprise any organic molecule. In one embodiment, the linker is polyethylene glycol (PEG). In another embodiment, the linker is amino acids. The linker can comprise 1-5 amino acids, 1-10 amino acids, 1-20 amino acids, 10-50 amino acids, 50-100 amino acids, 100-200 amino acids. In one embodiment, the linker is the eight amino acid linker, EFAGAAAV (SEQ ID NO: 50). Any of the linkers described herein may be used in the Factor VIII fusion, e.g., a monomer-dimer hybrid, including EFAGAAAV (SEQ ID NO: 50).

The linker can comprise the sequence $G_n$. The linker can comprise the sequence $(GA)_n$. The linker can comprise the sequence $(GGS)_n$. The linker can comprise the sequence $(GGS)_n(GGGGS)_n$ (SEQ ID NO: 63). In these instances, n may be an integer from 1-10, i.e., 1, 2, 3, 4, 5, 6, 7, 8, 9, 10. Examples of linkers include, but are not limited to, GGG, SGGSGGS (SEQ ID NO: 51), GGSGGSGGSGGSGGG (SEQ ID NO: 52), GGSGGSGGGGSGGGGS (SEQ ID NO: 53), GGSGGSGGSGGSGGSGGS (SEQ ID NO: 54). The linker does not eliminate or diminish the clotting activity of Factor VIII fusion protein. Optionally, the linker enhances the clotting activity of Factor VIII fusion protein, e.g., by further diminishing the effects of steric hindrance and making the Factor VIII portion more accessible to its target binding site.

In one embodiment, the linker for Factor VIII fusion is 15-25 amino acids long. In another embodiment, the linker for Factor VIII fusion is 15-20 amino acids long. In some embodiments, the linker for Factor VIII fusion is 10-25 amino acids long. In other embodiments, the linker for Factor VIII fusion is 15 amino acids long. In still other embodiments, the linker for Factor VIII fusion is $(GGGGS)_n$ (SEQ ID NO: 55) where G represents glycine, S represents serine and n is an integer from 1-10. In a specific embodiment, n is 3 (SEQ ID NO: 56).

The linker may also incorporate a moiety capable of being cleaved either chemically (e.g., hydrolysis of an ester bond), enzymatically (i.e., incorporation of a protease cleavage sequence) or photolytically (e.g., a chromophore such as 3-amino-3-(2-nitrophenyl) proprionic acid (ANP)) in order to release the biologically active molecule from the Fc protein.

Proprotein Convertases (Also Known as Prohormone Convertase)

The invention is based on the discovery that a proprotein convertase is capable of processing Factor VIII or Factor VIII variants at the corresponding residue by activating nonprocessed Factor VIII into processed Factor VIII. Proprotein convertases are also known as proprotein convertase subtilisin/kexin type proteins (PCSK), and there are nine subtypes of proprotein convertases (PCSK1, PCSK2, PCSK3, PCSK4, PCSK5, PCSK6, PCSK7, PCSK8, and PCSK9). In one embodiment, the proprotein convertase used for the present invention is selected from the group consisting of PCSK1, PCSK2, PCSK3, PCSK4, PCSK5, PCSK6, PCSK7, PCSK8, PCSK9, and a yeast Kex 2 protein. The proprotein convertase used for the purpose of this invention is an exogenous enzyme that is either added as a separate protein or expressed in a separate nucleotide sequence in the host cell expressing Factor VIII or expressed separately in a host cell different from the host cell expressing Factor VIII.

Proprotein convertase subtilisin/kexin type 1 (PCSK1) is also known as proprotein convertase 1 (PC1), proprotein convertase 3 (PC3), PC1/3, neuroendocrine convertase 1 (NEC 1), body mass index quantitative trait locus (BMIQ12), or prohormone convertase 1. The gene encoding PCSK1 is known as Pcsk1, Att-1, Nec-1, or Nec1 and has Accession Number M90753.1 in GenBank. The full-length human PCSK1 polypeptide has Accession Number P29120 in UniProtKB/Swiss-Prot entry and consists of a signal peptide (amino acids 1-27), a propeptide (amino acids 28-110), and the active protein domain (amino acids 111-753) including the catalytic domain (amino acids 122-410). The nucleotide and amino acid sequences of PCSK1 are represented herein as SEQ ID NO: 7 and SEQ ID NO: 8, respectively. Variants of human PCSK1 include, but are not limited to, the polypeptides with the following mutations: R80Q, N221D, S307L, G483R, Q665E, S690T, S357G, or S690T. Also included is PCSK1 from a different species, e.g., mouse, rat, monkey, dog, *drosophila*, or porcine.

PCSK1 Amino Acid Sequence (SEQ ID NO: 8)

```
MERRAWSLQC TAFVLFCAWC ALNSAKAKRQ FVNEWAAEIP GGPEAASAIA EELGYDLLGQ

IGSLENHYLF KHKNHPRRSR RSAFHITKRL SDDDRVIWAE QQYEKERSKR SALRDSALNL

FNDPMWNQQW YLQDTRMTAA LPKLDLHVIP VWQKGITGKG VVITVLDDGL EWNHTDIYAN

YDPEASYDFN DNDHDPFPRY DPTNENKHGT RCAGEIAMQA NNHKCGVGVA YNSKVGGIRM

LDGIVTDAIE ASSIGFNPGH VDIYSASWGP NDDGKTVEGP GRLAQKAFEY GVKQGRQGKG

SIFVWASGNG GRQGDNCDCD GYTDSIYTIS ISSASQQGLS PWYAEKCSST LATSYSSGDY

TDQRITSADL HNDCTETHTG TSASAPLAAG IFALALEANP NLTWRDMQHL VVWTSEYDPL

ANNPGWKKNG AGLMVNSRFG FGLLNAKALV DLADPRTWRS VPEKKECVVK DNDFEPRALK

ANGEVIIEIP TRACEGQENA IKSLEHVQFE ATIEYSRRGD LHVTLTSAAG TSTVLLAERE

RDTSPNGFKN WDFMSVHTWG ENPIGTWTLR ITDMSGRIQN EGRIVNWKLI LHGTSSQPEH

MKQPRVYTSY NTVQNDRRGV EKMVDPGEEQ PTQENPKENT LVSKSPSSSS VGGRRDELEE

GAPSQAMLRL LQSAFSKNSP PKQSPKKSPS AKLNIPYENF YEALEKLNKP SQLKDSEDSL

YNDYVDVFYN TKPYKHRDDR LLQALVDILN EEN
```

PCSK 1 Nucleic Acid Sequence (SEQ ID NO: 7)

```
atggagcgaa gagcctggag tctgcagtgc actgctttcg tcctcttttg cgcttggtgt

gcactgaaca gtgcaaaagc gaaaaggcaa tttgtcaatg aatgggcagc ggagatcccc

gggggcccgg aagcagcctc ggccatcgcc gaggagctgg gctatgacct tttgggtcag

attggttcac ttgaaaatca ctacttattc aaacataaaa accaccccag aaggtctcga

aggagtgcct ttcatatcac taagagatta tctgatgatg atcgtgtgat atgggctgaa

caacagtatg aaaaagaaag aagtaaacgt tcagctctaa gggactcagc actaaatctc

ttcaatgatc ccatgtggaa tcagcaatgg tacttgcaag ataccaggat gacggcagcc
```

-continued

```
ctgcccaagc tggaccttca tgtgatacct gtttggcaaa aaggcattac gggcaaagga
gttgttatca ccgtactgga tgatggtttg gagtggaatc acacggacat ttatgccaac
tatgatccag aggctagcta tgattttaat gataatgacc atgatccatt tccccgatat
gatcccacaa acgagaacaa acacgggacc agatgtgcag gagaaattgc catgcaagca
aataatcaca aatgcggggt tggagttgca tacaattcca aagttggagg cataagaatg
ctggatggca ttgtgacgga tgctattgag gccagttcaa ttggattcaa tcctggacac
gtggatattt acagtgcaag ctggggccct aatgatgatg ggaaaactgt ggaggggcct
ggccggctag cccagaaggc ttttgaatat ggtgtcaaac aggggagaca ggggaagggg
tccatcttcg tctgggcttc gggaaacggg gggcgtcagg gagataattg tgactgtgat
ggctacacag acagcatcta caccatctcc atcagcagtg cctcccagca aggcctatcc
ccctggtacg ctgagaagtg ctcctccaca ctggccacct cttacagcag cggagattac
accgaccaga gaatcacgag cgctgacctg cacaatgact gcacggagac gcacacaggc
acctcggcct ctgcacctct ggctgctggc atcttcgctc tggccctgga agcaaaccca
aatctcacct ggcgagatat gcagcacctg gttgtctgga cctctgagta tgacccgctg
gccaataacc ctggatggaa aaagaatgga gcaggcttga tggtgaatag tcgatttgga
tttggcttgc taaatgccaa agctctggtg gatttagctg accccaggac ctggaggagc
gtgcctgaga agaaagagtg tgttgtaaag gacaatgact ttgagcccag agccctgaaa
gctaatggag aagttatcat tgaaattcca acaagagctt gtgaaggaca agaaaatgct
atcaagtccc tggagcatgt acaatttgaa gcaacaattg aatattcccg aagaggagac
cttcatgtca cacttacttc tgctgctgga actagcactg tgctcttggc tgaaagagaa
cgggatacat ctcctaatgg ctttaagaac tgggacttca tgtctgttca cacatgggga
gagaacccta taggtacttg gactttgaga attacagaca tgtctggaag aattcaaaat
gaaggaagaa ttgtgaactg gaagctgatt ttgcacggga cctcttctca gccagagcat
atgaagcagc ctcgtgtgta cacgtcctac aacactgttc agaatgacag aagaggggtg
gagaagatgg tggatccagg ggaggagcag cccacacaag agaaccctaa ggagaacacc
ctggtgtcca aaagccccag cagcagcagc gtagggggcc ggagggatga gttggaggag
ggagcccctt cccaggccat gctgcgactc ctgcaaagtg ctttcagtaa aaactcaccg
ccaaagcaat caccaaagaa gtccccaagt gcaaagctca acatccctta tgaaaacttc
tacgaagccc tggaaaagct gaacaaacct tcccagctta aagactctga agacagtctg
tataatgact atgttgatgt tttttataac actaaacctt acaagcacag agacgaccgg
ctgcttcaag ctctggtgga cattctgaat gaggaaaatt aa
```

In one embodiment, the proprotein convertase used for the present invention comprises an amino acid sequence, which is at least 60%, 70%, 75%, 80%, 85%, 90%, 95%, 96%, 97%, 98%, 99%, or 100% identical to amino acids 122-410 of SEQ ID NO: 8, amino acids 111 to 753 of SEQ ID NO: 8, amino acids 28 to 753 of SEQ ID NO: 8, or SEQ ID NO: 8, wherein the amino acid sequence is capable of cleaving full-length Factor VIII at amino acid residue 1648.

Proprotein convertase subtilisin/kexin type 2 (PCSK2) is also known as proprotein convertase 2(PC2), neuroendocrine convertase 2 (NEC2), KEX2-like endoprotease 2, or prohormone convertase 2. The gene encoding PCSK2 is known as pcsk2 or nec2 has Accession Number AH002912 in GenBank. The full-length human PCSK2 polypeptide has Accession Number P16519 in UniProtKB/Swiss-Prot entry and consists of a signal peptide (amino acids 1-25), a propeptide (amino acids 26-109), and the active protein domain (amino acids 110-638) including the catalytic domain (amino acids 122-415). The nucleotide and amino acid sequences of PCSK2 are represented herein as SEQ ID NO: 9 and SEQ ID NO: 10, respectively. Variants of human PCSK2 include, but are not limited to, the polypeptides with the following mutations: D424N or EL283-284DV. Also included is PCSK2 from a different species, e.g., mouse, rat, monkey, dog, *drosophila*, or porcine.

PCSK2 Amino Acid Sequence (SEQ ID NO: 10)

MKGGCVSQWK AAAGFLFCVM VFASAERPVF TNHFLVELHK GGEDKARQVA AEHGFGVRKL

PFAEGLYHFY HNGLAKAKRR RSLHHKQQLE RDPRVKMALQ QEGFDRKKRG YRDINEIDIN

MNDPLFTKQW YLINTGQADG TPGLDLNVAE AWELGYTGKG VTIGIMDDGI DYLHPDLASN

YNAEASYDFS SNDPYPYPRY TDDWFNSHGT RCAGEVSAAA NNNICGVGVA YNSKVAGIRM

LDQPFMTDII EASSISHMPQ LIDIYSASWG PTDNGKTVDG PRELTLQAMA DGVNKGRGGK

GSIYVWASGD GGSYDDCNCD GYASSMWTIS INSAINDGRT ALYDESCSST LASTFSNGRK

RNPEAGVATT DLYGNCTLRH SGTSAAAPEA AGVFALALEA NLGLTWRDMQ HLTVLTSKRN

QLHDEVHQWR RNGVGLEFNH LFGYGVLDAG AMVKMAKDWK TVPERFHCVG GSVQDPEKIP

STGKLVLTLT TDACEGKENF VRYLEHVQAV ITVNATRRGD LNINMTSPMG TKSILLSRRP

RDDDSKVGFD KWPFMTTHTW GEDARGTWTL ELGFVGSAPQ KGVLKEWTLM LHGTQSAPYI

DQVVRDYQSK LAMSKKEELE EELDEAVERS LKSILNKN

PCSK 2 Nucleic Acid Sequence (SEQ ID NO: 9)

atgaagggtg gttgtgtctc ccagtggaag gcggccgccg ggttcctctt ctgtgtcatg gtttttgcat ctgctgagcg accggtcttc acgaatcatt ttcttgtgga gttgcataaa gggggagagg acaaagctcg ccaagttgca gcagaacacg gctttggagt ccgaaagctt ccctttgctg aaggtctgta ccacttttat cacaatggcc ttgcaaaggc caagagaaga cgcagcctac accacaagca gcagctggag agagacccca gggtaaagat ggctttgcag caggaaggat ttgaccgaaa aaagcgaggt tacagagaca tcaatgagat cgacatcaac atgaacgatc ctctttttac aaagcagtgg tatctgatca atactgggca agctgatggc actcctggcc ttgatttgaa tgtggctgaa gcctgggagc tgggatacac agggaaaggt gttaccattg gaattatgga tgatgggatt gactatctcc acccggacct ggcctccaac tataatgccg aagcaagtta cgacttcagc agcaacgacc cctatcctta ccctcggtac acagatgact ggtttaacag ccacgggacc cgatgtgcag gagaagtttc tgctgccgcc aacaacaata tctgtggagt tggagtagca tacaactcca aggttgcagg catccggatg ctggaccagc cattcatgac agacatcatc gaggcctcct ccatcagtca tatgccacag ctgattgaca tctacagcgc cagctggggc cccacagaca acggcaagac agtggatggg ccccgggagc tcacgctgca ggccatggcc gatggcgtga acaagggccg cggcggcaaa ggcagcatct acgtgtgggc ctccggggac ggcggcagct atgacgactg caactgcgac ggctacgcct ccagcatgtg gaccatctcc atcaactcag ccatcaacga cggcaggact gccctgtacg acgagagctg ctcttccacc ttggcttcca ccttcagcaa cgggaggaaa aggaaccccg aggccggtgt ggcaaccaca gatttgtacg gcaactgcac tctgaggcat tctgggacat ctgcagctgc ccccgaggca gctggtgtgt ttgcactggc tctggaggct aacctgggtc tgacctggcg ggacatgcag catctgactg tgctcacctc caaacggaac cagcttcacg acgaggtcca tcagtggcgg cgcaatgggg tcggcctgga atttaatcac ctctttggct acggggtcct tgatgcaggt gccatggtga aaatggctaa agactggaaa accgtgcctg agagattcca ctgtgtggga ggctccgtgc aggaccctga gaaaatacca tccactggca agttggtgct gacactcaca accgacgcct gtgaggggaa ggaaaatttt gtccgctacc tggagcatgt ccaggctgtc atcacggtca acgcaaccag aagaggagac ctgaacatca acatgacttc ccctatgggc accaagtcca ttttgctgag ccggcgtcca agggatgacg actccaaggt gggctttgac aagtggcctt tcatgaccac tcacacgtgg -continued

```
ggggaagacg cccgaggcac ctggaccctg gagctgggat ttgtcggcag cgccccgcag

aagggggtgc tgaaggagtg gaccctgatg ctgcatggca ctcagagtgc cccgtacatc

gaccaggtgg tgcgggatta ccagtccaag ttggccatgt ccaagaaaga ggagctggag

gaagagctgg acgaagccgt ggagagaagc ctgaaaagca tccttaacaa gaactag
```

In one embodiment, the proprotein convertase used for the present invention comprises an amino acid sequence, which is at least 60%, 70%, 75%, 80%, 85%, 90%, 95%, 96%, 97%, 98%, 99%, or 100% identical to amino acids 122-415 of SEQ ID NO: 10, amino acids 110 to 638 of SEQ ID NO: 10, amino acids 26 to 638 of SEQ ID NO: 10, or SEQ ID NO: 10, wherein the amino acid sequence is capable of cleaving full-length Factor VIII at amino acid residue 1648.

Proprotein convertase subtilisin/kexin type 3 (PCSK3) is also known as Furin, Paired Basic Amino Acid Residue Cleaving Enzyme (PACE), Dibasic-Processing Enzyme, or Prohormone Convertase 3. The gene encoding PCSK3 is known as Pcsk3, Furin, or Fur and has Accession Number BC012181 in GenBank. The full-length human PCSK3 polypeptide has Accession Number P09958 in UniProtKB/Swiss-Prot entry and consists of a signal peptide (amino acids 1-24), propeptide (amino acids 25-107), and the active protein domain (amino acids 108-794). The nucleotide and amino acid sequences of PCSK3 are represented herein as SEQ ID NO: 11 and SEQ ID NO: 12, respectively. Variants of human PCSK3 include, but are not limited to, the polypeptides with the following mutations: A43V or W547R. Also included is PCSK3 from a different species, e.g., mouse, rat, monkey, dog, *drosophila*, or porcine.

```
PCSK3 Amino Acid Sequence
                                                        (SEQ ID NO: 12)
MELRPWLLWV VAATGTLVLL AADAQGQKVF TNTWAVRIPG GPAVANSVAR KHGFLNLGQI

FGDYYHFWHR GVTKRSLSPH RPRHSRLQRE PQVQWLEQQV AKRRTKRDVY QEPTDPKFPQ

QWYLSGVTQR DLNVKAAWAQ GYTGHGIVVS ILDDGIEKNH PDLAGNYDPG ASFDVNDQDP

DPQPRYTQMN DNRHGTRCAG EVAAVANNGV CGVGVAYNAR IGGVRMLDGE VTDAVEARSL

GLNPNHIHIY SASWGPEDDG KTVDGPARLA EEAFFRGVSQ GRGGLGSIFV WASGNGGREH

DSCNCDGYTN SIYTLSISSA TQFGNVPWYS EACSSTLATT YSSGNQNEKQ IVTTDLRQKC

TESHTGTSAS APLAAGIIAL TLEANKNLTW RDMQHLVVQT SKPAHLNAND WATNGVGRKV

SHSYGYGLLD AGAMVALAQN WTTVAPQRKC IIDILTEPKD IGKRLEVRKT VTACLGEPNH

ITRLEHAQAR LTLSYNRRGD LAIHLVSPMG TRSTLLAARP HDYSADGFND WAFMTTHSWD

EDPSGEWVLE IENTSEANNY GTLTKFTLVL YGTAPEGLPV PPESSGCKTL TSSQACVVCE

EGFSLHQKSC VQHCPPGFAF QVLDTHYSTE NDVETIRASV CAPCHASCAT CQGPALTDCL

SCPSHASLDP VEQTCSRQSQ SSRESPPQQQ PPRLPPEVEA GQRLRAGLLP SHLPEVVAGL

SCAFIVLVFV TVFLVLQLRS GESERGVKVY TMDRGLISYK GLPPEAWQEE CPSDSEEDEG

RGERTAFIKD QSAL

PCSK 3 Nucleic Acid Sequence
                                                        (SEQ ID NO: 11)
atggagctga ggccctggtt gctatgggtg gtagcagcaa caggaacctt ggtcctgcta

gcagctgatg ctcagggcca gaaggtcttc accaacacgt gggctgtgcg catccctgga

ggcccagcgg tggccaacag tgtggcacgg aagcatgggt tcctcaacct gggccagatc

ttcggggact attaccactt ctggcatcga ggagtgacga agcggtccct gtcgcctcac

cgcccgcggc acagccggct gcagagggag cctcaagtac agtggctgga acagcaggtg

gcaaagcgac ggactaaacg ggacgtgtac caggagccca cagaccccaa gtttcctcag

cagtggtacc tgtctggtgt cactcagcgg gacctgaatg tgaaggcggc ctgggcgcag

ggctacacag ggcacggcat tgtggtctcc attctggacg atggcatcga gaagaaccac

ccggacttgg caggcaatta tgatcctggg gccagttttg atgtcaatga ccaggaccct

gacccccagc ctcggtacac acagatgaat gacaacaggc acggcacacg gtgtgcgggg

gaagtggctg cggtggccaa caacggtgtc tgtggtgtag gtgtggccta caacgcccgc
```

-continued

```
attggagggg tgcgcatgct ggatggcgag gtgacagatg cagtggaggc acgctcgctg
ggcctgaacc ccaaccacat ccacatctac agtgccagct ggggccccga ggatgacggc
aagacagtgg atgggccagc ccgcctcgcc gaggaggcct tcttccgtgg ggttagccag
ggccgagggg ggctgggctc catctttgtc tgggcctcgg ggaacggggg ccgggaacat
gacagctgca actgcgacgg ctacaccaac agtatctaca cgctgtccat cagcagcgcc
acgcagtttg gcaacgtgcc gtggtacagc gaggcctgct cgtccacact ggccacgacc
tacagcagtg gcaaccagaa tgagaagcag atcgtgacga ctgacttgcg gcagaagtgc
acggagtctc acacgggcac ctcagcctct gcccccttag cagccggcat cattgctctc
accctggagg ccaataagaa cctcacatgg cgggacatgc aacacctggt ggtacagacc
tcgaagccag cccacctcaa tgccaacgac tgggccacca atggtgtggg ccggaaagtg
agccactcat atggctacgg gcttttggac gcaggcgcca tggtggccct ggcccagaat
tggaccacag tggcccccca gcggaagtgc atcatcgaca tcctcaccga gcccaaagac
atcgggaaac ggctcgaggt gcggaagacc gtgaccgcgt gcctgggcga gcccaaccac
atcactcggc tggagcacgc tcaggcgcgg ctcaccctgt cctataatcg ccgtggcgac
ctggccatcc acctggtcag ccccatgggc acccgctcca ccctgctggc agccaggcca
catgactact ccgcagatgg gtttaatgac tgggccttca tgacaactca ttcctgggat
gaggatccct ctggcgagtg ggtcctagag attgaaaaca ccagcgaagc caacaactat
gggacgctga ccaagttcac cctcgtactc tatggcaccg cccctgaggg gctgcccgta
cctccagaaa gcagtggctg caagaccctc acgtccagtc aggcctgtgt ggtgtgcgag
gaaggcttct ccctgcacca gaagagctgt gtccagcact gccctccagg cttcgccccc
caagtcctcg atacgcacta tagcaccgag aatgacgtgg agaccatccg ggccagcgtc
tgcgccccct gccacgcctc atgtgccaca tgccaggggc cggccctgac agactgcctc
agctgcccca gccacgcctc cttggaccct gtggagcaga cttgctcccg gcaaagccag
agcagccgag agtccccgcc acagcagcag ccacctcggc tgcccccgga ggtggaggcg
gggcaacggc tgcgggcagg gctgctgccc tcacacctgc ctgaggtggt ggccggcctc
agctgcgcct tcatcgtgct ggtcttcgtc actgtcttcc tggtcctgca gctgcgctct
ggctttagtt ttcggggggt gaaggtgtac accatggacc gtggcctcat ctcctacaag
gggctgcccc ctgaagcctg gcaggaggag tgcccgtctg actcagaaga ggacgagggc
cggggcgaga ggaccgcctt tatcaaagac cagagcgccc tctga
```

In one embodiment, the proprotein convertase used for the present invention comprises an amino acid sequence, which is at least 60%, 70%, 75%, 80%, 85%, 90%, 95%, 96%, 97%, 98%, 99%, or 100% identical to amino acids 108 to 794 of SEQ ID NO: 12, amino acids 25 to 794 of SEQ ID NO: 12, or SEQ ID NO: 12, wherein the amino acid sequence is capable of cleaving full-length Factor VIII at amino acid residue 1648.

Proprotein convertase subtilisin/kexin type 4 (PCSK4) is also known as proprotein convertase 4 (PC4), Neuroendocrine convertase 3 (NEC3), prohormone convertase 3, or KEX2-like endoprotease 3. The gene encoding PCSK4 is known as Pcsk3, Nee-3, or Nec3 and has Accession Number AY358963 in GenBank. The full-length human PCSK3 polypeptide has Accession Number AAQ89322.1 in GenBank and consists of a signal peptide (amino acids 1-25), propeptide (amino acids 26-113), and the active protein domain (amino acids 114-755) including the catalytic domain (amino acids 124-417). The nucleotide and amino acid sequences of PCSK4 are represented herein as SEQ ID NO: 13 or 15 and SEQ ID NO: 14 or 16, respectively. Variants of human PCSK4 include, but are not limited to, the polypeptides with the mutation of T267M. Also included is PCSK4 from a different species, e.g., mouse, rat, monkey, dog, *drosophila*, or porcine.

PCSK4 Isoform 1 Amino Acid Sequence (SEQ ID NO: 14)

MRPAPIALWL RLVLALALVR PRAVGWAPVR APIYVSSWAV QVSQGNREVE RLARKFGFVN

LGPIFSDGQY FHLRHEGVVQ QSLTPHWGHR LHLKKNPKQV WFQQQTLQRR VKRSVVVPTD

PWFSKQWYMN SEAQPDLSIL QAWSQGLSGQ GIVVSVLDDG IEKDHPDLWA NYDPLASYDF

NDYDPDPQPR YTPSKENRHG TRCAGEVAAM ANNGFCGVGV AFNARIGGVR MLDGTITDVI

EAQSLSLQPQ HIHIYSASWG PEDDGRTVDG PGILTREAFR RGVTKGRGGL GTLFIWASGN

GGLHYDNCNC DGYTNSIHTL SVGSTTQQGR VPWYSEACAS TLTTTYSSGV ATDPQIVTTD

LHHGCTDQHT GTSASAPLAA GMIALALEAN PFLTWRDMQH LVVRASKPAH LQAEDWRTNG

VGRQVSHHYG YGLLDAGLLV DTARTWLPTQ PQRKCAVRVQ SRPTPILPLI YIRENVSACA

GLHNSIRSLE HVQAQLTLSY SRRGDLEISL TSPMGTRSTL VAIRPLDVST EGYNNWVFMS

THFWDENPQG VWTLGLENKG YYFNTGTLYR YTLLLYGTAE DMTARPTGPQ VTSSACVQRD

TEGLCQACDG PAYILGQLCL AYCPPRFFNH TRLVTAGPGH TAAPALRVCS SCHASCYTCR

GGSPRDCTSC PPSSTLDQQQ GSCMGPTTPD SRPRLRAAAC PHHRCPASAM VLSLLAVTLG

GPVLCGMSMD LPLYAWLSRA RATPTKPQVW LPAGT

PCSK 4 Isoform 1 Nucleic Acid Sequence (SEQ ID NO: 13)

atgcggcccg ccccgattgc gctgtggctg cgcctggtct tggccctggc ccttgtccgc ccccgggctg tggggtgggc cccggtccga gcccccatct atgtcagcag ctgggccgtc caggtgtccc agggtaaccg ggaggtcgag cgcctggcac gcaaattcgg cttcgtcaac ctggggccga tcttctctga cgggcagtac tttcacctgc ggcaccgggg cgtggtccag cagtccctga ccccgcactg gggccaccga ctgcacctga agaaaaaccc caaggtgcag tggttccagc agcagacgct gcagcggcgg gtgaaacgct ctgtcgtggt gcccacggac ccctggttct ccaagcagtg gtacatgaac agcgaggccc aaccagacct gagcatcctg caggcctgga gtcaggggct gtcaggccag ggcatcgtgg tctctgtgct ggacgatggc atcgagaagg accacccgga cctctgggcc aactacgacc ccctggccag ctatgacttc aatgactacg acccggaccc ccagccccgc tacaccccca gcaaagagaa ccggcacggg acccgctgtg ctggggaggt ggccgcgatg gccaacaatg gcttctgtgg tgtgggggtc gctttcaacg cccgaatcgg aggcgtacgg atgctggacg gtaccatcac cgatgtcatc gaggcccagt cgctgagcct gcagccgcag cacatccaca tttacagcgc cagctggggt cccgaggacg acggccgcac ggtggacggc cccggcatcc tcacccgcga ggccttccgg cgtggtgtga ccaagggccg cggcgggctg ggcacgctct tcatctgggc ctcgggcaac ggcggcctgc actacgacaa ctgcaactgc gacggctaca ccaacagcat ccacacgctt tccgtgggca gcaccaccca gcagggccgc gtgccctggt acagcgaagc ctgcgcctcc accctcacca ccacctacag cagcggcgtg gccaccgacc cccagatcgt caccacggac ctgcatcacg ggtgcacaga ccagcacacg ggcacctcgg cctcagcccc actggcggcc ggcatgatcg ccctagcgct ggaggccaac ccgttcctga cgtggagaga catgcagcac ctggtggtcc gcgcgtccaa gccggcgcac ctgcaggccg aggactggag gaccaacggc gtggggcgcc aagtgagcca tcactacgga tacgggctgc tggacgccgg gctgctggtg gacaccgccc gcacctggct gcccacccag ccgcagagga agtgcgccgt ccgggtccag agccgcccca cccccatcct gccgctgatc tacatcaggg aaaacgtatc ggcctgcgcc ggcctccaca actccatccg ctcgctggag cacgtgcagg cgcagctgac gctgtcctac agccggcgcg gagacctgga gatctcgctc accagcccca tgggcacgcg ctccacactc -continued gtggccatac gacccttgga cgtcagcact gaaggctaca acaactgggt cttcatgtcc acccacttct gggatgagaa cccacagggc gtgtggaccc tgggcctaga gaacaagggc tactatttca acacggggac gttgtaccgc tacacgctgc tgctctatgg gacggccgag gacatgacag cgcggcctac aggcccccag gtgaccagca gcgcgtgtgt gcagcgggac acagaggggc tgtgccaggc gtgtgacggc cccgcctaca tcctgggaca gctctgcctg gcctactgcc ccccgcggtt cttcaaccac acaaggctgg tgaccgctgg gcctgggcac acggcggcgc ccgcgctgag ggtctgctcc agctgccatg cctcctgcta cacctgccgc ggcggctccc cgagggactg cacctcctgt cccccatcct ccacgctgga ccagcagcag ggctcctgca tgggacccac cacccccgac agccgccccc ggcttagagc tgccgcctgt ccccaccacc gctgcccagc ctcggccatg gtgctgagcc tcctggccgt gaccctcgga ggccccgtcc tctgcggcat gtccatggac ctcccactat acgcctggct ctcccgtgcc agggccaccc ccaccaaacc ccaggtctgg ctgccagctg gaacctga PCSK 4 Isoform 2 Amino Acid Sequence (SEQ ID NO: 16)

MGTRSTLVAI RPLDVSTEGY NNWVFMSTHF WDENPQGVWT LGLENKGYYF NTGTLYRYTL

LLYGTAEDMT ARPTGPQVTS SACVQRDTEG LCQACDGPAY ILGQLCLAYC PPRFFNHTRL

VTAGPGHTAA PALRVCSSCH ASCYTCRGGS PRDCTSCPPS STLDQQQGSC MGPTTPDSRP

RLRAAACPHH RCPASAMVLS LLAVTLGGPV LCGMSMDLPL YAWLSRARAT PTKPQVWLPA

GT

PCSK 4 isoform 2 Nucleic Acid Sequence (SEQ ID NO: 15)

atgggcacgc gctccacact cgtggccata cgacccttgg acgtcagcac tgaaggctac aacaactggg tcttcatgtc cacccacttc tgggatgaga acccacaggg cgtgtggacc ctgggcctag agaacaaggg ctactatttc aacacgggga cgttgtaccg ctacacgctg ctgctctatg ggacggccga ggacatgaca gcgcggccta caggccccca ggtgaccagc agcgcgtgtg tgcagcggga cacagagggg ctgtgccagg cgtgtgacgg ccccgcctac atcctgggac agctctgcct ggcctactgc cccccgcggt tcttcaacca cacaaggctg gtgaccgctg ggcctgggca cacggcggcg cccgcgctga gggtctgctc cagctgccat gcctcctgct acacctgccg cggcggctcc ccgagggact gcacctcctg tcccccatcc tccacgctgg accagcagca gggctcctgc atgggaccca ccacccccga cagccgcccc cggcttagag ctgccgcctg tccccaccac cgctgcccag cctcggccat ggtgctgagc ctcctggccg tgaccctcgg aggccccgtc ctctgcggca tgtccatgga cctcccacta tacgcctggc tctcccgtgc cagggccacc cccaccaaac cccaggtctg gctgccagct ggaacctga In one embodiment, a proprotein convertase used for the present invention comprises an amino acid sequence, which is at least 60%, 70%, 75%, 80%, 85%, 90%, 95%, 96%, 97%, 98%, 99%, or 100% identical to amino acids 124 to 417 of SEQ ID NO: 14, amino acids 114-755 of SEQ ID NO: 14, amino acids 26 to 755 of SEQ ID NO: 14, SEQ ID NO: 14, amino acids 114-513 of SEQ ID NO: 14, amino acids 26 to 513 of SEQ ID NO: 14 or SEQ ID NO: 16, wherein the amino acid sequence is capable of cleaving full-length Factor VIII at amino acid residue 1648.

Proprotein convertase subtilisin/kexin type 5 (PCSK5) is also known as proprotein convertase 5 (PC5), proprotein convertase 6 (PC6), subtilisin/kexin-like protease PC5, or subtilisin-like proprotein convertase 6 (SPC6). The gene encoding PCSK5 is known as Pcsk5, furl, or PC5 and has Accession Number AL834522.1 in GenBank. The full-length human PCSK5 polypeptide has Accession Number NM-006200 in GenBank and consists of a signal peptide (amino acids 1-32), propeptide (amino acids 33-114), and the active protein domain (amino acids 115-913) including a catalytic domain (amino acids 115-454) and a cysteine-rich motif (amino acids 636-868). The nucleotide and amino acid sequences of PCSK5 are represented herein as SEQ ID NO: 17 and SEQ ID NO: 18, respectively. Variants of human PCSK5 include, but are not limited to, the polypeptides with the following mutations: G2D, G4E, F118S, A121V, R511A, and Q601R. An isoform is also available in GenBank as Accession No. NP_001177411 (SEQ ID NO: 57) for the amino acid sequence and Accession No. NM_001190482 (SEQ ID NO: 58) for the nucleotide sequence, both of which are incorporated herein by reference in its entirety. Also included is PCSK5 from a different species, e.g., mouse, rat, monkey, dog, *drosophila*, or porcine.

PCSK5 Amino Acid Sequence (SEQ ID NO: 18)

```
MGWGSRCCCP GRLDLLCVLA LLGGCLLPVC RTRVYTNHWA VKIAGGFPEA NRIASKYGFI
NIGQIGALKD YYHFYHSRTI KRSVISSRGT HSFISMEPKV EWIQQQVVKK RTKRDYDFSR
AQSTYFNDPK WPSMWYMHCS DNTHPCQSDM NIEGAWKRGY TGKNIVVTIL DDGIERTHPD
LMQNYDALAS CDVNGNDLDP MPRYDASNEN KHGTRCAGEV AAAANNSHCT VGIAFNAKIG
GVRMLDGDVT DMVEAKSVSF NPQHVHIYSA SWGPDDDGKT VDGPAPLTRQ AFENGVRMGR
RGLGSVFVWA SGNGGRSKDH CSCDGYTNSI YTISISSTAE SGKKPWYLEE CSSTLATTYS
SGESYDKKII TTDLRQRCTD NHTGTSASAP MAAGIIALAL EANPFLTWRD VQHVIVRTSR
AGHLNANDWK TNAAGFKVSH LYGFGLMDAE AMVMEAEKWT TVPRQHVCVE STDRQIKTIR
PNSAVRSIYK ASGCSDNPNR HVNYLEHVVV RITITHPRRG DLAIYLTSPS GTRSQLLANR
LFDHSMEGFK NWEFMTIHCW GERAAGDWVL EVYDTPSQLR NFKTPGKLKE WSLVLYGTSV
QPYSPTNEFP KVERFRYSRV EDPTDDYGTE DYAGPCDPEC SEVGCDGPGP DHCNDCLHYY
YKLKNNTRIC VSSCPPGHYH ADKKRCRKCA PNCESCFGSH GDQCMSCKYG YFLNEETNSC
VTHCPDGSYQ DTKKNLCRKC SENCKTCTEF HNCTECRDGL SLQGSRCSVS CEDGRYFNGQ
DCQPCHRFCA TCAGAGADGC INCTEGYFME DGRCVQSCSI SYYFDHSSEN GYKSCKKCDI
SCLTCNGPGF KNCTSCPSGY LLDLGMCQMG AICKDATEES WAEGGFCMLV KKNNLCQRKV
LQQLCCKTCT FQG
```

PCSK 5 Nucleic Acid Sequence (SEQ ID NO: 17)

```
atgggctggg ggagccgctg ctgctgcccg ggacgtttgg acctgctgtg cgtgctggcg
ctgctcgggg gctgcctgct ccccgtgtgt cggacgcgcg tctacaccaa ccactgggca
gtcaaaatcg ccgggggctt cccggaggcc aaccgtatcg ccagcaagta cggattcatc
aacataggac agataggggc cctgaaggac tactaccact tctaccatag caggacgatt
aaaaggtcag ttatctcgag cagagggacc cacagtttca tttcaatgga accaaaggtg
gaatggatcc aacagcaagt ggtaaaaaag cggacaaaga gggattatga cttcagtcgt
gcccagtcta cctatttcaa tgatcccaag tggcccagca tgtggtatat gcactgcagt
gacaatacac atccctgcca gtctgacatg aatatcgaag gagcctggaa gagaggctac
acgggaaaga acattgtggt cactatcctg gatgacggaa ttgagagaac ccatccagat
ctgatgcaaa actacgatgc tctggcaagt tgcgacgtga atgggaatga cttggaccca
atgcctcgtt atgatgcaag caacgagaac aagcatggga ctcgctgtgc tggagaagtg
gcagccgctg caaacaattc gcactgcaca gtcggaattg ctttcaacgc caagatcgga
ggagtgcgaa tgctggacgg agatgtcacg gacatggttg aagcaaaatc agttagcttc
aacccccagc acgtgcacat ttacagcgcc agctggggcc cggatgatga tggcaagact
gtggacggac cagcccccct cacccggcaa gcctttgaaa acggcgttag aatggggcgg
agaggcctcg gctctgtgtt tgtttgggca tctggaaatg gtggaaggag caaagaccac
tgctcctgtg atggctacac caacagcatc tacaccatct ccatcagcag cactgcagaa
agcggaaaga aaccttggta cctggaagag tgttcatcca cgctggccac aacctacagc
agcggggagt cctacgataa gaaaatcatc actacagatc tgaggcagcg ttgcacggac
aaccacactg ggacgtcagc ctcagccccc atggctgcag gcatcattgc gctggccctg
```

-continued

```
gaagccaatc cgtttctgac ctggagagac gtacagcatg ttattgtcag gacttcccgt
gcgggacatt tgaacgctaa tgactggaaa accaatgctg ctggttttaa ggtgagccat
ctttatggat ttggactgat ggacgcagaa gccatggtga tggaggcaga gaagtggacc
accgttcccc ggcagcacgt gtgtgtggag agcacagacc gacaaatcaa gacaatccgc
cctaacagtg cagtgcgctc catctacaaa gcttcaggct gctcggataa ccccaaccgc
catgtcaact acctggagca cgtcgttgtg cgcatcacca tcacccaccc caggagagga
gacctggcca tctacctgac ctcgccctct ggaactaggt ctcagctttt ggccaacagg
ctatttgatc actccatgga aggattcaaa aactgggagt tcatgaccat tcattgctgg
ggagaaagag ctgctggtga ctgggtcctt gaagtttatg atactccctc tcagctaagg
aactttaaga ctccaggtaa attgaaagaa tggtctttgg tcctctacgg cacctccgtg
cagccatatt caccaaccaa tgaatttccg aaagtggaac ggttccgcta tagccgagtt
gaagacccca cagacgacta tggcacagag gattatgcag gtccctgcga ccctgagtgc
agtgaggttg gctgtgacgg gccaggacca gaccactgca atgactgttt gcactactac
tacaagctga aaaacaatac caggatctgt gtctccagct gccccccctgg ccactaccac
gccgacaaga agcgctgcag gaagtgtgcc cccaactgtg agtcctgctt tgggagccat
ggtgaccaat gcatgtcctg caaatatgga tactttctga atgaagaaac caacagctgt
gttactcact gccctgatgg gtcatatcag gataccaaga aaaatctttg ccggaaatgc
agtgaaaact gcaagacatg tactgaattc cataactgta cagaatgtag ggatgggtta
agcctgcagg gatcccggtg ctctgtctcc tgtgaagatg gacggtattt caacggccag
gactgccagc cctgccaccg cttctgcgcc acttgtgctg gggcaggagc tgatgggtgc
attaactgca cagagggcta cttcatggag gatgggagat gcgtgcagag ctgtagtatc
agctattact ttgaccactc ttcagagaat ggatacaaat cctgcaaaaa atgtgatatc
agttgtttga cgtgcaatgg cccaggattc aagaactgta caagctgccc tagtgggtat
ctcttagact taggaatgtg tcaaatggga gccatttgca aggatgcaac ggaagagtcc
tgggcggaag gaggcttctg tatgcttgtg aaaaagaaca atctgtgcca acggaaggtt
cttcaacaac tttgctgcaa aacatgtaca tttcaaggct ga
```

In one embodiment, the proprotein convertase used for the present invention comprises an amino acid sequence, which is at least 60%, 70%, 75%, 80%, 85%, 90%, 95%, 96%, 97%, 98%, 99%, or 100% identical to amino acids 115 to 454 of SEQ ID NO: 18, amino acids 636 to 868 of SEQ ID NO: 18, amino acids 115 to 913 of SEQ ID NO: 18, amino acids 33 to 913 of SEQ ID NO: 18, or SEQ ID NO: 18, wherein the amino acid sequence is capable of cleaving full-length Factor VIII at amino acid residue 1648.

Proprotein convertase subtilisin/kexin type 6 (PCSK6) is also known as paired basic amino acid cleaving enzyme 4 (PACE4), subtilisin/kexin-like protease, subtilisin-like proprotein convertase 4 (SPC4). The gene encoding PCSK6 is known as Pcsk6 or pace4 and has Accession Number M80482.1 in GenBank. The full-length human PCSK6 polypeptide has Accession Number P29122 in UniProtKB/Swiss-Prot entry. Several isoforms produced by alternative splicing are also available as Accession Numbers P29122-1 (Isoform PACE4A-I), P29122-2 (Isoform PACE4A-II), P29122-3 (Isoform PACE4B), P29122-4 (isoform PACE4C), P29122-5 (isoform PACE4CS), P29122-6 (isoform PACE4D), P29122-7 (isoform PACE4E-I), and P29122-8 (isoform PACE4E-II). Isoform PACE4A-I consists of a signal peptide (amino acids 1-63), a propeptide (amino acids 64-149), and active protein domain (amino acids 150-969) including a catalytic domain (amino acids 150-454) and a cysteine-rich motif (amino acids 695-930). The nucleotide and amino acid sequences of isoform PACE4A-I are represented herein as SEQ ID NO: 19 and SEQ ID NO: 20, respectively. Variants of PACE4 include, but are not limited to, the polypeptides with the following mutations: KLK621-623NLD, C502R and T639I. Also included is PCSK6 from a different species, e.g., mouse, rat, monkey, dog, *drosophila*, or porcine.

PCSK6 Amino Acid Sequence (SEQ ID NO: 20)

MPPRAPPAPG PRPPPRAAAA TDTAAGAGGA GGAGGAGGPG FRPLAPRPWR WLLLLALPAA

CSAPPPRPVY TNHWAVQVLG GPAEADRVAA AHGYLNLGQI GNLEDYYHFY HSKTFKRSTL

SSRGPHTFLR MDPQVKWLQQ QEVKRRVKRQ VRSDPQALYF NDPIWSNMWY LHCGDKNSRC

RSEMNVQAAW KRGYTGKNVV VTILDDGIER NHPDLAPNYD SYASYDVNGN DYDPSPRYDA

SNENKHGTRC AGEVAASANN SYCIVGIAYN AKIGGIRMLD GDVTDVVEAK SLGIRPNYID

IYSASWGPDD DGKTVDGPGR LAKQAFEYGI KKGRQGLGSI FVWASGNGGR EGDYCSCDGY

TNSIYTISVS SATENGYKPW YLEECASTLA TTYSSGAFYE RKIVTTDLRQ RCTDGHTGTS

VSAPMVAGII ALALEANSQL TWRDVQHLLV KTSRPAHLKA SDWKVNGAGH KVSHFYGFGL

VDAEALVVEA KKWTAVPSQH MCVAASDKRP RSIPLVQVLR TTALTSACAE HSDQRVVYLE

HVVVRTSISH PRRGDLQIYL VSPSGTKSQL LAKRLLDLSN EGFTNWEFMT VHCWGEKAEG

QWTLEIQDLP SQVRNPEKQG KLKEWSLILY GTAEHPYHTF SAHQSRSRML ELSAPELEPP

KAALSPSQVE VPEDEEDYTA QSTPGSANIL QTSVCHPECG DKGCDGPNAD QCLNCVHFSL

GSVKTSRKCV SVCPLGYFGD TAARRCRRCH KGCETCSSRA ATQCLSCRRG FYHHQEMNTC

VTLCPAGFYA DESQKNCLKC HPSCKKCVDE PEKCTVCKEG FSLARGSCIP DCEPGTYFDS

ELIRCGECHH TCGTCVGPGR EECIHCAKNF HFHDWKCVPA CGEGFYPEEM PGLPHKVCRR

CDENCLSCAG SSRNCSRCKT GFTQLGTSCI TNHTCSNADE TFCEMVKSNR LCERKLFIQF

CCRTCLLAG

PCSK 6 Nucleic Acid Sequence (SEQ ID NO: 19)

atgcctccgc gcgcgccgcc tgcgcccggg ccccggccgc cgccccgggc cgccgccgcc accgacaccg ccgcgggcgc ggggggcgcg gggggcgcgg ggggcgccgg cgggcccggg ttccggccgc tcgcgccgcg tccctggcgc tggctgctgc tgctggcgct gcctgccgcc tgctccgcgc ccccgccgcg ccccgtctac accaaccact gggcggtgca agtgctgggc ggcccggccg aggcggaccg cgtggcggcg gcgcacggct acctcaactt gggccagatt ggaaacctgg aagattacta ccatttttat cacagcaaaa cctttaaaag atcaaccttg agtagcagag gccctcacac cttcctcaga atggaccccc aggtgaaatg gctccagcaa caggaagtga aacgaagggt gaagagacag gtgcgaagtg acccgcaggc cctttacttc aacgacccca tttggtccaa catgtggtac ctgcattgtg gcgacaagaa cagtcgctgc cggtcggaaa tgaatgtcca ggcagcgtgg aagaggggct acacaggaaa aaacgtggtg gtcaccatcc ttgatgatgg catagagaga aatcaccctg acctggcccc aaattatgat tcctacgcca gctacgacgt gaacggcaat gattatgacc catctccacg atatgatgcc agcaatgaaa ataaacacgg cactcgttgt gcgggagaag ttgctgcttc agcaaacaat tcctactgca tcgtgggcat agcgtacaat gccaaaatag gaggcatccg catgctggac ggcgatgtca cagatgtggt cgaggcaaag tcgctgggca tcagacccaa ctacatcgac atttacagtg ccagctgggg gccggacgac gacggcaaga cggtggacgg gcccggccga ctggctaagc aggctttcga gtatggcatt aaaaagggcc ggcagggcct gggctccatt ttcgtctggg catctgggaa tggcgggaga gagggggact actgctcgtg cgatggctac accaacagca tctacaccat ctccgtcagc agcgccaccg agaatggcta caagccctgg tacctggaag agtgtgcctc caccctggcc accacctaca gcagtggggc cttttatgag cgaaaaatcg tcaccacgga tctgcgtcag cgctgtaccg atggccacac tgggacctca gtctctgccc ccatggtggc gggcatcatc gccttggctc tagaagcaaa cagccagtta -continued

```
acctggaggg acgtccagca cctgctagtg aagacatccc ggccggccca cctgaaagcg
agcgactgga aagtaaacgg cgcgggtcat aaagttagcc atttctatgg atttggtttg
gtggacgcag aagctctcgt tgtggaggca aagaagtgga cagcagtgcc atcgcagcac
atgtgtgtgg ccgcctcgga caagagaccc aggagcatcc ccttagtgca ggtgctgcgg
actacggccc tgaccagcgc ctgcgcggag cactcggacc agcgggtggt ctacttggag
cacgtggtgg ttcgcacctc catctcacac ccacgccgag gagacctcca gatctacctg
gtttctccct cgggaaccaa gtctcaactt ttggcaaaga ggttgctgga tctttccaat
gaagggttta caaactggga attcatgact gtccactgct ggggagaaaa ggctgaaggg
cagtggacct tggaaatcca agatctgcca tcccaggtcc gcaacccgga gaagcaaggg
aagttgaaag aatggagcct catactgtat ggcacagcag agcacccgta ccacaccttc
agtgcccatc agtcccgctc gcggatgctg gagctctcag ccccagagct ggagccaccc
aaggctgccc tgtcaccctc ccaggtggaa gttcctgaag atgaggaaga ttacacagct
caatccaccc caggctctgc taatatttta cagaccagtg tgtgccatcc ggagtgtggt
gacaaaggct gtgatggccc caatgcagac cagtgcttga actgcgtcca cttcagcctg
gggagtgtca agaccagcag gaagtgcgtg agtgtgtgcc ccttgggcta ctttggggac
acagcagcaa gacgctgtcg ccggtgccac aaggggtgtg agacctgctc cagcagagct
gcgacgcagt gcctgtcttg ccgccgcggg ttctatcacc accaggagat gaacacctgt
gtgaccctct gtcctgcagg attttatgct gatgaaagtc agaaaaattg ccttaaatgc
cacccaagct gtaaaaagtg cgtggatgaa cctgagaaat gtactgtctg taaagaagga
ttcagccttg cacggggcag ctgcattcct gactgtgagc caggcaccta ctttgactca
gagctgatca gatgtgggga atgccatcac acctgcggaa cctgcgtggg gccaggcaga
gaagagtgca ttcactgtgc gaaaaacttc cacttccacg actggaagtg tgtgccagcc
tgtggtgagg gcttctaccc agaagagatg ccgggcttgc cccacaaagt gtgtcgaagg
tgtgacgaga actgcttgag ctgtgcaggc tccagcagga actgtagcag gtgtaagacg
ggcttcacac agctggggac ctcctgcatc accaaccaca cgtgcagcaa cgctgacgag
acattctgcg agatggtgaa gtccaaccgg ctgtgcgaac ggaagctctt cattcagttc
tgctgccgca cgtgcctcct ggccgggtaa
```

In one embodiment, the proprotein convertase used for the present invention comprises an amino acid sequence, which is at least 60%, 70%, 75%, 80%, 85%, 90%, 95%, 96%, 97%, 98%, 99%, or 100% identical to amino acids 150-454 of SEQ ID NO: 20, amino acids 695 to 930 of SEQ ID NO: 20, amino acids 150 to 969 of SEQ ID NO: 20, amino acids 64 to 969 of SEQ ID NO: 20, SEQ ID NO: 20, amino acids 168 to 664 of SEQ ID NO: 20, amino acids 1 to 472 of SEQ ID NO: 20, amino acids 150 to 472 of SEQ ID NO: 20, amino acids 64 to 472 of SEQ ID NO: 20 or any of the amino acid sequences of the isoforms, wherein the amino acid sequence is capable of cleaving full-length Factor VIII at amino acid residue 1648.

Proprotein convertase subtilisin/kexin type 7 (PCSK7) is also known as proprotein convertase 7 (PC7), subtilisin/kexin-like protease PC7, prohormone convertase PC7, hPC8, PC8, subtilisin-like proprotein convertase 7, or lymphoma proprotein convertase. The gene encoding PCSK7 is known as Pcsk7, LPC, PC7, PC8, SPC7 and has Accession Number BT006870.1 in GenBank. The full-length human PCSK7 polypeptide has Accession Number Q16549 in UniProtKB/Swiss-Prot entry and consists of a signal peptide (amino acids 1-37), a propeptide (amino acids 38-141), and the active protein domain (amino acids 142-785) including the catalytic domain (amino acids 142-474). The nucleotide and amino acid sequences of the full-length human PCSK7 are represented herein as SEQ ID NO: 21 and SEQ ID NO: 22, respectively. Variants of PCSK7 include, but are not limited to, the polypeptides with the following mutations: L688V, S689N, R700M, H708Y, R711Q, P52A, A112P, H228R, and A353T. Also included is PCSK7 from a different species, e.g., mouse, rat, monkey, dog, *drosophila*, or porcine.

PCSK7 Amino Acid Sequence (SEQ ID NO: 22)

MPKGRQKVPH LDAPLGLPTC LWLELAGLFL LVPWVMGLAG TGGPDGQGTG GPSWAVHLES

LEGDGEEETL EQQADALAQA AGLVNAGRIG ELQGHYLFVQ PAGHRPALEV EAIRQQVEAV

LAGHEAVRWH SEQRLLRRAK RSVHFNDPKY PQQWHLNNRR SPGRDINVTG VWERNVTGRG

VTVVVVDDGV EHTIQDIAPN YSPEGSYDLN SNDPDPMPHP DVENGNHHGT RCAGEIAAVP

NNSFCAVGVA YGSRIAGIRV LDGPLTDSME AVAFNKHYQI NDIYSCSWGP DDDGKTVDGP

HQLGKAALQH GVIAGRQGFG SIFVVASGNG GQHNDNCNYD GYANSIYTVT IGAVDEEGRM

PFYAEECASM LAVTFSGGDK MLRSIVTTDW DLQKGTGCTE GHTGTSAAAP LAAGMIALML

QVRPCLTWRD VQHIIVFTAT RYEDRRAEWV TNEAGFSHSH QHGFGLLNAW RLVNAAKIWT

SVPYLASYVS PVLKENKAIP QSPRSLEVLW NVSRMDLEMS GLKTLEHVAV TVSITHPRRG

SLELKLFCPS GMMSLIGAPR SMDSDPNGFN DWTFSTVRCW GERARGTYRL VIRDVGDESF

QVGILRQWQL TLYGSVWSAV DIRDRQRLLE SAMSGKYLHD DFALPCPPGL KIPEEDGYTI

TPNTLKTLVL VGCFTVFWTV YYMLEVYLGQ RNVASNQVCR SGPCHWPHRS RKAKEEGTEL

ESVPLCSSKD PDEVETESRG PPTTSDLLAP DLLEQGDWSL SQNKSALDCP HQHLDVPHCK

EEQIC

PCSK 7 Nucleic Acid Sequence (SEQ ID NO: 21)

atgccgaagg ggaggcagaa agtgccacac ttggatqccc ccctgggcct gcccacctgc ctctggctgg aattagccgg gctcttctta ctggttccct gggtcatggg cctggcaggg acaggtgggc ctgatggcca gggcacaggg gggccgagct gggctgtgca cctggaaagc ctggaaggtg acggggagga agagactctg gagcagcagg cggatgcctt ggcccaggca gcagggctgg tgaatgctgg acgcatcgga gagcttcagg ggcactacct ctttgtccag cctgctgggc acaggccggc cctggaggtg gaggccatcc ggcagcaggt ggaggctgtg ttggctgggc atgaagctgt gcgctggcac tcagagcaga ggctgctaag gcgggccaag cgcagcgtcc acttcaacga ccccaagtac ccgcagcaat ggcacctgaa taaccgacgg agcccgggca gggacatcaa cgtgacgggt gtgtgggaac gcaatgtgac tgggcgaggg gtgacggtgg tggtagtgga tgacggagtg gaacacacca tccaggacat tgcacccaac tatagccctg agggtagcta tgacctcaac tctaatgacc ctgaccccat gccccacccg gatgtggaga atggcaacca ccatggcacg cgatgtgcag gagagatcgc ggctgtgccc aacaacagct tctgtgccgt gggcgtggcc tacgggagcc gcatcgcagg tatccgggta ctggatggac ctctcacaga cagcatggag gcagtggcgt tcaacaagca ctatcagatc aatgacatct acagctgcag ctggggacca gatgacgatg ggaagacagt ggatggcccc catcagcttg gaaaggctgc cttacaacat ggggtgattg ctggtcgcca gggctttggg agcatctttg tggtagccag tggcaacgga ggccaacaca acgacaactg caactacgat ggctacgcca actccatcta caccgtcacc ataggagctg tggatgagga gggacgcatg cctttctatg cagaagaatg tgcctccatg ctggcagtca ccttcagtgg tggggacaag atgcttcgga gcattgtgac cactgactgg gaccttcaga agggcactgg ctgcactgag ggccacacag ggacctcagc tgcagcgcct ctggcagctg gcatgatgac cttaatgctg caggtgcggc cctgcctcac gtggcgtgac gtccagcaca tcattgtctt cacagccacc cggtatgagg atcgccgtgc agagtgggtc accaacgagg caggcttcag ccatagccac cagcacggtt tcggcctcct caacgcctgg aggctcgtga atgcagccaa gatctggaca tctgtccctt acttagcatc ctacgtcagt cccgtgttaa aagaaaacaa ggcgattccg -continued

```
cagtcccccc gttccctgga ggtcctgtgg aatgtcagca ggatggacct ggagatgtca
gggctgaaga ccctggagca tgtggcaqtg acagtctcca tcactcaccc acggcgcggc
agcttggagc tgaagctgtt ctgccccagt ggcatgatgt ccctcatcgg cgcccccgc
agcatggact cggatcccaa cggcttcaat gactggacct tctccactgt gcgatgctgg
ggggagagag cccgagggac ctacaggctt gtcatcaggg atgtcgggga tgagtcattc
caggtcggca tcctccggca atggcaqctg accctatatg gctctgtgtg gagtgcagta
gacatcaggg acagacaaag gctgttagag agtgccatga gtggaaaata cctgcacgat
gacttcgccc tgccctgccc accggggctg aaaattcctg aggaagatgg ttacaccatc
acccccaaca ccctcaagac cctggtgctg gtaggctgtt tcaccgtctt ctggactgtt
tactacatgc tggaagtata tttgagccag aggaatgtgg cttccaatca agtttgtagg
agtggaccct gccactggcc ccatcggagc cggaaagcca aggaggaagg gacagagcta
gaatcagtgc cactttgcag cagcaaggat ccagacgaag tggaaacaga gagcaggggc
cctcccacca cctctgacct ccttgcccca gacctgctgg agcaagggga ctggagcctg
tcccagaaca agagcgccct ggactgccct catcagcacc tagacgtacc gcacgggaag
gaggcgcaga tctgctag
```

In another embodiment, the proprotein convertase used for the present invention comprises an amino acid sequence, which is at least 60%, 70%, 75%, 80%, 85%, 90%, 95%, 96%, 97%, 98%, 99%, or 100% identical to amino acids 142 to 474 of SEQ ID NO: 22, amino acids 14 to 785 of SEQ ID NO: 22, amino acids 38 to 785 of SEQ ID NO: 22, or SEQ ID NO: 22, wherein the amino acid sequence is capable of cleaving full-length Factor VIII at amino acid residue 1648.

Proprotein convertase subtilisin/kexin type 8 (PCSK8) is also known as membrane-bound transcription factor peptidase, site 1 (MBTPS1), S1P endopeptidase, subtilisin/kexin-isozyme 1 (SKI-1), and site 1 protease (S1P). The gene encoding Pcsk8 is known as MBTPS1 and has Accession Number BC114555.1 in GenBank. The full-length human PCSK8 polypeptide has Accession Number Q14703 in UniProtKB/Swiss-Prot entry and consists of the signal peptide (amino acids 1-17), the propeptide (amino acids 18-186), and the active protein domain (amino acids 187-1052) including the serine protease domain (amino acids 218-414). The nucleotide and amino acid sequences of the full-length human PCSK8 are represented herein as SEQ ID NO: 23 and SEQ ID NO: 24, respectively. Variants of PCSK8 include, but are not limited to, the polypeptides with the following mutations: 16T and R90G. Also included is PCSK8 from a different species, e.g., mouse, rat, monkey, dog, *drosophila*, or porcine.

PCSK8 Amino Acid Sequence (SEQ ID NO: 24)

```
MKLVNIWLLL LVVLLCGKKA LGDRLEKKSF EKAPCPGCSH LTLKVEFSST VVEYEYIVAF
NGYFTAKARN SFISSALKSS EVDNWRIIPR NNPSSDYPSD FEVIQIKEKQ KAGLLTLEDH
PNIKRVTPQR KVFRSLKYAE SDPTVPCNET RWSQKWQSSR PLRRASLSLG SGFWHATGRH
SSRRLLRAIP RQVAQTLQAD VLWQMGYTGA NVRVAVFDTG LSEKHPHFKN VKERTNWTNE
RTLDDGLGHG TFVAGVIASM RECQGFAPDA ELHIFRVFTN NQVSYTSWFL DAFNYAILKK
IDVLNLSIGG PDFMDHPFVD KVWELTANNV IMVSAIGNDG PLYGTLNNPA DQMDVIGVGG
IDFEDNIARF SSRGMTTWEL PGGYGRMKPD IVTYGAGVRG SGVKGGCRAL SGTSVASPVV
AGAVTLLVST VQKRELVNPA SMKQALIASA RRLPGVNMFE QGHGKLDLLR AYQILNSYKP
QASLSPSYID LTECPYMWPY CSQPIYYGGM PTVVNVTILN GMGVTGRIVD KPDWQPYLPQ
NGDNIEVAFS YSSVLWPWSG YLAISISVTK KAASWEGIAQ GHVMITVASP AETESKNGAE
QTSTVKLPIK VKIIPTPPRS KRVLWDQYHN LRYPPGYFPR DNLRMKNDPL DWNGDHIHTN
FRDMYQHLRS MGYFVEVLGA PFTCFDASQY GTLLMVDSEE EYFPEEIAKL RRDVDNGLSL
VIFSDWYNTS VMRKVKFYDE NTRQWWMPDT GGANIPALNE LLSVWNMGFS DGLYEGEFTL
ANHDMYYASG CSIAKFPEDG VVITQTFKDQ GLEVLKQETA VVENVPILGL YQIPAEGGGR
IVLYGDSNCL DDSHRQKDCF WLLDALLQYT SYGVTPPSLS HSGNRQRPPS GAGSVTPERM
```

-continued

EGNHLHRYSK VLEAHLGDPK PRPLPACPRL SWAKPQPLNE TAPSNLWKHQ KLLSIDLDKV

VLPNFRSNRP QVRPLSPGES GAWDIPGGIM PGRYNQEVGQ TIPVFAFLGA MVVLAFFVVQ

INKAKSRPKR RKPRVKRPQL MQQVHPPKTP SV

PCSK 8 Nucleic Acid Sequence (SEQ ID NO: 23)

atgaagcttg tcaacatctg gctgcttctg ctcgtggttt tgctctgtgg gaagaaacat ctgggcgaca gactggaaaa gaaatctttt gaaaaggccc catgccctgg ctgttcccac ctgactttga aggtggaatt ctcatcaaca gttgtggaat atgaatatat tgtggctttc aatggatact ttacagccaa agctagaaat tcatttattt caagtgccct gaagagcagt gaagtagaca attggagaat tatacctcga aacaatccat ccagtgacta ccctagtgat tttgaggtga ttcagataaa agaaaaacaq aaagcggggc tgctaacact tgaagatcat ccaaacatca aacgggtcac gccccaacga aaagtctttc gttccctcaa gtatgctgaa tctgacccca cagtaccctg caatgaaacc cggtggagcc agaagtggca atcatcacgt cccctgcgaa gagccagcct ctccctgggc tctggcttct ggcatgctac gggaaggcat tcgagcagac ggctgctgag agccatcccg cgccaggttg cccagacact gcaggcagat gtgctctggc agatgggata tacaggtgct aatgtaagag ttgctgtttt tgacactggg ctgagcgaga agcatcccca cttcaaaaat gtgaaggaga gaaccaactg gaccaacgag cgaacgctgg acgatgggtt gggccatggc acattcgtgg caggtgtgat agccagcatg agggagtgcc aaggatttgc tccagatgca gaacttcaca ttttcagggt ctttaccaat aatcaggtat cttacacatc ttggtttttg gacgccctca actatgccat tttaaagaag atcgacgtgt taaacctcag catcggcggc ccggacttca tggatcatcc gtttgttgac aaggtgtggg aattaacagc taacaatgta atcatggttt ctgctattgg caatgacgga cctctttatg gcactctgaa taaccctgct gatcaaatgg atgtgattgg agtaggcggc attgactttg aagataacat cgcccgcttt tcttcaaggg gaatgactac ctgggagcta ccaggaggct acggtcgcat gaaacctgac attgtcacct atggtgctgg cgtgcggggt tctggcgtga aggggggtg ccgggccctc tcagggacca gtgttgcttc tccagtggtt gcaggtgctg tcaccttgtt agtgagcaca gtccagaagc gtgagctggt gaatcccgcc agtatgaagc aggccctgat cgcgtcagcc cggaggctcc ccggggtcaa catgtttgag caaggccacg gcaagctcga tctgctcaga gcctatcaqa tcctcaacag ctacaagcca caggcaagtt tgagccccag ctacatagat ctgactgagt gtccctacat gtggccctac tgctcccagc ccatctacta tggaggaatg ccgacagttg ttaatgtcac catcctcaac ggcatgggag tcacaggaag aattgtagat aagcctgact ggcagcccta tttgccacag aacggagaca acattgaagt tgccttctcc tactcctcgg tcttatggcc ttggtcgggc tacctggcca tctccatttc tgtgaccaag aaagcggctt cctgggaagg cattgctcag ggccatgtca tgatcactgt ggcttcccca gcagagacag agtcaaaaaa tggtgcagaa cagacttcaa ggataaagct ccccattaag gtgaagataa ttcctactcc cccgcgaagc aagagagttc tctgggatca gtaccacaac ctccgctatc cacctggcta tttccccagg gataatttaa ggatgaaqaa tgaccccttta gactggaatg gtgatcacat ccacaccaat ttcagggata tgtaccagca tctgagaagc atgggctact ttgtagaggt cctcggggcc cccttcacgt gttttgatgc cagtcagtat ggcactttgc tgatggtgga cagtgaggag gagtacttcc ctgaagagat cgccaagctc cggagggacg tggacaacgg cctctcgctc -continued

```
gtcatcttca gtgactggta caacacttct gttatgagaa aagtgaagtt ttatgatgaa
aacacaaggc agtggtggat gccggatacc ggaggagcta acatcccagc tctgaatgag
ctgctgtctg tgtggaacat ggggttcagc gatggcctgt atgaagggga gttcaccctg
gccaaccatg acatgtatta tgcgtcaggg tgcagcatcg cgaagtttcc agaagatggc
gtcgtgataa cacagacttt caaggaccaa ggattggagg ttttaaagca ggaaacagca
gttgttgaaa acgtccccat tttgggactt tatcagattc cagctgaggg tggaggccgg
attgtactgt atggggactc caattgcttg gatgacagtc accgacagaa ggactgcttt
tggcttctgg atgccctcct ccagtacaoa tcgtatgggg cgacaccgcc tagcctcagt
cactctggga accgccagcg ccctcccagt ggagcaggct cagtcactcc agagaggatg
gaaggaaacc arcttcatcg gtactccaag gttctggagg cccatttggg agacccaaaa
cctcggcctc taccagcctg tccacgcttg tcttgggcca agccacagcc tttaaacgag
acggcgccca gtaacctttg gaaacatcag aagctactct ccattgacct ggacaaggtg
gtgttaccca actttcgatc gaatcgccct caagtgaggc cctcgtcccc tggagagagc
ggcqcctggg acattcctgg agggatcatg cctggccgct acaaccagga ggtgggccag
accattcctg tctttgcctt cctgggagcc atggtggtcc tggccttctt tgtggtacaa
atcaacaagg ccaagagcag gccgaagcgg aggaagccca gggtgaagcg cccgcagctc
atgcagcagg ttcacccgcc aaagacccct tcggtgtga
```

In one embodiment, the proprotein convertase used for the present invention comprises an amino acid sequence, which is at least 60%, 70%, 75%, 80%, 85%, 90%, 95%, 96%, 97%, 98%, 99%, or 100% identical to amino acids 218 to 414 of SEQ ID NO: 24, amino acids 187 to 1052 of SEQ ID NO: 24, amino acids 18 to 1052 of SEQ ID NO: 24, or SEQ ID NO: 24, wherein the amino acid sequence is capable of cleaving full-length Factor VIII at amino acid residue 1648.

Proprotein convertase subtilisin/kexin type 9 (PCSK9) is also known as proprotein convertase 9 (PC9), subtilisin/kexin-like protease PC9, or neural apoptosis-regulated convertase 1 (NARC-1). The gene encoding Pcsk9 is known as psec0052, narc-1, and pc9 and has Accession Number AX127530 in GenBank. The fall-length human PCSK9 polypeptide has Accession Number Q8NBP7 in UniProtKB/Swiss-Prot entry and consists of the signal peptide (amino acids 1-30), the propeptide (amino acids 31-152), and the active protein domain (amino acids 153-692) including the peptidase S8 domain (amino acids 161-431). The nucleotide and amino acid sequences of the full-length human PCSK8 are represented herein as SEQ ID NO: 25 and SEQ ID NO: 26, respectively. Variants of PCSK9 include, but are not limited to, the polypeptides with the following mutations: L23LL, R46L, A53V, E57K, T77I, R93c, G106R, V114A, S127R, D129G, N157K, R215H, F216L, R218S, Q219E, R237W, A239D, L253F, R357H, D374H, D374Y, H391N, H417Q, N425S, A443T, G452D, R469W, 1474V, E482G, R496W, F515L, A522T, H553R, Q554E, P616L, Q619P, S668R, E670G, C67A, H226A, N533A, or V423A. Also included is PCSK9 from a different species, e.g., mouse, rat, monkey, dog, *drosophila*, or porcine.

PCSK9 Amino Acid Sequence (SEQ ID NO: 26)

```
MGTVSSRRSW WPLPLLLLLL LLLGPAGARA QEDEDGDYEE LVLALRSEED GLAEAPEHGT
TATFHRCAKD PWRLPGTYVV VLKEETHLSQ SERTARRLQA QAARRGYLTK ILHVFHGLLP
GFLVKMSGDL LELALKLPHV DYIEEDSSVF AQSIPWNLER ITPPRYRADE YQPPDGGSLV
EVYLLDTSIQ SDHREIEGRV MVTDFENVPE EDGTRFHRQA SKCDSHGTHL AGVVSGRDAG
VAKGASMRSL RVLNCQGKGT VSGTLIGLEF IRKSQLVQPV GPLVVLLPLA GGYSRVLNAA
CQRLARAGVV LVTAAGNFRD DACLYSPASA PEVITVGATN AQDQPVTLGT LGTNFGRCVD
LFAPGEDIIG ASSDCSTCFV SQSGTSQAAA HVAGIAAMML SAEPELTLAE LRQRLIHFSA
KDVINEAWFP EDQRVLTPNL VAALPPSTHG AGWQLFCRTV WSAHSGPTRM ATAIARCAPD
EELLSCSSFS RSGKRRGERM EAQGGKLVCR AHNAFGGEGV YAIARCCLLP QANCSVHTAP
PAEASMGTRV HCHQQGHVLT GCSSHWEVED LGHTKPPVLR PRGQPNQCVG HREASIGASC
```

-continued

CHAPGLECKV KEHGIPAPQE QVTVACEEGW TLTGCSALPG TSHVLGAYAV DNTCVVRSRD

VSTTGSTSEE AVTAVAICCR SRHLAQASQE LQ

PCSK9 Nucleic Acid Sequence (SEQ ID NO: 25)

atgggcaccg tcagctccag gcggtcctgg tggccgctgc cactgctgct gctgctgctg ctgctcctgg gtcccgcggg cgcccgtgcg caggaggacg aggacggcga ctacgaggag ctggtgctag ccttgcgttc cgaggaggac ggcctggccg aagcacccga gcacggaacc acagccacct tccaccgctg cgccaaggat ccgtggaggt tgcctggcac ctacgtggtg gtgctgaagg aggagaccca cctctcgcag tcagagcgca ctgcccgccg cctgcaggcc caggctgccc gccggggata cctcaccaag atcctgcatg tcttccatgg ccttcttcct ggcttcctgg tgaagatgag tggcgacctg ctggagctgg ccttgaagtt gccccatgtc gactacatcg aggaggactc ctctgtcttt gcccagagca tcccgtggaa cctggagcgg attacccctc cacggtaccg ggcggatgaa taccagcccc ccgacggagg cagcctggtg gaggtgtatc tcctagacac cagcatacag agtgaccacc gggaaatcga gggcagggtc atggtcaccg acttcgagaa tgtgcccgag gaggacggga cccgcttcca cagacaggcc agcaagtgtg acagtcatgg cacccacctg gcaggggtgg tcagcggccg ggatgccggc gtggccaagg gtgccagcat gcgcagcctg cgcgtgctca actgccaagg gaagggcacg gttagcggca ccctcatagg cctggagttt attcggaaaa gccagctggt ccagcctgtg gggccactgg tggtgctgct gcccctggcg ggtgggtaca gccgcgtcct caacgccgcc tgccagcgcc tggcgagggc tggggtcgtg ctggtcaccg ctgccggcaa cttccgggac gatgcctgcc tctactcccc agcctcagct cccgaggtca tcacagttgg ggccaccaat gcccaggacc agccggtgac cctggggact ttggggacca actttggccg ctgtgtggac ctctttgccc caggggagga catcattggt gcctccagcg actgcagcac ctgctttgtg tcacagagtg ggacatcaca ggctgctgcc cacgtggctg gcattgcagc catgatgctg tctgccgagc cggagctcac cctggccgag ttgaggcaga gactgatcca cttctctgcc aaagatgtca tcaatgaggc ctggttccct gaggaccagc gggtactgac ccccaacctg gtggccgccc tgccccccag cacccatggg gcaggttggc agctgttttg caggactgtg tggtcagcac actcggggcc tacacggatg gccacagcca tcgcccgctg cgccccagat gaggagctgc tgagctgctc cagtttctcc aggagtggga agcggcgggg cgagcgcatg gaggcccaag gggcaagct ggtctgccgg gcccacaacg cttttggggg tgagggtgtc tacgccattg ccaggtgctg cctgctaccc caggccaact gcagcgtcca cacagctcca ccagctgagg ccagcatggg gacccgtgtc cactgccacc aacagggcca cgtcctcaca ggctgcagct cccactggga ggtggaggac cttggcaccc acaagccgcc tgtgctgagg ccacgaggtc agcccaacca gtgcgtgggc cacagggagg ccagcatcca cgcttcctgc tgccatgccc caggtctgga atgcaaagtc aaggagcatg gaatcccggc ccctcaggag caggtgaccg tggcctgcga ggagggctgg accctgactg gctgcagtgc cctccctggg acctcccacg tcctgggggc ctacgccgta gacaacacgt gtgtagtcag gagccgggac gtcagcacta caggcagcac cagcgaagag gccgtgacag ccgttgccat ctgctgccgg agccggcacc tggcgcaggc ctcccaggag ctccagtga In one embodiment, the proprotein convertase used for the present invention comprises an amino acid sequence at least 60%, 70%, 75%, 80%, 85%, 90%, 95%, 96%, 97%, 98%, 99%, or 100% identical to amino acids 161 to 431 of SEQ ID NO: 26, amino acids 153 to 692 of SEQ ID NO: 26, amino acids 31 to 692 of SEQ ID NO: 26, or SEQ ID NO:

26, wherein the amino acid sequence is capable of cleaving full-length Factor VIII at amino acid residue 1648.

The proprotein convertase can comprise a yeast Kex2 protease, which is also known as Kexin or proteinase YSCF. The gene encoding the Kex2 protease is known as kex2 or qds1 and has Accession Number AAA3478.1 in GenBank. The full-length yeast Kex2 protease has Accession Number P13134 in UniProtKB/Swiss-Prot entry and comprises the signal peptide (amino acids 1-19), the propeptide (amino acids 20-113), and the active protein domain (amino acids 114-814) including the catalytic domain (amino acids 114-461). The nucleotide and amino acid sequences of the full-length yeast Kex2 protease are represented herein as SEQ ID NO: 27 and SEQ ID NO: 28, respectively.

```
Yeast Kex2 amino acid sequence
                                                      (SEQ ID NO: 28)
MKVRKYITLC FWWAFSTSAL VSSQQIPLKD HTSRQYFAVE SNETLSRLEE MHPNWKYEHD

VRGLPNHYVF SKELLKLGKR SSLEELQGDN NDHILSVHDL FPRNDLFKRL PVPAPPMDSS

LLPVKEAEDK LSINDPLFER QWHLVNPSFP GSDINVLDLW YNNITGAGVV AAIVDDGLDY

ENEDLKDNFC AEGSWDFNDN TNLPKPRLSD DYHGTRCAGE IAAKKGNNFC GVGVGYNAKI

SGIRILSGDI TTEDEAASLI YGLDVNDIYS CSWGPADDGR HLQGPSDLVK KALVKGVTEG

RDSKGAIYVF ASGNGGTRGD NCNYDGYTNS IYSITIGAID HKDLHPPYSE GCSAVMAVTY

SSGSGEYIHS SDINGRCSNS HGGTSAAAPL AAGVYTLLLE ANPNLTWRDV QYLSILSAVG

LEKNADGDWR DSAMGKKYSH RYGFGKIDAH KLIEMSKTWE NVNAQTWFYL PTLYVSQSTN

STEETLESVI TISEKSLQDA NFKRIEHVTV TVDIDTEIRG TTTVDLISPA GIISNLGVVR

PRDVSSEGFK DWTFMSVAHW GENGVGDWKI KVKTTENGHR IDFHSWRLKL FGESIDSSKT

ETFVFGNDKE EVEPAATEST VSQYSASSTS ISISATSTSS ISIGVETSAI PQTTTASTDP

DSDPNTPKKL SSPRQAMHYF LTIFLIGATF LVLYFMFFMK SRRRIRRSRA ETYEFDIIDT

DSEYDSTLDN GTSGITEPEE VEDFDFDLSD EDHLASLSSS ENGDAEHTID SVLTNENPFS

DPIKQKFPND ANAESASNKL QELQPDVPPS SGRS

Yeast Kex 2 Nucleic Acid Sequence
                                                      (SEQ ID NO: 27)
atgaaagtga ggaaatatat tactttatgc ttttggtggg ccttttcaac atccgctctt

gtatcatcac aacaaattcc attgaaggac catacgtcac gacagtattt tgctgtagaa

agcaatgaaa cattatcccg cttggaggaa atgcatccaa attggaaata tgaacatgat

gttcgagggc taccaaacca ttatgttttt tcaaaagagt tgctaaaatt gggcaaaaga

tcatcattag aagagttaca gggggataac aacgaccaca tattatctgt ccatgattta

ttcccgcgta acgacctatt taagagacta ccggtgcctg ctccaccaat ggactcaagc

ttgttaccgg taaaagaagc tgaggataaa ctcagcataa atgatccgct tttgagaggg

cagtggcact tggtcaatcc aagttttcct ggcagtgata taaatgttct tgatctgtgg

tacaataata ttacaggcgc aggggtcgtg gctgccattg ttgatgatgg ccttgactac

gaaaatgaag acttgaagga taatttttgc gctgaaggtt cttgggattt caacgacaat

accaatttac ctaaaccaag attatctgat gactaccatg gtacgagatg tgcaggtgaa

atagctgcca aaaaaggtaa caatttttgc ggtgtcgggg taggttacaa cgctaaaatc

tcaggcataa gaatcttatc cggtgatatc actacggaag atgaagctgc gtccttgatt

tatggtctag acgtaaacga tatatattca tgctcatggg gtcccgctga tgacggaaga

catttacaag gccctagtga cctggtgaaa aaggctttag taaaaggtgt tactgaggga

agagattcca aaggagcgat ttacgttttt gccagtggaa atggtggaac tcgtggtgat

aattgcaatt acgacggcta tactaattcc atatattcta ttactattgg ggctattgat

cacaaagatc tacatcctcc ttattccgaa ggttgttccg ccgtcatggc agtcacgtat

tcttcaggtt caggcgaata tattcattcg agtgatatca acggcagatg cagtaatagc

cacggtggaa cgtctgcggc tgctccatta gctgccggtg tttacacttt gttactagaa
```

-continued

```
gccaacccaa acctaacttg gagagacgta cagtatttat caatcttgtc tgcggtaggg

ttagaaaaga acgctgacgg agattggaga gatagcgcca tggggaagaa atactctcat

cgctatggct ttggtaaaat cgatgcccat aagttaattg aaatgtccaa gacctgggag

aatgttaacg cacaaacctg gttttacctg ccaacattgt atgtttccca gtccacaaac

tccacggaag agacattaga atccgtcata accatatcag aaaaaagtct tcaagatgct

aacttcaaga gaattgagca cgtcacggta actgtagata ttgatacaga aattagggga

actacgactg tcgatttaat atcaccagcg ggataatttt caaaccttgg cgttgtaaga

ccaagagatg tttcatcaga gggattcaaa gactggacat tcatgtctgt agcacattgg

ggtgagaacg gcgtaggtga ttggaaaatc aaggttaaga caacagaaaa tggacacagg

attgacttcc acagttggag gctgaagctc tttggggaat ccattgattc atctaaaaca

gaaactttcg tctttggaaa cgataaagag gaggttgaac cagctgctac agaaagtacc

gtatcacaat attctgccag ttcaacttct atttccatca gcgctacttc tacatcttct

atctcaattg gtgtggaaac gtcggccatt ccccaaacga ctactgcgag taccgatcct

gattctgatc caaacactcc taaaaaactt tcctctccta ggcaagccat gcattatttt

ttaacaatat ttttgattgg cgccacattt ttggtgttat acttcatgtt ttttatgaaa

tcaaggagaa ggatcagaag gtcaagagcg gaaacgtatg aattcgatat cattgataca

gactctgagt acgattctac tttggacaat ggaacttccg gaattactga gcccgaagag

gttgaggact tcgattttga tttgtccgat gaagaccatc ttgcaagttt gtcttcatca

gaaaacggtg atgctgaaca tacaattgat agtgtactaa caaacgaaaa tccatttagt

gaccctataa agcaaaagtt cccaaatgac gccaacgcag aatctgcttc caataaatta

caagaattac agcctgatgt tcctccatct tccggacgat cgtga
```

A proprotein convertase can comprise an amino acid sequence at least 60%, 70%, 75%, 80%, 85%, 90%, 95%, 96%, 97%, 98%, 99%, or 100% identical to amino acids 114-461 of SEQ ID NO: 28, amino acids 153 to 814 of SEQ ID NO: 28, or SEQ ID NO: 28, wherein the amino acid sequence is capable of cleaving fall-length Factor VIII at amino acid residue 1648.

In certain embodiments, the proprotein convertase used in this invention is selected from the group consisting of PCSK3, PCSK5, PCSK7, yeast Kex2, and a combination thereof. In some embodiments, the proprotein convertase is selected from the group consisting of PCSK5, PCSK7, and both.

In other embodiments, the proprotein convertase for this invention is selected from the group consisting of PCSK1, PCSK2, PCSK4, PCSK6, PCSK8, PCSK9, and a combination thereof.

In certain embodiments, the present invention is directed to a method of decreasing nonprocessed Factor VIII comprising (a) expressing Factor VIII from a polynucleotide in a host cell, wherein the endogenous processing enzymes of the host cell are insufficient to convert all of the Factor VIII to its processed form, (b) adding a proprotein convertase to the host cell, and (c) decreasing the nonprocessed Factor VIII by processing with the proprotein convertase.

In other embodiments, the present invention includes a method of decreasing nonprocessed Factor VIII comprising (a) expressing Factor VIII from a first polynucleotide in a first host cell, wherein the endogenous processing enzymes of the host cell are insufficient to convert all of the Factor VIII to its processed form, (b) expressing a proprotein convertase from a second polynucleotide in a second host cell, and (c) decreasing the nonprocessed Factor VIII by culturing the first host cell and the second host cell together, wherein the proprotein convertase expressed in the second host cell decreases the nonprocessed Factor VIII expressed in the first host cell.

Vector and Host Cells

When a proprotein convertase and an nonprocessed Factor VIII are to be coexpressed within a cell, in one embodiment, the cell contains a first nucleotide sequence encoding an nonprocessed Factor VIII or a fusion protein thereof, and a second nucleotide sequence encoding a functional protein convertase polypeptide. The first nucleotide sequence and the second nucleotide sequence can be in the same expression vector or different expression vector.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the invention will include polynucleotides encoding a protein convertase and Factor VIII.

In one embodiment, a coding sequence for Factor VIII or proprotein convertase is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired protein or polypeptide.

A gene expression control sequence as used herein is any regulatory nucleotide sequence, such as a promoter sequence or promoter-enhancer combination, which facilitates the efficient transcription and translation of the coding nucleic acid to which it is operably linked. The gene expression control sequence may, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression control sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined coding nucleic acid. The gene expression sequences optionally include enhancer sequences or upstream activator sequences as desired.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors not named but known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids may be custom designed using standard molecular biology techniques to remove and/or add specific fragments of DNA.

In one insect expression system that may be used to produce the proteins of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example, the polyhedron gene) of the virus and placed under control of an ACNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (see, e.g., Smith et al. (1983) *J Virol* 46:584; U.S. Pat. No. 4,215,051). Further examples of this expression system may be found in Ausubel et al., eds. (1989) Current Protocols in Molecular Biology, Vol. 2, Greene Publish. Assoc. & Wiley Interscience.

Another system which can be used to express the proteins of the invention is the glutamine synthetase gene expression system, also referred to as the "GS expression system" (Lonza Biologics PLC, Berkshire UK). This expression system is described in detail in U.S. Pat. No. 5,981,216.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. See, e.g., Logan & Shenk (1984) *Proc Natl Acad Sci USA* 81:3655). Alternatively, the vaccinia 7.5 K promoter may be used. See, e.g., Mackett et al. (1982) *Proc Natl Acad Sci USA* 79:7415; Mackett et al. (1984) *J Virol* 49:857; Panicali et al. (1982) *Proc Natl Acad Sci USA* 79:4927.

To increase efficiency of production, the polynucleotides can be designed to encode multiple units of the protein of the invention separated by enzymatic cleavage sites. The resulting polypeptide can be cleaved (e.g., by treatment with the appropriate enzyme) in order to recover the polypeptide units. This can increase the yield of polypeptides driven by a single promoter. When used in appropriate viral expression systems, the translation of each polypeptide encoded by the mRNA is directed internally in the transcript; e.g., by an internal ribosome entry site, IRES. Thus, the polycistronic construct directs the transcription of a single, large polycistronic mRNA which, in turn, directs the translation of multiple, individual polypeptides. This approach eliminates the production and enzymatic processing of polyproteins and may significantly increase yield of polypeptide driven by a single promoter.

Vectors used in transformation will usually contain a selectable marker used to identify transformants. In bacterial systems, this can include an antibiotic resistance gene such as ampicillin or kanamycin. Selectable markers for use in cultured mammalian cells include genes that confer resistance to drugs, such as neomycin, hygromycin, and methotrexate. The selectable marker may be an amplifiable selectable marker. One amplifiable selectable marker is the dihydrofolate reductase (DHFR) gene. Simonsen C C et al. (1983) *Proc Natl Acad Sci USA* 80:2495-9. Selectable markers are reviewed by Thilly (1986) Mammalian Cell Technology, Butterworth Publishers, Stoneham, Mass., and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, U.S. Pat. No. 4,713,339).

The expression vectors can encode for tags that permit for easy purification of the recombinantly produced protein. Examples include, but are not limited to vector pUR278 (Ruther et al. (1983) *EMBO J.* 2:1791) in which coding sequences for the protein to be expressed may be ligated into the vector in frame with the lac z coding region so that a tagged fusion protein is produced; pGEX vectors may be used to express proteins of the invention with a glutathione S-transferase (GST) tag. These proteins are usually soluble and can easily be purified from cells by adsorption to glutathione-agarose beads followed by elution in the presence of free glutathione. The vectors include cleavage sites (thrombin or Factor Xa protease or PRESCISSION PROTEASE™ (Pharmacia, Peapack, N.J.)) for easy removal of the tag after purification.

The expression vector or vectors are then transfected or co-transfected into a suitable target cell, which will express the polypeptides. Transfection techniques known in the art include, but are not limited to, calcium phosphate precipitation (Wigler et al. (1978) *Cell* 14:725), electroporation (Neumann et al. (1982) *EMBO J.* 1:841), and liposome-based reagents. A variety of host-expression vector systems may be utilized to express the proteins described herein including both prokaryotic and eukaryotic cells. These include, but are not limited to, microorganisms such as bacteria (e.g., *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems, including mammalian cells (e.g., HEK 293, CHO, Cos, HeLa, HKB11, and BHK cells).

In one embodiment, the host cell is a eukaryotic cell. As used herein, a eukaryotic cell refers to any animal or plant cell having a definitive nucleus. Eukaryotic cells of animals include cells of vertebrates, e.g., mammals, and cells of invertebrates, e.g., insects. Eukaryotic cells of plants specifically can include, without limitation, yeast cells. A eukaryotic cell is distinct from a prokaryotic cell, e.g., bacteria.

In certain embodiments, the eukaryotic cell is a mammalian cell. A mammalian cell is any cell derived from a mammal. Mammalian cells specifically include, but are not limited to, mammalian cell lines. In one embodiment, the mammalian cell is a human cell. In another embodiment, the mammalian cell is a HEK 293 cell, which is a human embryonic kidney cell line. HEK 293 cells are available as CRL-1533 from American Type Culture Collection, Manassas, Va., and as 293-H cells, Catalog No. 11631-017 or 293-F cells, Catalog No. 11625-019 from Invitrogen (Carlsbad, Calif.). In some embodiments, the mammalian cell is a PER.C6® cell, which is a human cell line derived from retina. PER.C6® cells are available from Crucell (Leiden, The Netherlands). In other embodiments, the mammalian cell is a Chinese hamster ovary (CHO) cell. CHO cells are available from American Type Culture Collection, Manassas, Va. (e.g., CHO-K1; CCL-61). In still other embodiments, the mammalian cell is a baby hamster kidney (BHK) cell. BHK cells are available from American Type Culture Collection, Manassas, Va. (e.g., CRL-1632). In some embodiments, the mammalian cell is a HKB11 cell, which is a hybrid cell line of a HEK293 cell and a human B cell line. Mei et al., *Mol. Biotechnol.* 34(2): 165-78 (2006).

In one embodiment, a plasmid including a Factor VIII-Fc fusion coding sequence and a selectable marker, e.g., zeocin resistance, is transfected into HEK 293 cells, for production of Factor VIII-Fc fusion.

In another embodiment, a first plasmid including a Factor VIII-Fc fusion coding sequence and a first selectable marker, e.g., a zeocin resistance gene, and a second plasmid including an Fc coding sequence and a second selectable marker, e.g., a neomycin resistance gene, are cotransfected into HEK 293 cells, for production of Factor VIII-Fc monomer-dimer hybrid. The first and second plasmids can be introduced in equal amounts (i.e., 1:1 ratio), or they can be introduced in unequal amounts.

In some embodiments, a first plasmid including a Factor VIII-Fc fusion coding sequence and a first selectable marker, e.g., a zeocin resistance gene, and a second plasmid including an Fc coding sequence and a second selectable marker, e.g., a neomycin resistance gene, and a third plasmid including a protein convertase coding sequence and a third selectable marker, e.g., a hygromycin resistance gene, are cotransfected into HEK 293 cells, for production of Factor VIII-Fc monomer-dimer hybrid. The first and second plasmids can be introduced in equal amounts (i.e., 1:1 molar ratio), or they can be introduced in unequal amounts.

In certain embodiments, a first plasmid, including a Factor VIII-Fc fusion coding sequence, an Fc coding sequence, and a first selectable marker, e.g., a zeocin resistance gene, and a second plasmid including a protein convertase coding sequence and a second selectable marker, e.g., a hygromycin resistance gene, are cotransfected into HEK 293 cells, for production of Factor VIII-Fc monomer-dimer hybrid. The promoters for the Factor VIII-Fc fusion coding sequence and the Fc coding sequence can be different or they can be the same.

In other embodiments, a first plasmid, including a Factor VIII-Fc fusion coding sequence, an Fc coding sequence, and a first selectable marker, e.g., a zeocin resistance gene, and a second plasmid including an Fc coding sequence and a second selectable marker, e.g., a neomycin resistance gene, and a third plasmid including a protein convertase coding sequence and a third selectable marker, e.g., a hygromycin resistance gene, are cotransfected into HEK 293 cells, for production of Factor VIII-Fc monomer-dimer hybrid. The promoters for the Factor VIII-Fc fusion coding sequence and the Fc coding sequence in the first plasmid can be different or they can be the same. The first and second plasmids can be introduced in equal amounts (i.e., 1:1 molar ratio), or they can be introduced in unequal amounts.

In still other embodiments, transfected cells are stably transfected. These cells can be selected and maintained as a stable cell line, using conventional techniques known to those of skill in the art.

Host cells containing DNA constructs of the protein are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals, and growth factors. Optionally the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment the medium is CD293 (Invitrogen, Carlsbad, Calif.). In one embodiment, the medium is CD17 (Invitrogen, Carlsbad, Calif.). Selection of a medium appropriate for the particular cell line used is within the level of ordinary skill in the art.

In order to co-express Factor VIII and a proprotein convertase, the host cells are cultured under conditions that allow expression of both the Factor VIII and the functional proprotein convertase. As used herein, culturing refers to maintaining living cells in vitro for at least a definite time. Maintaining can, but need not include, an increase in population of living cells. For example, cells maintained in culture can be static in population, but still viable and capable of producing a desired product, e.g., a recombinant protein or recombinant fusion protein. Suitable conditions for culturing eukaryotic cells are well known in the art and include appropriate selection of culture media, media supplements, temperature, pH, oxygen saturation, and the like. For commercial purposes, culturing can include the use of any of various types of scale-up systems including shaker flasks, roller bottles, hollow fiber bioreactors, stirred-tank bioreactors, airlift bioreactors, Wave bioreactors, and others.

The cell culture conditions are also selected to allow processing of Factor VIII by the functional proprotein convertase. Conditions that allow processing of Factor VIII by the functional proprotein convertase specifically may include the presence of a source of vitamin K. For example, in one embodiment, stably transfected HEK 293 cells are cultured in CD293 media (Invitrogen, Carlsbad, Calif.) supplemented with 4 mM glutamine In one aspect, the present invention is directed to a method of reducing nonprocessed Factor VIII in a culture medium expressing Factor VIII from a first polynucleotide in a host cell, where the endogenous processing enzymes of the host cell are insufficient to convert all of the Factor VIII to its processed isoform; b) expressing a proprotein convertase from a second polynucleotide in the host cell; and c) reducing the nonprocessed Factor VIII by processing with said proprotein convertase. In one embodiment, a present method reduces the nonprocessed Factor VIII completely, e.g., to an undetectable level as measured by SDS-PAGE. In another embodiment, a present method reduces the level of the nonprocessed Factor VIII partially or completely, e.g., less than 25%, 20%, 15%, 10%, 9%, 8%, 7%, 6%, 5%, 4%, 3%, 2%, or 1% in the Factor VIII yield from the culture compared to the level of the nonprocessed Factor VIII without co-transfection with a proprotein convertase encoding gene, thereby generating a Factor VIII product comprising more than 75%, 80%, 85%, 90%, 91%, 92%, 93%, 94%, 95%, 96%, 97%, 98%, 99%, or 100% processed Factor VIII.

The invention, in another aspect, relates to a method for increasing yield of a functional Factor VIII. As used herein, increasing yield refers to inducing a measurable increase in amount or activity of Factor VIII, obtained with a proprotein convertase and under specified conditions, as compared to a reference amount or activity of Factor VIII, obtained without a proprotein convertase and under the specified conditions. In one embodiment, the measurable increase is at least 5 percent. In another embodiment, the measurable increase is at least 10 percent. In some embodiments, the measurable increase is at least 20 percent, at least 30 percent, at least 40 percent, at least 50 percent, at least 60 percent, at least 70 percent, at least 80 percent, at least 90 percent, or at least 100 percent.

In further embodiments, the protein product containing the Factor VIII protein or a fusion protein thereof is secreted into the media. Media is separated from the cells, concentrated, filtered, and then passed over two or three affinity columns, e.g., a protein A column and one or two anion exchange columns.

In one aspect, the present invention relates to an isolated polypeptide comprising the Factor VIII protein or a fusion protein thereof produced by the methods described herein. For example, an isolated Factor VIII, which comprises expressing Factor VIII from a first polynucleotide in a host cell, wherein the endogenous processing enzymes of the host cell are insufficient to convert all of the Factor VIII to its processed isoform, expressing Methods of Using Chimeric Proteins The Factor VIII protein or a fusion protein thereof prepared by the invention has many uses as will be recognized by one skilled in the art, including, but not limited to methods of treating a subject having a hemostatic disorder and methods of treating a subject in need of a general hemostatic agent. In one embodiment, the invention relates to a method of treating a subject having a hemostatic disorder comprising administering a therapeutically effective amount of Factor VIII produced by the present invention.

The Factor VIII protein or a fusion protein thereof prepared by the invention treats or prevents a hemostatic disorder by serving as a cofactor to Factor IX on a negatively charged phospholipid surface, thereby forming a Xase complex. The binding of activated coagulation factors to a phospholipid surface localizes this process to sites of vascular damage. On a phospholipid surface, Factor VIIIa increases the maximum velocity of Factor X activation by Factor IXa, by approximately 200,000-fold, leading to the large second burst of thrombin generation.

The Factor VIII protein or a fusion protein thereof prepared by the invention can be used to treat any hemostatic disorder. The hemostatic disorders that may be treated by administration of Factor VIII of the invention include, but are not limited to, hemophilia A, as well as deficiencies or structural abnormalities relating to Factor VIII. In one embodiment, the hemostatic disorder is hemophilia A.

The Factor VIII protein or a fusion protein thereof prepared by the invention can be used to prophylactically treat a subject with a hemostatic disorder. The chimeric protein of the invention can be used to treat an acute bleeding episode in a subject with a hemostatic disorder. In another embodiment, the hemostatic disorder can be the result of a defective clotting factor, e.g., von Willebrand's factor. In one embodiment, the hemostatic disorder is an inherited disorder. In another embodiment, the hemostatic disorder is an acquired disorder. The acquired disorder can result from an underlying secondary disease or condition. The unrelated condition can be, as an example, but not as a limitation, cancer, an auto-immune disease, or pregnancy. The acquired disorder can result from old age or from medication to treat an underlying secondary disorder (e.g. cancer chemotherapy).

The invention also relates to methods of treating a subject that does not have a hemostatic disorder or a secondary disease or condition resulting in acquisition of a hemostatic disorder. The invention thus relates to a method of treating a subject in need of a general hemostatic agent comprising administering a therapeutically effective amount of the Factor VIII protein or a fusion protein thereof prepared by the present methods.

In one embodiment, the subject in need of a general hemostatic agent is undergoing, or is about to undergo, surgery. The Factor VIII or a fusion protein thereof can be administered prior to, during, or after surgery as a prophylactic. The Factor VIII or a fusion protein thereof can be administered prior to, during, or after surgery to control an acute bleeding episode. The surgery can include, but is not limited to liver transplantation, liver resection, or stem cell transplantation.

The Factor VIII protein or a fusion protein thereof prepared by the invention can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding.

In one embodiment, the Factor VIII protein or a fusion protein thereof of the invention is administered intravenously, subcutaneously, intramuscularly, or via any mucosal surface, e.g., orally, sublingually, buccally, nasally, rectally, vaginally or via pulmonary route. The Factor VIII or a fusion protein thereof can be implanted within or linked to a biopolymer solid support that allows for the slow release of the chimeric protein to the site of bleeding or implanted into bandage/dressing. The dose of the Factor VIII protein or the fusion protein thereof will vary depending on the subject and upon the particular route of administration used. Dosages can range from 0.1 to 100,000 μg/kg body weight. In one embodiment, the dosing range is 0.1-1,000 μg/kg. The protein can be administered continuously or at specific timed intervals. In vitro assays may be employed to determine optimal dose ranges and/or schedules for administration. In vitro assays that measure clotting factor activity are known in the art, e.g., STA-CLOT VIIa-rTF clotting assay. Additionally, effective doses may be extrapolated from dose-response curves obtained from animal models, e.g., a hemophiliac dog (Mount et al. 2002, *Blood* 99(8):2670).

The invention also relates to a pharmaceutical composition comprising Factor VIII or fusion protein of the invention. Examples of suitable pharmaceutical carriers are described in Remington's Pharmaceutical Sciences by E. W. Martin. Examples of excipients can include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition may take the form of tablets or lozenges according to conventional protocols.

For administration by inhalation, the compounds for use according to the present invention are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can be formulated for parenteral administration (i.e. intravenous or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

The pharmaceutical composition can also be formulated for rectal administration as a suppository or retention enema, e.g., containing conventional suppository bases such as cocoa butter or other glycerides.

In certain embodiments, the invention relates to a method of treating a subject with a hemostatic disorder comprising administering a therapeutically effective amount of Factor VIII or fusion proteins thereof prepared by the present invention in combination with at least one other clotting factor or -agent that promotes hemostasis. Said other clotting factor or agent that promotes hemostasis can be any therapeutic with demonstrated clotting activity. As an example, but not as a limitation, the clotting factor or hemostatic agent can include factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include anti-fibrinolytic drugs, e.g., epsilon-amino-caproic acid, tranexamic acid.

Kits

The invention provides a kit for the diagnosis of a hemostatic disorder. The kit can include a container and Factor VIII or fusion protein thereof. The Factor VIII or fusion proteins thereof can be provided in an appropriate buffer or solvent. The buffer can be an aqueous buffer, e.g., PBS or alternatively the chimeric protein can be lyophilized. The kit can also provide instructions for detecting the presence of a clotting factor in a sample, e.g., contacting an aliquot of a sample with the chimeric protein of the invention and detecting the presence of a clot. Detection can include visible detection. The kit can optionally provide an aliquot of blood lacking a known clotting factor.

Having now described the present invention in detail, the same will be more clearly understood by reference to the following examples, which are included herewith for purposes of illustration only and are not intended to be limiting of the invention. All patents and publications referred to herein are expressly incorporated by reference.

EXAMPLES

Example 1

Cloning of Factor VIII-Fc Expressing Constructs

The coding sequence of human recombinant B-domain deleted FVIII was obtained by reverse transcription-polymerase chain reaction (RT-PCR) from human liver poly A RNA (Clontech) using FVIII-specific primers. The FVIII sequence includes the native signal sequence for FVIII. The B-domain deletion starts after serine 743 (S743; 2287 bp) and ends before glutamine 1638 (Q1638; 4969 bp) for a total deletion of 2682 by (SQ version, which is represented by SEQ ID NO: 2).

The coding sequence for human recombinant Fc was obtained by RT-PCR from a human leukocyte cDNA library (Clontech) using Fc specific primers. Primers were designed such that the B-domain deleted FVIII sequence was fused directly to the N-terminus of the Fc sequence with no intervening linker. The FVIIIFc DNA sequence was cloned into the mammalian dual expression vector pBUDCE4.1 (Invitrogen) under control of the CMV promoter.

A second identical Fc sequence including the mouse Igk signal sequence was obtained by RT-PCR and cloned downstream of the second promoter, EF1α, in the expression vector pBUDCE4.1. This final construct was designated pSYN-FVIII-013.

A second plasmid was created from similar constructs using PCR and standard molecular biology techniques, in order to express rFVIIIBDD-Fc-Fc in which the rFVIIIBDDFc coding sequence was fused to the second Fc sequence with a $(GGGGS)_4$ linker, allowing for production of only the rFVIIIBDD-Fc monomer-dimer hybrid in transient transfection. This construct was designated pSYN-FVIII-041.

Example 2

Cloning of PC5

The coding sequence for human PC5 was obtained by RT-PCR. The following primers were used (areas that anneal to the cDNA are indicated in bold):

| Primers | SEQ ID NO | Sequences |
|---|---|---|
| PC5-KpnI-F: | 29 | 5'-**ATCTACACCATCTCCATCAGCAGC**-3' |
| PC5 NotI-R: | 30 | 5'-AAGGCGGCCGC**TCAGCCTTGAAATGTACATGTTTTGC**-3' |
| PC5-UTR-F: | 31 | 5'-**AGCGAGGGAGCAGCGAGG**-3' |
| PC5-HindIII-R: | 32 | 5'-**GGTAGTTGACATGGCGGTTGG**-3' |
| PC5-Afl2-F: | 33 | 5'-CAGCGACTTAAGCCACC**ATGGGCTGGGGGAGCCG**-3' |

-continued

| Primers | SEQ ID NO | Sequences |
|---|---|---|
| PC5-KpnI-R: | 34 | 5'-**GTAGGTTGTGGCCAGCGTGG**-3' |

Coding sequence for human PC5 (GenBank accession no. NM-006200) was obtained in two pieces. The 3' ~1750 bp were obtained using the primers PC5-KpnI-F and PC5-NotI-R with the Invitogen SUPERSCRIPT™ RT-PCR with PLATINUM™ Taq kit according to the manufacturer's standard protocol, from human liver mRNA. The cycle used for the reverse transcription was 30 min at 50° C. followed by denaturing at 94° C. for 2 min and 35 cycles of 94° C. for 15 sec, 54° C. for 30 sec, 72° C. for 3 min, followed by 10 min extension at 72° C. and then storage at 4° C. This produced a fragment from the internal KpnI site in the PC5 coding sequence through the stop codon, with a NotI site added at the 3' end. This fragment was then cloned into pCR2.1 TOPO according to manufacturer's protocol to generate pSYN-PC5-001 (pCR2.1/PC5 (KpnI-NotI)). This fragment was then subcloned into pcDNA3.1/hygro using the KpnI and NotI restriction sites to generate pSYN-PC5-002 (pcDNA3.1/hygro/PC5 (KpnI-NotI)).

The 5' ~1100 bp of PC5 was obtained in two steps. It was first amplified by RT-PCR using the primers PC5-UTR-F and PC5-HindIII-R to amplify a ~1520 bp fragment from human liver mRNA, using similar conditions as above, with an annealing temperature of 57° C. These primers have complete homology to the native PC5 sequence, in the untranslated 5' sequence and sequence 3' from the internal unique HindIII site, respectively. Note that this HindIII site is not present in the final construct due to a silent nucleotide substitution. This DNA fragment was then gel purified and used as a template for a second PCR reaction with PC5-Af12-F, which adds an AflII cloning site followed by a Kozak sequence to the N-terminal coding sequence at the 5' end, and PC5-KpnI-R, which anneals 3' to the internal unique KpnI site, to generate an ~1100 bp fragment. The reaction was carried out with the EXPAND™ High Fidelity System according to the manufacturer's standard protocol in a MJ Thermocycler using the following cycles: 94° C., 2 min; 14 cycles of (94° C., 30 sec, 57° C., 30 sec, 72° C., 2 min), followed by 72° C., 10 min. This fragment was then subcloned into pSYN-PC5-002 using the AflII and KpnI restriction sites to generate pSYN-PC5-003 (pcDNA3.1/hygro/PC5).

The nucleotide sequence encoding PC5 in pSYN-PC5-003 has the following sequence (SEQ ID NO: 35):

```
atgggctggg ggagccgctg ctgctgcccg ggacgtttgg acctgctgtg cgtgctggcg
ctgctcgggg gctgcctgct ccccgtgtgt cggacgcgcg tctacaccaa ccactgggca
gtcaaaatcg ccgggggctt cccggaggcc aaccgtatcg ccagcaagta cggattcatc
aacataggac agataggggc cctgaaggac tactaccact tctaccatag caggacgatt
aaaaggtcag ttatctcgag cagagggacc cacagtttca tttcaatgga accaaaggtg
gaatggatcc aacagcaagt ggtaaaaaag cggacaaaga gggattatga cttcagtcgt
gcccagtcta cctatttcaa tgatcccaag tggcccagta tgtggtatat gcactgcagt
gacaatacac atccctgcca gtctgacatg aatatcgaag gagcctggaa gagaggctac
acgggaaaga acattgtggt cactatcctg gatgacggaa ttgagagaac ccatccagat
ctgatgcaaa actacgatgc tctggcaagt tgcgacgtga atgggaatga cttggaccca
atgcctcgtt atgatgcaag caacgagaac aagcatggga ctcgctgtgc tggagaagtg
gcagccgctg caaacaattc gcactgcaca gtcggaattg ctttcaacgc caagatcgga
ggagtgcgaa tgctggacgg agatgtcacg gacatggttg aagcaaaatc agttagcttc
aacccccagc acgtgcacat ttacagcgcc agctggggcc cggatgatga tggcaagact
gtggacggac cagcccccct cacccggcaa gcctttgaaa acggcgttag aatggggcgg
agaggcctcg gctctgtgtt tgtttgggca tctggaaatg gtggaaggag caaagaccac
tgctcctgtg atggctacac caacagcatc tacaccatct ccatcagcag cactgcagaa
agcggaaaga aaccttggta cctggaagag tgttcatcca cgctggccac aacctacagc
agcggggagt cctacgataa gaaaatcatc actacagatc tgaggcagcg ttgcacggac
aaccacactg ggacgtcagc ctcagccccc atggctgcag gcatcattgc gctggccctg
gaagccaatc cgtttctgac ctggagagac gtacagcatg ttattgtcag gacttcccgt
```

-continued

```
gcgggacatt tgaacgctaa tgactggaaa accaatgctg ctggttttaa ggtgagccat
ctttatggat ttggactgat ggacgcagaa gccatggtga tggaggcaga gaagtggacc
accgttcccc ggcagcacgt gtgtgtggag agcacagacc gacaaatcaa gacaatccgc
cctaacagtg cagtgcgctc catctacaaa gcctcaggct gctcagataa ccccaaccgc
catgtcaact acctggagca cgtcgttgtg cgcatcacca tcacccaccc caggagagga
gacctggcca tctacctgac ctcgccctct ggaactaggt ctcagctttt ggccaacagg
ctatttgatc actccatgga aggattcaaa aactgggagt tcatgacoat tcattgctgg
ggagaaagag ctgctggtga ctgggtcctt gaagtttatg atactccctc tcagctaagg
aactttaaga ctccaggtaa attgaaagaa tggtctttgg tcctctacgg cacctccgtg
cagccatatt caccaaccaa tgaatttccg aaagtggaac ggttccgcta tagccgagtt
gaagacccca cagacgacta tggcacagag gattatgcag gtccctgcga ccctgagtgc
agtgaggttg gctgtgacgg gccaggacca gaccactgca atgactgttt gcactactac
tacaagctga aaaacaatac caggatctgt gtctccagct gcccccctgg ccactaccac
gccgacaaga agcgctgcag gaagtgtggc cccaactgtg agtcctgctt tgggagccat
ggtgaccaat gcatgtcctg caaatatgga tactttctga atgaagaaac caacagctgt
gttactcact gccctgatgg gtcatatcag gataccaaga aaaatctttg ccggaaatgc
agtgaaaact gcaagacatg tactgaattc cataactgta cagaatgtag ggatgggtta
agcctgcagg gatcccggtg ctctgtctcc tgtgaagatg gacggtattt caacggccag
gactgccagc cctgccaccg cttctgcgcc acttgtgctg ggcaggagc tgatgggtgc
attaactgca cagagggcta cttcatggag gatgggagat gcgtgcagag ctgtagtatc
agctattact ttgaccactc ttcagagaat ggatacaaat cctgcaaaaa atgtgatatc
agttgtttga cgtgcaatgg cccaggattc aagaactgta caagctgccc tagtgggtat
ctcttagact taggaatgtg tcaaatggga gccatttgca aggatgcaac ggaagagtcc
tgggcggaag gaggcttctg tatgcttgtg aaaaagaaca atctgtgcca acggaaggtt
cttcaacaac tttgctgcaa aacatgtaca tttcaaggc
```

SEQ ID NO:35 contains substitutions from the GenBank sequence that do not affect the amino acid coding sequence. Specifically, the nucleotide at position 399 (corresponding to position 876 of GenBank accession no. NM-006200) is a T instead of a C, but preserves the amino acid Ser 133 (corresponding to amino acid numbering in GenBank accession no. NP-006191); nucleotide position 1473 (GenBank position 1950) is a C instead of a T, but preserves the amino acid Ala 491; and nucleotide position 1485 (GenBank position 1962) is an A instead of a G, but preserves the amino acid Ser 496. The nucleotide change at position 1473 eliminates a HindIII restriction site.

Example 3

Cloning of PACE-SOL

The coding sequence for human PACE was obtained by RT-PCR. The following primers were used (areas that anneal to the cDNA are indicated in bold):

| | SEQ ID NO | |
|---|---|---|
| PACE-F1: | 36 | 5'-GGTAAGCTTGCC**ATGGAGCTGAGGCCCTGGTTGC**-3' |
| PACE-R1: | 37 | 5'-**GTTTTCAATCTCTAGGACCCACTCGCC**-3' |
| PACE-F2: | 38 | 5'-**GCCAGGCCACATGACTACTCCGC**-3' |
| PACE-R2: | 39 | 5'-GGTGAATTCTCAC**TCAGGCAGGTGTGAGGGCAGC**-3' |

The primer PACE-F 1 adds a HindIII site to the 5' end of the PACE sequence beginning with 3 nucleotides before the start codon, while the primer PACE-R2 adds a stop codon after amino acid 715, which occurs at the end of the extracellular domain of PACE, as well as adding an EcoRI site to the 3' end of the stop codon. The PACE-R1 and PACE-F2 primers anneal on the 3' and 5' sides of an internal BamHI site, respectively. Two RT-PCR reactions were then set up using 25 pmol each of the primer pairs of PACE-F1/R1 or PACE-F2/R2 with 20 ng of adult human liver RNA (Clontech; Palo Alto, Calif.) in a 50 μl RT-PCR reaction using the SUPERSCRIPT™ One-Step RT-PCR with PLATINUM® Taq system (Invitrogen, Carlsbad, Calif.)

according to manufacturer's protocol. The reaction was carried out in a MJ Thermocycler using the following cycles: 50° C. 30 minutes; 94° C. 2 minutes; 30 cycles of (94° C. 30 seconds, 58° C. 30 seconds, 72° C. 2 minutes), followed by 72° C. 10 minutes. Each of these fragments was ligated into the vector pGEM T-Easy (Promega, Madison, Wis.) and sequenced fully. The F2-R2 fragment was then subcloned into pcDNA6 V5/His (Invitrogen, Carlsbad, Calif.) using the BamHI/EcoRI sites, and then the F1-R1 fragment was cloned into this construct using the HindIII/BamHI sites. The final plasmid, pcDNA6-PACE, produces a soluble form of PACE (amino acids 1-715), as the transmembrane region has been deleted. The sequence of PACE in pcDNA6-PACE is essentially as described in Harrison S et al., (1998) Semin Hematol 35(2 Suppl 2):4-10.

Example 4

Cloning of Kex2-SOL

The coding sequence for the yeast endoprotease, KEX2, was obtained by RT-PCR from *Saccharomyces cerevisiae* polyA+ mRNA (BD Clontech, cat #6999-1) using the following primers (areas that anneal to the cDNA are indicated in bold):

| Primers | SEQ ID NO | Sequences |
|---|---|---|
| KEX2-F: | 40 | 5'-GCGCTAGCCGTACGGCCGCCACC**ATGAAAGTGAGGAAATATATTAC-TTTATGC**-3' |
| KEX2-BglII-F: | 41 | 5'-**GCTATTGATCACAAAGATCTACATCCTCC**-3' |
| KEX2-BglII-R: | 42 | 5'-**GGAGGATGTAGATCTTTGTGATCAATAGC**-3' |
| KEX2-675-R: | 43 | 5'-GCGAATTCCGGTCCGTCA**TTGCCTAGGGCTCGAGAGTTTTTTAGGA-GTGTTTGGATCAG**-3' |

These primers were used to obtain coding sequence for KEX2 (amino acids 1-675), the yeast homolog to PACE, in two pieces in a manner similar to that used for PACE-SOL, Example 3 above; similarly, the transmembrane region was removed to generate the soluble form of the protein.

Example 5

Cloning of PC7-SOL

The coding sequence for PC7 was obtained by RT-PCR from human adult liver mRNA using the following primers (areas that anneal to the cDNA are indicated in bold):

| | SEQ ID NO | |
|---|---|---|
| PC7-BamMut-F: | 44 | 5'-**GCATGGACTCCGATCCCAACG**-3' |
| PC7-BamMut-R: | 45 | 5'-**CGTTGGGATCGGAGTCCATGC**-3' |
| PC7-F: | 46 | 5'-GGTAAGCTTGCCGCCACC**ATGCCGAAGGGGAGGCAGAAAG**-3' |
| PC7-SOL-R: | 47 | 5'-TTTGAATTCTCA**GTTGGGGGTGATGGTGTAACC**-3' |
| PC7-Xma-F: | 48 | 5'-**GGCACCTGAATAACCGACGG**-3' |
| PC7-Xma-R: | 49 | 5'-**CGTCACGTTGATGTCCCTGC**-3' |

These primers were used to obtain coding sequence for PC7 (amino acids 1-663) in three pieces in a manner similar to that used for PACE-SOL, Example 3 above; similarly, the transmembrane region was removed to generate the soluble form of the protein.

Example 6

Transient Transfection of FVIIIFc Constructs in HEK293 Cells

HEK293 cells were transiently transfected with 25 μg pSYN-FVIII-041, or cotransfected with 12.5 μg pSYN-FVIII-041 and with 12.5 μg pSYN-PC5-003 or PACE expressing construct described in Example 3, yeast Kex2 expressing construct described in Example 5, or PC7 expressing construct described in Example 5 using PEI transfection reagent.

Example 7

Protein A Immunoprecipitation for SDS-PAGE and Western Blot Analysis

In order to analyze the FVIII-Fc from the transient transfection, the transfectants conditioned media on day 5 of transfection was subject to protein A immunoprecipitation. Specifically, conditioned media from HEK293 transfectants ((1) FVIIIFc alone, (2) FVIIIFc+Kex2, (3) FVIIIFc+PC7, (4) FVIIIFc+PACE, and (5) FVIIIFc+PC5) were supplemented with 1/10 volume of 5 ml of 4M NaCl, 5 mM $CaCl_2$, and 10 mM HEPES buffer and incubated for 30 minutes. The cells were then centrifuged at 1000 rpm for 5 minutes. The collected supernatant was mixed with 25 μl of Protein A resin (Peirce #20338) and 50 ml conditioned media and incubated at 4° C. with rocking. The mixture was centrifuged for 5 minutes at 2,000 rpm, and the pellets were resuspended in 1 ml DPBS without Ca2+ and Mg2+. The resuspended mixture was again centrifuged for 30 minutes at 2,000 rpm, and the pellets were resuspended in 40 μl 2×TG SDS Sample loading buffer with a reducing agent. The resuspended mixture was heated for 5 minutes at 100° C.

Example 8

For Western Blot Analysis

For the Western blot analysis, 5 μl of the eluted mixture was loaded per lane on a 4-20% SDS TG gel. The gel was transferred to Nitrocellulose membrane (whatman Protran cat #10401396) at 25 V constant for 1.5 hours. For detection of the heavy chain alone, the membrane was incubated in 15 ml blocking buffer with 15 μA mouse monoclonal a-human FVIII A2 Domain antibody at 1:1000 dilution (cat #GMA-012) at 4° C., washed 3×5 min in PBST, followed by incubation with goat anti-mouse IgG peroxidase conjugate at 1:10,000 in 15 ml blocking buffer for 30 min, washed 3×5 min with PBST, and then incubated with then in ECL plus Western blotting detection system (GE Healthcare, cat #RPN2132) for five minutes. The membrane was then scanned.

For detection of the light chain (LC-Fc), anti-human IgG (Fc specific)-horseradish peroxidase conjugate was used at 1:10,000 dilution (Thermo Scientific cat #31413) at 4° C. The membrane was then washed 3×5 minutes in PBST at room temperature and then incubated in ECL plus Western blotting detection system (GE Healthcare, cat #RPN 2132) for five minutes.

As FIGS. 3A and 3B show, the HEK293 cells transfected only with the FVIIIFc expressing construct shows nonprocessed FVIIIFc (NP) as well as processed FVIIIFc (LC-Fc and HC) while the HEK293 cells co-transfected with the FVIIIFc expressing construct and the Kex2 expressing construct (lane 2), the PC7 expressing constructs (lane 3), the PACE expressing construct (lane 4), or the PC5 expressing construct (lane 5) show no nonprocessed Factor VIII, only LC-Fc and HC. These figures also indicated that the HEK293 cells co-transfected with the FVIIIFc expressing construct and the Kex2 expressing construct (lane 2) or the PACE expressing construct (lane 4) result in lower levels of the FVIII heavy chain, possibly due to degradation by the processing enzyme, while the HEK293 cells co-transfected with the PC7 expressing constructs (lane 3) or the PC5 expressing construct (lane 5) show relatively higher recovery of the heavy chain. Note that the lane with FVIIIFc alone was generated with twice the amount of FVIIIFc construct DNA, therefore a direct comparison to the amount of reduction of yield by PC7 and PC5 is difficult to make. In all cases the processing enzyme eliminated the amount of nonprocessed FVIII.

Example 10

SYPRO™ Ruby Gel Staining and Coomassie Gel Staining

Alternative to the Western blotting, an SDS-PAGE gel was run with 6.7 μl of eluted material and was stained with SYPRO RUBY™ (Bio-Rad Laboratories,), imaged, and then stained with Coomassie blue. As FIGS. 4A and 4B show, SYPRO RUBY™ gel staining and Coomassie gel staining show consistent results that Kex2, PC7, PACE, and PC5 decrease nonprocessed Factor VIII. Similarly, the staining methods also confirm lower levels of the FVIII heavy chain by cotransfection with Kex2 and PACE, but relatively higher levels of FVIII heavy chain by cotransfection with PC7 and PC5.

Example 11

Stable Transfection in HEK293 Cells

A stable cell line expressing rFVIIIFc (3C4-22) was generated by transfecting HEK293 cells with pSYN-FVIII-013 described in Example 1 using Lipofectamine 2000 transfection reagent (Invitrogen, Carlsbad, Calif.) according to manufacturers protocols. Stable cell lines were selected with 200 μg/mL zeocin, adapted to serum free suspension; line 3C4 was chosen for cloning due to high levels of expression, and line 3C4-22 was ultimately chosen due to high levels of expression, growth profile, and stability.

Stable Factor VIII-Fc expressing cell line 3C4-22 was further transfected with pSYN-PC5-003 After 48 hours, cells were distributed in 96 well plates (2500-10000 cells/well), and stable lines selected with 50 μg/ml hygromycin. Cell lines were adapted to serum free suspension culture, and the cell line with best growth properties and expression levels (1D9) was chosen for further analysis.

Cell lines 3C4-22 and 3C4-22/PC5-003 1D9 were both expanded and rFVIIIFc protein purified from the cell culture media using a combination of affinity chromatography and standard chromatographic techniques.

Example 12

SDS PAGE Analysis of rFVIIIFc and rFVIIIFc/PC5

Protein was analyzed by both reducing and nonreducing SDS-PAGE. Lane 1 was contains rFVIIIFc purified from 3C4-22/PC5-003 1D9, lane 2 contains rFVIIIFc purified from 3C4-22. FIGS. 5A and 5B show that the FVIIIFc produced from line 3C4-22 (HEK293 cells transfected only with the FVIIIFc expressing construct) shows nonprocessed FVIIIBDDFc (NP) as well as processed FVIIIBDDFc (LC-Fc/LC-Fc2 and HC), but the FVIIIFc produced from line 3C4-22/PC5-003 1D9 (HEK293 cells co-transfected with the FVIIIFc expressing construct and PC5 expressing construct) express Example 13

Cloning of BDD Factor VIII Expressing Construct

The coding sequence of human recombinant B-domain deleted FVIII was obtained by PCR from pSYN-FVIII-041 using specific primers designed to express the coding sequence for the BDD FVIII alone, without Fc, and cloned into the mammalian expression vector pcDNA4, under control of the CMV promoter.

Example 14

Transient Transfection of FVIII Construct in HEK293 Cells, and FVIII-Affinity Resin Pull Down HEK293 cells were transiently transfected with 37.5 μg pSYN-FVIII-066, or cotransfected with 18.75 μg pSYN-FVIII-066 and with 18.75 μg pSYN-PC5-003 or PACE expressing construct described in Example 3, yeast Kex2 expressing construct described in Example 5, or PC7 expressing construct described in Example 5 using a modified protocol with FREESTYLE™ MAX reagent (Invitrogen, Carlsbad Calif.). Briefly, FreeStyle 293-F cells were split to 6-7×$10^5$ cells/ml 24 hours before transfection.

Plasmid DNAs (37.5 μg) were diluted into OPTIPRO™ SFM to a total volume of 0.6 ml and further mixed with diluted FREESTYLE™ MAX Reagent to obtain a total volume of 1.2 ml. The DNA-lipid mixture were incubated for 10-20 minutes at room temperature to allow complexes to form and then added into each of 125 ml flasks containing 30 ml of the FREESTYLE™ 293-F cells prepared as shown above. The cells were incubated at 37° C., 8% CO2 on an orbital shaker set to 135 rpm.

Example 15

FVIII Affinity Resin Pull Down for SDS-PAGE and Western Blot Analysis

In order to analyze the FVIII from the transient transfection, the transfectants conditioned media on day 5 of transfection was subject to small scale FVIII Affinity resin pull down. Specifically, conditioned media from HEK293 transfectants ((1) FVIII alone, (2) FVIII+Kex2, (3) FVIII+PC7, (4) FVIII+PACE, and (5) FVIII+PC5) were supplemented with 1/10 volume of 3 ml of 4M NaCl, 5 mM $CaCl_2$, and 10 mM HEPES buffer and incubated for 30 minutes. The cells were then centrifuged at 1000 rpm for 5 minutes. The FVIII protein was then purified by adding 15 μl of FVIIISelect Resin (GE Healthcare #17-5450-01) to 14 ml conditioned media and incubated at 4° C. with rotation overnight. The mixture was centrifuged for 5 minutes at 2,000 rpm, and the pellets were resuspended in 1 ml DPBS without Ca2+ and Mg2+. The resuspended mixture was transferred to eppendorf tubes, washed three times with 1 ml DBS, split into two tubes, and the final pellets resuspended in 23 μl 1×TG SDS Sample loading buffer with a reducing agent. The resuspended mixture was heated for 9 minutes at 100° C.

Example 16

For Western Blot Analysis

For the Western blot analysis, the 23 μl from the split tubes were loaded in each lane of a 4-20% SDS TG gel, and two gels analyzed in parallel. The gels were transferred to Nitrocellulose membrane using the iBlot (Invitrogen) standard protocol. For detection of the heavy chain alone, the membrane was incubated in 15 ml blocking buffer with 15 μl mouse monoclonal a-human FVIII A2 Domain antibody at 1:1000 dilution (cat #GMA-012) at 4° C., washed 3×5 min in PBST, followed by incubation with goat anti-mouse IgG peroxidase conjugate at 1:10,000 in 15 ml blocking buffer for 30 min, washed 3×5 min with PBST, and then incubated with ECL plus Western blotting detection system (GE Healthcare, cat #RPN2132) for five minutes. For the detection of the light chain, a similar analysis was performed, using a monoclonal anti-human FVIII antibody against the N-terminal region of the 83 kD light chain of Factor VIII (cat #10101-10104, QEDBioscience Inc) at 1:10,000 dilution. The membranes were then scanned. As FIGS. 6A and 6B show, the HEK293 cells transfected only with the FVIII expressing construct shows nonprocessed FVIII (NP) as well as processed FVIII (LC and HC) while the HEK293 cells co-transfected with the FVIII expressing construct and the Kex2 expressing construct (lane 2), the PACE expressing construct (lane 4), or the PC5 expressing construct (lane 5) show no nonprocessed Factor VIII, and the PC7 cotransfection (lane 3) showed reduced nonprocessed isoform. These figures also indicated that the HEK293 cells co-transfected with the FVIII expressing construct and the Kex2 expressing construct (lane 2) resulted in almost undetectable levels of the HC, and the PACE expressing construct (lane 4) resulted in lower levels of the FVIII heavy chain, possibly due to degradation by the processing enzyme, compared to HEK293 cells co-transfected with the PC7 expressing constructs (lane 3) or the PC5 expressing construct (lane 5), which show higher recovery of the heavy chain by comparison. Note that these pulldowns were performed with FVIIISelect affinity resin, which binds to FVIII, and therefore it cannot conclude whether the Kex2 cotransfection lead to greater degradation of the HC, or cleaved it in such a way that the FVIII was no longer able to interact with the resin. Note that the lane with FVIII alone was generated with twice the amount of FVIII construct DNA, therefore a direct comparison to the amount of reduction of yield by PC7 and PC5 is difficult to make. In all cases the processing enzyme reduced or eliminated the amount of nonprocessed FVIII.

Tables

TABLE 1

Polynucleotide Sequences

A. B-Domain Deleted FVIIIFc
(i) B-Domain Deleted FVIIIFc Chain DNA Sequence (FVIII signal peptide underlined,
Fc region in bold) (SEQ ID NO: 59, which encodes SEQ ID NO: 60)

```
 661                                   A TGCAAATAGA GCTCTCCACC TGCTTCTTTC
 721 TGTGCCTTTT GCGATTCTGC TTTAGTGCCA CCAGAAGATA CTACCTGGGT GCAGTGGAAC
 781 TGTCATGGGA CTATATGCAA AGTGATCTCG GTGAGCTGCC TGTGGACGCA AGATTTCCTC
 841 CTAGAGTGCC AAAATCTTTT CCATTCAACA CCTCAGTCGT GTACAAAAAG ACTCTGTTTG
 901 TAGAATTCAC GGATCACCTT TTCAACATCG CTAAGCCAAG GCCACCCTGG ATGGGTCTGC
 961 TAGGTCCTAC CATCCAGGCT GAGGTTTATG ATACAGTGGT CATTACACTT AAGAACATGG
1021 CTTCCCATCC TGTCAGTCTT CATGCTGTTG GTGTATCCTA CTGGAAAGCT TCTGAGGGAG
1081 CTGAATATGA TGATCAGACC AGTCAAAGGG AGAAAGAAGA TGATAAAGTC TTCCCTGGTG
1141 GAAGCCATAC ATATGTCTGG CAGGTCCTGA AAGAGAATGG TCCAATGGCC TCTGACCCAC
1201 TGTGCCTTAC CTACTCATAT CTTTCTCATG TGGACCTGGT AAAAGACTTG AATTCAGGCC
1261 TCATTGGAGC CCTACTAGTA TGTAGAGAAG GGAGTCTGGC CAAGGAAAAG ACACAGACCT
1321 TGCACAAATT TATACTACTT TTTGCTGTAT TTGATGAAGG GAAAAGTTGG CACTCAGAAA
1381 CAAAGAACTC CTTGATGCAG GATAGGGATG CTGCATCTGC TCGGGCCTGG CCTAAAATGC
1441 ACACAGTCAA TGGTTATGTA AACAGGTCTC TGCCAGGTCT GATTGGATGC CACAGGAAAT
1501 CAGTCTATTG GCATGTGATT GGAATGGGCA CCACTCCTGA AGTGCACTCA ATATTCCTCG
1561 AAGGTCACAC ATTTCTTGTG AGGAACCATC GCCAGGCGTC CTTGGAAATC TCGCCAATAA
1621 CTTTCCTTAC TGCTCAAACA CTCTTGATGG ACCTTGGACA GTTTCTACTG TTTTGTCATA
1681 TCTCTTCCCA CCAACATGAT GGCATGGAAG CTTATGTCAA AGTAGACAGC TGTCCAGAGG
```

TABLE 1-continued

Polynucleotide Sequences

1741 AACCCCAACT ACGAATGAAA AATAATGAAG AAGCGGAAGA CTATGATGAT GATCTTACTG
1801 ATTCTGAAAT GGATGTGGTC AGGTTTGATG ATGACAACTC TCCTTCCTTT ATCCAAATTC
1861 GCTCAGTTGC CAAGAAGCAT CCTAAAACTT GGGTACATTA CATTGCTGCT GAAGAGGAGG
1921 ACTGGGACTA TGCTCCCTTA GTCCTCGCCC CCGATGACAG AAGTTATAAA AGTCAATATT
1981 TGAACAATGG CCCTCAGCGG ATTGGTAGGA AGTACAAAAA AGTCCGATTT ATGGCATACA
2041 CAGATGAAAC CTTTAAGACT CGTGAAGCTA TTCAGCATGA ATCAGGAATC TTGGGACCTT
2101 TACTTTATGG GGAAGTTGGA GACACACTGT TGATTATATT TAAGAATCAA GCAAGCAGAC
2161 CATATAACAT CTACCCTCAC GGAATCACTG ATGTCCGTCC TTTGTATTCA AGGAGATTAC
2221 CAAAAGGTGT AAAACATTTG AAGGATTTTC CAATTCTGCC AGGAGAAATA TTCAAATATA
2281 AATGGACAGT GACTGTAGAA GATGGGCCAA CTAAATCAGA TCCTCGGTGC CTGACCCGCT
2341 ATTACTCTAG TTTCGTTAAT ATGGAGAGAG ATCTAGCTTC AGGACTCATT GGCCCTCTCC
2401 TCATCTGCTA CAAAGAATCT GTAGATCAAA GAGGAAACCA GATAATGTCA GACAAGAGGA
2461 ATGTCATCCT GTTTTCTGTA TTTGATGAGA ACCGAAGCTG GTACCTCACA GAGAATATAC
2521 AACGCTTTCT CCCCAATCCA GCTGGAGTGC AGCTTGAGGA TCCAGAGTTC CAAGCCTCCA
2581 ACATCATGCA CAGCATCAAT GGCTATGTTT TTGATAGTTT GCAGTTGTCA GTTTGTTTGC
2641 ATGAGGTGGC ATACTGGTAC ATTCTAAGCA TTGGAGCACA GACTGACTTC CTTTCTGTCT
2701 TCTTCTCTGG ATATACCTTC AAACACAAAA TGGTCTATGA AGACACACTC ACCCTATTCC
2761 CATTCTCAGG AGAAACTGTC TTCATGTCGA TGGAAAACCC AGGTCTATGG ATTCTGGGGT
2821 GCCACAACTC AGACTTTCGG AACAGAGGCA TGACCGCCTT ACTGAAGGTT TCTAGTTGTG
2881 ACAAGAACAC TGGTGATTAT TACGAGGACA GTTATGAAGA TATTTCAGCA TACTTGCTGA
2941 GTAAAAACAA TGCCATTGAA CCAAGAAGCT TCTCTCAAAA CCCACCAGTC TTGAAACGCC
3001 ATCAACGGGA AATAACTCGT ACTACTCTTC AGTCAGATCA AGAGGAAATT GACTATGATG
3061 ATACCATATC AGTTGAAATG AAGAAGGAAG ATTTTGACAT TTATGATGAG GATGAAAATC
3121 AGAGCCCCCG CAGCTTTCAA AAGAAAACAC GACACTATTT TATTGCTGCA GTGGAGAGGC
3181 TCTGGGATTA TGGGATGAGT AGCTCCCCAC ATGTTCTAAG AAACAGGGCT CAGAGTGGCA
3241 GTGTCCCTCA GTTCAAGAAA GTTGTTTTCC AGGAATTTAC TGATGGCTCC TTTACTCAGC
3301 CCTTATACCG TGGAGAACTA AATGAACATT TGGGACTCCT GGGGCCATAT ATAAGAGCAG
3361 AAGTTGAAGA TAATATCATG GTAACTTTCA GAAATCAGGC CTCTCGTCCC TATTCCTTCT
3421 ATTCTAGCCT TATTTCTTAT GAGGAAGATC AGAGGCAAGG AGCAGAACCT AGAAAAAACT
3481 TTGTCAAGCC TAATGAAACC AAAACTTACT TTTGGAAAGT GCAACATCAT ATGGCACCCA
3541 CTAAAGATGA GTTTGACTGC AAAGCCTGGG CTTATTTCTC TGATGTTGAC CTGGAAAAAG
3601 ATGTGCACTC AGGCCTGATT GGACCCCTTC TGGTCTGCCA CACTAACACA CTGAACCCTG
3661 CTCATGGGAG ACAAGTGACA GTACAGGAAT TTGCTCTGTT TTTCACCATC TTTGATGAGA
3721 CCAAAAGCTG GTACTTCACT GAAAATATGG AAAGAAACTG CAGGGCTCCC TGCAATATCC
3781 AGATGGAAGA TCCCACTTTT AAAGAGAATT ATCGCTTCCA TGCAATCAAT GGCTACATAA
3841 TGGATACACT ACCTGGCTTA GTAATGGCTC AGGATCAAAG GATTCGATGG TATCTGCTCA
3901 GCATGGGCAG CAATGAAAAC ATCCATTCTA TTCATTTCAG TGGACATGTG TTCACTGTAC
3961 GAAAAAAAGA GGAGTATAAA ATGGCACTGT ACAATCTCTA TCCAGGTGTT TTTGAGACAG
4021 TGGAAATGTT ACCATCCAAA GCTGGAATTT GGCGGGTGGA ATGCCTTATT GGCGAGCATC
4081 TACATGCTGG GATGAGCACA CTTTTTCTGG TGTACAGCAA TAAGTGTCAG ACTCCCCTGG
4141 GAATGGCTTC TGGACACATT AGAGATTTTC AGATTACAGC TTCAGGACAA TATGGACAGT
4201 GGGCCCCAAA CCTGGCCAGA CTTCATTATT CCGGATCAAT CAATGCCTGG AGCACCAAGG
4261 AGCCCTTTTC TTGGATCAAG GTGGATCTGT TGGCACCAAT GATTATTCAC GGCATCAAGA
4321 CCCAGGGTGC CCGTCAGAAG TTCTCCAGCC TCTACATCTC TCAGTTTATC ATCATGTATA
4381 GTCTTGATGG GAAGAAGTGG CAGACTTATC GAGGAAATTC CACTGGAACC TTAATGGTCT
4441 TCTTTGGCAA TGTGGATTCA TCTGGGATAA AACACAATAT TTTTAACCCT CCAATTATTG
4501 CTCGATACAT CCGTTTGCAC CCAACTCATT ATAGCATTCG CAGCACTCTT CGCATGGAGT
4561 TGATGGGCTG TGATTTAAAT AGTTGCAGCA TGCCATTGGG AATGGAGAGT AAAGCAATAT
4621 CAGATGCACA GATTACTGCT TCATCCTACT TTACCAATAT GTTTGCCACC TGGTCTCCTT
4681 CAAAAGCTCG ACTTCACCTC CAAGGGAGGA GTAATGCCTG GAGACCTCAG GTGAATAATC
4741 CAAAAGAGTG GCTGCAAGTG GACTTCCAGA AGACAATGAA AGTCACAGGA GTAACTACTC
4801 AGGGAGTAAA ATCTCTGCTT ACCAGCATGT ATGTGAAGGA GTTCCTCATC TCCAGCAGTC
4861 AAGATGGCCA TCAGTGGACT CTCTTTTTTC AGAATGGCAA AGTAAAGGTT TTTCAGGGAA
4921 ATCAAGACTC CTTCACACCT GTGGTGAACT CTCTAGACCC ACCGTTACTG ACTCGCTACC
4981 TTCGAATTCA CCCCCAGAGT TGGGTGCACC AGATTGCCCT GAGGATGGAG GTTCTGGGCT
5041 GCGAGGCACA GGACCTCTAC GACAAAACTC ACACATGCCC ACCGTGCCCA GCTCCAGAAC
5101 TCCTGGGCGG ACCGTCAGTC TTCCTCTTCC CCCCAAAACC CAAGGACACC CTCATGATCT
5161 CCCGGACCCC TGAGGTCACA TGCGTGGTGG TGGACGTGAG CCACGAAGAC CCTGAGGTCA
5221 AGTTCAACTG GTACGTGGAC GGCGTGGAGG TGCATAATGC CAAGACAAAG CCGCGGGAGG
5281 AGCAGTACAA CAGCACGTAC CGTGTGGTCA GCGTCCTCAC CGTCCTGCAC CAGGACTGGC
5341 TGAATGGCAA GGAGTACAAG TGCAAGGTCT CCAACAAAGC CCTCCCAGCC CCCATCGAGA
5401 AAACCATCTC CAAAGCCAAA GGGCAGCCCC GAGAACCACA GGTGTACACC CTGCCCCCAT
5461 CCCGGGATGA GCTGACCAAG AACCAGGTCA GCCTGACCTG CCTGGTCAAA GGCTTCTATC
5521 CCAGCGACAT CGCCGTGGAG TGGGAGAGCA ATGGGCAGCC GGAGAACAAC TACAAGACCA
5581 CGCCTCCCGT GTTGGACTCC GACGGCTCCT TCTTCCTCTA CAGCAAGCTC ACCGTGGACA
5641 AGAGCAGGTG GCAGCAGGGG AACGTCTTCT CATGCTCCGT GATGCATGAG GCTCTGCACA
5701 ACCACTACAC GCAGAAGAGC CTCTCCCTGT CTCCGGGTAA A

(ii) Fc DNA sequence (mouse Igκ signal peptide underlined) (SEQ ID NO: 3, which encodes SEQ ID NO: 4)

7981 ATGGA GACAGACACA
8041 CTCCTGCTAT GGGTACTGCT GCTCTGGGTT CCAGGTTCCA CTGGTGACAA AACTCACACA
8101 TGCCCACCGT GCCCAGCACC TGAACTCCTG GGAGGACCGT CAGTCTTCCT CTTCCCCCCA
8161 AAACCCAAGG ACACCCTCAT GATCTCCCGG ACCCCTGAGG TCACATGCGT GGTGGTGGAC
8221 GTGAGCCACG AAGACCCTGA GGTCAAGTTC AACTGGTACG TGGACGGCGT GGAGGTGCAT
8281 AATGCCAAGA CAAAGCCGCG GGAGGAGCAG TACAACAGCA CGTACCGTGT GGTCAGCGTC
8341 CTCACCGTCC TGCACCAGGA CTGGCTGAAT GGCAAGGAGT ACAAGTGCAA GGTCTCCAAC
8401 AAAGCCCTCC CAGCCCCCAT CGAGAAAACC ATCTCCAAAG CCAAAGGGCA GCCCCGAGAA

TABLE 1-continued

Polynucleotide Sequences

8461 CCACAGGTGT ACACCCTCCC CCCATCCCGC GATGAGCTGA CCAAGAACCA GGTCAGCCTG
8521 ACCTGCCTGG TCAAAGGCTT CTATCCCAGC GACATCGCCG TGGAGTGGGA GAGCAATGGG
8581 CAGCCGGAGA ACAACTACAA GACCACGCCT CCCGTGTTGG ACTCCGACGG CTCCTTCTTC
8641 CTCTACAGCA AGCTCACCGT GGACAAGAGC AGGTGGCAGC AGGGGAACGT CTTCTCATGC
8701 TCCGTGATGC ATGAGGCTCT GCACAACCAC TACACGCAGA AGAGCCTCTC CCTGTCTCCG
8761 GGTAAA

B. Full-length FVIIIFc
(i) Full-length FVIIIFc DNA Sequence (FVIII signal peptide underlined, Fc region in bold) (SEQ ID NO: 61, which encodes SEQ ID NO: 62)
661 ATG CAAATAGAGC TCTCCACCTG
721 CTTCTTTCTG TGCCTTTTGC GATTCTGCTT TAGTGCCACC AGAAGATACT ACCTGGGTGC
781 AGTGGAACTG TCATGGGACT ATATGCAAAG TGATCTCGGT GAGCTGCCTG TGGACGCAAG
841 ATTTCCTCCT AGAGTGCCAA AATCTTTTCC ATTCAACACC TCAGTCGTGT ACAAAAAGAC
901 TCTGTTTGTA GAATTCACGG ATCACCTTTT CAACATCGCT AAGCCAAGGC CACCCTGGAT
961 GGGTCTGCTA GGTCCTACCA TCCAGGCTGA GGTTTATGAT ACAGTGGTCA TTACACTTAA
1021 GAACATGGCT TCCCATCCTG TCAGTCTTCA TGCTGTTGGT GTATCCTACT GGAAAGCTTC
1081 TGAGGGAGCT GAATATGATG ATCAGACCAG TCAAAGGGAG AAAGAAGATG ATAAAGTCTT
1141 CCCTGGTGGA AGCCATACAT ATGTCTGGCA GGTCCTGAAA GAGAATGGTC CAATGGCCTC
1201 TGACCCACTG TGCCTTACCT ACTCATATCT TTCTCATGTG GACCTGGTAA AAGACTTGAA
1261 TTCAGGCCTC ATTGGAGCCC TACTAGTATG TAGAGAAGGG AGTCTGGCCA AGGAAAAGAC
1321 ACAGACCTTG CACAAATTTA TACTACTTTT TGCTGTATTT GATGAAGGGA AAAGTTGGCA
1381 CTCAGAAACA AAGAACTCCT TGATGCAGGA TAGGGATGCT GCATCTGCTC GGGCCTGGCC
1441 TAAAATGCAC ACAGTCAATG GTTATGTAAA CAGGTCTCTG CCAGGTCTGA TTGGATGCCA
1501 CAGGAAATCA GTCTATTGGC ATGTGATTGG AATGGGCACC ACTCCTGAAG TGCACTCAAT
1561 ATTCCTCGAA GGTCACACAT TTCTTGTGAG GAACCATCGC CAGGCGTCCT TGGAAATCTC
1621 GCCAATAACT TTCCTTACTG CTCAAACACT CTTGATGGAC CTTGGACAGT TTCTACTGTT
1681 TTGTCATATC TCTTCCCACC AACATGATGG CATGGAAGCT TATGTCAAAG TAGACAGCTG
1741 TCCAGAGGAA CCCCAACTAC GAATGAAAAA TAATGAAGAA GCGGAAGACT ATGATGATGA
1801 TCTTACTGAT TCTGAAATGG ATCTGGTCAG GTTTGATGAT GACAACTCTC CTTCCTTTAT
1861 CCAAATTCGC TCAGTTGCCA AGAAGCATCC TAAAACTTGG GTACATTACA TTGCTGCTGA
1921 AGAGGAGGAC TGGGACTATG CTCCCTTAGT CCTCGCCCCC GATGACAGAA GTTATAAAAG
1981 TCAATATTTG AACAATGGCC CTCAGCGGAT TGGTAGGAAG TACAAAAAAG TCCGATTTAT
2041 GGCATACACA GATGAAACCT TTAAGACTCG TGAAGCTATT CAGCATGAAT CAGGAATCTT
2101 GGGACCTTTA CTTTATGGGG AAGTTGGAGA CACACTGTTG ATTATATTTA AGAATCAAGC
2161 AAGCAGACCA TATAACATCT ACCCTCACGG AATCACTGAT GTCCGTCCTT TGTATTCAAG
2221 GAGATTACCA AAAGGTGTAA AACATTTGAA GGATTTTCCA ATTCTGCCAG GAGAAATATT
2281 CAAATATAAA TGGACAGTGA CTGTAGAAGA TGGGCCAACT AAATCAGATC CTCGGTGCCT
2341 GACCCGCTAT TACTCTAGTT TCGTTAATAT GGAGAGAGAT CTAGCTTCAC GACTCATTGG
2401 CCCTCTCCTC ATCTGCTACA AAGAATCTGT AGATCAAAGA GGAAACCAGA TAATGTCAGA
2461 CAAGAGGAAT GTCATCCTGT TTTCTGTATT TGATGAGAAC CGAAGCTGGT ACCTCACAGA
2521 GAATATACAA CGCTTTCTCC CCAATCCAGC TGGAGTGCAG CTTGAGGATC CAGAGTTCCA
2581 AGCCTCCAAC ATCATGCACA GCATCAATGG CTATGTTTTT GATAGTTTGC AGTTGTCAGT
2641 TTGTTTGCAT GAGGTGGCAT ACTGGTACAT TCTAAGCATT GGAGCACAGA CTGACTTCCT
2701 TTCTGTCTTC TTCTCTGGAT ATACCTTCAA ACACAAAATG GTCTATGAAG ACACACTCAC
2761 CCTATTCCCA TTCTCAGGAG AAACTGTCTT CATGTCGATG GAAAACCCAG GTCTATGGAT
2821 TCTGGGGTGC CACAACTCAG ACTTTCGGAA CAGAGGCATG ACCGCCTTAC TGAAGGTTTC
2881 TAGTTGTGAC AAGAACACTG GTGATTATTA CGAGGACAGT TATGAACATA TTTCAGCATA
2941 CTTGCTGAGT AAAAACAATG CCATTGAACC AAGAAGCTTC TCCCAGAATT CAAGACACCC
3001 TAGCACTAGG CAAAAGCAAT TTAATGCCAC CACAATTCCA GAAAATGACA TAGAGAAGAC
3061 TGACCCTTGG TTTGCACACA GAACACCTAT GCCTAAAATA CAAAATGTCT CCTCTAGTGA
3121 TTTGTTGATG CTCTTGCGAC AGAGTCCTAC TCCACATGGG CTATCCTTAT CTGATCTCCA
3181 AGAAGCCAAA TATGAGACTT TTTCTGATGA TCCATCACCT GGAGCAATAG ACAGTAATAA
3241 CAGCCTGTCT GAAATGACAC ACTTCAGGCC ACAGCTCCAT CACAGTGGGG ACATGGTATT
3301 TACCCCTGAG TCAGGCCTCC AATTAAGATT AAATGAGAAA CTGGGGACAA CTGCAGCAAC
3361 AGAGTTGAAG AAACTTGATT TCAAAGTTTC TAGTACATCA AATAATCTGA TTTCAACAAT
3421 TCCATCAGAC AATTTGGCAG CAGGTACTGA TAATACAAGT TCCTTAGGAC CCCCAAGTAT
3481 GCCAGTTCAT TATGATAGTC AATTAGATAC CACTCTATTT GGCAAAAAGT CATCTCCCCT
3541 TACTGAGTCT GGTGGACCTC TGAGCTTGAG TGAAGAAAAT AATGATTCAA AGTTGTTAGA
3601 ATCAGGTTTA ATGAATAGCC AAGAAAGTTC ATGGGGAAAA AATGTATCGT CAACAGAGAG
3661 TGGTAGGTTA TTTAAAGGGA AAAGAGCTCA TGGACCTGCT TTGTTGACTA AAGATAATGC
3721 CTTATTCAAA GTTAGCATCT CTTTGTTAAA GACAAACAAA ACTTCCAATA ATTCAGCAAC
3781 TAATAGAAAG ACTCACATTG ATGGCCCATC ATTATTAATT GAGAATAGTC CATCAGTCTG
3841 GCAAAATATA TTAGAAAGTG ACACTGAGTT TAAAAAAGTG ACACCTTTGA TTCATGACAa
3901 AATGCTTATG GACAAAAATG CTACAGCTTT GAGGCTAAAT CATATGTCAA ATAAAACTAC
3961 TTCATCAAAA AACATGGAAA TGGTCCAACA GAAAAAAGAG GGCCCCATTC CACCAGATGC
4021 ACAAAATCCA GATATGTCGT TCTTTAAGAT GCTATTCTTG CCAGAATCAG CAAGGTGGAT
4081 ACAAAGGACT CATGGAAAGA ACTCTCTGAA CTCTGGGCAA GGCCCCAGTC CAAAGCAATT
4141 AGTATCCTTA GGACCAGAAA AATCTGTGGA AGGTCAGAAT TTCTTGTCTG AGAAAAACAA
4201 AGTGGTAGTA GGAAAGGGTG AATTTACAAA GGACGTAGGA CTCAAAGAGA TGCTTTTTCC
4261 AAGCAGCAGA AACCTATTTC TTACTAACTT GGATAATTTA CATGAAAATA ATACACACAA
4321 TCAAGAAAAA AAAATTCAGG AAGAAATAGA AAAGAAGGAA ACATTAATCC AAGAGAATGT
4381 AGTTTTGCCT CAGATACATA CAGTGACTGG CACTAAGAAT TTCATGAAGA ACCTTTTCTT
4441 ACTGAGCACT AGGCAAAATG TAGAAGGTTC ATATGACGGG GCATATGCTC CAGTACTTCA
4501 AGATTTTAGG TCATTAAATG ATTCAACAAA TAGAACAAAG AAACACACAG CTCATTTCTC
4561 AAAAAAAGGG GAGGAAGAAA ACTTGGAAGG CTTGGGAAAT CAAACCAAGC AAATTGTAGA
4621 GAAATATGCA TGCACCACAA GGATATCTCC TAATACAAGC CAGCAGAATT TTGTCACGCA
4681 ACGTAGTAAG AGAGCTTTGA AACAATTCAG ACTCCCACTA GAAGAAACAG AACTTGAAAA TABLE 1-continued Polynucleotide Sequences 4741 AAGGATAATT GTGGATGACA CCTCAACCCA GTGGTCCAAA AACATGAAAC ATTTGACCCC
4801 GAGCACCCTC ACACAGATAG ACTACAATGA GAAGGAGAAA GGGGCCATTA CTCAGTCTCC
4861 CTTATCAGAT TGCCTTACGA GGAGTCATAG CATCCCTCAA GCAAATAGAT CTCCATTACC
4921 CATTGCAAAG GTATCATCAT TTCCATCTAT TAGACCTATA TATCTGACCA GGGTCCTATT
4981 CCAAGACAAC TCTTCTCATC TTCCAGCAGC ATCTTATAGA AAGAAAGATT CTGGGGTCCA
5041 AGAAAGCAGT CATTTCTTAC AAGGAGCCAA AAAAAATAAC CTTTCTTTAG CCATTCTAAC
5101 CTTGGAGATG ACTGGTGATC AAAGAGAGGT TGGCTCCCTG GGGACAAGTG CCACAAATTC
5161 AGTCACATAC AAGAAAGTTG AGAACACTGT TCTCCCGAAA CCAGACTTGC CCAAAACATC
5221 TGGCAAAGTT GAATTGCTTC CAAAAGTTCA CATTTATCAG AAGGACCTAT TCCCTACGGA
5281 AACTAGCAAT GGGTCTCCTG GCCATCTGGA TCTCGTGGAA GGGAGCCTTC TTCAGGGAAC
5341 AGAGGGAGCG ATTAAGTGGA ATGAAGCAAA CAGACCTGGA AAAGTTCCCT TTCTGAGAGT
5401 AGCAACAGAA AGCTCTGCAA AGACTCCCTC CAAGCTATTG GATCCTCTTG CTTGGGATAA
5461 CCACTATGGT ACTCAGATAC CAAAAGAAGA GTGGAAATCC CAAGAGAAGT CACCAGAAAA
5521 AACAGCTTTT AAGAAAAAGG ATACCATTTT GTCCCTGAAC GCTTGTGAAA GCAATCATGC
5581 AATAGCAGCA ATAAATGAGG GACAAAATAA GCCCGAAATA GAAGTCACCT GGGCAAAGCA
5641 AGGTAGGACT GAAAGGCTGT GCTCTCAAAA CCCACCAGTC TTGAAACGCC ATCAACGGGA
5701 AATAACTCGT ACTACTCTTC AGTCAGATCA AGAGGAAATT GACTATGATG ATACCATATC
5761 ACTTGAAATG AAGAAGGAAG ATTTTGACAT TTATGATGAG GATGAAAATC AGAGCCCCCG
5821 CAGCTTTCAA AAGAAAACAC GACACTATTT TATTGCTGCA GTGGAGAGGC TCTGGGATTA
5881 TGGGATGAGT AGCTCCCCAC ATGTTCTAAG AAACAGGGCT CACAGTGGCA GTGTCCCTCA
5941 GTTCAAGAAA GTTGTTTTCC AGGAATTTAC TGATGGCTCC TTTACTCAGC CCTTATACCG
6001 TGGAGAACTA AATGAACATT TGGGACTCCT GGGGCCATAT ATAAGAGCAG AAGTTGAAGA
6061 TAATATCATG GTAACTTTCA GAAATCAGGC CTCTCGTCCC TATTCCTTCT ATTCTAGCCT
6121 TATTTCTTAT GAGGAAGATC AGAGGCAAGG AGCAGAACCT AGAAAAAACT TTGTCAAGCC
6181 TAATGAAACC AAAACTTACT TTTGGAAAGT GCAACATCAT ATGGCACCCA CTAAAGATGA
6241 GTTTGACTGC AAAGCCTGGG CTTATTTCTC TGATGTTGAC CTGGAAAAAG ATGTGCACTC
6301 AGGCCTGATT GGACCCCTTC TGGTCTGCCA CACTAACACA CTGAACCCTG CTCATGGGAG
6361 ACAAGTGACA GTACAGGAAT TTGCTCTGTT TTTCACCATC TTTGATGAGA CCAAAAGCTG
6421 GTACTTCACT GAAAATATGG AAAGAAACTG CAGGGCTCCC TGCAATATCC AGATGGAAGA
6481 TCCCACTTTT AAAGAGAATT ATCGCTTCCA TGCAATCAAT GGCTACATAA TGGATACACT
6541 ACCTGGCTTA GTAATGGCTC AGGATCAAAG GATTCGATGG TATCTGCTCA GCATGGGCAG
6601 CAATGAAAAC ATCCATTCTA TTCATTTCAG TGGACATGTG TTCACTGTAC GAAAAAAAGA
6661 GGAGTATAAA ATGGCACTGT ACAATCTCTA TCCAGGTGTT TTTGAGACAG TGGAAATGTT
6721 ACCATCCAAA GCTGGAATTT GGCGGGTGGA ATGCCTTATT GGCGAGCATC TACATGCTGG
6781 GATGAGCACA CTTTTTCTGG TGTACAGCAA TAAGTGTCAG ACTCCCCTGG GAATGGCTTC
6841 TGGACACATT AGAGATTTTC AGATTACAGC TTCAGGACAA TATGGACAGT CGCCCCCAAA
6901 GCTGGCCAGA CTTCATTATT CCGGATCAAT CAATGOCTOG AGCACCAAGG AGCCCTTTTC
6961 TTGGATCAAG GTGGATCTGT TGGCACCAAT GATTATTCAC GGCATCAAGA CCCAGGGTGC
7021 CCGTCAGAAG TTCTCCAGCC TCTACATCTC TCAGTTTATC ATCATGTATA GTCTTGATGG
7081 GAAGAAGTOG CAGACTTATC GAGGAAATTC CACTGGAACC TTAATGGTCT TCTTTGGCAA
7141 TGTGGATTCA TCTGGGATAA AACACAATAT TTTTAACCCT CCAATTATTG CTCGATACAT
7201 CCGTTTGCAC CCAACTCATT ATAGCATTCG CAGCACTCTT CGCATGGAGT TGATGGGCTG
7261 TGATTTAAAT AGTTGCAGCA TGCCATTGGG AATGGAGAGT AAAGCAATAT CAGATGCACA
7321 GATTACTGCT TCATCCTACT TTACCAATAT GTTTGCCACC TGGTCTCCTT CAAAAGCTCG
7381 ACTTCACCTC CAAGGGAGGA GTAATGCCTG GAGACCTCAG GTGAATAATC CAAAAGAGTG
7441 GCTGCAAGTG GACTTCCAGA AGACAATGAA AGTCACAGGA GTAACTACTC AGGGAGTAAA
7501 ATCTCTGCTT ACCAGCATGT ATGTGAAGGA GTTCCTCATC TCCAGCAGTC AAGATGGCCA
7561 TCAGTGGACT CTCTTTTTTC AGAATGGCAA AGTAAAGGTT TTTCAGGGAA ATCAAGACTC
7621 CTTCACACCT GTGGTGAACT CTCTAGACCC ACCGTTACTG ACTCGCTACC TTCGAATTCA
7681 CCCCCAGAGT TGGGTGCACC AGATTGCCCT GAGGATGGAG GTTCTGGGCT GCGAGGCACA
7741 GGACCTCTAC GACAAAACTC ACACATGCCC ACCGTGCCCA GCTCCAGAAC TCCTGGGCGG
7801 ACCGTCAGTC TTCCTCTTCC CCCCAAAACC CAAGGACACC CTCATGATCT CCCGGACCCC
7861 TGAGGTCACA TGCGTGGTGG TGGACGTGAG CCACGAAGAC CCTGAGGTCA AGTTCAACTG
7921 GTACGTGGAC GGCGTGGAGG TGCATAATGC CAAGACAAAG CCGCGGGAGG AGCAGTACAA
7981 CAGCACGTAC CGTGTGGTCA GCGTCCTCAC CGTCCTGCAC CAGGACTGGC TGAATGGCAA
8041 GGAGTACAAG TGCAAGGTCT CCAACAAAGC CCTCCCAGCC CCCATCGAGA AAACCATCTC
8101 CAAAGCCAAA GGGCAGCCCC GAGAACCACA GGTGTACACC CTGCCCCCAT CCCGGGATGA
8161 GCTGACCAAG AACCAGGTCA GCCTGACCTG CCTGGTCAAA GGCTTCTATC CCAGCGACAT
8221 CGCCGTGGAG TGGGAGAGCA ATGGGCAGCC GGAGAACAAC TACAAGACCA CGCCTCCCGT
8281 GTTGGACTCC GACGGCTCCT TCTTCCTCTA CAGCAAGCTC ACCGTGGACA AGAGCAGGTG
8341 GCAGCAGGGG AACGTCTTCT CATGCTCCGT GATGCATGAG GCTCTGCACA ACCACTACAC
8401 GCAGAAGAGC CTCTCCCTGT CTCCGGGTAA A

(ii) Fc (same sequence as A (ii) (SEQ ID NO:3))]
C. B-Domain Deleted FVIII Encoding Nucleotide Sequence (SEQ ID NO: 1)
gccaccagaa gatactacct gggtgcagtg gaactgtcat gggactatat gcaaagtgat 60
ctcggtgagc tgcctgtgga cgcaagattt cctcctagag tgccaaaatc ttttccattc 120
aacacctcag tcgtgtacaa aaagactctg tttgtagaat tcacggatca cctttttcaac 180
atcgctaagc caaggccacc ctggatgggt ctgctaggtc ctaccatcca ggctgaggtt 240
tatgatacag tggtcattac acttaagaac atggcttccc atcctgtcag tcttcatgct 300
gttggtgtat cctactggaa agcttctgag ggagctgaat atgatgatca gaccagtcaa 360
agggagaaag aagatgataa agtcttccct ggtggaagcc atacatatgt ctggcaggtc 420
ctgaaagaga atggtccaat ggcctctgac ccactgtgcc ttacctactc atatctttct 480
catgtggacc tggtaaaaga cttgaattca ggcctcattg gagccctact agtatgtaga 540
gaagggagtc tggccaagga aaagacacag accttgcaca aatttatact actttttgct 600
gtatttgatg aagggaaaag ttggcactca gaaacaaaga actccttgat gcaggatagg 660
gatgctgcat ctgctcgggc ctggcctaaa atgcacacag tcaatggtta tgtaaacagg 720
tctctgccag gtctgattgg atgccacagg aaatcagtct attggcatgt gattggaatg 780

TABLE 1-continued

| Polynucleotide Sequences |
|---|
| ggcaccactc ctgaagtgca ctcaatattc ctcgaaggtc acacatttct tgtgaggaac 840<br>catcgccagg cgtccttgga aatctcgcca ataactttcc ttactgctca aacactcttg 900<br>atggaccttg gacagtttct actgttttgt catatctctt cccaccaaca tgatggcatg 960<br>gaagcttatg tcaaagtaga cagctgtcca gaggaacccc aactacgaat gaaaaataat 1020<br>gaagaagcgg aagactatga tgatgatctt actgattctg aaatggatgt ggtcaggttt 1080<br>gatgatgaca actctccttc ctttatccaa attcgctcag ttgccaagaa gcatcctaaa 1140<br>acttgggtac attacattgc tgctgaagag gaggactggg actatgctcc cttagtcctc 1200<br>gcccccgatg acagaagtta taaaagtcaa tatttgaaca atggccctca gcggattggt 1260<br>aggaagtaca aaaaagtccg atttatggca tacacagatg aaacctttaa gactcgtgaa 1320<br>gctattcagc atgaatcagg aatcttggga cctttacttt atggggaagt tggagacaca 1380<br>ctgttgatta tatttaagaa tcaagcaagc agaccatata acatctaccc tcacggaatc 1440<br>actgatgtcc gtcctttgta ttcaaggaga ttaccaaaag gtgtaaaaca tttgaaggat 1500<br>tttccaattc tgccaggaga aatattcaaa tataaatgga cagtgactgt agaagatggg 1560<br>ccaactaaat cagatcctcg gtgcctgacc cgctattact ctagtttcgt taatatggag 1620<br>agagatctag cttcaggact cattggccct ctcctcatct gctacaaaga atctgtagat 1680<br>caaagaggaa accagataat gtcagacaag aggaatgtca tcctgttttc tgtatttgat 1740<br>gagaaccgaa gctggtacct cacagagaat atacaacgct ttctccccaa tccagctgga 1800<br>gtgcagcttg aggatccaga gttccaagcc tccaacatca tgcacagcat caatggctat 1860<br>gtttttgata gtttgcagtt gtcagtttgt ttgcatgagg tggcatactg gtacattcta 1920<br>agcattggag cacagactga cttcctttct gtcttcttct ctggatatac cttcaaacac 1980<br>aaaatggtct atgaagacac actcacccta ttcccattct caggagaaac tgtcttcatg 2040<br>tcgatggaaa acccaggtct atggattctg gggtgccaca actcagactt tcggaacaga 2100<br>ggcatgaccg ccttactgaa ggtttctagt tgtgacaaga acactggtga ttattacgag 2160<br>gacagttatg aagatatttc agcatacttg ctgagtaaaa acaatgccat tgaaccaaga 2220<br>agcttctctc aaaacccacc agtcttgaaa cgccatcaac gggaaataac tcgtactact 2280<br>cttcagtcag atcaagagga aattgactat gatgatacca tatcagttga aatgaagaag 2340<br>gaagattttg acatttatga tgaggatgaa aatcagagcc cccgcagctt tcaaaagaaa 2400<br>acacgacact attttattgc tgcagtggag aggctctggg attatgggat gagtagctcc 2460<br>ccacatgttc taagaaacag ggctcagagt ggcagtgtcc ctcagttcaa gaaagttgtt 2520<br>ttccaggaat ttactgatgg ctcctttact cagcccttat accgtggaga actaaatgaa 2580<br>catttgggac tcctggggcc atatataaga gcagaagttg aagataatat catggtaact 2640<br>ttcagaaatc aggcctctcg tccctattcc ttctattcta gccttatttc ttatgaggaa 2700<br>gatcagaggc aaggagcaga acctagaaaa aactttgtca agcctaatga aaccaaaact 2760<br>tacttttgga aagtgcaaca tcatatggca cccactaaag atgagtttga ctgcaaagcc 2820<br>tgggcttatt tctctgatgt tgacctggaa aaagatgtgc actcaggcct gattggaccc 2880<br>cttctggtct gccacactaa cacactgaac cctgctcatg ggagacaagt gacagtacag 2940<br>gaatttgctc tgtttttcac catctttgat gagaccaaaa gctggtactt cactgaaaat 3000<br>atggaaagaa actgcagggc tccctgcaat atccagatgg aagatcccac ttttaaagag 3060<br>aattatcgct tccatgcaat caatggctac ataatggata cactacctgg cttagtaatg 3120<br>gctcaggatc aaaggattcg atggtatctg ctcagcatgg gcagcaatga aaacatccat 3180<br>tctattcatt tcagtggaca tgtgttcact gtacgaaaaa aagaggagta taaaatggca 3240<br>ctgtacaatc tctatccagg tgtttttgag acagtggaaa tgttaccatc caaagctgga 3300<br>atttggcggg tggaatgcct tattggcgag catctacatg ctgggatgag cacacttttt 3360<br>ctggtgtaca gcaataagtg tcagactccc ctgggaatgg cttctggaca cattagagat 3420<br>tttcagatta cagcttcagg acaatatgga cagtgggccc caaagctggc cagacttcat 3480<br>tattccggat caatcaatgc ctggagcacc aaggagccct tttcttggat caaggtggat 3540<br>ctgttggcac caatgattat tcacggcatc aagacccagg gtgcccgtca gaagttctcc 3600<br>agcctctaca tctctcagtt tatcatcatg tatagtcttg atgggaagaa gtggcagact 3660<br>tatcgaggaa attccactgg aaccttaatg gtcttctttg gcaatgtgga ttcatctggg 3720<br>ataaaacaca atatttttaa ccctccaatt attgctcgat acatccgttt gcacccaact 3780<br>cattatagca ttcgcagcac tcttcgcatg gagttgatgg gctgtgattt aaatagttgc 3840<br>agcatgccat tgggaatgga gagtaaagca atatcagatg cacagattac tgcttcatcc 3900<br>tactttacca atatgtttgc cacctggtct ccttcaaaag ctcgacttca cctccaaggg 3960<br>aggagtaatg cctggagacc tcaggtgaat aatccaaaag agtggctgca agtggacttc 4020<br>cagaagacaa tgaaagtcac aggagtaact actcagggag taaaatctct gcttaccagc 4080<br>atgtatgtga aggagttcct catctccagc agtcaagatg gccatcagtg gactctcttt 4140<br>tttcagaatg gcaaagtaaa ggtttttcag ggaaatcaag actccttcac acctgtggtg 4200<br>aactctctag acccaccgtt actgactcgc taccttcgaa ttcacccccca gagttgggtg 4260<br>caccagattg ccctgaggat ggaggttctg ggctgcgagg cacaggacct ctac 4314<br><br>D. Full-length FVIII Encoding Nucleotide Sequence (SEQ ID NO: 5)<br>gccaccagaa gatactacct gggtgcagtg gaactgtcat gggactatat gcaaagtgat 60<br>ctcggtgagc tgcctgtgga cgcaagattt cctcctagag tgccaaaatc ttttccattc 120<br>aacacctcag tcgtgtacaa aaagactctg tttgtagaat tcacggatca ccttttcaac 180<br>atcgctaagc caaggccacc ctggatgggt ctgctaggtc ctaccatcca ggctgaggtt 240<br>tatgatacag tggtcattac acttaagaac atggcttccc atcctgtcag tcttcatgct 300<br>gttggtgtat cctactggaa agcttctgag ggagctgaat atgatgatca gaccagtcaa 360<br>agggagaaag aagatgataa agtcttccct ggtggaagcc atacatatgt ctggcaggtc 420<br>ctgaaagaga atggtccaat ggcctctgac ccactgtgcc ttacctactc atatctttct 480<br>catgtggacc tggtaaaaga cttgaattca ggcctcattg gagccctact agtatgtaga 540<br>gaagggagtc tggccaagga aaagacacag accttgcaca aatttatact actttttgct 600<br>gtatttgatg aagggaaaag ttggcactca gaaacaaaga actccttgat gcaggatagg 660<br>gatgctgcat ctgctcgggc ctggcctaaa atgcacacag tcaatggtta tgtaaacagg 720<br>tctctgccag gtctgattgg atgccacagg aaatcagtct attggcatgt gattggaatg 780<br>ggcaccactc ctgaagtgca ctcaatattc ctcgaaggtc acacatttct tgtgaggaac 840<br>catcgccagg cgtccttgga aatctcgcca ataactttcc ttactgctca aacactcttg 900<br>atggaccttg gacagtttct actgttttgt catatctctt cccaccaaca tgatggcatg 960<br>gaagcttatg tcaaagtaga cagctgtcca gaggaacccc aactacgaat gaaaaataat 1020 |

TABLE 1-continued

| Polynucleotide Sequences |
|---|
| gaagaagcgg aagactatga tgatgatctt actgattctg aaatggatgt ggtcaggttt 1080 |
| gatgatgaca actctccttc ctttatccaa attcgctcag ttgccaagaa gcatcctaaa 1140 |
| acttgggtac attacattgc tgctgaagag gaggactggg actatgctcc cttagtcctc 1200 |
| gcccccgatg acagaagtta taaaagtcaa tatttgaaca atggccctca gcggattggt 1260 |
| aggaagtaca aaaaagtccg atttatggca tacacagatg aaacctttaa gactcgtgaa 1320 |
| gctattcagc atgaatcagg aatcttggga cctttacttt atggggaagt tggagacaca 1380 |
| ctgttgatta tatttaagaa tcaagcaagc agaccatata acatctaccc tcacggaatc 1440 |
| actgatgtcc gtcctttgta ttcaaggaga ttaccaaaag gtgtaaaaca tttgaaggat 1500 |
| tttccaattc tgccaggaga aatattcaaa tataaatgga cagtgactgt agaagatggg 1560 |
| ccaactaaat cagatcctcg gtgcctgacc cgctattact ctagtttcgt taatatggag 1620 |
| agagatctag cttcaggact cattggccct ctcctcatct gctacaaaga atctgtagat 1680 |
| caaagaggaa accagataat gtcagacaag aggaatgtca tcctgttttc tgtatttgat 1740 |
| gagaaccgaa gctggtacct cacagagaat atacaacgct ttctccccaa tccagctgga 1800 |
| gtgcagcttg aggatccaga gttccaagcc tccaacatca tgcacagcat caatggctat 1860 |
| gtttttgata gtttgcagtt gtcagtttgt ttgcatgagg tggcatactg gtacattcta 1920 |
| agcattggag cacagactga cttcctttct gtcttcttct ctggatatac cttcaaacac 1980 |
| aaaatggtct atgaagacac actcacccta ttcccattct caggagaaac tgtcttcatg 2040 |
| tcgatggaaa acccaggtct atggattctg gggtgccaca actcagactt tcggaacaga 2100 |
| ggcatgaccg ccttactgaa ggtttctagt tgtgacaaga acactggtga ttattacgag 2160 |
| gacagttatg aagatatttc agcatacttg ctgagtaaaa acaatgccat tgaaccaaga 2220 |
| agcttctccc agaattcaag acaccctagc actaggcaaa agcaatttaa tgccaccaca 2280 |
| attccagaaa atgacataga gaagactgac ccttggtttg cacacagaac acctatgcct 2340 |
| aaaatacaaa atgtctcctc tagtgatttg ttgatgctct tqcgacagag tcctactcca 2400 |
| catgggctat ccttatctga tctccaagaa gccaaatatg agactttttc tgatgatcca 2460 |
| tcacctggag caatagacag taataacagc ctgtctgaaa tgacacactt caggccacag 2520 |
| ctccatcaca gtggggacat ggtatttacc cctgagtcag gcctccaatt aagattaaat 2580 |
| gagaaactgg ggacaactgc agcaacagag ttgaagaaac ttgatttcaa agtttctagt 2640 |
| acatcaaata atctgatttc aacaattcca tcagacaatt tggcagcagg tactgataat 2700 |
| acaagttcct taggaccccc aagtatgcca gttcattatg atagtcaatt agataccact 2760 |
| ctatttggca aaaagtcatc tccccttact gagtctggtg gacctctgag cttgagtgaa 2820 |
| gaaaataatg attcaaagtt gttagaatca ggtttaatga atagccaaga aagttcatgg 2880 |
| ggaaaaaatg tatcgtcaac agagagtggt aggttattta aagggaaaag agctcatgga 2940 |
| cctgctttgt tgactaaaga taatgcctta ttcaaagtta gcatctcttt gttaaagaca 3000 |
| aacaaaactt ccaataattc agcaactaat agaaagactc acattgatgg cccatcatta 3060 |
| ttaattgaga atagtccatc agtctggcaa aatatattag aaagtgacac tgagtttaaa 3120 |
| aaagtgacac ctttgattca tgacagaatg cttatggaca aaaatgctac agctttgagg 3180 |
| ctaaatcata tgtcaaataa aactacttca tcaaaaaaca tggaaatggt ccaacagaaa 3240 |
| aaagagggcc ccattccacc agatgcacaa aatccagata tgtcgttctt taagatgcta 3300 |
| ttcttgccag aatcagcaag gtggatacaa aggactcatg gaaagaactc tctgaactct 3360 |
| gggcaaggcc ccagtccaaa gcaattagta tccttaggac cagaaaaatc tgtggaaggt 3420 |
| cagaatttct tgtctgagaa aaacaaagtq gtagtaggaa agggtgaatt tacaaaggac 3480 |
| gtaggactca aagagatggt tttccaagc agcagaaacc tatttcttac taacttggat 3540 |
| aatttacatg aaaataatac acacaatcaa gaaaaaaaaa ttcaggaaga aatagaaaag 3600 |
| aaggaaacat taatccaaga gaatgtagtt ttgcctcaga tacatacagt gactggcact 3660 |
| aagaatttca tgaagaacct tttcttactg agcactaggc aaaatgtaga aggttcatat 3720 |
| gacggggcat atgctccagt acttcaagat tttaggtcat taaatgattc aacaaataga 3780 |
| acaaagaaac acacagctca tttctcaaaa aaaggggagg aagaaaactt ggaaggcttg 3840 |
| ggaaatcaaa ccaagcaaat tgtagagaaa tatgcatgca ccacaaggat atctcctaat 3900 |
| acaagccagc agaattttgt cacgcaacgt agtaagagag ctttgaaaca attcagactc 3960 |
| ccactagaag aaacagaact tgaaaaaagg ataattgtgg atgacacctc aacccagtgg 4020 |
| tccaaaaaca tgaaacattt qaccccgagc accctcacac agatagacta caatgagaag 4080 |
| gagaaagggg ccattactca gtctccctta tcagattgcc ttacgaggag tcatagcatc 4140 |
| cctcaagcaa atagatctcc attacccatt gcaaaggtat catcatttcc atctattaga 4200 |
| cctatatatc tgaccagggt cctattccaa gacaactctt ctcatcttcc agcagcatct 4260 |
| tatagaaaga aagattctgg ggtccaagaa agcagtcatt tcttacaagg agccaaaaaa 4320 |
| aataaccttt ctttagccat tctaaccttg gagatgactg gtgatcaaag agaggttggc 4380 |
| tccctgggga caagtgccac aaattcagtc acatacaaga aagttgagaa cactgttctc 4440 |
| ccgaaaccag acttgcccaa aacatctggc aaagttgaat tgcttccaaa agttcacatt 4500 |
| tatcagaagg acctattccc tacggaaact agcaatgggt ctcctggcca tctggatctc 4560 |
| gtggaaggga gccttcttca gggaacagag ggagcgatta agtggaatga agcaaacaga 4620 |
| cctggaaaag ttccctttct gagagtagca acagaaagct ctgcaaagac tccctccaag 4680 |
| ctattggatc ctcttgcttg ggataaccac tatggtactc agataccaaa agaagagtgg 4740 |
| aaatcccaag agaagtcacc agaaaaaaca gcttttaaga aaaaggatac cattttgtcc 4800 |
| ctgaacgctt gtgaaagcaa tcatgcaata gcagcaataa atgagggaca aaataagccc 4860 |
| gaaatagaag tcacctgggc aaagcaaggt aggactgaaa ggctgtgctc tcaaaaccca 4920 |
| ccagtcttga aacgccatca acgggaaata actcgtacta ctcttcagtc agatcaagag 4980 |
| gaaattgact atgatgatac catatcagtt gaaatgaaga aggaagattt tgacatttat 5040 |
| gatgaggatg aaaatcagag cccccgcagc tttcaaaaga aaacacgaca ctattttatt 5100 |
| gctgcagtgg agaggctctg ggattatggg atgagtagct ccccacatgt tctaagaaac 5160 |
| agggctcaga gtggcagtgt ccctcagttc aagaaagttg ttttccagga atttactgat 5220 |
| ggctccttta ctcagccctt ataccgtgga gaactaaatg aacatttggg actcctgggg 5280 |
| ccatatataa gagcagaagt tgaagataat atcatggtaa ctttcagaaa tcaggcctct 5340 |
| cgtccctatt ccttctattc tagccttatt tcttatgagg aagatcagag gcaaggagca 5400 |
| gaacctagaa aaaactttgt caagcctaat gaaaccaaaa cttacttttg gaaagtgcaa 5460 |
| catcatatgg cacccactaa agatgagttt gactgcaaag cctgggctta tttctctgat 5520 |
| gttgacctgg aaaaagatgt gcactcaggc ctgattggac cccttctggt ctgccacact 5580 |
| aacacactga accctgctca tgggagacaa gtgacagtac aggaatttgc tctgtttttc 5640 |
| accatctttg atgagaccaa aagctggtac ttcactgaaa atatggaaag aaactgcagg 5700 |

TABLE 1-continued

| Polynucleotide Sequences |
|---|
| gctccctgca atatccagat ggaagatccc acttttaaag agaattatcg cttccatgca 5760 |
| atcaatggct acataatgga tacactacct ggcttagtaa tggctcagga tcaaaggatt 5820 |
| cgatggtatc tgctcagcat gggcagcaat gaaaacatcc attctattca tttcagtgga 5880 |
| catgtgttca ctgtacgaaa aaaagaggag tataaaatgg cactgtacaa tctctatcca 5940 |
| ggtgtttttg agacagtgga aatgttacca tccaaagctg gaatttggcg ggtggaatgc 6000 |
| cttattggcg agcatctaca tgctgggatg agcacacttt ttctggtgta cagcaataag 6060 |
| tgtcagactc ccctgggaat ggcttctgga cacattagag attttcagat tacagcttca 6120 |
| ggacaatatg gacagtgggc cccaaagctg gccagacttc attattccgg atcaatcaat 6180 |
| gcctggagca ccaaggagcc cttttcttgg atcaaggtgg atctgttggc accaatgatt 6240 |
| attcacggca tcaagaccca gggtgcccgt cagaagttct ccagcctcta catctctcag 6300 |
| tttatcatca tgtatagtct tgatgggaag aagtggcaga cttatcgagg aaattccact 6360 |
| ggaaccttaa tggtcttctt tggcaatgtg gattcatctg ggataaaaca caatattttt 6420 |
| aaccctccaa ttattgctcg atacatccgt ttgcacccaa ctcattatag cattcgcagc 6480 |
| actcttcgca tggagttgat gggctgtgat ttaaatagtt gcagcatgcc attgggaatg 6540 |
| gagagtaaag caatatcaga tgcacagatt actgcttcat cctactttac caatatgttt 6600 |
| gccacctggt ctccttcaaa agctcgactt cacctccaag ggaggagtaa tgcctggaga 6660 |
| cctcaggtga ataatccaaa agagtggctg caagtggact tccagaagac aatgaaagtc 6720 |
| acaggagtaa ctactcaggg agtaaaatct ctgcttacca gcatgtatgt gaaggagttc 6780 |
| ctcatctcca gcagtcaaga tggccatcag tggactctct tttttcagaa tggcaaagta 6840 |
| aaggtttttc agggaaatca agactccttc acacctgtgg tgaactctct agacccaccg 6900 |
| ttactgactc gctaccttcg aattcacccc cagagttggg tgcaccagat tgccctgagg 6960 |
| atggaggttc tgggctgcga ggcacaggac ctctac 6996 |

TABLE 2

Polypeptide Sequences

A. B-Domain Deleted FVIII-Fc Monomer Hybrid: created by coexpressing BDD FVIIIFc and Fc chains.

Construct = HC-LC-Fc fusion. An Fc expression cassette is cotransfected with BDDFVIII-Fc to generate the BDD FVIIIFc monomer-. For the BDD FVIIIFc chain, the Fc sequence is shown in bold; HC sequence is shown in double underline; remaining B domain sequence is shown in italics. Signal peptides are underlined.

i) B domain deleted FVIII-Fc chain (19 amino acid signal sequence underlined) (SEQ ID NO: 60)

MQIELSICFFLCLLRFCFS
ATRRYYLGAVELSWDYMQSDLGELPVDARFPPRVPKSFPFNTSVVYKKTLFVEFTDHLFNIAKPR
PPWMGLLGPTIQAEVYDTVVITLKNMASHPVSLHAVGVSYWKASEGAEYDDQTSQREKEDDKVFP
GGSHTYVWQVLKENGPMASDPLCLTYSYLSHVDLVKDLNSGLIGALLVCREGSLAKEKTQTLHKF
ILLFAVFDEGKSWHSETKNSLMQDRDAASARAWPKMHTVNGYVNRSLPGLIGCHRKSVYWHVIGM
GTTPEVHSIFLEGHTFLVRNHRQASLEISPITFLTAQTLLMDLGQFLLFCHISSHQRDGMEAYVK
VDSCPEEPQLRMKNNEEAEDYDDDLTDSEMDVVREDDDNSPSFIQIRSVAKKHPKTWVHYIAAEE
EDWDYAPLVLAPDDRSYKSQYLNNGPQRIGRKYKKVRFMAYTDETFKTREAIOHESGILGPLLYG
EVGDTLLIIFKNQASRPYNIYPHGITDVRPLYSRRLPKGVKHLKDFPILPGEIFKYKWTVTVEDG
PIKSDPRCLTRYYSSFVNMERDLASGLIGPLLICYKESVDQRGNQIMSDKRNVILFSVFDENRSW
YLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNT
GDYYEDSYEDISAYLLSKNNAIEPR*SFSQNPPVLKRHQR*EITRTTLQSDQEEIDYDDTISVEMKK
EDFDIYDEDENQSPRSFQKKTRHYFIAAVERLWDYGMSSSPHVLRNRAQSGSVPQFKKVVFQEFT
DGSFTQPLYRGELNEHLGLLGPYIRAEVEDNIMVTFRNQASRPYSFYSSLISYEEDQRQGAEPRK
NFVKPNETKTYFWKVQHHMAPTKDEFDCKAWAYFSDVDLEKDVHSGLIGFLLVCHTNTLNPAHGR
QVTVQEFALFFTIFDETKSWYFTENMERNCRAPCNIQMEDPTFKENYRFHAINGYIMDTLPGLVM
AQDQRIRWYLLSMGSNENIHSIHFSGHVFTVRKKEEYKMALYNLYPGVFETVEMLPSKAGIWRVE
CLIGEHLHAGMSTLFLVYSNKCQTPLGMASGHIRDFQITASGQYGQWAPKLARLHYSGSINAWST
KEPFSWIKVDLLAPMIIHGIKTQGARQKFSSLYISQFIIMYSLDGKKWQTYRGNSTGTLMVFFGN
VDSSGIKHNIFNPPIIARYIRLHPTHYSIRSTLRMELMGCDLNSCSMPLGMESKAISDAQITASS
YFTNMFATWSPSKARLHLQGRSNAWRPQVNNPKEWLQVDFQKTMKVTGVITQGVKSLLTSMYVKE
FLISSSQDGHQWTLFFQNGKVKVFQGNQDSFTPVVNSLDPPLLTRYLRIHPQSWVHQIALRMEVL
GCEAQDLYDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK ii) Fc chain (20 amino acid heterologous signal peptide from mouse Igκ chain underlined) (SEQ ID NO: 4)

METDTLLLWVLLLWVPGSTG
DKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK ii) B-Domain Deleted FVIII Without Signal Peptide (SEQ ID NO: 2)

ATRRYYLGAVELSWDYMQSDLGELPVDARFPPRVPKSFPFNTSVVYKKTLFVEFTDHLFNIAKPR
PPWMGLLGPTIQAEVYDTVVITLKNMASHPVSLHAVGVSYWKASEGAEYDDQTSQREKEDDKVFP
GGSHTYVWQVLKENGPMASDPLCLTYSYLSHVDLVKDLNSGLIGALLVCREGSLAKEKTQTLHKF

TABLE 2-continued

Polypeptide Sequences

ILLFAVFDEGKSWHSETKNSLMQDRDAASARAWPKMHTVNGYVNRSLPGLIGCHRKSVYWHVIGM
GTTPEVHSIFLEGHTFLVRNHRQASLEISPITFLTAQTLLMDLGQFLLFCHISSHQHDGMEAYVK
VDSCPEEPQLRMKNNEEAEDYDDDLTDSEMDVVRFDDDNSPSFIQIRSVAKKHPKTWVHYIAAEE
EDWDYAPLVLAPDDRSYKSQYLNNGPQRIGRKYKKVRFMAYTDETFKTREAIQHESGILGPLLYG
EVGDTLLIIFKNQASRPYNIYPHGITDVRPLYSRRLPKGVKHLKDFPILPGEIFKYKWTVTVEDG
PTKSDPRCLTRYYSSFVNMERDLASGLIGPLLICYKESVDQRGNQIMSDKRNVILFSVFDENRSW
YLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNT
GDYYEDSYEDISAYLLSKNNAIEPRSFSQNPPVLKRHQREITRTTLQSDQEEIDYDDTISVEMKK
EDFDIYDEDENQSPRSFQKKTRHYFIAAVERLWDYGMSSSPHVLRNRAQSGSVPQFKKVVFQEFT
DGSFTQPLYRGELNEHLGLLGPYIRAEVEDNIMVTFRNQASRPYSFYSSLISYEEDQRQGAEPRK
NFVKPNETKTYFWKVQHHMAPTKDEFDCKAWAYFSDVDLEKDVHSGLIGPLLVCHTNTLNPAHGR
QVTVQEFALFFTIFDETKSWYFTENMERNCRAPCNIQMEDPTFKENYRFHAINGYIMDTLPGLVM
AQDQRIRWYLLSMGSNENIHSIHFSGHVFTVRKKEEYKMALYNLYPGVFETVEMLPSKAGIWRVE
CLIGEHLHAGMSTLFLVYSNKCQTPLGMASGHIRDFQITASGQYGQWAPKLARLHYSGSINAWST
KEPFSWIKVDLLAPMIIHGIKTQGARQKFSSLYISQFIIMYSLDGKKWQTYRGNSTGTLMVFFGN
VDSSGIKHNIFNPPIIARYIRLHPTHYSIRSTLRMELMGCDLNSCSMPLGMESKAISDAQITASS
YFTNMFATWSPSKARLHLQGRSNAWRPQVNNPKEWLQVDFQKTMKVTGVTTQGVKSLLTSMYVKE
FLISSSQDGHQWTLFFQNGKVKVFQGNQDSFTPVVNSLDPPLLTRYLRIHPQSWVHQIALRMEVL
GCEAQDLY

B. Full-length FVIIIFc monomer hybrid: created by coexpressing FVIIIFc and Fc chains.
Construct = HC-B-LC-Fc fusion. An Fc expression cassette is cotransfected with full-length FVIII-Fc to generate the full-length FVIIIFc monomer. For the FVIIIFc chain, the Fc sequence is shown in bold; HC sequence is shown in double underline; B domain sequence is shown in italics. Signal peptides are underlined.
i) Full-length FVIIIFc chain (FVIII signal peptide underlined (SEQ ID NO: 62)
MQIELSTCFFLCLLRFCFS
ATRRYYLGAVELSWDYMQSDLGELPVDARFPPRVPKSFPFNTSVVYKKTLFVEFTDHLFNIAKPR
PPWMGLLGPTIQAEVYDTVVITLKNMASHPVSLHAVGVSYWKASEGAEYDDQTSQREKEDDKVFP
GGSHTYVWQVLKENGPMASDPLCLTYSYLSHVDLVKDLNSGLIGALLVCREGSLAKEKTQTLHKF
ILLFAVFDEGKSWHSETKNSLMQDRDAASARAWPKMHTVNGYVNRSLPGLIGCHRKSVYWHVIGM
GTTPEVHSIFLEGHTFLVRNHRQASLEISPITFLTAQTLLMDLGQFLLFCHISSHQHDGMEAYVK
VDSCPEEPQLRMKNNEEAEDYDDDLTDSEMDVVRFDDDNSPSFIQIRSVAKKHPKTWVHYIAAEE
EDWDYAPLVLAPDDRSYKSQYLNNGPQRIGRKYKKVRFMAYTDETFKTREAIQHESGILGPLLYG
EVGDTLLIIFKNQASRPYNIYPHGITDVRPLYSRRLPKGVKHLKDFPILPGEIFKYKWTVTVEDG
PIKSDPRCLTRYYSSEVNMERDLASGLIGPLLICYKESVDQRGNQIMSDKRNVILFSVFDENRSW
YLTENIQRFLPNPAGVQLEDREFQASNIMHSINGYVFDSLALSVCLHEVAYWYILSIGAQTDFLS
VFFSGYTEKHKMVYEDTLTLFPFSGETVFMSMENPGLWILGCHNSDERNRGMTALLKVSSCDKNT
GDYYEDSYEDISAYLLSKNNAIEPR*SFSQNSRHPSTRQKQFNATTIPENDIEKTDPWFAHRTPMP*
*KIQNVSSSDLLMLLRQSPTPHGLSLSDLQEAKYETFSDDPSPGAIDSNNSLSEMTHFRPQLHHSG*
*DMVFTPESGLQLRLNEKLGTTAATELKKLDFKVSSTSNNLISTIPSDNLAAGTDNTSSLGPPSMP*
*VHYDSQLDTTLFGKKSSPLTESGGPLSLSEENNDSKLLESGLMNSQESSWGKNVSSTESGRLFKG*
*KRAHGPALLTKDNALFKVSISLLKTNKTSNNSATNRKTHIDGPSLLIENSPSVWQNILESDTEFK*
*KVTPLIHDRMLMDKNATALRLNHMSNKTTSSKNMEMVQQKKEGPIPPDAQNPDMSFFKMLFLPES*
*ARWIQRTHGKNSLNSGQGPSPKQLVSLGPEKSVEGQNFLSEKNKVVVGKGEFTKDVGLKEMVFPS*
*SRNLFLTNLDNLHENNTHNQEKKIQEEIEKKETLIQENVVLPQIHTVTGTKNFMKNLFLLSTRQN*
*VEGSYDGAYAPVLQDFRSLNDSTNRTKKHTAHFSKKGEEENLEGLGNQTKQTVEKYACTTRISPN*
*TSQQNFVTQRSKRALKQFRLPLEETELEKRIIVDDTSTQWSKNMKHLTPSTLTQIDYNEKEKGAI*
*TQSPLSDCLTRSHSIPQANRSPLPIAKVSSFPSIRPIYLTRVLFQDNSSHLPAASYRKKDSGVQE*
*SSHFLOGAKKNNLSLAILTLEMTGDQREVGSLGTSATNSVTYKKVENTVlPKPDLPKTSGKVELL*
*PKVHIYQKDLFPTETSNGSPGHLDLVEGSLLQGTEGAIKWNEANRPGKVPFLRVATESSAKTPSK*
*LLDPLAWDNHYGTQIPKEEWKSQEKSPEKTAFKKKDTILSLNACESNHAIAAINEGQNKPETEVT*
*WAKQGRTERLCSQNPPVLKRHQR*EITRTTLQSDQEEIDYDDTISVEMKKEDFDIYDEDENQSPRS
FQKKTRHYFIAAVERLWDYGMSSSPHVLRNRAQSGSVPQFKKVVFQEFTDGSFTQPLYRGELNEH
LGLLGPYIRAEVEDNIMVTFRNQASRPYSFYSSLISYEEDQRQGAEPRKNFVKPNETKTYFWKVQ
HHMAPTKDEFDCKAWAYFSDVDLEKDVHSGLIGPLLVCHTNTLNPAHGRQVTVQEFALFFTIFDE
TKSWYFTENMERNCRAPCNIQMEDPTFKENYRFHAINGYIMDTLPGLVMAQDQRIRWYLLSMGSN
ENIHSIHFSGHVFTVRKKEEYKMALYNLYPGVFETVEMLPSKAGIWRVECLIGEHLHAGMSTLFL
VYSNKCQTPLGMASGHIRDFQITASGQYGQWAPKLARLHYSGSINAWSTKEPFSWIKVDLLAPMI
IHGIKTQGARQKFSSLYISQFIIMYSLDGKKWQTYRGNSTGTLMVFFGNVDSSGIKHNIFNPPII
ARYIRLHPTHYSIRSTLRMELMGCDLNSCSMPLGMESKAISDAQITASSYFTNMFATWSPSKARL
HLQGRSNAWRPQVNNPKEWLQVDFQKTMKVTGVTTQGVKSLLTSMYVKEFLISSSQDGHQWTLFF
QNGKVKVFQGNQDSFTPVVNSLDPPLLTRYLRIHPQSWVHQIALRMEVLGCEAQDLYDKTHTCPP
CPAPELLGGPSVPLFPPKPKDTLMISRTPEVTCVVVDVSHEDPEVKFNWYVDGVEVENAKTKPRE
EQYNSTYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQQGNVF
SCSVNBEALHNHYTQKSLSLSPGK ii) Fc chain (20 amino acid heterologous signal peptide from mouse Igκ chain underlined) (SEQ ID NO: 4)
METDTLLLWVLLLWVPGSTG
DKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK TABLE 2-continued

| Polypeptide Sequences |
|---|
| iii) Full-length FVIII Without Signal Peptide (SEQ ID NO: 6)<br>ATRRYYLGAVELSWDYMQSDLGELPVDARFPPRVPKSFPFNTSVVYKKTLFVEF<br>TDHLFNIAKPRPPWMGLLGPTIQAEVYDTVVITLKNMASHPVSLHAVGVSYWKASEGAEYDDQTS<br>QREKEDDKVFPGGSHTYVWQVLKENGPMASDPLCLTYSYLSHVDLVKDLNSGLIGALLVCREGSL<br>AKEKTQTLHKFILLFAVFDEGKSWHSETKNSLMQDRDAASARAWPKMHTVNGYVNRSLPGLIGCH<br>RKSVYWHVIGMGTTPEVHSIFLEGHTFLVRNHRQASLEISPITFLTAQTLLMDLGQFLLFCHISS<br>HQHDGMEAYVKVDSCPEEPQLRMKNNEEAEDYDDDLTDSEMDVVRFDDDNSPSFIQIRSVAKKHP<br>KTWVHYTAAEEEDWDYAPLVLAPDDRSYKSQYLNNGPQRIGRKYKKVREMAYTDETFKTREAIQH<br>ESGILGPLLYGEVGDTLLIIFKNQASRPYNIYPHGITDVRPLYSRRLPKGVKHLKDEPILPGEIF<br>KYKWTVTVEDGPTKSDPRCLTRYYSSFVNMERDLASGLIGPLLICYKESVDQRGNQIMSDKRNVI<br>LFSVEDENRSWYLTENIQRFLPNPAGVQLEDPEFQASNIMHSINGYVEDSLQLSVCLHEVAYWYI<br>LSIGAQTDFLSVFFSGYTFKHKMVYEDTLTLFPFSGETVFMSMENPGLWILGCHNSDERNRGMTA<br>LLKVSSCDKNTGDYYEDSYEDISAYLLSKNNAIEPRSFSQNSRHPSTRQKQFNATTIPENDIEKT<br>DPWFAHRTPMPKIQNVSSSDLLMLLRQSPTPHGLSLSDLQEAKYETFSDDPSPGAIDSNNSLSEM<br>THFRPQLHHSGDMVFTPESGLQLRLNEKLGTTAATELKKLDEKVSSTSNNLISTIPSDNLAAGTD<br>NTSSLGPPSMPVHYDSQLDTTLFGKKSSPLTESGGPLSLSEENNDSKLLESGLMNSQESSWGKNV<br>SSTESGRLFKGKRAHGPALLTKDNALFKVSISLLKTNKTSNNSATNRKTHIDGPSLLIENSPSVW<br>QNILESDTEFKKVTPLIHDRMLMDKNATALRLNHMSNKTTSSKNMEMVQQKKEGPIPPDAQNPDM<br>SFFKMLFLPESARWIQRTHGKNSLNSGQGPSPKQLVSLGPEKSVEGQNFLSEKNKVVVGKGEFTK<br>DVGLKEMVETSSRNLFLTNLDNLHENNTHNQEKKIQEETEKKETLIQENVVLPQIHTVTGTKNEM<br>KNLFLLSTRQNVEGSYDGAYAPVLQDFRSLNDSTNRTKKHTAHFSKKGEEENLEGLGNQTKQIVE<br>KYACTTRISPNTSQQNFVTQRSKRALKQERLPLEETELEKRIIVDDTSTQWSKNMKHLTPSTLTQ<br>IDYNEKEKGAITQSPLSDCLTRSHSIPQANRSPLPIAKVSSFPSIRPIYLTRVLFQDNSSHLPAA<br>SYRKKDSGVQESSHFLQGAKKNNLSLAILTLEMTGDQREVGSLGTSATNSVTYKKVENTVLPKPD<br>LPKTSGKVELLPKVHIYQKDLFPTETSNGSPGHLDLVEGSLLQGTEGAIKWNEANRPGKVPFLRV<br>ATESSAKTPSKLLDPLAWDNHYGTQIPKEEWKSQEKSPEKTAFKKKDTILSLNACESNHAIAAIN<br>EGQNKPEIEVTWAKQGRTERLCSQNPPVLKRHQREITRTTLQSDQEEIDYDDTISVEMKKEDFDI<br>YDEDENQSPRSFQKKTRHYFIAAVERLWDYGMSSSPHVLRNRAQSGSVPQFKKVVFQEFTDGSFT<br>QPLYRGELNEHLGLLGPYIRAEVEDNIMVTFRNQASRPYSFYSSLISYEEDQRQGAEPRKNEVKP<br>NETKTYFWKVQHHMAPTKDEFDCKAWAYFSDVDLEKDVHSGLIGPLLVCHTNTLNPAHGRQVTVQ<br>EFALFFTIFDETKSWYFTENMERNCRAPCNIQMEDPTEKENYRFHAINGYINDTLPGLVMAQDQR<br>IRWYLLSMGSNENIHSIHFSGHVFTVRKKEEYKMALYNLYPGVFETVEMLPSKAGIWRVECLIGE<br>HLHAGMSTLFLVYSNKCQTPLGMASGHIRDFQITASGQYGQWAPKLARLHYSGSINAWSTKEPFS<br>WIKVDLLAPMIIHGIKTQGARQKFSSLYISQFIIMYSLDGKKWQTYRGNSIGTLMVFEGNVDSSG<br>IKHNIFNPPIIARYIRLHPTHYSIRSTLRMELMGCDLNSCSMPLGMESKAISDAQITASSYFTNM<br>FATWSPSKARLHLQGRSNAWRPQVNNPKEWLQVDFQKTMKVTGVTTQGVKSLLTSMYVKEFLISS<br>SQDGHQWTLFFQNGKVKVFQGNQDSFTPVVNSLDPPLLTRYLRIHPQSWVHQIALRMEVLGCEAQ<br>DLY |

What is claimed is:

1. A method for decreasing nonprocessed Factor VIII (FVIII) in a culturing medium, comprising contacting a nonprocessed FVIII polypeptide expressed from a polynucleotide in a host cell with proprotein convertase subtilisin/kexin type 5 (PC5), wherein the PC5 is expressed from a second polynucleotide in the host cell expressing the FVIII, wherein the host cell is a mammalian cell, and wherein the PC5 processes the nonprocessed FVIII polypeptide to a processed FVIII polypeptide, which comprises a FVIII heavy chain and a FVIII light chain associated by a non-covalent bond.

2. The method of claim 1, wherein the proprotein convertase cleaves Arginine in the nonprocessed FVIII polypeptide at an amino acid residue corresponding to amino acid 1648 of SEQ ID NO: 6 or amino acid 754 of SEQ ID NO: 2.

3. The method of claim 1, wherein the FVIII heavy chain and the FVIII light chain are associated by a metal-ion mediated non-covalent bond.

4. The method of claim 1, wherein the level of the nonprocessed FVIII polypeptide is decreased such that more than 75%, 80%, 85%, 90%, 95%, and 100% of the FVIII is the processed FVIII polypeptide.

5. The method of claim 1, wherein the nonprocessed FVIII polypeptide is expressed as full-length FVIII or partial or full B-domain deleted FVIII.

6. The method of claim 1, wherein the FVIII polypeptides are fused to an immunoglobulin constant region or a portion thereof.

7. The method of claim 6, wherein the immunoglobulin constant region or a portion thereof comprises a neonatal Fc Receptor (FcRn) binding domain.

8. The method of claim 1, wherein the polynucleotide encoding the nonprocessed FVIII polypeptide and the second polynucleotide encoding PC5 are located on the same vector or on two different vectors.

9. The method of claim 1, wherein the host cell is a CHO cell, a HEK293 cell, a HKB11 cell, or a BHK cell.

10. The method of claim 1, wherein the polynucleotide encoding the nonprocessed FVIII polypeptide and the second polynucleotide encoding the PC5 are expressed from two different vectors.

11. The method of claim 1, wherein the processed FVIII polypeptide is produced in a large manufacturing process.

12. The method of claim 1, wherein the PC5 comprises an amino acid sequence at least 80% identical to the sequence set forth as SEQ ID NO: 18 and wherein the PC5 is capable of cleaving full-length FVIII or B domain-deleted FVIII.

13. The method of claim 1, wherein the PC5 comprises an amino acid sequence at least 95% identical to the sequence set forth as SEQ ID NO: 18 and wherein the PC5 is capable of cleaving full-length FVIII or B domain-deleted FVIII.

14. The method of claim 1, wherein the PC5 comprises the amino acid sequence set forth as SEQ ID NO: 18.

15. The method of claim 1, wherein the processed FVIII polypeptide is further cleaved by thrombin and is activated.

16. The method of claim 1, wherein the FVIII polypeptide comprises human full-length FVIII.

17. The method of claim 1, wherein the FVIII polypeptide comprises human B domain-deleted FVIII.

18. The method of claim 6, wherein the immunoglobulin constant region or portion thereof comprises an Fc fragment.

19. The method of claim 6, wherein the host cell further comprises a second polynucleotide encoding a second immunoglobulin constant region or portion thereof, which comprises a neonatal Fc Receptor (FcRn) binding domain.

20. The method of claim 19, wherein the second immunoglobulin constant region or portion thereof comprises an Fc fragment.

21. The method of claim 8, wherein each of the polynucleotide encoding the nonprocessed FVIII polypeptide and the second polynucleotide encoding the PC5 is operably linked to a promoter.

22. The method of claim 8, wherein the polynucleotide encoding the nonprocessed FVIII polypeptide and the second polynucleotide encoding the PC5 are operably linked to a single promoter.

23. A method of increasing the yield of processed Factor VIII polypeptides in a host cell comprising contacting a nonprocessed FVIII polypeptide expressed from a polynucleotide in a host cell with proprotein convertase subtilisin/kexin type 5 (PC5), wherein the PC5 is expressed from a second polynucleotide in the host cell, wherein the host cell is a mammalian cell, and wherein the PC5 processes the nonprocessed FVIII polypeptide to a processed FVIII polypeptide, which comprises a FVIII heavy chain and a FVIII light chain associated by a non-covalent bond.

24. The method of claim 23, wherein the polynucleotide encoding the nonprocessed FVIII polypeptide and the second polynucleotide encoding the PC5 are on the same vector or on the different vectors.

25. A method of reducing the level of nonprocessed Factor VIII polypeptides in a host cell comprising contacting a nonprocessed FVIII polypeptide expressed from a polynucleotide in the host cell with PC5 expressed from a second polynucleotide in the host cell, wherein the host cell is a mammalian cell, and wherein the PC5 processes the nonprocessed FVIII polypeptide to a processed FVIII polypeptide, which comprises a FVIII heavy chain and a FVIII light chain.

* * * * *